US012678067B1

(12) United States Patent  
Goldberg et al.

(10) Patent No.: US 12,678,067 B1  
(45) Date of Patent: Jul. 14, 2026

(54) TELEMETRY IMPLANTS

(71) Applicant: Biological Art Group, Inc., Miami, FL (US)

(72) Inventors: Barry A. Goldberg, Miami, FL (US); Steven M. Hoffberg, West Harrison, NY (US)

(*) Notice: Subject to any disclaimer, the term of this patent is extended or adjusted under 35 U.S.C. 154(b) by 596 days.

(21) Appl. No.: 16/826,027

(22) Filed: Mar. 20, 2020

Related U.S. Application Data

(60) Provisional application No. 62/821,013, filed on Mar. 20, 2019.

(51) Int. Cl.  
A61B 5/07 (2006.01)  
A61B 5/00 (2006.01)  
(Continued)

(52) U.S. Cl.  
CPC ............ A61B 5/076 (2013.01); A61B 5/1459 (2013.01); A61B 5/1473 (2013.01); A61B 90/98 (2016.02);  
(Continued)

(58) Field of Classification Search  
CPC ..... A61B 5/076; A61B 5/1459; A61B 5/1473; A61B 90/98; A61B 5/002; A61B 5/0071; A61B 5/1032; A61B 5/14532; A61B 5/14539; A61B 5/14542; A61B 5/14546; A61B 5/318; A61B 5/369; A61B 5/389; A61B 2560/0219; A61B 2562/0204; A61B 2562/0219; A61B 2562/0247; A61B 2562/0261; A61B 2562/028; A61B 2562/0285; A61B 5/07; A61B 5/073;

G08C 17/02; H04Q 2209/43; H04Q 2209/86; H04Q 9/00; H04W 4/80; H04W 12/06; H04W 12/041; H04W 12/33; H04W 12/47; H04W 12/50; H04W 52/028; H04W 64/00; H04W 76/10; H04W 76/14; H04W 76/30; H04W 80/00; H04W 88/02; H04W 80/10;  
(Continued)

(56) References Cited

U.S. PATENT DOCUMENTS 4,698,631 A 10/1987 Kelly, Jr. et al.  
4,734,698 A 3/1988 Nysen et al.  
(Continued)

OTHER PUBLICATIONS

"Near Field Communication versus Bluetooth." Near Field Communication versus Bluetooth—NearFieldCommunication.org, Jun. 6, 2012, <https://web.archive.org/web/20120606132133/http://nearfieldcommunication.org/bluetooth.html> (Year: 2012).*  
(Continued)

*Primary Examiner* — Aurelie H Tu  
*Assistant Examiner* — Andrew E Hoffpauir

(57) ABSTRACT

An implantable device having a sensor configured to detect a physiological condition, e.g., temperature, dynamics, sounds, amount of an analyte, pH, temperature, strain, pressure, bioelectric activity, an optical sensor, etc., a microcontroller, configured to process data from the sensor and store processed data in a memory, a rechargeable electrical power source, and a telemetry system. The telemetry system optionally harvests power to recharge the rechargeable electrical power source, or to directly power the system. The implantable device is encapsulated in a biocompatible shell.

20 Claims, 6 Drawing Sheets

(51) Int. Cl.

| | | |
|---|---|---|
| *A61B 5/103* | (2006.01) |
| *A61B 5/145* | (2006.01) |
| *A61B 5/1459* | (2006.01) |
| *A61B 5/1473* | (2006.01) |
| *A61B 5/318* | (2021.01) |
| *A61B 5/369* | (2021.01) |
| *A61B 5/389* | (2021.01) |
| *A61B 90/98* | (2016.01) |
| *H04W 4/80* | (2018.01) |

(52) U.S. Cl.

CPC ............. *A61B 5/002* (2013.01); *A61B 5/0071* (2013.01); *A61B 5/1032* (2013.01); *A61B 5/14532* (2013.01); *A61B 5/14539* (2013.01); *A61B 5/14542* (2013.01); *A61B 5/14546* (2013.01); *A61B 5/318* (2021.01); *A61B 5/369* (2021.01); *A61B 5/389* (2021.01); *A61B 2503/40* (2013.01); *A61B 2560/0219* (2013.01); *A61B 2562/0204* (2013.01); *A61B 2562/0219* (2013.01); *A61B 2562/0247* (2013.01); *A61B 2562/0261* (2013.01); *A61B 2562/0271* (2013.01); *H04Q 2209/43* (2013.01); *H04W 4/80* (2018.02)

(58) Field of Classification Search

CPC ........ H02J 50/20; H02J 7/00034; H02J 50/00; H02J 50/40; H02J 50/80; H04L 2209/88; H04L 63/04

See application file for complete search history.

(56) References Cited

U.S. PATENT DOCUMENTS

| | | | |
|---|---|---|---|
| 4,737,789 | A | 4/1988 | Nysen |
| 5,095,240 | A | 3/1992 | Nysen et al. |
| 5,129,394 | A | 7/1992 | Mehra |
| 5,182,570 | A | 1/1993 | Nysen et al. |
| 5,246,008 | A | 9/1993 | Mueller |
| 5,506,420 | A | 4/1996 | Kossovsky et al. |
| 5,585,646 | A | 12/1996 | Kossovsky et al. |
| 5,764,518 | A | 6/1998 | Collins |
| 5,899,929 | A | 5/1999 | Thompson et al. |
| 5,967,986 | A | 10/1999 | Cimochowski et al. |
| 5,986,382 | A | 11/1999 | Nysen |
| 6,001,067 | A | 12/1999 | Shults et al. |
| 6,052,621 | A | 4/2000 | Begemann et al. |
| 6,060,815 | A | 5/2000 | Nysen |
| 6,107,910 | A | 8/2000 | Nysen |
| 6,114,971 | A | 9/2000 | Nysen |
| 6,141,592 | A | 10/2000 | Pauly |
| 6,170,318 | B1 | 1/2001 | Lewis |
| 6,208,062 | B1 | 3/2001 | Nysen et al. |
| 6,230,059 | B1 | 5/2001 | Duffin |
| 6,232,139 | B1 | 5/2001 | Casalnuovo et al. |
| 6,259,991 | B1 | 7/2001 | Nysen |
| 6,287,765 | B1 | 9/2001 | Cubicciotti |
| 6,292,659 | B1 | 9/2001 | Olds et al. |
| 6,306,598 | B1 | 10/2001 | Charych et al. |
| 6,319,469 | B1 | 11/2001 | Mian et al. |
| 6,375,612 | B1 | 4/2002 | Guichon et al. |
| 6,379,669 | B1 | 4/2002 | Sinha |
| 6,381,494 | B1 | 4/2002 | Gilkerson et al. |
| 6,383,815 | B1 | 5/2002 | Potyrailo |
| 6,388,360 | B1 | 5/2002 | Nysen et al. |
| 6,403,944 | B1 | 6/2002 | Mackenzie et al. |
| 6,424,847 | B1 | 7/2002 | Mastrototaro et al. |
| 6,424,916 | B2 | 7/2002 | Nysen |
| 6,428,484 | B1 | 8/2002 | Battmer et al. |
| 6,433,671 | B1 | 8/2002 | Nysen |
| 6,442,413 | B1 | 8/2002 | Silver |
| 6,444,321 | B1 | 9/2002 | Arnebrant et al. |
| 6,477,395 | B2 | 11/2002 | Schulman et al. |
| 6,477,424 | B1 | 11/2002 | Thompson et al. |

| | | | |
|---|---|---|---|
| 6,484,046 | B1 | 11/2002 | Say et al. |
| 6,495,892 | B2 | 12/2002 | Goodman et al. |
| 6,512,939 | B1 | 1/2003 | Colvin et al. |
| 6,531,957 | B1 | 3/2003 | Nysen |
| 6,545,791 | B1 | 4/2003 | McCaughan et al. |
| 6,565,509 | B1 | 5/2003 | Say et al. |
| 6,567,259 | B2 | 5/2003 | Stevenson et al. |
| 6,567,753 | B2 | 5/2003 | Potyrailo |
| 6,569,092 | B1 | 5/2003 | Guichon et al. |
| 6,579,235 | B1 | 6/2003 | Abita et al. |
| 6,579,690 | B1 | 6/2003 | Bonnecaze et al. |
| 6,580,358 | B1 | 6/2003 | Nysen |
| 6,586,133 | B1* | 7/2003 | Teeters .............. H01M 10/0565 |
| | | | 29/623.5 |
| 6,611,224 | B1 | 8/2003 | Nysen et al. |
| 6,611,758 | B1 | 8/2003 | Nysen |
| 6,627,154 | B1 | 9/2003 | Goodman et al. |
| 6,633,226 | B1 | 10/2003 | Nysen |
| 6,643,650 | B1 | 11/2003 | Slaughter et al. |
| 6,656,430 | B2 | 12/2003 | Sheppard, Jr. et al. |
| 6,684,683 | B2 | 2/2004 | Potyrailo et al. |
| 6,700,535 | B2 | 3/2004 | Gilkes et al. |
| 6,709,869 | B2 | 3/2004 | Mian et al. |
| 6,720,710 | B1 | 4/2004 | Wenzel et al. |
| 6,721,542 | B1 | 4/2004 | Anttila et al. |
| 6,735,479 | B2 | 5/2004 | Fabian et al. |
| 6,744,753 | B2 | 6/2004 | Heinonen et al. |
| 6,746,960 | B2 | 6/2004 | Goodman |
| 6,762,025 | B2 | 7/2004 | Cubicciotti |
| 6,772,331 | B1 | 8/2004 | Hind et al. |
| 6,775,616 | B1 | 8/2004 | Nysen |
| 6,789,077 | B1 | 9/2004 | Slaughter et al. |
| 6,789,126 | B1 | 9/2004 | Saulpaugh et al. |
| 6,792,466 | B1 | 9/2004 | Saulpaugh et al. |
| 6,810,363 | B2 | 10/2004 | Newman et al. |
| 6,813,501 | B2 | 11/2004 | Kinnunen et al. |
| 6,833,540 | B2 | 12/2004 | Mackenzie et al. |
| 6,845,097 | B2 | 1/2005 | Haller et al. |
| 6,846,428 | B2 | 1/2005 | McCaughan et al. |
| 6,848,295 | B2 | 2/2005 | Auner et al. |
| 6,850,979 | B1 | 2/2005 | Saulpaugh et al. |
| 6,862,465 | B2 | 3/2005 | Shults et al. |
| 6,862,594 | B1 | 3/2005 | Saulpaugh et al. |
| 6,867,275 | B2 | 3/2005 | Alexander, IV et al. |
| 6,868,447 | B1 | 3/2005 | Slaughter et al. |
| 6,879,574 | B2 | 4/2005 | Naghian et al. |
| 6,885,388 | B2 | 4/2005 | Gunter et al. |
| 6,886,095 | B1 | 4/2005 | Hind et al. |
| 6,889,079 | B2 | 5/2005 | Bocek et al. |
| 6,895,265 | B2 | 5/2005 | Silver |
| 6,898,445 | B2 | 5/2005 | Slettengren et al. |
| 6,898,618 | B1 | 5/2005 | Slaughter et al. |
| 6,908,391 | B2 | 6/2005 | Gatto et al. |
| 6,912,657 | B2 | 6/2005 | Gehrmann |
| 6,916,247 | B2 | 7/2005 | Gatto et al. |
| 6,917,976 | B1 | 7/2005 | Slaughter et al. |
| 6,918,084 | B1 | 7/2005 | Slaughter et al. |
| 6,922,725 | B2 | 7/2005 | Lamming et al. |
| 6,925,562 | B2 | 8/2005 | Gulcu et al. |
| 6,931,327 | B2 | 8/2005 | Goode, Jr. et al. |
| 6,944,502 | B2 | 9/2005 | Charvin et al. |
| 6,945,870 | B2 | 9/2005 | Gatto et al. |
| 6,947,995 | B2 | 9/2005 | Chang et al. |
| 6,948,066 | B2 | 9/2005 | Hind et al. |
| 6,950,009 | B1 | 9/2005 | Nysen |
| 6,950,875 | B1 | 9/2005 | Slaughter et al. |
| 6,950,946 | B1 | 9/2005 | Droz et al. |
| 6,959,212 | B2 | 10/2005 | Hsu et al. |
| 6,961,541 | B2 | 11/2005 | Overy et al. |
| 6,965,816 | B2 | 11/2005 | Walker |
| 6,965,868 | B1 | 11/2005 | Bednarek |
| 6,967,428 | B2 | 11/2005 | Edmonson et al. |
| 6,968,453 | B2 | 11/2005 | Doyle et al. |
| 6,970,869 | B1 | 11/2005 | Slaughter et al. |
| 6,973,493 | B1 | 12/2005 | Slaughter et al. |
| 6,975,205 | B1 | 12/2005 | French et al. |
| 6,980,660 | B1 | 12/2005 | Hind et al. |
| 6,985,773 | B2 | 1/2006 | Von Arx et al. |
| 6,986,739 | B2 | 1/2006 | Warren et al. |

(56) References Cited

U.S. PATENT DOCUMENTS

| | | | |
|---|---|---|---|
| 6,990,444 B2 | 1/2006 | Hind et al. |
| 6,993,393 B2 | 1/2006 | Von Arx et al. |
| 7,006,858 B2 | 2/2006 | Silver et al. |
| 7,010,573 B1 | 3/2006 | Saulpaugh et al. |
| 7,015,826 B1 | 3/2006 | Chan et al. |
| 7,016,966 B1 | 3/2006 | Saulpaugh et al. |
| 7,023,323 B1 | 4/2006 | Nysen |
| 7,023,955 B2 | 4/2006 | Chen et al. |
| 7,025,727 B2 | 4/2006 | Brockway et al. |
| 7,028,184 B2 | 4/2006 | Hind et al. |
| 7,031,945 B1 | 4/2006 | Donner |
| 7,033,322 B2 | 4/2006 | Silver |
| 7,042,988 B2 | 5/2006 | Juitt et al. |
| 7,047,076 B1 | 5/2006 | Li et al. |
| 7,058,243 B2 | 6/2006 | Tao et al. |
| 7,061,061 B2 | 6/2006 | Goodman et al. |
| 7,065,574 B1 | 6/2006 | Saulpaugh et al. |
| 7,065,579 B2 | 6/2006 | Traversat et al. |
| 7,072,718 B2 | 7/2006 | Von Arx et al. |
| 7,072,967 B1 | 7/2006 | Saulpaugh et al. |
| 7,080,078 B1 | 7/2006 | Slaughter et al. |
| 7,081,195 B2 | 7/2006 | Simpson et al. |
| 7,082,200 B2 | 7/2006 | Aboba et al. |
| 7,084,736 B2 | 8/2006 | Ritter |
| 7,085,599 B2 | 8/2006 | Kim et al. |
| 7,089,089 B2 | 8/2006 | Cumming et al. |
| 7,089,298 B2 | 8/2006 | Nyman et al. |
| 7,096,137 B2 | 8/2006 | Shipton et al. |
| 7,097,662 B2 | 8/2006 | Evans, III et al. |
| 7,103,313 B2 | 9/2006 | Heinonen et al. |
| 7,110,372 B2 | 9/2006 | Kovacs et al. |
| 7,116,661 B2 | 10/2006 | Patton |
| 7,120,667 B2 | 10/2006 | Derocher et al. |
| 7,121,639 B2 | 10/2006 | Plunkett |
| 7,132,778 B1 | 11/2006 | Nysen et al. |
| 7,136,689 B2 | 11/2006 | Shults et al. |
| 7,136,927 B2 | 11/2006 | Traversat et al. |
| 7,146,307 B2 | 12/2006 | Mocek |
| 7,147,695 B2 | 12/2006 | Mitra |
| 7,152,942 B2 | 12/2006 | Walmsley et al. |
| 7,155,518 B2 | 12/2006 | Forslow |
| 7,162,454 B1 | 1/2007 | Donner et al. |
| 7,165,107 B2 | 1/2007 | Pouyoul et al. |
| 7,165,824 B2 | 1/2007 | Walmsley et al. |
| 7,167,892 B2 | 1/2007 | Defosse et al. |
| 7,167,920 B2 | 1/2007 | Traversat et al. |
| 7,171,323 B2 | 1/2007 | Shipton et al. |
| 7,177,699 B2 | 2/2007 | Fabian et al. |
| 7,181,261 B2 | 2/2007 | Silver et al. |
| 7,181,572 B2 | 2/2007 | Walmsley |
| 7,181,614 B1 | 2/2007 | Gehrmann et al. |
| 7,185,199 B2 | 2/2007 | Balfanz et al. |
| 7,187,974 B2 | 3/2007 | Haeg et al. |
| 7,188,251 B1 | 3/2007 | Slaughter et al. |
| 7,188,282 B2 | 3/2007 | Walmsley |
| 7,197,565 B2 | 3/2007 | Abdelaziz et al. |
| 7,200,848 B1 | 4/2007 | Slaughter et al. |
| 7,203,665 B2 | 4/2007 | Donner |
| 7,203,753 B2 | 4/2007 | Yeager et al. |
| 7,205,701 B2 | 4/2007 | Liu et al. |
| 7,206,841 B2 | 4/2007 | Traversat et al. |
| 7,206,934 B2 | 4/2007 | Pabla et al. |
| 7,209,790 B2 | 4/2007 | Thompson et al. |
| 7,213,047 B2 | 5/2007 | Yeager et al. |
| 7,215,775 B2 | 5/2007 | Noguchi et al. |
| 7,216,109 B1 | 5/2007 | Donner |
| 7,216,231 B2 | 5/2007 | Gehrmann |
| 7,216,365 B2 | 5/2007 | Bhagwat et al. |
| 7,218,967 B2 | 5/2007 | Bergelson et al. |
| 7,222,187 B2 | 5/2007 | Yeager et al. |
| 7,243,356 B1 | 7/2007 | Saulpaugh et al. |
| 7,249,182 B1 | 7/2007 | Heinonen et al. |
| 7,251,331 B2 | 7/2007 | Kansala et al. |
| 7,254,608 B2 | 8/2007 | Yeager et al. |
| 7,256,695 B2 | 8/2007 | Hamel et al. |
| 7,259,019 B2 | 8/2007 | Pawliszyn et al. |
| 7,260,432 B2 | 8/2007 | Kramer et al. |
| 7,260,538 B2 | 8/2007 | Calderone et al. |
| 7,260,543 B1 | 8/2007 | Saulpaugh et al. |
| 7,262,709 B2 | 8/2007 | Borleske et al. |
| 7,263,560 B2 | 8/2007 | Abdelaziz et al. |
| 7,263,612 B2 | 8/2007 | Yamazaki et al. |
| 7,270,633 B1 | 9/2007 | Goscha et al. |
| 7,275,102 B2 | 9/2007 | Yeager et al. |
| 7,275,156 B2 | 9/2007 | Balfanz et al. |
| 7,278,034 B2 | 10/2007 | Shipton |
| 7,278,697 B2 | 10/2007 | Plunkett |
| 7,280,975 B1 | 10/2007 | Donner |
| 7,283,803 B2 | 10/2007 | Karaoguz et al. |
| 7,290,132 B2 | 10/2007 | Aboba et al. |
| 7,293,047 B2 | 11/2007 | Dunn et al. |
| 7,295,119 B2 | 11/2007 | Rappaport et al. |
| 7,297,062 B2 | 11/2007 | Gatto et al. |
| 7,299,007 B2 | 11/2007 | Eskin |
| 7,300,631 B2 | 11/2007 | Miller et al. |
| 7,302,592 B2 | 11/2007 | Shipton et al. |
| 7,308,496 B2 | 12/2007 | Yeager et al. |
| 7,310,544 B2 | 12/2007 | Brister et al. |
| 7,312,721 B2 | 12/2007 | Mason, Jr. et al. |
| 7,318,049 B2 | 1/2008 | Iannacci |
| 7,318,086 B2 | 1/2008 | Chang et al. |
| 7,319,901 B2 | 1/2008 | Dublin et al. |
| 7,328,243 B2 | 2/2008 | Yeager et al. |
| 7,332,327 B2 | 2/2008 | Vikholm et al. |
| 7,333,013 B2 | 2/2008 | Berger |
| 7,337,776 B2 | 3/2008 | Fishman et al. |
| 7,339,914 B2 | 3/2008 | Bhagwat et al. |
| 7,340,214 B1 | 3/2008 | Hamberg |
| 7,340,438 B2 | 3/2008 | Nordman et al. |
| 7,340,500 B2 | 3/2008 | Traversat et al. |
| 7,340,770 B2 | 3/2008 | Freund |
| 7,343,350 B1 | 3/2008 | Donner |
| 7,346,167 B2 | 3/2008 | Billhartz et al. |
| 7,347,822 B2 | 3/2008 | Brockway et al. |
| 7,348,895 B2 | 3/2008 | Lagassey |
| 7,356,329 B2 | 4/2008 | Willey et al. |
| 7,366,901 B2 | 4/2008 | Hapamas et al. |
| 7,370,091 B1 | 5/2008 | Slaughter et al. |
| 7,371,825 B2 | 5/2008 | Das et al. |
| 7,377,608 B2 | 5/2008 | Walmsley et al. |
| 7,379,891 B1 | 5/2008 | Donner et al. |
| 7,379,913 B2 | 5/2008 | Steele et al. |
| 7,383,433 B2 | 6/2008 | Yeager et al. |
| 7,386,517 B1 | 6/2008 | Donner |
| 7,392,092 B2 | 6/2008 | Li et al. |
| 7,392,375 B2 | 6/2008 | Bartram et al. |
| 7,392,387 B2 | 6/2008 | Balfanz et al. |
| 7,395,333 B1 | 7/2008 | Saulpaugh et al. |
| 7,395,536 B2 | 7/2008 | Verbeke et al. |
| 7,398,533 B1 | 7/2008 | Slaughter et al. |
| 7,399,043 B2 | 7/2008 | Walmsley et al. |
| 7,401,152 B2 | 7/2008 | Traversat et al. |
| 7,401,153 B2 | 7/2008 | Traversat et al. |
| 7,408,147 B2 | 8/2008 | Blick et al. |
| 7,409,434 B2 | 8/2008 | Lamming et al. |
| 7,409,569 B2 | 8/2008 | Illowsky et al. |
| 7,412,518 B1 | 8/2008 | Duigou et al. |
| 7,414,534 B1 | 8/2008 | Kroll et al. |
| 7,415,424 B1 | 8/2008 | Donner |
| 7,415,439 B2 | 8/2008 | Kontio et al. |
| 7,415,537 B1 | 8/2008 | Maes |
| 7,418,593 B2 | 8/2008 | Paatero et al. |
| 7,420,956 B2 | 9/2008 | Karaoguz et al. |
| 7,421,411 B2 | 9/2008 | Kontio et al. |
| 7,424,285 B2 | 9/2008 | Jei |
| 7,426,271 B2 | 9/2008 | Conley et al. |
| 7,426,411 B2 | 9/2008 | Bocek et al. |
| 7,426,721 B1 | 9/2008 | Saulpaugh et al. |
| 7,433,649 B2 | 10/2008 | Toulis et al. |
| 7,433,773 B2 | 10/2008 | Tengler et al. |
| 7,444,644 B1 | 10/2008 | Slaughter et al. |
| 7,445,605 B2 | 11/2008 | Overall et al. |
| 7,454,542 B2 | 11/2008 | Illowsky et al. |
| 7,454,619 B2 | 11/2008 | Smetters et al. |

(56) References Cited

U.S. PATENT DOCUMENTS

| | | | |
|---|---|---|---|
| 7,458,082 B1 | 11/2008 | Slaughter et al. |
| 7,461,172 B2 | 12/2008 | Newman et al. |
| 7,473,551 B2 | 1/2009 | Warthoe |
| 7,475,244 B2 | 1/2009 | Sugikawa |
| 7,477,873 B2 | 1/2009 | Tanaka et al. |
| 7,478,108 B2 | 1/2009 | Townsend et al. |
| 7,484,225 B2 | 1/2009 | Hugly et al. |
| 7,487,509 B2 | 2/2009 | Hugly et al. |
| 7,494,465 B2 | 2/2009 | Brister et al. |
| 7,497,827 B2 | 3/2009 | Brister et al. |
| 7,500,104 B2 | 3/2009 | Goland |
| 7,504,365 B2 | 3/2009 | Carlson |
| 7,509,387 B2 | 3/2009 | Hirsch |
| 7,510,882 B2 | 3/2009 | Vikholm et al. |
| 7,512,649 B2 | 3/2009 | Faybishenko et al. |
| 7,516,325 B2 | 4/2009 | Willey |
| 7,522,549 B2 | 4/2009 | Karaoguz et al. |
| 7,523,111 B2 | 4/2009 | Walmsley |
| 7,529,713 B1 | 5/2009 | Donner |
| 7,533,141 B2 | 5/2009 | Nadgir et al. |
| 7,533,161 B2 | 5/2009 | Hugly et al. |
| 7,533,172 B2 | 5/2009 | Traversat et al. |
| 7,536,177 B2 | 5/2009 | Karaoguz et al. |
| 7,536,723 B1 | 5/2009 | Bhagwat et al. |
| 7,545,941 B2 | 6/2009 | Sovio et al. |
| 7,546,254 B2 | 6/2009 | Bednarek |
| 7,548,946 B1 | 6/2009 | Saulpaugh et al. |
| 7,549,056 B2 | 6/2009 | Carr |
| 7,550,310 B2 | 6/2009 | Goodman et al. |
| 7,562,028 B1 | 7/2009 | Donner |
| 7,562,051 B1 | 7/2009 | Donner |
| 7,565,328 B1 | 7/2009 | Donner |
| 7,565,529 B2 | 7/2009 | Beck et al. |
| 7,570,943 B2 | 8/2009 | Sorvari et al. |
| 7,571,346 B2 | 8/2009 | Illowsky et al. |
| 7,573,855 B2 | 8/2009 | Hohl et al. |
| 7,574,523 B2 | 8/2009 | Traversat et al. |
| 7,577,479 B2 | 8/2009 | Hartley et al. |
| 7,577,575 B1 | 8/2009 | Donner et al. |
| 7,577,619 B1 | 8/2009 | Donner et al. |
| 7,577,620 B1 | 8/2009 | Donner |
| 7,577,834 B1 | 8/2009 | Traversat et al. |
| 7,581,096 B2 | 8/2009 | Balfanz et al. |
| 7,583,998 B2 | 9/2009 | Meyer et al. |
| 7,584,360 B2 | 9/2009 | Kasaura et al. |
| 7,587,196 B2 | 9/2009 | Hansen |
| 7,590,589 B2 | 9/2009 | Hoffberg |
| 7,592,829 B2 | 9/2009 | Walmsley et al. |
| 7,593,776 B2 | 9/2009 | Loeb et al. |
| 7,596,227 B2 | 9/2009 | Illowsky et al. |
| 7,597,250 B2 | 10/2009 | Finn |
| 7,598,094 B2 | 10/2009 | Masters et al. |
| 7,599,305 B2 | 10/2009 | Bui |
| 7,600,252 B2 | 10/2009 | Illowsky et al. |
| 7,606,242 B2 | 10/2009 | Whelan et al. |
| 7,606,570 B2 | 10/2009 | Karaoguz et al. |
| 7,607,012 B2 | 10/2009 | Nyberg |
| 7,610,065 B2 | 10/2009 | Vallapureddy et al. |
| 7,611,908 B2 | 11/2009 | Miller et al. |
| 7,613,522 B2 | 11/2009 | Christman et al. |
| 7,613,881 B2 | 11/2009 | Illowsky et al. |
| 7,615,381 B2 | 11/2009 | Masters et al. |
| 7,617,159 B1 | 11/2009 | Donner |
| 7,620,452 B1 | 11/2009 | Russie |
| 7,623,922 B2 | 11/2009 | Bange et al. |
| 7,624,143 B2 | 11/2009 | Newman et al. |
| 7,629,137 B2 | 12/2009 | Sauer-Budge et al. |
| 7,630,941 B2 | 12/2009 | Berstis |
| 7,632,638 B2 | 12/2009 | Sauer-Budge et al. |
| 7,634,230 B2 | 12/2009 | Ji et al. |
| 7,640,048 B2 | 12/2009 | Dobbles et al. |
| 7,648,844 B2 | 1/2010 | Srivastava et al. |
| 7,649,872 B2 | 1/2010 | Naghian et al. |
| 7,651,596 B2 | 1/2010 | Petisce et al. |
| 7,654,956 B2 | 2/2010 | Brister et al. |
| 7,657,255 B2 | 2/2010 | Abel et al. |
| 7,657,314 B2 | 2/2010 | Sathaye et al. |
| 7,657,597 B2 | 2/2010 | Arora et al. |
| 7,660,990 B1 | 2/2010 | Thomsen et al. |
| 7,660,998 B2 | 2/2010 | Walmsley |
| 7,666,284 B2 | 2/2010 | Heller et al. |
| 7,668,596 B2 | 2/2010 | Von Arx et al. |
| 7,672,662 B2 | 3/2010 | Hamberg |
| 7,680,133 B2 | 3/2010 | Karaoguz et al. |
| 7,681,572 B2 | 3/2010 | Fishman |
| 7,684,374 B2 | 3/2010 | Karaoguz et al. |
| 7,689,508 B2 | 3/2010 | Davis et al. |
| 7,697,894 B2 | 4/2010 | Zilliacus et al. |
| 7,698,393 B2 | 4/2010 | Milstein et al. |
| 7,701,912 B2 | 4/2010 | Thompson et al. |
| 7,702,387 B2 | 4/2010 | Stevenson et al. |
| 7,702,821 B2 | 4/2010 | Feinberg et al. |
| 7,703,073 B2 | 4/2010 | Illowsky et al. |
| 7,705,736 B1 | 4/2010 | Kedziora |
| 7,707,415 B2 | 4/2010 | Braskich et al. |
| 7,707,621 B2 | 4/2010 | Walmsley |
| 7,708,194 B2 | 5/2010 | Vawter |
| 7,712,111 B2 | 5/2010 | Illowsky et al. |
| 7,712,777 B2 | 5/2010 | Breed |
| 7,713,574 B2 | 5/2010 | Brister et al. |
| 7,713,923 B2 | 5/2010 | Genove et al. |
| 7,715,351 B2 | 5/2010 | Karaoguz et al. |
| 7,716,492 B1 | 5/2010 | Saulpaugh et al. |
| 7,720,535 B2 | 5/2010 | Ni et al. |
| 7,720,544 B2 | 5/2010 | Christman et al. |
| 7,724,717 B2 | 5/2010 | Porras et al. |
| 7,725,195 B2 | 5/2010 | Lima et al. |
| 7,727,143 B2 | 6/2010 | Birk et al. |
| 7,729,776 B2 | 6/2010 | Von Arx et al. |
| 7,730,482 B2 | 6/2010 | Illowsky et al. |
| 7,733,804 B2 | 6/2010 | Hardjono et al. |
| 7,736,330 B2 | 6/2010 | Bardy |
| 7,738,964 B2 | 6/2010 | Von Arx et al. |
| 7,741,956 B1 | 6/2010 | Nysen |
| 7,743,074 B1 | 6/2010 | Parupudi et al. |
| 7,747,980 B2 | 6/2010 | Illowsky et al. |
| 7,748,618 B2 | 7/2010 | Vawter |
| 7,749,445 B2 | 7/2010 | Masters |
| 7,757,076 B2 | 7/2010 | Stewart et al. |
| 7,760,654 B2 | 7/2010 | Adya et al. |
| 7,761,159 B2 | 7/2010 | Yost et al. |
| 7,761,863 B2 | 7/2010 | Illowsky et al. |
| 7,761,885 B2 | 7/2010 | Labrou et al. |
| 7,761,910 B2 | 7/2010 | Ransom et al. |
| 7,762,470 B2 | 7/2010 | Finn et al. |
| 7,765,005 B2 | 7/2010 | Stevenson |
| 7,769,420 B2 | 8/2010 | Silver et al. |
| 7,770,008 B2 | 8/2010 | Walmsley |
| 7,771,352 B2 | 8/2010 | Shults et al. |
| 7,774,145 B2 | 8/2010 | Brauker et al. |
| 7,774,495 B2 | 8/2010 | Pabla et al. |
| 7,778,927 B2 | 8/2010 | Kawakami |
| 7,780,590 B2 | 8/2010 | Birk et al. |
| 7,783,041 B2 | 8/2010 | Asokan et al. |
| 7,783,777 B1 | 8/2010 | Pabla et al. |
| 7,783,886 B2 | 8/2010 | Walmsley |
| 7,786,867 B2 | 8/2010 | Hamel et al. |
| 7,787,865 B2 | 8/2010 | Willey et al. |
| 7,787,958 B2 | 8/2010 | Stevenson |
| 7,788,663 B2 | 8/2010 | Illowsky et al. |
| 7,792,588 B2 | 9/2010 | Harding |
| 7,801,058 B2 | 9/2010 | Wang |
| 7,801,612 B2 | 9/2010 | Johnson et al. |
| 7,801,781 B2 | 9/2010 | Olin et al. |
| 7,804,807 B2 | 9/2010 | Korus et al. |
| 7,813,778 B2 | 10/2010 | Benaron et al. |
| 7,818,056 B2 | 10/2010 | Kim et al. |
| 7,818,519 B2 | 10/2010 | Plunkett |
| 7,818,811 B2 | 10/2010 | Kirovski et al. |
| 7,822,863 B2 | 10/2010 | Balfanz et al. |
| 7,823,772 B2 | 11/2010 | Vawter |
| 7,826,981 B2 | 11/2010 | Goode, Jr. et al. |
| 7,831,238 B2 | 11/2010 | Hamberg |
| 7,831,752 B2 | 11/2010 | Illowsky et al. |

(56) References Cited

U.S. PATENT DOCUMENTS

| | | | |
|---|---|---|---|
| 7,831,827 B2 | 11/2010 | Walmsley | |
| 7,842,092 B2 | 11/2010 | Otto et al. | |
| 7,844,834 B2 | 11/2010 | Leone et al. | |
| 7,848,746 B2 | 12/2010 | Juels | |
| 7,848,813 B2 | 12/2010 | Bergelson et al. | |
| 7,849,140 B2 | 12/2010 | Abdel-Aziz et al. | |
| 7,853,255 B2 | 12/2010 | Karaoguz et al. | |
| 7,853,324 B2 | 12/2010 | Stevenson et al. | |
| 7,853,780 B2 | 12/2010 | Rotondo et al. | |
| 7,857,756 B2 | 12/2010 | Warren et al. | |
| 7,857,760 B2 | 12/2010 | Brister et al. | |
| 7,860,574 B2 | 12/2010 | Von Arx et al. | |
| 7,860,922 B2 | 12/2010 | Singer et al. | |
| 7,860,923 B2 | 12/2010 | Singer et al. | |
| 7,864,673 B2 | 1/2011 | Bonner | |
| 7,869,601 B2 | 1/2011 | Ando et al. | |
| 7,870,097 B2 | 1/2011 | Dunn et al. | |
| 7,876,228 B2 | 1/2011 | Kroll et al. | |
| 7,877,145 B2 | 1/2011 | Russie | |
| 7,881,667 B2 | 2/2011 | Ji et al. | |
| 7,885,697 B2 | 2/2011 | Brister et al. | |
| 7,886,962 B2 | 2/2011 | Vawter | |
| 7,890,180 B2 | 2/2011 | Quiles | |
| 7,896,809 B2 | 3/2011 | Simpson et al. | |
| 7,899,187 B2 | 3/2011 | Messerges et al. | |
| 7,899,511 B2 | 3/2011 | Shults et al. | |
| 7,899,915 B2 | 3/2011 | Reisman | |
| 7,901,354 B2 | 3/2011 | Shults et al. | |
| 7,904,074 B2 | 3/2011 | Karaoguz et al. | |
| 7,904,169 B2 | 3/2011 | Bange et al. | |
| 7,904,170 B2 | 3/2011 | Harding | |
| 7,905,833 B2 | 3/2011 | Brister et al. | |
| 7,907,935 B2 | 3/2011 | Le Saint et al. | |
| 7,912,544 B1 | 3/2011 | Min et al. | |
| 7,914,460 B2 | 3/2011 | Melker et al. | |
| 7,914,468 B2 | 3/2011 | Shalon et al. | |
| 7,916,013 B2 | 3/2011 | Stevenson | |
| 7,916,090 B2 | 3/2011 | Nysen | |
| 7,916,861 B2 | 3/2011 | Conley et al. | |
| 7,917,226 B2 | 3/2011 | Nghiem et al. | |
| 7,920,518 B2 | 4/2011 | Thompson et al. | |
| 7,920,534 B2 | 4/2011 | Nakayama | |
| 7,920,851 B2 | 4/2011 | Moshir et al. | |
| 7,920,906 B2 | 4/2011 | Goode, Jr. et al. | |
| 7,925,356 B2 | 4/2011 | Li et al. | |
| 7,927,274 B2 | 4/2011 | Rasdal et al. | |
| 7,930,543 B2 | 4/2011 | Corndorf | |
| 7,932,825 B2 | 4/2011 | Berger | |
| 7,937,089 B2 | 5/2011 | Smetters et al. | |
| 7,937,159 B2 | 5/2011 | Lima et al. | |
| 7,940,933 B2 | 5/2011 | Corndorf | |
| 7,944,577 B2 | 5/2011 | Chang et al. | |
| 7,945,322 B2 | 5/2011 | Stevenson et al. | |
| 7,945,959 B2 | 5/2011 | Ilechko | |
| 7,946,984 B2 | 5/2011 | Brister et al. | |
| 7,949,381 B2 | 5/2011 | Brister et al. | |
| 7,950,047 B2 | 5/2011 | Risher et al. | |
| 7,952,528 B2 | 5/2011 | Nysen | |
| 7,953,818 B2 | 5/2011 | Chang et al. | |
| 7,955,258 B2 | 6/2011 | Goscha et al. | |
| 7,956,162 B2 | 6/2011 | Chahal et al. | |
| 7,960,311 B2 | 6/2011 | Carlson | |
| 7,962,164 B2 | 6/2011 | Karaoguz et al. | |
| 7,962,209 B2 | 6/2011 | Bocek et al. | |
| 7,966,075 B2 | 6/2011 | Johnson et al. | |
| 7,967,751 B2 | 6/2011 | Goscha et al. | |
| 7,969,307 B2 * | 6/2011 | Peeters | A61B 5/02028 340/572.1 |
| 7,970,734 B2 | 6/2011 | Townsend et al. | |
| 7,970,894 B1 | 6/2011 | Patwardhan | |
| 7,972,865 B2 | 7/2011 | Yi et al. | |
| 7,974,234 B2 | 7/2011 | Gustave et al. | |
| 7,974,296 B2 | 7/2011 | Karaoguz et al. | |
| 7,975,002 B2 | 7/2011 | Newman et al. | |
| 7,975,051 B2 | 7/2011 | Saint Clair et al. | |
| 7,976,492 B2 | 7/2011 | Brauker et al. | |
| 7,978,062 B2 | 7/2011 | LaLonde et al. | |
| 7,979,692 B1 | 7/2011 | Washington et al. | |
| 7,981,025 B2 | 7/2011 | Pool et al. | |
| 7,983,435 B2 | 7/2011 | Moses | |
| 7,983,615 B2 | 7/2011 | Bryce et al. | |
| 7,983,763 B2 | 7/2011 | Stevenson et al. | |
| 7,983,835 B2 | 7/2011 | Lagassey | |
| 7,985,715 B2 | 7/2011 | Carlson | |
| 7,986,704 B2 | 7/2011 | Karaoguz et al. | |
| 7,987,491 B2 | 7/2011 | Reisman | |
| 7,989,851 B2 | 8/2011 | Lu et al. | |
| 7,990,947 B2 | 8/2011 | Twitchell, Jr. et al. | |
| 7,991,764 B2 | 8/2011 | Rathod | |
| 7,998,071 B2 | 8/2011 | Goode, Jr. et al. | |
| 8,000,314 B2 | 8/2011 | Brownrigg et al. | |
| 8,000,801 B2 | 8/2011 | Stevenson et al. | |
| 8,000,901 B2 | 8/2011 | Brauker et al. | |
| 8,001,232 B1 | 8/2011 | Saulpaugh et al. | |
| 8,004,021 B2 | 8/2011 | Miller et al. | |
| 8,005,476 B2 | 8/2011 | Karaoguz et al. | |
| 8,005,524 B2 | 8/2011 | Brauker et al. | |
| 8,009,608 B2 | 8/2011 | Karaoguz et al. | |
| 8,010,174 B2 | 8/2011 | Goode, Jr. et al. | |
| RE42,725 E | 9/2011 | Chang et al. | |
| 8,013,732 B2 | 9/2011 | Petite et al. | |
| 8,014,722 B2 | 9/2011 | Abel et al. | |
| 8,019,352 B2 | 9/2011 | Rappaport et al. | |
| 8,023,425 B2 | 9/2011 | Raleigh | |
| 8,028,329 B2 | 9/2011 | Whitcomb | |
| RE42,871 E | 10/2011 | Forslow | |
| 8,031,650 B2 | 10/2011 | Petite et al. | |
| 8,032,486 B2 | 10/2011 | Townsend et al. | |
| 8,032,939 B2 | 10/2011 | Palnitkar et al. | |
| 8,036,195 B2 | 10/2011 | Thompson et al. | |
| 8,036,736 B2 | 10/2011 | Snyder et al. | |
| 8,037,202 B2 | 10/2011 | Yeager et al. | |
| 8,038,239 B2 | 10/2011 | Walmsley et al. | |
| 8,041,432 B2 | 10/2011 | Von Arx et al. | |
| 8,046,080 B2 | 10/2011 | Von Arx et al. | |
| 8,046,328 B2 | 10/2011 | Rhodes et al. | |
| 8,046,504 B2 | 10/2011 | Feinberg et al. | |
| 8,049,671 B2 | 11/2011 | Nysen | |
| 8,050,405 B2 | 11/2011 | Camp, Jr. et al. | |
| 8,050,771 B2 | 11/2011 | Yamamoto et al. | |
| 8,057,401 B2 | 11/2011 | Wolf | |
| 8,057,472 B2 | 11/2011 | Walker et al. | |
| 8,059,046 B2 | 11/2011 | Nysen | |
| 8,060,173 B2 | 11/2011 | Goode, Jr. et al. | |
| 8,064,412 B2 | 11/2011 | Petite | |
| 8,064,879 B2 | 11/2011 | Willey et al. | |
| 8,064,926 B2 | 11/2011 | Howarter et al. | |
| 8,068,831 B2 | 11/2011 | Karaoguz et al. | |
| 8,070,768 B2 | 12/2011 | Kim et al. | |
| 8,073,519 B2 | 12/2011 | Goode, Jr. et al. | |
| 8,073,520 B2 | 12/2011 | Kamath et al. | |
| 8,073,839 B2 | 12/2011 | Rathod | |
| 8,078,282 B2 | 12/2011 | Nycz | |
| 8,079,518 B2 | 12/2011 | Turner et al. | |
| 8,081,925 B2 | 12/2011 | Parramon et al. | |
| 8,082,491 B1 | 12/2011 | Abdelaziz et al. | |
| 8,090,399 B2 | 1/2012 | Howarter et al. | |
| 8,090,443 B2 | 1/2012 | Min et al. | |
| 8,092,549 B2 | 1/2012 | Hillis et al. | |
| 8,093,991 B2 | 1/2012 | Stevenson et al. | |
| 8,097,926 B2 | 1/2012 | De Graff et al. | |
| 8,102,999 B2 | 1/2012 | Corndorf | |
| 8,103,691 B2 | 1/2012 | Chunilal | |
| 8,103,718 B2 | 1/2012 | O'Shea et al. | |
| 8,108,455 B2 | 1/2012 | Yeager et al. | |
| 8,109,920 B2 | 2/2012 | Boyden et al. | |
| 8,114,021 B2 | 2/2012 | Robertson et al. | |
| 8,114,345 B2 | 2/2012 | Dlugos, Jr. et al. | |
| 8,114,350 B1 | 2/2012 | Silver et al. | |
| 8,114,964 B2 | 2/2012 | Das et al. | |
| 8,115,618 B2 | 2/2012 | Robertson et al. | |
| 8,116,734 B2 | 2/2012 | Vawter | |
| 8,116,862 B2 | 2/2012 | Stevenson et al. | |
| 8,117,547 B2 | 2/2012 | Parupudi et al. | |

(56) References Cited

U.S. PATENT DOCUMENTS

| | | | |
|---|---|---|---|
| 8,123,687 B2 | 2/2012 | Dacquay et al. |
| 8,127,039 B2 | 2/2012 | Patton et al. |
| 8,128,562 B2 | 3/2012 | Goode, Jr. et al. |
| 8,130,146 B2 | 3/2012 | Belcea et al. |
| 8,131,645 B2 | 3/2012 | Lin et al. |
| 8,133,178 B2 | 3/2012 | Brauker et al. |
| 8,133,698 B2 | 3/2012 | Silver |
| 8,135,796 B1 | 3/2012 | Slaughter et al. |
| 8,136,149 B2 | 3/2012 | Freund |
| 8,139,588 B2 | 3/2012 | Hardjono et al. |
| 8,143,681 B2 | 3/2012 | Zaghloul et al. |
| 8,144,725 B2 | 3/2012 | Bienas et al. |
| 8,145,219 B2 | 3/2012 | Karaoguz et al. |
| 8,145,295 B2 | 3/2012 | Boyden et al. |
| 8,145,301 B2 | 3/2012 | Kim et al. |
| 8,149,848 B2 | 4/2012 | Karaoguz et al. |
| 8,150,312 B2 | 4/2012 | Bappu et al. |
| 8,150,372 B2 | 4/2012 | Orlassino |
| 8,150,416 B2 | 4/2012 | Ribaudo et al. |
| 8,150,488 B2 | 4/2012 | Goode, Jr. et al. |
| 8,151,336 B2 | 4/2012 | Savoor |
| 8,155,723 B2 | 4/2012 | Shults et al. |
| 8,156,337 B2 | 4/2012 | Balfanz et al. |
| 8,159,985 B2 | 4/2012 | Karaoguz et al. |
| 8,160,077 B2 | 4/2012 | Traversat et al. |
| 8,160,669 B2 | 4/2012 | Brauker et al. |
| 8,160,671 B2 | 4/2012 | Kamath et al. |
| 8,160,680 B2 | 4/2012 | Boyden et al. |
| 8,161,172 B2 | 4/2012 | Reisman |
| 8,165,142 B2 | 4/2012 | Karaoguz et al. |
| 8,165,684 B2 | 4/2012 | Putz et al. |
| 8,165,691 B2 | 4/2012 | Ellingson et al. |
| 8,166,296 B2 | 4/2012 | Buer et al. |
| 8,166,551 B2 | 4/2012 | King |
| 8,167,801 B2 | 5/2012 | Goode, Jr. et al. |
| 8,170,667 B2 | 5/2012 | Sanders |
| 8,170,680 B2 | 5/2012 | Ameri |
| 8,170,803 B2 | 5/2012 | Kamath et al. |
| 8,171,136 B2 | 5/2012 | Petite |
| 8,171,292 B2 | 5/2012 | Brown et al. |
| 8,175,528 B2 | 5/2012 | He et al. |
| 8,179,911 B2 | 5/2012 | Karaoguz et al. |
| 8,180,436 B2 | 5/2012 | Boyden et al. |
| 8,180,438 B2 | 5/2012 | Brockway et al. |
| 8,180,448 B2 | 5/2012 | Stevenson et al. |
| 8,182,340 B2 | 5/2012 | Korp |
| 8,182,435 B2 | 5/2012 | Dacquay et al. |
| 8,183,998 B2 | 5/2012 | Rao et al. |
| 8,185,119 B2 | 5/2012 | Karaoguz et al. |
| 8,185,195 B2 | 5/2012 | Kim et al. |
| 8,185,204 B2 | 5/2012 | Bange et al. |
| 8,190,256 B2 | 5/2012 | Hartley et al. |
| 8,190,900 B2 | 5/2012 | Corndorf |
| 8,192,406 B2 | 6/2012 | Wells et al. |
| 8,193,930 B2 | 6/2012 | Petite et al. |
| 8,195,233 B2 | 6/2012 | Morikuni et al. |
| 8,195,265 B2 | 6/2012 | Goode, Jr. et al. |
| 8,195,305 B2 | 6/2012 | Nghiem et al. |
| 8,195,934 B1 | 6/2012 | Lawrence |
| 8,197,454 B1 | 6/2012 | Mann et al. |
| 8,200,195 B2 | 6/2012 | Le Saint et al. |
| 8,200,328 B2 | 6/2012 | Stevenson et al. |
| 8,200,342 B2 | 6/2012 | Stevenson et al. |
| 8,200,700 B2 | 6/2012 | Moore et al. |
| 8,202,260 B2 | 6/2012 | Mann et al. |
| 8,204,522 B2 | 6/2012 | Karaoguz et al. |
| 8,204,992 B2 | 6/2012 | Arora et al. |
| 8,206,297 B2 | 6/2012 | Kamath et al. |
| 8,207,316 B1 | 6/2012 | Bentwich |
| 8,212,667 B2 | 7/2012 | Petite et al. |
| 8,213,907 B2 | 7/2012 | Etchegoyen |
| 8,214,228 B2 | 7/2012 | Butler et al. |
| 8,214,645 B2 | 7/2012 | Brown et al. |
| 8,216,135 B2 | 7/2012 | Goscha et al. |
| 8,216,139 B2 | 7/2012 | Brauker et al. |
| 8,219,204 B2 | 7/2012 | Mateychuk |
| 8,223,010 B2 | 7/2012 | Petite et al. |
| 8,224,443 B2 | 7/2012 | KenKnight et al. |
| 8,224,893 B2 | 7/2012 | Newman et al. |
| 8,225,094 B2 | 7/2012 | Willey |
| 8,225,380 B2 | 7/2012 | Moshir et al. |
| 8,226,474 B2 | 7/2012 | Nguyen et al. |
| 8,228,861 B1 | 7/2012 | Nix |
| 8,229,534 B2 | 7/2012 | Brister et al. |
| 8,229,536 B2 | 7/2012 | Goode, Jr. et al. |
| 8,229,785 B2 | 7/2012 | Fung et al. |
| 8,229,812 B2 | 7/2012 | Raleigh |
| 8,229,813 B2 | 7/2012 | Olin et al. |
| 8,229,888 B1 | 7/2012 | Roskind et al. |
| 8,231,531 B2 | 7/2012 | Brister et al. |
| 8,233,471 B2 | 7/2012 | Brownrigg et al. |
| 8,233,958 B2 | 7/2012 | Brauker et al. |
| 8,233,959 B2 | 7/2012 | Kamath et al. |
| 8,234,387 B2 | 7/2012 | Bradley et al. |
| 8,238,975 B2 | 8/2012 | Vallapureddy et al. |
| 8,242,907 B2 | 8/2012 | Butler et al. |
| 8,242,908 B2 | 8/2012 | Butler et al. |
| 8,245,315 B2 | 8/2012 | Cassett et al. |
| 8,246,533 B2 | 8/2012 | Chang et al. |
| 8,248,238 B2 | 8/2012 | Butler et al. |
| 8,248,239 B2 | 8/2012 | Butler et al. |
| 8,249,028 B2 | 8/2012 | Porras et al. |
| 8,249,559 B1 | 8/2012 | Meiss et al. |
| 8,249,684 B2 | 8/2012 | Kamath et al. |
| 8,250,207 B2 | 8/2012 | Raleigh |
| 8,250,628 B2 | 8/2012 | Brodfuehrer et al. |
| 8,251,906 B2 | 8/2012 | Brauker et al. |
| 8,251,946 B2 | 8/2012 | Bardy |
| 8,253,567 B2 | 8/2012 | Butler et al. |
| 8,257,259 B2 | 9/2012 | Brauker et al. |
| 8,257,295 B2 | 9/2012 | Rickard et al. |
| 8,257,729 B2 | 9/2012 | Schmitz et al. |
| 8,260,274 B2 | 9/2012 | Moshir et al. |
| 8,260,320 B2 | 9/2012 | Herz |
| 8,260,422 B2 | 9/2012 | Ellingson et al. |
| 8,261,338 B2 | 9/2012 | Brown et al. |
| 8,263,192 B2 | 9/2012 | Koberstein et al. |
| 8,265,725 B2 | 9/2012 | Brauker et al. |
| 8,265,738 B1 | 9/2012 | Min et al. |
| 8,265,754 B2 | 9/2012 | Yost et al. |
| 8,266,212 B2 | 9/2012 | Brunet de Courssou |
| 8,266,438 B2 | 9/2012 | Orsini et al. |
| 8,266,676 B2 | 9/2012 | Hardjono et al. |
| 8,267,863 B2 | 9/2012 | Najafi et al. |
| 8,269,630 B2 | 9/2012 | Butler et al. |
| 8,269,635 B2 | 9/2012 | Kroll et al. |
| 8,269,636 B2 | 9/2012 | Kroll et al. |
| 8,270,310 B2 | 9/2012 | Raleigh |
| 8,270,952 B2 | 9/2012 | Raleigh |
| 8,271,087 B2 | 9/2012 | Sathaye et al. |
| 8,271,800 B2 | 9/2012 | Carr |
| 8,271,802 B2 | 9/2012 | Orsini et al. |
| 8,274,373 B2 | 9/2012 | Nysen |
| 8,275,395 B2 | 9/2012 | Howarter et al. |
| 8,275,437 B2 | 9/2012 | Brauker et al. |
| 8,275,438 B2 | 9/2012 | Simpson et al. |
| 8,275,672 B1 | 9/2012 | Nguyen et al. |
| 8,277,713 B2 | 10/2012 | Petisce et al. |
| 8,279,065 B2 | 10/2012 | Butler et al. |
| 8,279,067 B2 | 10/2012 | Berger et al. |
| 8,280,359 B2 | 10/2012 | Moshir et al. |
| 8,280,475 B2 | 10/2012 | Brister et al. |
| 8,280,499 B2 | 10/2012 | Brockway et al. |
| 8,281,169 B2 | 10/2012 | Borras et al. |
| 8,281,408 B2 | 10/2012 | Corndorf |
| 8,282,549 B2 | 10/2012 | Brauker et al. |
| 8,282,550 B2 | 10/2012 | Rasdal et al. |
| 8,284,055 B2 | 10/2012 | Butler et al. |
| 8,284,748 B2 | 10/2012 | Borghei |
| 8,285,387 B2 | 10/2012 | Utsi et al. |
| 8,287,453 B2 | 10/2012 | Li et al. |
| 8,289,886 B2 | 10/2012 | McDonald et al. |
| 8,290,498 B2 | 10/2012 | Karaoguz et al. |
| 8,290,559 B2 | 10/2012 | Shariati et al. |

(56) References Cited

U.S. PATENT DOCUMENTS

| | | | |
|---|---|---|---|
| 8,290,560 B2 | 10/2012 | Kamath et al. |
| 8,290,561 B2 | 10/2012 | Brauker et al. |
| 8,292,810 B2 | 10/2012 | Goode, Jr. et al. |
| 8,294,579 B2 | 10/2012 | Butler et al. |
| 8,296,825 B2 | 10/2012 | Leone et al. |
| 8,298,142 B2 | 10/2012 | Simpson et al. |
| 8,299,899 B2 | 10/2012 | Frysz et al. |
| 8,301,110 B2 | 10/2012 | Roberts et al. |
| 8,301,243 B2 | 10/2012 | Stevenson et al. |
| 8,301,254 B2 | 10/2012 | Mosesov et al. |
| 8,301,784 B2 | 10/2012 | Hascalovici et al. |
| 8,302,167 B2 | 10/2012 | Mennes et al. |
| 8,303,573 B2 | 11/2012 | Boyden et al. |
| 8,305,935 B2 | 11/2012 | Wang |
| 8,305,936 B2 | 11/2012 | Wang |
| 8,305,980 B1 | 11/2012 | Nix |
| 8,311,214 B2 | 11/2012 | Buskey et al. |
| 8,311,628 B2 | 11/2012 | Stevenson et al. |
| 8,311,749 B2 | 11/2012 | Brauker et al. |
| 8,311,939 B1 | 11/2012 | Bent et al. |
| 8,313,434 B2 | 11/2012 | Brister et al. |
| 8,316,091 B2 | 11/2012 | Hirvela et al. |
| 8,316,438 B1 | 11/2012 | Bush et al. |
| 8,317,776 B2 | 11/2012 | Ferren et al. |
| 8,320,879 B2 | 11/2012 | Willey et al. |
| 8,321,032 B2 | 11/2012 | Frysz et al. |
| 8,321,149 B2 | 11/2012 | Brauker et al. |
| 8,321,330 B2 | 11/2012 | Kerschner et al. |
| 8,321,526 B2 | 11/2012 | Raleigh |
| 8,321,534 B1 | 11/2012 | Roskind et al. |
| 8,322,346 B2 | 12/2012 | Najafi et al. |
| 8,322,607 B2 | 12/2012 | Lapstun et al. |
| 8,323,193 B2 | 12/2012 | Skerl et al. |
| 8,323,232 B2 | 12/2012 | Bardy |
| 8,323,982 B2 | 12/2012 | LeBoeuf et al. |
| 8,325,011 B2 | 12/2012 | Butler et al. |
| 8,325,031 B1 | 12/2012 | Rao et al. |
| 8,326,435 B2 | 12/2012 | Stevenson |
| 8,326,958 B1 | 12/2012 | Raleigh |
| 8,327,131 B1 | 12/2012 | Hardjono et al. |
| 8,331,901 B2 | 12/2012 | Raleigh |
| 8,332,024 B2 | 12/2012 | Rapoport et al. |
| 8,333,754 B2 | 12/2012 | Boyden et al. |
| 8,335,222 B2 | 12/2012 | Karaoguz et al. |
| 8,335,304 B2 | 12/2012 | Petite |
| 8,336,373 B2 | 12/2012 | Kwon |
| 8,337,482 B2 | 12/2012 | Wood, Jr. |
| 8,341,141 B2 | 12/2012 | Krislov |
| 8,341,291 B2 | 12/2012 | Twitchell, Jr. |
| 8,341,292 B2 | 12/2012 | Twitchell, Jr. |
| 8,343,068 B2 | 1/2013 | Najafi et al. |
| 8,345,881 B2 | 1/2013 | Rekimoto |
| 8,346,248 B2 | 1/2013 | Howarter et al. |
| 8,346,338 B2 | 1/2013 | Goode, Jr. et al. |
| 8,346,482 B2 | 1/2013 | Fernandez |
| 8,347,088 B2 | 1/2013 | Moore et al. |
| 8,347,093 B1 | 1/2013 | Ahmed |
| 8,348,882 B2 | 1/2013 | Bardy |
| 8,351,898 B2 | 1/2013 | Raleigh |
| 8,352,044 B2 | 1/2013 | Christman et al. |
| 8,352,342 B1 | 1/2013 | Bent, II et al. |
| 8,352,636 B2 | 1/2013 | Twitchell, Jr. |
| 8,353,052 B2 | 1/2013 | Larsson et al. |
| 8,353,896 B2 | 1/2013 | Hillis et al. |
| 8,355,337 B2 | 1/2013 | Raleigh |
| 8,359,016 B2 | 1/2013 | Lindeman et al. |
| 8,359,397 B2 | 1/2013 | Traversat et al. |
| 8,360,069 B2 | 1/2013 | Kim et al. |
| 8,361,013 B2 | 1/2013 | Wood, Jr. |
| 8,364,411 B2 | 1/2013 | Fernandez |
| 8,364,413 B2 | 1/2013 | Fernandez |
| 8,364,961 B2 | 1/2013 | Tanaka et al. |
| 8,366,633 B2 | 2/2013 | Wolf |
| 8,369,830 B2 | 2/2013 | Sperti et al. |
| 8,369,950 B2 | 2/2013 | Rawat et al. |
| 8,369,959 B2 | 2/2013 | Meskens |
| 8,369,961 B2 | 2/2013 | Christman et al. |
| 8,370,068 B1 | 2/2013 | Fernandez |
| 8,370,070 B2 | 2/2013 | Fernandez |
| 8,370,071 B2 | 2/2013 | Fernandez |
| 8,370,072 B2 | 2/2013 | Fernandez |
| 8,370,073 B2 | 2/2013 | Fernandez |
| 8,370,078 B2 | 2/2013 | Fernandez |
| 8,370,236 B1 | 2/2013 | Bent et al. |
| 8,372,139 B2 | 2/2013 | Bailey et al. |
| 8,373,556 B2 | 2/2013 | LaLonde et al. |
| 8,374,667 B2 | 2/2013 | Brauker et al. |
| 8,374,697 B2 | 2/2013 | Berger |
| 8,374,796 B2 | 2/2013 | Fernandez |
| 8,375,202 B2 | 2/2013 | Moore et al. |
| 8,379,564 B2 | 2/2013 | Petite et al. |
| 8,380,982 B2 | 2/2013 | Miyabayashi et al. |
| 8,381,262 B2 | 2/2013 | Risher et al. |
| 8,382,756 B2 | 2/2013 | Pool et al. |
| 8,385,240 B2 | 2/2013 | Krishnaswamy |
| 8,385,916 B2 | 2/2013 | Raleigh |
| 8,386,004 B2 | 2/2013 | Kamath et al. |
| 8,386,043 B2 | 2/2013 | Bange et al. |
| 8,386,394 B1 | 2/2013 | Nguyen et al. |
| 8,388,553 B2 | 3/2013 | James et al. |
| 8,389,286 B2 | 3/2013 | Chahal et al. |
| 8,391,981 B2 | 3/2013 | Mosesov |
| 8,391,990 B2 | 3/2013 | Smith et al. |
| 8,392,289 B1 | 3/2013 | Nguyen |
| 8,394,021 B2 | 3/2013 | Goode et al. |
| 8,395,498 B2 | 3/2013 | Gaskill et al. |
| 8,396,458 B2 | 3/2013 | Raleigh |
| 8,397,762 B2 | 3/2013 | Masters et al. |
| 8,403,881 B2 | 3/2013 | Ferren et al. |
| 8,412,301 B2 | 4/2013 | Goode, Jr. et al. |
| 8,415,837 B2 | 4/2013 | Theilmann et al. |
| 8,417,312 B2 | 4/2013 | Kamath et al. |
| 8,419,673 B2 | 4/2013 | Rickard |
| 8,419,734 B2 | 4/2013 | Walker et al. |
| 8,421,630 B2 | 4/2013 | Butler et al. |
| 8,423,298 B2 | 4/2013 | Fernandez |
| 8,428,678 B2 | 4/2013 | Kamath et al. |
| 8,435,179 B2 | 5/2013 | Goode, Jr. et al. |
| 8,435,208 B2 | 5/2013 | Bardy |
| 8,441,081 B2 | 5/2013 | Arora et al. |
| 8,442,631 B2 | 5/2013 | KenKnight et al. |
| 8,444,653 B2 | 5/2013 | Nycz et al. |
| 8,447,376 B2 | 5/2013 | Shariati et al. |
| 8,447,389 B2 | 5/2013 | Koh et al. |
| 8,447,414 B2 | 5/2013 | Johnson et al. |
| 8,449,464 B2 | 5/2013 | Simpson et al. |
| 8,452,368 B2 | 5/2013 | Brister et al. |
| 8,454,552 B2 | 6/2013 | Bardy |
| 8,457,708 B2 | 6/2013 | Brister et al. |
| 8,457,757 B2 | 6/2013 | Cauller et al. |
| 8,457,760 B2 | 6/2013 | Johnson et al. |
| 8,460,231 B2 | 6/2013 | Brauker et al. |
| 8,463,350 B2 | 6/2013 | Kamath et al. |
| 8,463,375 B2 | 6/2013 | Stevenson et al. |
| 8,469,886 B2 | 6/2013 | Brauker et al. |
| 8,474,397 B2 | 7/2013 | Brister et al. |
| 8,475,373 B2 | 7/2013 | Brister et al. |
| 8,478,377 B2 | 7/2013 | Shariati et al. |
| 8,478,378 B2 | 7/2013 | Lal et al. |
| 8,483,791 B2 | 7/2013 | Brister et al. |
| 8,483,793 B2 | 7/2013 | Simpson et al. |
| 8,483,838 B2 | 7/2013 | Nghiem et al. |
| 8,483,840 B2 | 7/2013 | Stevenson et al. |
| 8,486,070 B2 | 7/2013 | Morgan et al. |
| 8,491,474 B2 | 7/2013 | Goode, Jr. et al. |
| 8,493,187 B2 | 7/2013 | Rowland et al. |
| 8,494,647 B2 | 7/2013 | Quiles |
| 8,496,657 B2 | 7/2013 | Bonutti et al. |
| 8,497,804 B2 | 7/2013 | Haubrich et al. |
| 8,502,675 B2 | 8/2013 | Hamel et al. |
| 8,509,911 B2 | 8/2013 | Li et al. |
| 8,509,913 B2 | 8/2013 | Johnson et al. |
| 8,512,219 B2 | 8/2013 | Ferren et al. |
| 8,514,067 B2 | 8/2013 | Hyde et al. |

(56)                References Cited

U.S. PATENT DOCUMENTS

| | | | |
|---|---|---|---|
| 8,515,516 B2 | 8/2013 | Kamath et al. |
| 8,515,519 B2 | 8/2013 | Brister et al. |
| 8,515,547 B2 | 8/2013 | Mass et al. |
| 8,517,013 B2 | 8/2013 | Ni et al. |
| 8,527,026 B2 | 9/2013 | Shults et al. |
| 8,536,667 B2 | 9/2013 | de Graff et al. |
| 8,538,528 B2 | 9/2013 | Von Arx et al. |
| 8,540,632 B2 | 9/2013 | Robertson et al. |
| 8,540,644 B2 | 9/2013 | Husheer |
| 8,543,199 B2 | 9/2013 | Snyder et al. |
| 8,545,402 B2 | 10/2013 | Hafezi et al. |
| 8,545,431 B2 | 10/2013 | Rickard |
| 8,545,436 B2 | 10/2013 | Robertson et al. |
| 8,547,248 B2 | 10/2013 | Zdeblick et al. |
| 8,548,551 B2 | 10/2013 | Kamath et al. |
| 8,548,553 B2 | 10/2013 | Kamath et al. |
| 8,557,772 B2 | 10/2013 | Popel et al. |
| 8,558,563 B2 | 10/2013 | Zdeblick |
| 8,558,699 B2 | 10/2013 | Butler et al. |
| 8,562,528 B2 | 10/2013 | Leach et al. |
| 8,562,558 B2 | 10/2013 | Kamath et al. |
| 8,565,848 B2 | 10/2013 | Brister et al. |
| 8,565,849 B2 | 10/2013 | Kamath et al. |
| 8,565,891 B2 | 10/2013 | Mumbru et al. |
| 8,570,187 B2 | 10/2013 | Janna et al. |
| 8,571,625 B2 | 10/2013 | Kamath et al. |
| 8,574,146 B2 | 11/2013 | Gillespie, Jr. et al. |
| 8,574,164 B2 | 11/2013 | Mashiach |
| 8,577,453 B1 | 11/2013 | Stevenson et al. |
| 8,577,464 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,579,848 B2 | 11/2013 | Field et al. |
| 8,583,210 B2 | 11/2013 | Doerr et al. |
| 8,583,231 B2 | 11/2013 | Bocek et al. |
| 8,585,631 B2 | 11/2013 | Dacquay |
| 8,587,427 B2 | 11/2013 | LaLonde et al. |
| 8,588,924 B2 | 11/2013 | Dion |
| 8,588,941 B2 | 11/2013 | Mashiach |
| 8,599,009 B2 | 12/2013 | Hyde et al. |
| 8,603,024 B2 | 12/2013 | Bohm et al. |
| 8,608,310 B2 | 12/2013 | Otis et al. |
| 8,609,426 B2 | 12/2013 | Silver |
| 8,615,282 B2 | 12/2013 | Brister et al. |
| RE44,695 E | 1/2014 | Simpson et al. |
| 8,623,023 B2 | 1/2014 | Ritchey et al. |
| 8,626,257 B2 | 1/2014 | Li et al. |
| 8,626,310 B2 | 1/2014 | Barror et al. |
| 8,634,927 B2 | 1/2014 | Olson et al. |
| 8,636,670 B2 | 1/2014 | Ferren et al. |
| 8,639,524 B2 | 1/2014 | Solomon |
| 8,644,957 B2 | 2/2014 | Mashiach |
| 8,647,861 B2 | 2/2014 | Ingber et al. |
| 8,649,757 B2 | 2/2014 | Roberts et al. |
| 8,649,857 B2 | 2/2014 | Stevenson et al. |
| 8,649,859 B2 | 2/2014 | Smith et al. |
| 8,652,409 B2 | 2/2014 | LeBoeuf et al. |
| 8,653,966 B2 | 2/2014 | Rao et al. |
| 8,657,745 B2 | 2/2014 | Brauker et al. |
| 8,657,747 B2 | 2/2014 | Kamath et al. |
| 8,660,642 B2 | 2/2014 | Ferren et al. |
| 8,660,659 B2 | 2/2014 | Mosesov et al. |
| 8,661,663 B2 | 3/2014 | Wolfe et al. |
| 8,663,109 B2 | 3/2014 | Brister et al. |
| 8,663,201 B2 | 3/2014 | Hill et al. |
| 8,663,202 B2 | 3/2014 | Yomtov et al. |
| 8,664,364 B2 | 3/2014 | Schmidt et al. |
| 8,666,471 B2 | 3/2014 | Rogers et al. |
| 8,672,845 B2 | 3/2014 | Kamath et al. |
| 8,673,194 B2 | 3/2014 | Lee et al. |
| 8,674,825 B2 | 3/2014 | Zdeblick et al. |
| 8,680,233 B2 | 3/2014 | Bolduc et al. |
| 8,681,000 B2 | 3/2014 | August et al. |
| 8,682,446 B2 | 3/2014 | Albu |
| 8,690,775 B2 | 4/2014 | Brister et al. |
| 8,690,929 B2 | 4/2014 | Stein et al. |
| 8,690,934 B2 | 4/2014 | Boyden et al. |
| 8,694,092 B2 | 4/2014 | Ferren et al. |
| 8,700,181 B2 | 4/2014 | Bornzin et al. |
| 8,700,183 B2 | 4/2014 | Mashiach |
| 8,702,607 B2 | 4/2014 | LeBoeuf et al. |
| 8,704,124 B2 | 4/2014 | Wilson et al. |
| 8,706,208 B2 | 4/2014 | Chiao et al. |
| 8,706,226 B2 | 4/2014 | Johnson et al. |
| 8,707,040 B2 | 4/2014 | Andersen |
| 8,707,964 B2 | 4/2014 | Boyden et al. |
| 8,712,541 B2 | 4/2014 | Olson et al. |
| 8,715,159 B2 | 5/2014 | Pool et al. |
| 8,715,269 B2 | 5/2014 | Wolff et al. |
| 8,718,193 B2 | 5/2014 | Arne et al. |
| 8,718,776 B2 | 5/2014 | Mashiach et al. |
| 8,718,787 B2 | 5/2014 | Utsi et al. |
| 8,721,520 B2 | 5/2014 | Caira et al. |
| 8,721,545 B2 | 5/2014 | Brister et al. |
| 8,721,580 B2 | 5/2014 | Rickard et al. |
| 8,721,643 B2 | 5/2014 | Morgan et al. |
| 8,723,640 B2 | 5/2014 | Hyde et al. |
| 8,730,032 B2 | 5/2014 | Torgerson et al. |
| 8,731,630 B2 | 5/2014 | Kamath et al. |
| 8,731,668 B2 | 5/2014 | Rawat et al. |
| 8,736,441 B2 | 5/2014 | Rao et al. |
| 8,738,139 B2 | 5/2014 | Lanning et al. |
| 8,744,572 B1 | 6/2014 | Greenhut et al. |
| 8,744,581 B2 | 6/2014 | Mosesov |
| 8,747,315 B2 | 6/2014 | Brauker et al. |
| 8,750,955 B2 | 6/2014 | Brister et al. |
| 8,751,013 B2 | 6/2014 | Johnson et al. |
| 8,753,305 B2 | 6/2014 | Field et al. |
| 8,761,856 B2 | 6/2014 | Goode et al. |
| 8,771,187 B2 | 7/2014 | Goode, Jr. et al. |
| 8,774,888 B2 | 7/2014 | Kamath et al. |
| 8,777,853 B2 | 7/2014 | Kamath et al. |
| 8,781,581 B2 | 7/2014 | KenKnight et al. |
| 8,784,332 B2 | 7/2014 | Wolf, II |
| 8,784,425 B2 | 7/2014 | Ritchey et al. |
| 8,785,151 B2 | 7/2014 | Geierstanger et al. |
| 8,788,007 B2 | 7/2014 | Brauker et al. |
| 8,788,008 B2 | 7/2014 | Goode, Jr. et al. |
| 8,788,057 B2 | 7/2014 | Stevenson et al. |
| 8,789,536 B2 | 7/2014 | Boyden et al. |
| 8,790,260 B2 | 7/2014 | Goode, Jr. et al. |
| 8,790,400 B2 | 7/2014 | Boyden et al. |
| 8,792,953 B2 | 7/2014 | Brister et al. |
| 8,792,954 B2 | 7/2014 | Brister et al. |
| 8,792,955 B2 | 7/2014 | Brister et al. |
| 8,792,983 B2 | 7/2014 | Von Arx et al. |
| 8,795,177 B2 | 8/2014 | Goode, Jr. et al. |
| 8,795,260 B2 | 8/2014 | Drew |
| 8,795,359 B2 | 8/2014 | Boyden et al. |
| 8,798,773 B2 | 8/2014 | Mashiach |
| 8,801,610 B2 | 8/2014 | Brauker et al. |
| 8,801,611 B2 | 8/2014 | Brister et al. |
| 8,801,612 B2 | 8/2014 | Goode et al. |
| 8,805,478 B2 | 8/2014 | Powers et al. |
| 8,805,530 B2 | 8/2014 | John |
| 8,808,163 B2 | 8/2014 | Pool et al. |
| 8,808,182 B2 | 8/2014 | Goode et al. |
| 8,808,224 B2 | 8/2014 | Rickard |
| 8,808,271 B2 | 8/2014 | Boyden et al. |
| 8,808,276 B2 | 8/2014 | Boyden et al. |
| 8,808,373 B2 | 8/2014 | Boyden et al. |
| 8,811,926 B2 | 8/2014 | Otis et al. |
| 8,812,073 B2 | 8/2014 | Goode, Jr. et al. |
| 8,814,868 B2 | 8/2014 | Janna et al. |
| 8,816,814 B2 | 8/2014 | Hyde et al. |
| 8,818,522 B2 | 8/2014 | Mass et al. |
| 8,821,400 B2 | 9/2014 | Goode, Jr. et al. |
| 8,825,127 B2 | 9/2014 | Kamath et al. |
| 8,838,249 B2 | 9/2014 | Nycz |
| 8,838,254 B2 | 9/2014 | McClure et al. |

(56) References Cited

U.S. PATENT DOCUMENTS

| | | | |
|---|---|---|---|
| 8,840,578 | B2 | 9/2014 | Dos Santos et al. |
| 8,843,187 | B2 | 9/2014 | Goode, Jr. et al. |
| 8,845,536 | B2 | 9/2014 | Brauker et al. |
| 8,847,766 | B2 | 9/2014 | Zdeblick et al. |
| 8,849,368 | B2 | 9/2014 | Madsen et al. |
| 8,855,785 | B1 | 10/2014 | Johnson et al. |
| 8,858,432 | B2 | 10/2014 | Robertson et al. |
| 8,858,434 | B2 | 10/2014 | Kamath et al. |
| 8,868,201 | B2 | 10/2014 | Roberts et al. |
| 8,870,813 | B2 | 10/2014 | Ferren et al. |
| 8,875,714 | B2 | 11/2014 | Boyden et al. |
| 8,882,741 | B2 | 11/2014 | Brauker et al. |
| 8,884,779 | B2 | 11/2014 | Herman et al. |
| 8,886,272 | B2 | 11/2014 | Brister et al. |
| 8,886,273 | B2 | 11/2014 | Li et al. |
| 8,886,300 | B2 | 11/2014 | Sathaye et al. |
| 8,886,334 | B2 | 11/2014 | Ghaffari et al. |
| 8,901,084 | B2 | 12/2014 | Genove et al. |
| 8,903,500 | B2 | 12/2014 | Smith et al. |
| 8,911,486 | B1 | 12/2014 | Drnek et al. |
| 8,914,131 | B2 | 12/2014 | Bornzin et al. |
| 8,915,849 | B2 | 12/2014 | Brauker et al. |
| 8,920,401 | B2 | 12/2014 | Brauker et al. |
| 8,923,947 | B2 | 12/2014 | Shults et al. |
| 8,926,573 | B2 | 1/2015 | Smith et al. |
| 8,926,933 | B2 | 1/2015 | Zhang et al. |
| 8,929,999 | B2 | 1/2015 | Maschiach |
| 8,932,221 | B2 | 1/2015 | Colliou et al. |
| 8,933,848 | B2 | 1/2015 | Nghiem et al. |
| 8,936,629 | B2 | 1/2015 | Boyden et al. |
| 8,941,470 | B2 | 1/2015 | Butler et al. |
| 8,945,005 | B2 | 2/2015 | Hafezi et al. |
| 8,946,390 | B2 | 2/2015 | Chahal et al. |
| 8,947,233 | B2 | 2/2015 | Butler et al. |
| 8,947,301 | B2 | 2/2015 | Nghiem et al. |
| 8,951,203 | B2 | 2/2015 | Patangay et al. |
| 8,956,288 | B2 | 2/2015 | Hafezi et al. |
| 8,961,412 | B2 | 2/2015 | Hafezi et al. |
| 8,963,737 | B2 | 2/2015 | Makdissi |
| 8,968,198 | B2 | 3/2015 | Brauker et al. |
| 8,968,377 | B2 | 3/2015 | Boyden et al. |
| 8,970,392 | B2 | 3/2015 | LaLonde et al. |
| 8,975,372 | B2 | 3/2015 | Ju et al. |
| 8,979,885 | B2 | 3/2015 | Hyde et al. |
| 8,979,887 | B2 | 3/2015 | Hyde et al. |
| 8,983,618 | B2 | 3/2015 | Yamamoto et al. |
| 8,986,209 | B2 | 3/2015 | Brauker et al. |
| 8,986,337 | B2 | 3/2015 | Hyde et al. |
| 8,989,833 | B2 | 3/2015 | Brauker et al. |
| 8,989,867 | B2 | 3/2015 | Chow et al. |
| 8,989,868 | B2 | 3/2015 | Mashiach et al. |
| 8,989,870 | B2 | 3/2015 | Johnson et al. |
| 8,995,949 | B2 | 3/2015 | Roberts et al. |
| 9,002,467 | B2 | 4/2015 | Smith et al. |
| 9,002,471 | B2 | 4/2015 | Stevenson et al. |
| 9,011,329 | B2 | 4/2015 | Ferren et al. |
| 9,011,330 | B2 | 4/2015 | Sadek et al. |
| 9,011,361 | B2 | 4/2015 | de Juan, Jr. et al. |
| 9,011,510 | B2 | 4/2015 | Boyden et al. |
| 9,014,661 | B2 | 4/2015 | deCharms |
| 9,014,815 | B2 | 4/2015 | Yang et al. |
| 9,017,380 | B2 | 4/2015 | Mayer et al. |
| 9,026,792 | B2 | 5/2015 | Andersen |
| 9,031,637 | B2 | 5/2015 | Ritchey et al. |
| 9,031,658 | B2 | 5/2015 | Chiao et al. |
| 9,037,258 | B2 | 5/2015 | Johnson et al. |
| 9,041,730 | B2 | 5/2015 | Johnson et al. |
| 9,042,999 | B2 | 5/2015 | Stevenson et al. |
| 9,044,182 | B2 | 6/2015 | Silver |
| 9,044,199 | B2 | 6/2015 | Brister et al. |
| 9,044,209 | B2 | 6/2015 | Dayton et al. |
| 9,044,612 | B2 | 6/2015 | Mashiach et al. |
| 9,045,973 | B2 | 6/2015 | Potyrailo et al. |
| 9,050,413 | B2 | 6/2015 | Brauker et al. |
| 9,055,791 | B2 | 6/2015 | Proud et al. |
| 9,055,901 | B2 | 6/2015 | Brister et al. |
| 9,060,742 | B2 | 6/2015 | Brister et al. |
| 9,061,139 | B2 | 6/2015 | Stevenson et al. |
| 9,061,151 | B2 | 6/2015 | Mashiach et al. |
| 9,067,073 | B2 | 6/2015 | Simms, Jr. |
| 9,072,560 | B2 | 7/2015 | Doherty |
| 9,072,588 | B2 | 7/2015 | Bohm et al. |
| 9,072,914 | B2 | 7/2015 | Greenhut et al. |
| 9,078,613 | B2 | 7/2015 | Irazoqui et al. |
| 9,078,626 | B2 | 7/2015 | Brister et al. |
| 9,078,956 | B2 | 7/2015 | Thompson et al. |
| 9,083,424 | B2 | 7/2015 | Otis et al. |
| 9,083,589 | B2 | 7/2015 | Arne et al. |
| 9,107,623 | B2 | 8/2015 | Brauker et al. |
| 9,110,836 | B1 | 8/2015 | Fernandez |
| 9,111,026 | B1 | 8/2015 | Fernandez |
| 9,113,844 | B2 | 8/2015 | Hollstien |
| 9,119,533 | B2 | 9/2015 | Ghaffari |
| 9,119,554 | B2 | 9/2015 | Zdeblick et al. |
| 9,125,981 | B2 | 9/2015 | Mann et al. |
| 9,126,031 | B2 | 9/2015 | Tekmen et al. |
| 9,126,825 | B2 | 9/2015 | Molin et al. |
| 9,135,402 | B2 | 9/2015 | Mensinger et al. |
| 9,144,488 | B2 | 9/2015 | Boyden et al. |
| 9,144,489 | B2 | 9/2015 | Boyden et al. |
| 9,147,144 | B2 | 9/2015 | Potyrailo et al. |
| 9,149,189 | B2 | 10/2015 | Proud |
| 9,149,219 | B2 | 10/2015 | Goode, Jr. et al. |
| 9,149,233 | B2 | 10/2015 | Kamath et al. |
| 9,149,234 | B2 | 10/2015 | Kamath et al. |
| 9,149,423 | B2 | 10/2015 | Duck et al. |
| 9,149,577 | B2 | 10/2015 | Robertson et al. |
| 9,155,496 | B2 | 10/2015 | Shults et al. |
| 9,155,843 | B2 | 10/2015 | Brauker et al. |
| 9,159,223 | B2 | 10/2015 | Proud |
| 9,161,693 | B2 | 10/2015 | Rizwan |
| 9,166,655 | B2 | 10/2015 | Meskens et al. |
| 9,168,005 | B2 | 10/2015 | Najafi et al. |
| 9,168,380 | B1 | 10/2015 | Greenhut et al. |
| 9,173,837 | B2 | 11/2015 | Hillis et al. |
| 9,174,058 | B2 | 11/2015 | Ellingson et al. |
| 9,179,960 | B2 | 11/2015 | Walker et al. |
| 9,185,087 | B2 | 11/2015 | Carlson et al. |
| 9,186,060 | B2 | 11/2015 | De Graff et al. |
| 9,187,539 | B2 | 11/2015 | Popel et al. |
| 9,192,328 | B2 | 11/2015 | Brauker et al. |
| 9,198,563 | B2 | 12/2015 | Ferren et al. |
| 9,198,591 | B2 | 12/2015 | Brockway et al. |
| 9,198,911 | B2 | 12/2015 | Christiano et al. |
| 9,204,798 | B2 | 12/2015 | Proud |
| 9,205,258 | B2 | 12/2015 | Simon et al. |
| 9,205,268 | B2 | 12/2015 | Yoon et al. |
| 9,211,185 | B2 | 12/2015 | Boyden et al. |
| 9,220,917 | B2 | 12/2015 | Boyden et al. |
| 9,226,851 | B2 | 1/2016 | Gunn |
| 9,237,012 | B2 | 1/2016 | Andersen |
| 9,238,133 | B2 | 1/2016 | Boyden et al. |
| 9,242,103 | B2 | 1/2016 | Perryman et al. |
| 9,242,113 | B2 | 1/2016 | Smith et al. |
| 9,247,900 | B2 | 2/2016 | Brister et al. |
| 9,247,901 | B2 | 2/2016 | Kamath et al. |
| 9,248,291 | B2 | 2/2016 | Mashiach |
| 9,248,302 | B2 | 2/2016 | Mashiach et al. |
| 9,251,960 | B2 | 2/2016 | Brendel et al. |
| 9,265,949 | B2 | 2/2016 | Salo et al. |
| 9,269,251 | B2 | 2/2016 | LaLonde et al. |
| 9,270,025 | B2 | 2/2016 | Robertson et al. |
| 9,270,137 | B2 | 2/2016 | Greene |
| 9,271,781 | B2 | 3/2016 | Walker et al. |
| 9,271,857 | B2 | 3/2016 | Pool et al. |
| 9,282,925 | B2 | 3/2016 | Kamath et al. |
| 9,283,115 | B2 | 3/2016 | Lind et al. |
| 9,288,614 | B1 | 3/2016 | Young et al. |
| 9,289,614 | B2 | 3/2016 | Wu et al. |
| 9,289,619 | B2 | 3/2016 | Kramer et al. |
| 9,291,636 | B1 | 3/2016 | Otis et al. |
| 9,302,093 | B2 | 4/2016 | Mashiach |
| 9,308,381 | B2 | 4/2016 | Mashiach et al. |
| 9,314,613 | B2 | 4/2016 | Mashiach |

(56) References Cited

U.S. PATENT DOCUMENTS

| | | | |
|---|---|---|---|
| 9,316,469 | B2 | 4/2016 | Parker et al. |
| 9,317,920 | B2 | 4/2016 | Gluncic |
| 9,318,916 | B2 | 4/2016 | Olson et al. |
| 9,320,455 | B2 | 4/2016 | Hafezi et al. |
| 9,320,466 | B2 | 4/2016 | Simpson et al. |
| 9,320,908 | B2 | 4/2016 | Fletcher et al. |
| 9,326,720 | B2 | 5/2016 | McLaughlin |
| 9,326,726 | B2 | 5/2016 | Lanning et al. |
| 9,326,730 | B2 | 5/2016 | Boyden et al. |
| 9,327,061 | B2 | 5/2016 | Govil et al. |
| 9,333,071 | B2 | 5/2016 | Boyden et al. |
| 9,333,365 | B2 | 5/2016 | Zhao |
| 9,339,188 | B2 | 5/2016 | Proud |
| 9,339,238 | B2 | 5/2016 | Shariati et al. |
| 9,339,372 | B2 | 5/2016 | Boyden et al. |
| 9,345,404 | B2 | 5/2016 | Proud |
| 9,351,124 | B1 | 5/2016 | Shelton |
| 9,351,668 | B2 | 5/2016 | Brauker et al. |
| 9,352,164 | B2 | 5/2016 | Smith et al. |
| 9,356,473 | B2 | 5/2016 | Ghovanloo |
| 9,357,922 | B2 | 6/2016 | Proud |
| 9,358,378 | B2 | 6/2016 | Hanson et al. |
| 9,358,392 | B2 | 6/2016 | Mashiach |
| 9,361,572 | B2 | 6/2016 | Proud et al. |
| 9,364,173 | B2 | 6/2016 | Brauker et al. |
| 9,367,793 | B2 | 6/2016 | Proud et al. |
| 9,370,618 | B2 | 6/2016 | Mann et al. |
| 9,370,619 | B2 | 6/2016 | Mann et al. |
| 9,386,360 | B2 | 7/2016 | Sagan et al. |
| 9,389,260 | B2 | 7/2016 | Potyrailo et al. |
| 9,390,362 | B2 | 7/2016 | Butler et al. |
| 9,392,939 | B2 | 7/2016 | Proud |
| 9,392,949 | B2 | 7/2016 | Ortega et al. |
| 9,393,424 | B2 | 7/2016 | Demmer et al. |
| 9,393,434 | B2 | 7/2016 | Olson et al. |
| 9,398,854 | B2 | 7/2016 | Proud |
| 9,399,139 | B2 | 7/2016 | Demmer et al. |
| 9,399,143 | B2 | 7/2016 | Yamamoto et al. |
| 9,402,583 | B2 | 8/2016 | Stein et al. |
| 9,402,994 | B2 | 8/2016 | Chow et al. |
| 9,403,009 | B2 | 8/2016 | Mashiach |
| 9,403,021 | B2 | 8/2016 | Dronov |
| 9,408,530 | B2 | 8/2016 | Ferren et al. |
| 9,409,013 | B2 | 8/2016 | Mashiach et al. |
| 9,409,018 | B2 | 8/2016 | Tourrel et al. |
| 9,414,651 | B2 | 8/2016 | Proud et al. |
| 9,414,775 | B2 | 8/2016 | Colvin, Jr. et al. |
| 9,414,777 | B2 | 8/2016 | Brister et al. |
| 9,415,163 | B2 | 8/2016 | Ricotti et al. |
| 9,415,215 | B2 | 8/2016 | Mashiach |
| 9,415,216 | B2 | 8/2016 | Mashiach |
| 9,420,856 | B2 | 8/2016 | Proud et al. |
| 9,420,857 | B2 | 8/2016 | Proud et al. |
| 9,420,965 | B2 | 8/2016 | Brauker et al. |
| 9,420,968 | B2 | 8/2016 | Kamath et al. |
| 9,421,372 | B2 | 8/2016 | Mashiach et al. |
| 9,421,388 | B2 | 8/2016 | John |
| 9,424,508 | B2 | 8/2016 | Proud et al. |
| 9,427,053 | B2 | 8/2016 | Proud et al. |
| 9,427,160 | B2 | 8/2016 | Proud et al. |
| 9,427,183 | B2 | 8/2016 | Goode, Jr. et al. |
| 9,427,189 | B2 | 8/2016 | Proud et al. |
| 9,427,190 | B1 | 8/2016 | Proud |
| 9,427,584 | B2 | 8/2016 | Kaula et al. |
| 9,433,371 | B2 | 9/2016 | Hafezi et al. |
| 9,433,376 | B2 | 9/2016 | Estes et al. |
| 9,433,515 | B2 | 9/2016 | Bailey et al. |
| 9,433,775 | B2 | 9/2016 | Boyden et al. |
| 9,433,790 | B2 | 9/2016 | Kaula et al. |
| 9,436,903 | B2 | 9/2016 | Proud et al. |
| 9,436,923 | B1 | 9/2016 | Sriram et al. |
| 9,439,589 | B2 | 9/2016 | Shults et al. |
| 9,444,503 | B2 | 9/2016 | Arne et al. |
| 9,445,651 | B2 | 9/2016 | Proud et al. |
| 9,445,720 | B2 | 9/2016 | Janna et al. |
| 9,445,730 | B2 | 9/2016 | Snyder et al. |
| 9,446,194 | B2 | 9/2016 | Kamath et al. |
| 9,448,219 | B2 | 9/2016 | Arora et al. |
| 9,451,908 | B2 | 9/2016 | Kamath et al. |
| 9,451,910 | B2 | 9/2016 | Brister et al. |
| 9,462,856 | B2 | 10/2016 | Proud et al. |
| 9,462,962 | B2 | 10/2016 | Doerr |
| 9,463,012 | B2 | 10/2016 | Bonutti et al. |
| 9,465,559 | B2 | 10/2016 | Butler et al. |
| 9,468,766 | B2 | 10/2016 | Sheldon et al. |
| 9,468,772 | B2 | 10/2016 | Demmer |
| 9,474,461 | B2 | 10/2016 | Fisher et al. |
| 9,474,888 | B2 | 10/2016 | Wiley et al. |
| 9,481,949 | B2 | 11/2016 | Zhang et al. |
| 9,486,168 | B2 | 11/2016 | Bonmassar et al. |
| 9,492,656 | B2 | 11/2016 | Chow et al. |
| 9,492,671 | B2 | 11/2016 | O'Brien et al. |
| 9,492,677 | B2 | 11/2016 | Greenhut et al. |
| 9,492,678 | B2 | 11/2016 | Chow |
| 9,496,733 | B2 | 11/2016 | Van Funderburk |
| 9,497,928 | B2 | 11/2016 | Garner et al. |
| 9,498,155 | B2 | 11/2016 | Brauker et al. |
| 9,498,164 | B2 | 11/2016 | Johnson et al. |
| 9,498,165 | B2 | 11/2016 | Johnson et al. |
| 9,498,195 | B2 | 11/2016 | Schutt et al. |
| 9,501,735 | B2 | 11/2016 | Proud et al. |
| 9,504,430 | B2 | 11/2016 | Johnson et al. |
| 9,504,830 | B2 | 11/2016 | Kaula et al. |
| 9,510,780 | B2 | 12/2016 | Silver |
| 9,510,782 | B2 | 12/2016 | Kamath et al. |
| 9,512,545 | B2 | 12/2016 | Zhang et al. |
| 9,514,338 | B1 | 12/2016 | Bromberg et al. |
| 9,517,023 | B2 | 12/2016 | McMillan et al. |
| 9,522,282 | B2 | 12/2016 | Chow et al. |
| 9,526,422 | B2 | 12/2016 | Proud |
| 9,526,650 | B2 | 12/2016 | Pool et al. |
| 9,526,800 | B2 | 12/2016 | Hynes et al. |
| 9,528,633 | B2 | 12/2016 | Dos Santos et al. |
| 9,530,089 | B2 | 12/2016 | Proud et al. |
| 9,532,716 | B2 | 1/2017 | Proud |
| 9,532,738 | B2 | 1/2017 | Delbeke et al. |
| 9,533,165 | B1 | 1/2017 | Gunderson |
| 9,538,946 | B2 | 1/2017 | Rasdal et al. |
| 9,539,037 | B2 | 1/2017 | Janna et al. |
| 9,542,685 | B2 | 1/2017 | Proud et al. |
| 9,545,506 | B2 | 1/2017 | Quigley |
| 9,549,692 | B2 | 1/2017 | Hughes et al. |
| 9,550,064 | B2 | 1/2017 | Mashiach |
| 9,551,635 | B2 | 1/2017 | Kalra et al. |
| 9,553,486 | B2 | 1/2017 | Proud et al. |
| 9,561,381 | B2 | 2/2017 | Rao et al. |
| 9,564,777 | B2 | 2/2017 | Yeh et al. |
| 9,567,642 | B2 | 2/2017 | Feldser et al. |
| 9,569,719 | B2 | 2/2017 | Proud et al. |
| 9,569,720 | B2 | 2/2017 | Proud et al. |
| 9,569,771 | B2 | 2/2017 | Lesavich et al. |
| 9,572,992 | B2 | 2/2017 | Shahandeh et al. |
| 9,576,236 | B2 | 2/2017 | Proud et al. |
| 9,579,422 | B2 | 2/2017 | Ju et al. |
| 9,579,510 | B2 | 2/2017 | Meskens |
| 9,582,748 | B2 | 2/2017 | Proud et al. |
| 9,582,749 | B2 | 2/2017 | Proud et al. |
| 9,585,607 | B2 | 3/2017 | Kamath et al. |
| 9,585,722 | B2 | 3/2017 | Ritchey et al. |
| 9,592,010 | B2 | 3/2017 | Stein |
| 9,592,392 | B2 | 3/2017 | Demmer et al. |
| 9,595,187 | B2 | 3/2017 | Kotz et al. |
| 9,596,988 | B2 | 3/2017 | Irazoqui et al. |
| 9,597,513 | B2 | 3/2017 | Sheldon et al. |
| 9,603,557 | B2 | 3/2017 | Brister et al. |
| 9,603,997 | B2 | 3/2017 | Humayun et al. |
| 9,605,363 | B2 | 3/2017 | Zhang et al. |
| 9,610,031 | B2 | 4/2017 | Brister et al. |
| 9,610,391 | B2 | 4/2017 | Vollmers et al. |
| 9,610,450 | B2 | 4/2017 | Zhao |
| 9,615,970 | B2 | 4/2017 | Rickard et al. |
| 9,616,237 | B2 | 4/2017 | Pare et al. |
| 9,624,520 | B2 | 4/2017 | Geierstanger et al. |
| 9,629,586 | B2 | 4/2017 | Ghaffari et al. |

(56)                References Cited

U.S. PATENT DOCUMENTS

| | | | |
|---|---|---|---|
| 9,631,301 B2 | 4/2017 | Zhang et al. |
| 9,634,921 B2 | 4/2017 | Proud et al. |
| 9,636,509 B2 | 5/2017 | Hintz |
| 9,641,342 B2 | 5/2017 | Sriram et al. |
| 9,649,069 B2 | 5/2017 | Goode et al. |
| 9,649,493 B2 | 5/2017 | Mashiach |
| 9,649,503 B2 | 5/2017 | Delp et al. |
| 9,655,558 B2 | 5/2017 | Proud et al. |
| 9,655,777 B2 | 5/2017 | Gelvin |
| 9,656,056 B2 | 5/2017 | Boyden et al. |
| 9,656,074 B2 | 5/2017 | Simon et al. |
| 9,656,087 B2 | 5/2017 | Ghosh |
| 9,659,423 B2 | 5/2017 | Robertson et al. |
| 9,662,015 B2 | 5/2017 | Proud et al. |
| 9,662,069 B2 | 5/2017 | De Graff et al. |
| 9,662,392 B2 | 5/2017 | Altschul et al. |
| 9,662,508 B2 | 5/2017 | Delp et al. |
| 9,668,677 B2 | 6/2017 | Brister et al. |
| 9,668,682 B2 | 6/2017 | Brister et al. |
| 9,669,217 B2 | 6/2017 | Kaula et al. |
| 9,669,224 B2 | 6/2017 | Carney et al. |
| 9,669,227 B2 | 6/2017 | Kaula et al. |
| 9,672,393 B1 | 6/2017 | Zhu et al. |
| 9,675,261 B2 | 6/2017 | Cao et al. |
| 9,675,270 B2 | 6/2017 | Sarkar |
| 9,675,273 B2 | 6/2017 | Gluncic |
| 9,675,809 B2 | 6/2017 | Chow |
| 9,681,842 B2 | 6/2017 | Zdeblick et al. |
| 9,687,654 B2 | 6/2017 | Sheldon et al. |
| 9,688,536 B2 | 6/2017 | Zhang et al. |
| 9,688,743 B2 | 6/2017 | Schmidt et al. |
| 9,693,708 B2 | 7/2017 | Towe |
| 9,693,777 B2 | 7/2017 | Schellin et al. |
| 9,693,813 B2 | 7/2017 | Walker et al. |
| 9,700,234 B2 | 7/2017 | Mickle et al. |
| 9,700,253 B2 | 7/2017 | Estes et al. |
| 9,700,712 B2 | 7/2017 | Towe |
| 9,704,209 B2 | 7/2017 | Proud et al. |
| 9,707,405 B2 | 7/2017 | Shishilla et al. |
| 9,717,449 B2 | 8/2017 | Kamath et al. |
| 9,717,916 B2 | 8/2017 | Ortega et al. |
| 9,719,147 B1 | 8/2017 | Fernandez |
| 9,723,898 B2 | 8/2017 | Proud et al. |
| 9,724,028 B2 | 8/2017 | Brauker et al. |
| 9,724,045 B1 | 8/2017 | Goode, Jr. et al. |
| 9,724,098 B2 | 8/2017 | Baxter, III et al. |
| 9,724,183 B2 | 8/2017 | Mayer et al. |
| 9,729,001 B2 | 8/2017 | Olson et al. |
| 9,731,104 B2 | 8/2017 | Linden et al. |
| 9,732,322 B2 | 8/2017 | Dalton et al. |
| 9,741,139 B2 | 8/2017 | Kamath et al. |
| 9,743,357 B2 | 8/2017 | Tabe |
| 9,748,986 B2 | 8/2017 | Makdissi |
| 9,750,441 B2 | 9/2017 | Brauker et al. |
| 9,750,460 B2 | 9/2017 | Goode et al. |
| 9,750,939 B2 | 9/2017 | Carcieri et al. |
| 9,750,946 B2 | 9/2017 | Kaula et al. |
| 9,756,549 B2 | 9/2017 | Perdomo |
| 9,757,061 B2 | 9/2017 | Shults et al. |
| 9,757,124 B2 | 9/2017 | Schellin et al. |
| 9,757,200 B2 | 9/2017 | Magee et al. |
| 9,764,139 B2 | 9/2017 | Christensen |
| 9,770,189 B2 | 9/2017 | Hyde et al. |
| 9,775,543 B2 | 10/2017 | Brister et al. |
| 9,788,756 B2 | 10/2017 | Demmer |
| 9,789,236 B2 | 10/2017 | Bonde |
| 9,789,317 B2 | 10/2017 | Greenhut et al. |
| 9,801,527 B2 | 10/2017 | Ferren et al. |
| 9,801,572 B2 | 10/2017 | Brister et al. |
| 9,801,989 B2 | 10/2017 | Vollmers et al. |
| 9,804,672 B2 | 10/2017 | Anderson et al. |
| 9,814,389 B2 | 11/2017 | DeHennis |
| 9,814,414 B2 | 11/2017 | Brister et al. |
| 9,814,900 B2 | 11/2017 | Lundmark et al. |
| 9,815,699 B1 | 11/2017 | Zhang et al. |
| 9,818,092 B2 | 11/2017 | Pennanen |
| 9,820,120 B2 | 11/2017 | deCharms |
| 9,821,166 B2 | 11/2017 | Nolan et al. |
| 9,821,170 B2 | 11/2017 | Lundmark et al. |
| 9,823,737 B2 | 11/2017 | Mazed et al. |
| 9,826,963 B2 | 11/2017 | Scott et al. |
| 9,833,143 B2 | 12/2017 | Brister et al. |
| 9,833,176 B2 | 12/2017 | Brister et al. |
| 9,833,199 B2 | 12/2017 | Johnson et al. |
| 9,833,353 B2 | 12/2017 | Witt et al. |
| 9,833,628 B2 | 12/2017 | Yoder et al. |
| 9,837,704 B2 | 12/2017 | Andersen et al. |
| 9,839,395 B2 | 12/2017 | Shariati et al. |
| 9,839,422 B2 | 12/2017 | Schellin et al. |
| 9,839,423 B2 | 12/2017 | Vendely et al. |
| 9,845,554 B2 | 12/2017 | Zhang et al. |
| 9,848,775 B2 | 12/2017 | Tee et al. |
| 9,848,789 B2 | 12/2017 | Hu et al. |
| 9,849,288 B2 | 12/2017 | Meadows et al. |
| 9,849,364 B2 | 12/2017 | Tran et al. |
| 9,853,819 B2 | 12/2017 | Truu et al. |
| 9,854,370 B2 | 12/2017 | Meskens |
| 9,855,433 B2 | 1/2018 | Shahandeh et al. |
| 9,855,785 B1 | 1/2018 | Nagelberg et al. |
| 9,862,222 B1 | 1/2018 | Nagelberg et al. |
| 9,862,607 B2 | 1/2018 | Zhang et al. |
| 9,872,988 B2 | 1/2018 | Kaula et al. |
| 9,874,923 B1 | 1/2018 | Brown et al. |
| 9,876,537 B2 | 1/2018 | Zhu et al. |
| 9,878,138 B2 | 1/2018 | Altschul et al. |
| 9,878,139 B2 | 1/2018 | Altschul et al. |
| 9,878,159 B2 | 1/2018 | Mashiach |
| 9,878,168 B2 | 1/2018 | Shishilla et al. |
| 9,883,815 B2 | 2/2018 | Einarsson et al. |
| 9,884,150 B2 | 2/2018 | Jho et al. |
| 9,884,191 B2 | 2/2018 | Meadows et al. |
| 9,884,456 B2 | 2/2018 | Schellin et al. |
| 9,895,089 B2 | 2/2018 | Goode, Jr. et al. |
| 9,895,301 B2 | 2/2018 | Christiano et al. |
| 9,895,532 B2 | 2/2018 | Kaula et al. |
| 9,895,540 B2 | 2/2018 | Mashiach |
| 9,901,269 B2 | 2/2018 | Hu et al. |
| 9,901,276 B2 | 2/2018 | Sarkar |
| 9,901,307 B2 | 2/2018 | Kamath et al. |
| 9,907,497 B2 | 3/2018 | Simpson et al. |
| 9,910,053 B2 | 3/2018 | Bakhru et al. |
| 9,913,989 B2 | 3/2018 | Schilling et al. |
| 9,915,641 B2 | 3/2018 | Shapiro et al. |
| 9,918,716 B2 | 3/2018 | Baxter, III et al. |
| 9,919,088 B2 | 3/2018 | Bonde et al. |
| 9,919,099 B2 | 3/2018 | Tai et al. |
| 9,919,158 B2 | 3/2018 | Ellingson et al. |
| 9,922,380 B2 | 3/2018 | Isaacson et al. |
| 9,922,381 B2 | 3/2018 | Isaacson et al. |
| 9,931,067 B2 | 4/2018 | Shults et al. |
| 9,936,877 B2 | 4/2018 | Kotz et al. |
| 9,936,890 B2 | 4/2018 | Sarkar et al. |
| 9,939,449 B2 | 4/2018 | May et al. |
| 9,942,051 B1 | 4/2018 | Poltorak |
| 9,942,304 B2 | 4/2018 | Gold |
| 9,943,686 B2 | 4/2018 | Mashiach |
| 9,943,697 B2 | 4/2018 | John |
| 9,944,529 B2 | 4/2018 | Zhang et al. |
| 9,950,166 B2 | 4/2018 | Mashiach et al. |
| 9,958,515 B2 | 5/2018 | Ellingson et al. |
| 9,960,916 B2 | 5/2018 | Corndorf |
| 9,964,384 B2 | 5/2018 | Parker |
| 9,974,492 B1 | 5/2018 | Dicks et al. |
| 9,974,705 B2 | 5/2018 | Rapoport |
| 9,974,965 B2 | 5/2018 | Perryman et al. |
| 9,981,135 B2 | 5/2018 | Cho et al. |
| 9,986,924 B2 | 6/2018 | Rogers et al. |
| 9,989,535 B2 | 6/2018 | Verdine et al. |
| 9,993,173 B2 | 6/2018 | Bellock et al. |
| 9,993,654 B2 | 6/2018 | Smith et al. |
| 9,996,669 B2 | 6/2018 | Goetz et al. |
| 9,999,774 B2 | 6/2018 | Cinbis et al. |
| 9,999,775 B2 | 6/2018 | Ghosh |
| 10,003,862 B2 | 6/2018 | Rowland et al. |

(56) References Cited

U.S. PATENT DOCUMENTS

| | | | |
|---|---|---|---|
| 10,005,564 B1 | 6/2018 | Bhatia et al. |
| 10,010,703 B2 | 7/2018 | Altschul et al. |
| 10,014,571 B2 | 7/2018 | Andersen et al. |
| 10,015,720 B2 | 7/2018 | Perdomo |
| 10,016,135 B2 | 7/2018 | Wolf, II |
| 10,022,078 B2 | 7/2018 | Brauker et al. |
| 10,022,552 B2 | 7/2018 | Stahler et al. |
| 10,022,553 B2 | 7/2018 | Lundmark et al. |
| 10,022,613 B2 | 7/2018 | Tran et al. |
| 10,022,614 B1 | 7/2018 | Tran et al. |
| 10,024,860 B2 | 7/2018 | Hynes et al. |
| 10,026,118 B2 | 7/2018 | Castinado et al. |
| 10,028,659 B2 | 7/2018 | Schwartz et al. |
| 10,028,743 B2 | 7/2018 | Shelton, IV et al. |
| 10,034,743 B2 | 7/2018 | Boyden et al. |
| 10,039,113 B2 | 7/2018 | Ogrinz |
| 10,039,469 B2 | 8/2018 | Higgins et al. |
| 10,039,661 B2 | 8/2018 | Pool et al. |
| 10,045,697 B2 | 8/2018 | Wolf, II |
| 10,045,710 B2 | 8/2018 | Higgins et al. |
| 10,045,764 B2 | 8/2018 | Scott et al. |
| 10,045,798 B2 | 8/2018 | Beyar et al. |
| 10,046,228 B2 | 8/2018 | Tran et al. |
| 10,052,055 B2 | 8/2018 | Li et al. |
| 10,052,490 B2 | 8/2018 | Kaula et al. |
| 10,055,715 B1 | 8/2018 | Grassadonia et al. |
| 10,060,860 B2 | 8/2018 | Popp |
| 10,064,624 B2 | 9/2018 | Shelton, IV et al. |
| 10,065,042 B2 | 9/2018 | Ortega et al. |
| 10,066,203 B2 | 9/2018 | Fryer et al. |
| 10,070,905 B2 | 9/2018 | Bottlang et al. |
| 10,070,992 B2 | 9/2018 | Pagani |
| 10,078,839 B1 | 9/2018 | Mullins et al. |
| 10,080,498 B1 | 9/2018 | Gibson |
| 10,080,897 B2 | 9/2018 | Kaula et al. |
| 10,080,900 B2 | 9/2018 | Ghosh et al. |
| 10,080,903 B2 | 9/2018 | Willis et al. |
| 10,092,363 B2 | 10/2018 | Magee et al. |
| 10,103,936 B2 | 10/2018 | Kurian et al. |
| 10,105,081 B2 | 10/2018 | Delbeke et al. |
| 10,105,550 B2 | 10/2018 | Stahler et al. |
| 10,108,938 B1 | 10/2018 | Brock et al. |
| 10,115,068 B2 | 10/2018 | Vivier |
| 10,117,621 B2 | 11/2018 | Berger et al. |
| 10,118,037 B2 | 11/2018 | Kaula et al. |
| 10,118,054 B2 | 11/2018 | Maharbiz et al. |
| 10,119,798 B2 | 11/2018 | Parker |
| 10,120,888 B2 | 11/2018 | Almasan et al. |
| 10,121,186 B2 | 11/2018 | Isaacson et al. |
| 10,123,882 B2 | 11/2018 | Stevenson et al. |
| 10,124,171 B2 | 11/2018 | Kaula et al. |
| 10,124,182 B2 | 11/2018 | Kivi et al. |
| 10,127,247 B1 | 11/2018 | Arora et al. |
| 10,129,032 B2 | 11/2018 | Vandervort |
| 10,130,282 B2 | 11/2018 | Goetz et al. |
| 10,130,476 B2 | 11/2018 | Nycz et al. |
| 10,135,835 B1 | 11/2018 | Kandel et al. |
| 10,136,816 B2 | 11/2018 | Bernstein et al. |
| 10,137,288 B2 | 11/2018 | Altschul et al. |
| 10,142,312 B2 | 11/2018 | Johnsrud et al. |
| 10,147,076 B2 | 12/2018 | Zhou et al. |
| 10,152,756 B2 | 12/2018 | Isaacson et al. |
| 10,159,847 B2 | 12/2018 | Rasmussen et al. |
| 10,160,251 B1 | 12/2018 | Nagelberg et al. |
| 10,163,079 B1 | 12/2018 | Brock et al. |
| 10,163,080 B2 | 12/2018 | Chow et al. |
| 10,164,685 B2 | 12/2018 | Dobyns et al. |
| 10,164,952 B2 | 12/2018 | Vandervort |
| 10,165,986 B2 | 1/2019 | Johnson et al. |
| 10,168,257 B2 | 1/2019 | Kalra |
| 10,168,693 B2 | 1/2019 | Kingston et al. |
| 10,172,409 B1 | 1/2019 | Andon |
| 10,176,412 B2 | 1/2019 | Geissler et al. |
| 10,176,418 B1 | 1/2019 | Osborn et al. |
| 10,176,481 B2 | 1/2019 | Aljawhari |
| 10,177,609 B2 | 1/2019 | Olson et al. |
| 10,178,105 B2 | 1/2019 | Kurian et al. |
| 10,178,890 B1 | 1/2019 | Andon et al. |
| 10,179,065 B2 | 1/2019 | Drnek et al. |
| 10,182,751 B2 | 1/2019 | Kamath et al. |
| 10,182,819 B2 | 1/2019 | Shelton, IV |
| 10,185,513 B1 | 1/2019 | Vandewater et al. |
| 10,186,546 B2 | 1/2019 | De Graff et al. |
| 10,186,760 B2 | 1/2019 | Heppell |
| 10,188,394 B2 | 1/2019 | Shelton, IV et al. |
| 10,188,870 B2 | 1/2019 | Lundmark et al. |
| 10,192,198 B2 | 1/2019 | Nazzari et al. |
| 10,193,217 B2 | 1/2019 | Andersen et al. |
| 10,193,695 B1 | 1/2019 | Endress et al. |
| 10,194,802 B2 | 2/2019 | Windolf |
| 10,195,513 B2 | 2/2019 | Tran et al. |
| 10,196,271 B2 | 2/2019 | Zhang et al. |
| 10,196,596 B2 | 2/2019 | Glazier et al. |
| 10,200,199 B2 | 2/2019 | Truu et al. |
| 10,200,834 B2 | 2/2019 | Tran et al. |
| 10,204,160 B1 | 2/2019 | Yelton et al. |
| 10,207,116 B2 | 2/2019 | Sheldon et al. |
| 10,213,617 B2 | 2/2019 | Lundmark et al. |
| 10,219,229 B1 | 2/2019 | Mulligan, IV |
| 10,220,217 B2 | 3/2019 | Chow et al. |
| 10,225,085 B2 | 3/2019 | Drouin et al. |
| 10,238,322 B2 | 3/2019 | Vanslyke et al. |
| 10,254,173 B2 | 4/2019 | Choi et al. |
| 10,476,382 B2 | 11/2019 | Wu et al. |
| 10,671,077 B2 | 6/2020 | Ros Sanchez |
| 2001/0055812 A1 | 12/2001 | Mian et al. |
| 2002/0001588 A1 | 1/2002 | Sinha |
| 2002/0005580 A1 | 1/2002 | Goodman et al. |
| 2002/0024450 A1 | 2/2002 | Townsend et al. |
| 2002/0034757 A1 | 3/2002 | Cubicciotti |
| 2002/0049482 A1 | 4/2002 | Fabian et al. |
| 2002/0069278 A1 | 6/2002 | Forslow |
| 2002/0072975 A1 | 6/2002 | Steele et al. |
| 2002/0075844 A1 | 6/2002 | Hagen |
| 2002/0095194 A1 | 7/2002 | Charvin et al. |
| 2002/0098119 A1 | 7/2002 | Goodman |
| 2002/0115198 A1 | 8/2002 | Nerenberg et al. |
| 2002/0128546 A1 | 9/2002 | Silver |
| 2002/0133534 A1 | 9/2002 | Forslow |
| 2002/0137218 A1 | 9/2002 | Mian et al. |
| 2002/0143655 A1 | 10/2002 | Elston et al. |
| 2002/0143855 A1 | 10/2002 | Traversat et al. |
| 2002/0143944 A1 | 10/2002 | Traversat et al. |
| 2002/0147771 A1 | 10/2002 | Traversat et al. |
| 2002/0147810 A1 | 10/2002 | Traversat et al. |
| 2002/0152299 A1 | 10/2002 | Traversat et al. |
| 2002/0161476 A1 | 10/2002 | Panofsky et al. |
| 2002/0173922 A1 | 11/2002 | Potyrailo |
| 2002/0177522 A1 | 11/2002 | Alexander et al. |
| 2002/0182322 A1 | 12/2002 | McCaughan et al. |
| 2002/0184310 A1 | 12/2002 | Traversat et al. |
| 2002/0184311 A1 | 12/2002 | Traversat et al. |
| 2002/0184357 A1 | 12/2002 | Traversat et al. |
| 2002/0184358 A1 | 12/2002 | Traversat et al. |
| 2002/0188657 A1 | 12/2002 | Traversat et al. |
| 2003/0002521 A1 | 1/2003 | Traversat et al. |
| 2003/0009093 A1 | 1/2003 | Silver |
| 2003/0010898 A1 | 1/2003 | Mackenzie et al. |
| 2003/0028226 A1 | 2/2003 | Thompson et al. |
| 2003/0040780 A1 | 2/2003 | Haeg et al. |
| 2003/0041141 A1 | 2/2003 | Abdelaziz et al. |
| 2003/0049204 A1 | 3/2003 | Leyland-Jones |
| 2003/0053284 A1 | 3/2003 | Stevenson et al. |
| 2003/0053950 A1 | 3/2003 | Leyland-Jones |
| 2003/0059954 A1 | 3/2003 | Vikholm et al. |
| 2003/0065525 A1 | 4/2003 | Giacchetti et al. |
| 2003/0068273 A1 | 4/2003 | Leyland-Jones |
| 2003/0072710 A1 | 4/2003 | Leyland-Jones |
| 2003/0073133 A1 | 4/2003 | Leyland-Jones |
| 2003/0077222 A1 | 4/2003 | Leyland-Jones |
| 2003/0087629 A1 | 5/2003 | Juitt et al. |
| 2003/0091975 A1 | 5/2003 | Leyland-Jones |
| 2003/0093691 A1 | 5/2003 | Simon et al. |
| 2003/0100369 A1 | 5/2003 | Gatto et al. |

(56) References Cited

U.S. PATENT DOCUMENTS

| | | |
|---|---|---|
| 2003/0100370 A1 | 5/2003 | Gatto et al. |
| 2003/0100371 A1 | 5/2003 | Gatto et al. |
| 2003/0100372 A1 | 5/2003 | Gatto et al. |
| 2003/0100824 A1 | 5/2003 | Warren et al. |
| 2003/0103901 A1 | 6/2003 | Leyland-Jones |
| 2003/0108484 A1 | 6/2003 | Leyland-Jones |
| 2003/0114735 A1 | 6/2003 | Silver et al. |
| 2003/0114897 A1 | 6/2003 | Von Arx et al. |
| 2003/0114898 A1 | 6/2003 | Von Arx et al. |
| 2003/0124636 A1 | 7/2003 | Leyland-Jones |
| 2003/0130702 A1 | 7/2003 | Kramer et al. |
| 2003/0133639 A1 | 7/2003 | Tao et al. |
| 2003/0136960 A1 | 7/2003 | Goodman et al. |
| 2003/0138375 A1 | 7/2003 | Leyland-Jones |
| 2003/0138377 A1 | 7/2003 | Leyland-Jones |
| 2003/0149459 A1 | 8/2003 | Von Arx et al. |
| 2003/0154031 A1 | 8/2003 | Potyrailo et al. |
| 2003/0160194 A1 | 8/2003 | Potyrailo et al. |
| 2003/0170176 A1 | 9/2003 | Leyland-Jones |
| 2003/0175210 A1 | 9/2003 | Leyland-Jones |
| 2003/0180823 A1 | 9/2003 | Leyland-Jones |
| 2003/0186339 A1 | 10/2003 | Leyland-Jones |
| 2003/0190671 A1 | 10/2003 | Leyland-Jones |
| 2003/0195350 A1 | 10/2003 | Leyland-Jones |
| 2003/0195572 A1 | 10/2003 | Bocek et al. |
| 2003/0196477 A1 | 10/2003 | Auner et al. |
| 2003/0229900 A1 | 12/2003 | Reisman |
| 2004/0005582 A1 | 1/2004 | Shipwash |
| 2004/0011671 A1 | 1/2004 | Shults et al. |
| 2004/0019807 A1 | 1/2004 | Freund |
| 2004/0023413 A1 | 2/2004 | Opalsky |
| 2004/0030743 A1 | 2/2004 | Hugly et al. |
| 2004/0030794 A1 | 2/2004 | Hugly et al. |
| 2004/0031038 A1 | 2/2004 | Hugly et al. |
| 2004/0031058 A1 | 2/2004 | Reisman |
| 2004/0044727 A1 | 3/2004 | Abdelaziz et al. |
| 2004/0053425 A1 | 3/2004 | Link et al. |
| 2004/0064512 A1 | 4/2004 | Arora et al. |
| 2004/0064568 A1 | 4/2004 | Arora et al. |
| 2004/0064693 A1 | 4/2004 | Pabla et al. |
| 2004/0072208 A1 | 4/2004 | Warthoe et al. |
| 2004/0072263 A1 | 4/2004 | Link et al. |
| 2004/0073795 A1 | 4/2004 | Jablon |
| 2004/0078219 A1 | 4/2004 | Kaylor et al. |
| 2004/0082973 A1 | 4/2004 | Kim et al. |
| 2004/0084867 A1 | 5/2004 | Leyland-Jones |
| 2004/0088347 A1 | 5/2004 | Yeager et al. |
| 2004/0088348 A1 | 5/2004 | Yeager et al. |
| 2004/0088369 A1 | 5/2004 | Yeager et al. |
| 2004/0088646 A1 | 5/2004 | Yeager et al. |
| 2004/0098447 A1 | 5/2004 | Verbeke et al. |
| 2004/0100376 A1 | 5/2004 | Lye et al. |
| 2004/0101477 A1 | 5/2004 | Leyland-Jones |
| 2004/0106967 A1 | 6/2004 | Von Arx et al. |
| 2004/0129270 A1 | 7/2004 | Fishman |
| 2004/0133092 A1 | 7/2004 | Kain |
| 2004/0133640 A1 | 7/2004 | Yeager et al. |
| 2004/0148326 A1 | 7/2004 | Nadgir et al. |
| 2004/0162871 A1 | 8/2004 | Pabla et al. |
| 2004/0167587 A1 | 8/2004 | Thompson |
| 2004/0176672 A1 | 9/2004 | Silver et al. |
| 2004/0194628 A1 | 10/2004 | Mitra |
| 2004/0198220 A1 | 10/2004 | Whelan et al. |
| 2004/0199221 A1 | 10/2004 | Fabian et al. |
| 2004/0215240 A1 | 10/2004 | Lovett et al. |
| 2004/0230229 A1 | 11/2004 | Lovett et al. |
| 2004/0234954 A1 | 11/2004 | Nusslein et al. |
| 2004/0253365 A1 | 12/2004 | Warren et al. |
| 2004/0260346 A1 | 12/2004 | Overall et al. |
| 2005/0004615 A1 | 1/2005 | Sanders |
| 2005/0027463 A1 | 2/2005 | Goode, Jr. et al. |
| 2005/0028816 A1 | 2/2005 | Fishman et al. |
| 2005/0036583 A1 | 2/2005 | Chen et al. |
| 2005/0043598 A1 | 2/2005 | Goode, Jr. et al. |
| 2005/0043894 A1 | 2/2005 | Fernandez |
| 2005/0069461 A1 | 3/2005 | Thundat et al. |
| 2005/0069913 A1 | 3/2005 | Mian et al. |
| 2005/0070962 A1 | 3/2005 | Echt et al. |
| 2005/0070968 A1 | 3/2005 | Bergelson et al. |
| 2005/0086300 A1 | 4/2005 | Yeager et al. |
| 2005/0089890 A1 | 4/2005 | Cubicciotti |
| 2005/0098843 A1 | 5/2005 | Touzov |
| 2005/0101841 A9 | 5/2005 | Kaylor et al. |
| 2005/0106630 A1 | 5/2005 | Carlson |
| 2005/0107839 A1 | 5/2005 | Sanders |
| 2005/0109841 A1 | 5/2005 | Ryan et al. |
| 2005/0118617 A1 | 6/2005 | Carlson |
| 2005/0121999 A1 | 6/2005 | Edmonson et al. |
| 2005/0124873 A1 | 6/2005 | Shults et al. |
| 2005/0129240 A1 | 6/2005 | Balfanz et al. |
| 2005/0141706 A1 | 6/2005 | Regli et al. |
| 2005/0143635 A1 | 6/2005 | Kamath et al. |
| 2005/0144437 A1 | 6/2005 | Ransom et al. |
| 2005/0154271 A1 | 7/2005 | Rasdal et al. |
| 2005/0181018 A1 | 8/2005 | Peyman |
| 2005/0181973 A1 | 8/2005 | Genove et al. |
| 2005/0192557 A1 | 9/2005 | Brauker et al. |
| 2005/0197677 A1 | 9/2005 | Stevenson |
| 2005/0203360 A1 | 9/2005 | Brauker et al. |
| 2005/0215764 A1 | 9/2005 | Tuszynski et al. |
| 2005/0233811 A1 | 10/2005 | Gatto et al. |
| 2005/0247319 A1 | 11/2005 | Berger |
| 2005/0249667 A1 | 11/2005 | Tuszynski et al. |
| 2005/0256417 A1 | 11/2005 | Fischell et al. |
| 2005/0259611 A1 | 11/2005 | Bhagwat et al. |
| 2005/0261970 A1 | 11/2005 | Vucina et al. |
| 2005/0273850 A1 | 12/2005 | Freund |
| 2005/0276727 A1 | 12/2005 | Pawliszyn et al. |
| 2005/0283196 A1 | 12/2005 | Bocek et al. |
| 2006/0002331 A1 | 1/2006 | Bhagwat et al. |
| 2006/0010251 A1 | 1/2006 | Mrsic-Flogel et al. |
| 2006/0010485 A1 | 1/2006 | Gorman |
| 2006/0016700 A1 | 1/2006 | Brister et al. |
| 2006/0019327 A1 | 1/2006 | Brister et al. |
| 2006/0019408 A1 | 1/2006 | Waggoner et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0024813 A1 | 2/2006 | Warthoe |
| 2006/0025834 A1 | 2/2006 | Von Arx et al. |
| 2006/0030904 A1 | 2/2006 | Quiles |
| 2006/0032312 A1 | 2/2006 | Auner et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040248 A1 | 2/2006 | Aaron |
| 2006/0041445 A1 | 2/2006 | Aaron |
| 2006/0041446 A1 | 2/2006 | Aaron |
| 2006/0041460 A1 | 2/2006 | Aaron |
| 2006/0041891 A1 | 2/2006 | Aaron |
| 2006/0047283 A1 | 3/2006 | Evans et al. |
| 2006/0049714 A1 | 3/2006 | Liu et al. |
| 2006/0062206 A1 | 3/2006 | Krishnaswamy |
| 2006/0063205 A1 | 3/2006 | Carlson |
| 2006/0064037 A1 | 3/2006 | Shalon et al. |
| 2006/0074479 A1 | 4/2006 | Bailey et al. |
| 2006/0079740 A1 | 4/2006 | Silver et al. |
| 2006/0092043 A1 | 5/2006 | Lagassey |
| 2006/0095199 A1 | 5/2006 | Lagassey |
| 2006/0116744 A1 | 6/2006 | Von Arx et al. |
| 2006/0122863 A1 | 6/2006 | Gottesman et al. |
| 2006/0122864 A1 | 6/2006 | Gottesman et al. |
| 2006/0142651 A1 | 6/2006 | Brister et al. |
| 2006/0142820 A1 | 6/2006 | Von Arx et al. |
| 2006/0147922 A1 | 7/2006 | Watts et al. |

(56) References Cited

U.S. PATENT DOCUMENTS

| | | |
|---|---|---|
| 2006/0149330 A1* | 7/2006 | Mann ............... A61N 1/37229 |
| | | 607/34 |
| 2006/0153736 A1 | 7/2006 | Kalra et al. |
| 2006/0155180 A1 | 7/2006 | Brister et al. |
| 2006/0156054 A1 | 7/2006 | Brown et al. |
| 2006/0161225 A1 | 7/2006 | Sormann et al. |
| 2006/0167784 A1 | 7/2006 | Hoffberg |
| 2006/0174017 A1 | 8/2006 | Robertson |
| 2006/0178841 A1 | 8/2006 | Fernandez |
| 2006/0183984 A1 | 8/2006 | Dobbles et al. |
| 2006/0183985 A1 | 8/2006 | Brister et al. |
| 2006/0194615 A1 | 8/2006 | Vallapureddy et al. |
| 2006/0195029 A1 | 8/2006 | Shults et al. |
| 2006/0195161 A1 | 8/2006 | Li et al. |
| 2006/0200020 A1 | 9/2006 | Brister et al. |
| 2006/0200970 A1 | 9/2006 | Brister et al. |
| 2006/0208066 A1 | 9/2006 | Finn et al. |
| 2006/0208254 A1 | 9/2006 | Goodman et al. |
| 2006/0212080 A1 | 9/2006 | Hartley et al. |
| 2006/0212084 A1 | 9/2006 | Yost et al. |
| 2006/0212085 A1 | 9/2006 | Fischell et al. |
| 2006/0212096 A1 | 9/2006 | Stevenson |
| 2006/0217621 A1 | 9/2006 | Kim et al. |
| 2006/0219776 A1 | 10/2006 | Finn |
| 2006/0222566 A1 | 10/2006 | Brauker et al. |
| 2006/0224206 A1 | 10/2006 | Dublin et al. |
| 2006/0224207 A1 | 10/2006 | Dublin et al. |
| 2006/0229512 A1 | 10/2006 | Petisce et al. |
| 2006/0234678 A1 | 10/2006 | Juitt et al. |
| 2006/0235285 A1 | 10/2006 | Brister et al. |
| 2006/0247711 A1 | 11/2006 | Verhoef et al. |
| 2006/0253259 A1 | 11/2006 | Fernandez |
| 2006/0265018 A1 | 11/2006 | Smith et al. |
| 2006/0282662 A1 | 12/2006 | Whitcomb |
| 2006/0287685 A1 | 12/2006 | Meyer et al. |
| 2006/0291455 A1 | 12/2006 | Katz et al. |
| 2006/0293714 A1 | 12/2006 | Salo et al. |
| 2006/0293717 A1 | 12/2006 | Sathaye et al. |
| 2007/0004436 A1 | 1/2007 | Stirbu |
| 2007/0016381 A1 | 1/2007 | Kamath et al. |
| 2007/0022474 A1 | 1/2007 | Rowett et al. |
| 2007/0022479 A1 | 1/2007 | Sikdar et al. |
| 2007/0023621 A1 | 2/2007 | Blick et al. |
| 2007/0025245 A1 | 2/2007 | Porras et al. |
| 2007/0025265 A1 | 2/2007 | Porras et al. |
| 2007/0027371 A1 | 2/2007 | Benaron et al. |
| 2007/0027385 A1 | 2/2007 | Brister et al. |
| 2007/0032706 A1 | 2/2007 | Kamath et al. |
| 2007/0032718 A1 | 2/2007 | Shults et al. |
| 2007/0032749 A1 | 2/2007 | Overall et al. |
| 2007/0038044 A1 | 2/2007 | Dobbles et al. |
| 2007/0049976 A1 | 3/2007 | Ni et al. |
| 2007/0055324 A1 | 3/2007 | Thompson et al. |
| 2007/0059196 A1 | 3/2007 | Brister et al. |
| 2007/0060099 A1 | 3/2007 | Ramer et al. |
| 2007/0060109 A1 | 3/2007 | Ramer et al. |
| 2007/0060114 A1 | 3/2007 | Ramer et al. |
| 2007/0060129 A1 | 3/2007 | Ramer et al. |
| 2007/0060136 A1 | 3/2007 | Ramer et al. |
| 2007/0060173 A1 | 3/2007 | Ramer et al. |
| 2007/0061197 A1 | 3/2007 | Ramer et al. |
| 2007/0061198 A1 | 3/2007 | Ramer et al. |
| 2007/0061211 A1 | 3/2007 | Ramer et al. |
| 2007/0061229 A1 | 3/2007 | Ramer et al. |
| 2007/0061242 A1 | 3/2007 | Ramer et al. |
| 2007/0061243 A1 | 3/2007 | Ramer et al. |
| 2007/0061244 A1 | 3/2007 | Ramer et al. |
| 2007/0061245 A1 | 3/2007 | Ramer et al. |
| 2007/0061246 A1 | 3/2007 | Ramer et al. |
| 2007/0061247 A1 | 3/2007 | Ramer et al. |
| 2007/0061300 A1 | 3/2007 | Ramer et al. |
| 2007/0061301 A1 | 3/2007 | Ramer et al. |
| 2007/0061302 A1 | 3/2007 | Ramer et al. |
| 2007/0061303 A1 | 3/2007 | Ramer et al. |
| 2007/0061317 A1 | 3/2007 | Ramer et al. |
| 2007/0061328 A1 | 3/2007 | Ramer et al. |
| 2007/0061331 A1 | 3/2007 | Ramer et al. |
| 2007/0061332 A1 | 3/2007 | Ramer et al. |
| 2007/0061333 A1 | 3/2007 | Ramer et al. |
| 2007/0061334 A1 | 3/2007 | Ramer et al. |
| 2007/0061335 A1 | 3/2007 | Ramer et al. |
| 2007/0061336 A1 | 3/2007 | Ramer et al. |
| 2007/0061363 A1 | 3/2007 | Ramer et al. |
| 2007/0066873 A1 | 3/2007 | Kamath et al. |
| 2007/0067004 A1 | 3/2007 | Boveja et al. |
| 2007/0068523 A1 | 3/2007 | Fishman |
| 2007/0073717 A1 | 3/2007 | Ramer et al. |
| 2007/0073718 A1 | 3/2007 | Ramer et al. |
| 2007/0073719 A1 | 3/2007 | Ramer et al. |
| 2007/0073722 A1 | 3/2007 | Ramer et al. |
| 2007/0073723 A1 | 3/2007 | Ramer et al. |
| 2007/0087756 A1 | 4/2007 | Hoffberg |
| 2007/0094042 A1 | 4/2007 | Ramer et al. |
| 2007/0097885 A1 | 5/2007 | Traversat et al. |
| 2007/0100385 A1 | 5/2007 | Rawat et al. |
| 2007/0100650 A1 | 5/2007 | Ramer et al. |
| 2007/0100651 A1 | 5/2007 | Ramer et al. |
| 2007/0100652 A1 | 5/2007 | Ramer et al. |
| 2007/0100653 A1 | 5/2007 | Ramer et al. |
| 2007/0100805 A1 | 5/2007 | Ramer et al. |
| 2007/0100806 A1 | 5/2007 | Ramer et al. |
| 2007/0106138 A1 | 5/2007 | Beiski et al. |
| 2007/0106333 A1 | 5/2007 | Fernandez |
| 2007/0106346 A1 | 5/2007 | Bergelson et al. |
| 2007/0112398 A1 | 5/2007 | Stevenson et al. |
| 2007/0118030 A1 | 5/2007 | Bruce et al. |
| 2007/0118533 A1 | 5/2007 | Ramer et al. |
| 2007/0120683 A1 | 5/2007 | Flippen et al. |
| 2007/0134420 A1 | 6/2007 | Koberstein et al. |
| 2007/0134721 A1 | 6/2007 | Laitenberger et al. |
| 2007/0135803 A1 | 6/2007 | Belson |
| 2007/0136817 A1 | 6/2007 | Nguyen |
| 2007/0143629 A1 | 6/2007 | Hardjono et al. |
| 2007/0143827 A1 | 6/2007 | Nicodemus et al. |
| 2007/0143851 A1 | 6/2007 | Nicodemus et al. |
| 2007/0154030 A1 | 7/2007 | Moses |
| 2007/0156895 A1 | 7/2007 | Vuong |
| 2007/0163880 A1 | 7/2007 | Woo et al. |
| 2007/0167867 A1 | 7/2007 | Wolf |
| 2007/0168354 A1 | 7/2007 | Ramer et al. |
| 2007/0169184 A1 | 7/2007 | Krywaniuk |
| 2007/0171885 A1 | 7/2007 | Bhagwat et al. |
| 2007/0173708 A9 | 7/2007 | Dobbles et al. |
| 2007/0173709 A1 | 7/2007 | Petisce et al. |
| 2007/0173710 A1 | 7/2007 | Petisce et al. |
| 2007/0179549 A1 | 8/2007 | Russie |
| 2007/0179558 A1 | 8/2007 | Gliner et al. |
| 2007/0179562 A1 | 8/2007 | Nycz |
| 2007/0192294 A1 | 8/2007 | Ramer et al. |
| 2007/0192318 A1 | 8/2007 | Ramer et al. |
| 2007/0197889 A1 | 8/2007 | Brister et al. |
| 2007/0197890 A1 | 8/2007 | Boock et al. |
| 2007/0198432 A1 | 8/2007 | Pitroda et al. |
| 2007/0198485 A1 | 8/2007 | Ramer et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0210349 A1 | 9/2007 | Lu et al. |
| 2007/0210923 A1 | 9/2007 | Butler et al. |
| 2007/0213611 A1 | 9/2007 | Simpson et al. |
| 2007/0219639 A1 | 9/2007 | Otto et al. |
| 2007/0232879 A1 | 10/2007 | Brister et al. |
| 2007/0239724 A1 | 10/2007 | Ramer et al. |
| 2007/0249992 A1 | 10/2007 | Bardy |
| 2007/0250020 A1 | 10/2007 | Kim et al. |
| 2007/0254382 A1 | 11/2007 | Vikholm et al. |
| 2007/0260635 A1 | 11/2007 | Ramer et al. |
| 2007/0263783 A1 | 11/2007 | Speranza |
| 2007/0265515 A1 | 11/2007 | Brister et al. |
| 2007/0265704 A1 | 11/2007 | Mayer et al. |
| 2007/0282196 A1 | 12/2007 | Birk et al. |
| 2007/0282634 A1 | 12/2007 | Johnson et al. |
| 2007/0286546 A1 | 12/2007 | Masson et al. |

(56)                    References Cited

U.S. PATENT DOCUMENTS

| | | |
|---|---|---|
| 2007/0288065 A1 | 12/2007 | Christman et al. |
| 2007/0288066 A1 | 12/2007 | Christman et al. |
| 2007/0288069 A1 | 12/2007 | Goscha et al. |
| 2007/0288427 A1 | 12/2007 | Ramer et al. |
| 2007/0293323 A1 | 12/2007 | Gatto et al. |
| 2007/0299386 A1 | 12/2007 | Peyman |
| 2007/0299420 A1 | 12/2007 | Peyman |
| 2008/0004642 A1 | 1/2008 | Birk et al. |
| 2008/0004671 A1 | 1/2008 | Anderson et al. |
| 2008/0009268 A1 | 1/2008 | Ramer et al. |
| 2008/0015494 A1 | 1/2008 | Santini et al. |
| 2008/0015655 A1 | 1/2008 | Bange et al. |
| 2008/0015656 A1 | 1/2008 | Bange et al. |
| 2008/0020012 A1 | 1/2008 | Ju et al. |
| 2008/0021522 A1 | 1/2008 | Verhoef et al. |
| 2008/0021524 A1 | 1/2008 | Goscha et al. |
| 2008/0026486 A1 | 1/2008 | Cooper et al. |
| 2008/0032801 A1 | 2/2008 | Brunet de Courssou |
| 2008/0033254 A1 | 2/2008 | Kamath et al. |
| 2008/0033869 A1 | 2/2008 | Steele et al. |
| 2008/0039904 A1 | 2/2008 | Bulkes et al. |
| 2008/0041937 A1 | 2/2008 | Vawter |
| 2008/0044014 A1 | 2/2008 | Corndorf |
| 2008/0044025 A1 | 2/2008 | Corndorf |
| 2008/0045825 A1 | 2/2008 | Melker et al. |
| 2008/0046037 A1 | 2/2008 | Haubrich et al. |
| 2008/0046038 A1 | 2/2008 | Hill et al. |
| 2008/0046039 A1 | 2/2008 | Corndorf |
| 2008/0046057 A1 | 2/2008 | Kramer et al. |
| 2008/0048855 A1 | 2/2008 | Berger |
| 2008/0049376 A1 | 2/2008 | Stevenson et al. |
| 2008/0052769 A1 | 2/2008 | Leone et al. |
| 2008/0063201 A1 | 3/2008 | Wormald et al. |
| 2008/0065181 A1 | 3/2008 | Stevenson |
| 2008/0071156 A1 | 3/2008 | Brister et al. |
| 2008/0071313 A1 | 3/2008 | Stevenson et al. |
| 2008/0071328 A1 | 3/2008 | Haubrich et al. |
| 2008/0076572 A1 | 3/2008 | Nguyen et al. |
| 2008/0077375 A1 | 3/2008 | Fernandez |
| 2008/0083617 A1 | 4/2008 | Simpson et al. |
| 2008/0092181 A1 | 4/2008 | Britt |
| 2008/0095180 A1 | 4/2008 | Vucina et al. |
| 2008/0097496 A1 | 4/2008 | Chang et al. |
| 2008/0097858 A1 | 4/2008 | Vucina et al. |
| 2008/0098212 A1 | 4/2008 | Helms et al. |
| 2008/0102096 A1 | 5/2008 | Molin et al. |
| 2008/0106419 A1 | 5/2008 | Sakama et al. |
| 2008/0108942 A1 | 5/2008 | Brister et al. |
| 2008/0109879 A1 | 5/2008 | Bhagwat et al. |
| 2008/0119703 A1 | 5/2008 | Brister et al. |
| 2008/0129465 A1 | 6/2008 | Rao |
| 2008/0140154 A1 | 6/2008 | Loeb et al. |
| 2008/0140160 A1 | 6/2008 | Goetz et al. |
| 2008/0141360 A1 | 6/2008 | Hicks et al. |
| 2008/0142366 A1 | 6/2008 | Tamirisa et al. |
| 2008/0157928 A1 | 7/2008 | Butler et al. |
| 2008/0161886 A1 | 7/2008 | Stevenson et al. |
| 2008/0164975 A1 | 7/2008 | Butler et al. |
| 2008/0164977 A1 | 7/2008 | Butler et al. |
| 2008/0167600 A1 | 7/2008 | Peyman |
| 2008/0167954 A1 | 7/2008 | Kawakami |
| 2008/0170982 A1 | 7/2008 | Zhang et al. |
| 2008/0176271 A1 | 7/2008 | Silver et al. |
| 2008/0180242 A1 | 7/2008 | Cottingham |
| 2008/0180249 A1 | 7/2008 | Butler et al. |
| 2008/0182270 A1 | 7/2008 | Carlson |
| 2008/0183072 A1 | 7/2008 | Robertson et al. |
| 2008/0183247 A1 | 7/2008 | Harding |
| 2008/0183853 A1 | 7/2008 | Manion et al. |
| 2008/0186137 A1 | 8/2008 | Butler et al. |
| 2008/0186138 A1 | 8/2008 | Butler et al. |
| 2008/0186139 A1 | 8/2008 | Butler et al. |
| 2008/0186180 A1 | 8/2008 | Butler et al. |
| 2008/0188731 A1 | 8/2008 | Brister et al. |
| 2008/0194935 A1 | 8/2008 | Brister et al. |
| 2008/0195180 A1 | 8/2008 | Stevenson et al. |
| 2008/0207983 A1 | 8/2008 | Boyden et al. |
| 2008/0208010 A1 | 8/2008 | Boyden et al. |
| 2008/0208025 A1 | 8/2008 | Shults et al. |
| 2008/0211630 A1 | 9/2008 | Butler et al. |
| 2008/0214915 A1 | 9/2008 | Brister et al. |
| 2008/0220535 A1 | 9/2008 | LeBoeuf et al. |
| 2008/0222715 A1 | 9/2008 | Bansal et al. |
| 2008/0229402 A1 | 9/2008 | Smetters et al. |
| 2008/0230859 A1 | 9/2008 | Zaghloul et al. |
| 2008/0234047 A1 | 9/2008 | Nguyen |
| 2008/0234598 A1 | 9/2008 | Snyder et al. |
| 2008/0234599 A1 | 9/2008 | Chiao et al. |
| 2008/0234784 A1 | 9/2008 | Li et al. |
| 2008/0242279 A1 | 10/2008 | Ramer et al. |
| 2008/0242961 A1 | 10/2008 | Brister et al. |
| 2008/0242976 A1 | 10/2008 | Robertson et al. |
| 2008/0243200 A1 | 10/2008 | Scinicariello et al. |
| 2008/0252459 A1 | 10/2008 | Butler et al. |
| 2008/0252485 A1 | 10/2008 | Lagassey |
| 2008/0256618 A1 | 10/2008 | Bansal et al. |
| 2008/0269573 A1 | 10/2008 | Najafi et al. |
| 2008/0275312 A1 | 11/2008 | Mosesov et al. |
| 2008/0275313 A1 | 11/2008 | Brister et al. |
| 2008/0281371 A1 | 11/2008 | KenKnight et al. |
| 2008/0288027 A1 | 11/2008 | Kroll et al. |
| 2008/0296155 A1 | 12/2008 | Shults et al. |
| 2008/0300658 A1 | 12/2008 | Meskens |
| 2008/0303728 A1 | 12/2008 | Lee et al. |
| 2008/0306359 A1 | 12/2008 | Zdeblick et al. |
| 2008/0319280 A1 | 12/2008 | August et al. |
| 2009/0004231 A1 | 1/2009 | Popp |
| 2009/0005656 A1 | 1/2009 | Najafi et al. |
| 2009/0011946 A1 | 1/2009 | Majumdar et al. |
| 2009/0012372 A1 | 1/2009 | Burnett et al. |
| 2009/0013380 A1 | 1/2009 | Chandrasiri et al. |
| 2009/0016529 A1 | 1/2009 | Gopinath et al. |
| 2009/0018403 A1* | 1/2009 | Black ................... A61B 5/0031 |
| | | 600/300 |
| 2009/0024161 A1 | 1/2009 | Bonutti et al. |
| 2009/0028957 A1 | 1/2009 | Daniloff |
| 2009/0036111 A1 | 2/2009 | Danford et al. |
| 2009/0036910 A1 | 2/2009 | Kim et al. |
| 2009/0043347 A1 | 2/2009 | Bocek et al. |
| 2009/0044804 A1 | 2/2009 | Fishman |
| 2009/0046591 A1 | 2/2009 | Krishnaswamy et al. |
| 2009/0046598 A1 | 2/2009 | Krishnaswamy et al. |
| 2009/0046644 A1 | 2/2009 | Krishnaswamy et al. |
| 2009/0046676 A1 | 2/2009 | Krishnaswamy et al. |
| 2009/0046861 A1 | 2/2009 | Krishnaswamy |
| 2009/0047930 A1 | 2/2009 | Krishnaswamy et al. |
| 2009/0047966 A1 | 2/2009 | Krishnaswamy et al. |
| 2009/0049158 A1 | 2/2009 | Krishnaswamy et al. |
| 2009/0058635 A1 | 3/2009 | LaLonde et al. |
| 2009/0058636 A1 | 3/2009 | Gaskill et al. |
| 2009/0060201 A1 | 3/2009 | Rhodes et al. |
| 2009/0062825 A1 | 3/2009 | Pool et al. |
| 2009/0062887 A1 | 3/2009 | Mass et al. |
| 2009/0063193 A1 | 3/2009 | Barton et al. |
| 2009/0065001 A1 | 3/2009 | Fishman |
| 2009/0069869 A1 | 3/2009 | Stouffer et al. |
| 2009/0071474 A1 | 3/2009 | Fishman |
| 2009/0071475 A1 | 3/2009 | Fishman |
| 2009/0071476 A1 | 3/2009 | Fishman |
| 2009/0071481 A1 | 3/2009 | Fishman |
| 2009/0073943 A1 | 3/2009 | Krishnaswamy et al. |
| 2009/0076360 A1 | 3/2009 | Brister et al. |
| 2009/0076361 A1 | 3/2009 | Kamath et al. |
| 2009/0088133 A1 | 4/2009 | Orlassino |
| 2009/0088609 A1 | 4/2009 | Schmitz-Rode et al. |
| 2009/0099626 A1 | 4/2009 | de Juan, Jr. et al. |
| 2009/0102682 A1 | 4/2009 | Corndorf |
| 2009/0104250 A1 | 4/2009 | Boyden et al. |
| 2009/0105561 A1 | 4/2009 | Boyden et al. |
| 2009/0105694 A1 | 4/2009 | Boyden et al. |
| 2009/0110714 A1 | 4/2009 | Boyden et al. |
| 2009/0112048 A1 | 4/2009 | Boyden et al. |
| 2009/0112189 A1 | 4/2009 | Boyden et al. |
| 2009/0112190 A1 | 4/2009 | Boyden et al. |

(56)　　　　References Cited

U.S. PATENT DOCUMENTS

| | | |
|---|---|---|
| 2009/0112191 A1 | 4/2009 | Boyden et al. |
| 2009/0112523 A1 | 4/2009 | Townsend et al. |
| 2009/0118597 A1 | 5/2009 | Mills et al. |
| 2009/0118683 A1 | 5/2009 | Hanson et al. |
| 2009/0119741 A1 | 5/2009 | Palnitkar et al. |
| 2009/0119776 A1 | 5/2009 | Palnitkar et al. |
| 2009/0124513 A1 | 5/2009 | Berg et al. |
| 2009/0124879 A1 | 5/2009 | Brister et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137866 A1 | 5/2009 | Boyden et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143696 A1 | 6/2009 | Najafi et al. |
| 2009/0148496 A1 | 6/2009 | Schmitz et al. |
| 2009/0155900 A1 | 6/2009 | Vemuri et al. |
| 2009/0156919 A1 | 6/2009 | Brister et al. |
| 2009/0156988 A1 | 6/2009 | Ferren et al. |
| 2009/0157056 A1 | 6/2009 | Ferren et al. |
| 2009/0157057 A1 | 6/2009 | Ferren et al. |
| 2009/0157058 A1 | 6/2009 | Ferren et al. |
| 2009/0157141 A1 | 6/2009 | Chiao et al. |
| 2009/0157147 A1 | 6/2009 | Cauller et al. |
| 2009/0157151 A1 | 6/2009 | Cauller et al. |
| 2009/0163790 A1 | 6/2009 | Brister et al. |
| 2009/0163791 A1 | 6/2009 | Brister et al. |
| 2009/0163894 A1 | 6/2009 | Boyden et al. |
| 2009/0163980 A1 | 6/2009 | Stevenson |
| 2009/0163981 A1 | 6/2009 | Stevenson et al. |
| 2009/0168990 A1 | 7/2009 | Makagon et al. |
| 2009/0178459 A1 | 7/2009 | Li et al. |
| 2009/0182217 A1 | 7/2009 | Li et al. |
| 2009/0192381 A1 | 7/2009 | Brockway et al. |
| 2009/0192449 A1 | 7/2009 | Boyden et al. |
| 2009/0192574 A1 | 7/2009 | Von Arx et al. |
| 2009/0192724 A1 | 7/2009 | Brauker et al. |
| 2009/0194181 A1 | 8/2009 | Masters et al. |
| 2009/0198293 A1 | 8/2009 | Cauller et al. |
| 2009/0198450 A1 | 8/2009 | Fernandez |
| 2009/0198451 A1 | 8/2009 | Fernandez |
| 2009/0199009 A1 | 8/2009 | Chia et al. |
| 2009/0202387 A1 | 8/2009 | Dlugos, Jr. et al. |
| 2009/0203980 A1 | 8/2009 | Carlson et al. |
| 2009/0204379 A1 | 8/2009 | Fernandez |
| 2009/0204805 A1 | 8/2009 | Robba et al. |
| 2009/0204964 A1 | 8/2009 | Foley et al. |
| 2009/0206087 A1 | 8/2009 | Reinmuller |
| 2009/0216103 A1 | 8/2009 | Brister et al. |
| 2009/0221439 A1 | 9/2009 | Carlson |
| 2009/0222215 A1 | 9/2009 | Fernandez |
| 2009/0227855 A1 | 9/2009 | Hill et al. |
| 2009/0227862 A1 | 9/2009 | Smith et al. |
| 2009/0228075 A1 | 9/2009 | Dion |
| 2009/0228076 A1 | 9/2009 | Ameri |
| 2009/0248112 A1 | 10/2009 | Mumbru et al. |
| 2009/0248450 A1 | 10/2009 | Fernandez |
| 2009/0253587 A1 | 10/2009 | Fernandez |
| 2009/0254179 A1 | 10/2009 | Burnett |
| 2009/0254572 A1 | 10/2009 | Redlich et al. |
| 2009/0254646 A1 | 10/2009 | Brown et al. |
| 2009/0270948 A1 | 10/2009 | Nghiem et al. |
| 2009/0274737 A1 | 11/2009 | Borck |
| 2009/0275403 A1 | 11/2009 | Proctor |
| 2009/0281589 A1 | 11/2009 | Hartley et al. |
| 2009/0281597 A1 | 11/2009 | Parramon et al. |
| 2009/0281872 A1 | 11/2009 | Kalaboukis |
| 2009/0284378 A1 | 11/2009 | Ferren et al. |
| 2009/0287093 A1 | 11/2009 | Ferren et al. |
| 2009/0287094 A1 | 11/2009 | Ferren et al. |
| 2009/0287101 A1 | 11/2009 | Ferren et al. |
| 2009/0287109 A1 | 11/2009 | Ferren et al. |
| 2009/0287110 A1 | 11/2009 | Ferren et al. |
| 2009/0287120 A1 | 11/2009 | Ferren et al. |
| 2009/0287191 A1 | 11/2009 | Ferren et al. |
| 2009/0292212 A1 | 11/2009 | Ferren et al. |
| 2009/0292213 A1 | 11/2009 | Ferren et al. |
| 2009/0292214 A1 | 11/2009 | Ferren et al. |
| 2009/0292222 A1 | 11/2009 | Ferren et al. |
| 2009/0299156 A1 | 12/2009 | Simpson et al. |
| 2009/0299438 A1 | 12/2009 | Nolan et al. |
| 2009/0305972 A1 | 12/2009 | Chahal et al. |
| 2009/0309614 A1 | 12/2009 | Goodman et al. |
| 2009/0319672 A1 | 12/2009 | Reisman |
| 2009/0320073 A1 | 12/2009 | Reisman |
| 2009/0322510 A1 | 12/2009 | Berger et al. |
| 2009/0327729 A1 | 12/2009 | Rhodes et al. |
| 2010/0004500 A1 | 1/2010 | Gliner et al. |
| 2010/0004523 A1 | 1/2010 | August et al. |
| 2010/0007444 A1 | 1/2010 | Nordin et al. |
| 2010/0015201 A1 | 1/2010 | Borck et al. |
| 2010/0016925 A1 | 1/2010 | Christman et al. |
| 2010/0036209 A1 | 2/2010 | Ferren et al. |
| 2010/0036263 A1 | 2/2010 | Ferren et al. |
| 2010/0036268 A1 | 2/2010 | Ferren et al. |
| 2010/0036269 A1 | 2/2010 | Ferren et al. |
| 2010/0036463 A1 | 2/2010 | Bange et al. |
| 2010/0045480 A1 | 2/2010 | Vallapureddy et al. |
| 2010/0055801 A1 | 3/2010 | Yi et al. |
| 2010/0056888 A1 | 3/2010 | Skerl et al. |
| 2010/0057801 A1 | 3/2010 | Ramer et al. |
| 2010/0063347 A1 | 3/2010 | Yomtov et al. |
| 2010/0069987 A1 | 3/2010 | Min et al. |
| 2010/0073016 A1 | 3/2010 | Arora et al. |
| 2010/0076845 A1 | 3/2010 | Ramer et al. |
| 2010/0081908 A1 | 4/2010 | Dobbles et al. |
| 2010/0082080 A1 | 4/2010 | Mateychuk |
| 2010/0082102 A1 | 4/2010 | Govil et al. |
| 2010/0082430 A1 | 4/2010 | Ramer et al. |
| 2010/0082431 A1 | 4/2010 | Ramer et al. |
| 2010/0085160 A1 | 4/2010 | Fu |
| 2010/0094654 A1 | 4/2010 | Stewart |
| 2010/0094981 A1 | 4/2010 | Cordray et al. |
| 2010/0095077 A1 | 4/2010 | Lockwood |
| 2010/0099396 A1 | 4/2010 | Huq et al. |
| 2010/0100157 A1 | 4/2010 | Nghiem et al. |
| 2010/0100930 A1 | 4/2010 | King |
| 2010/0106224 A1 | 4/2010 | Von Arx et al. |
| 2010/0109958 A1 | 5/2010 | Haubrich et al. |
| 2010/0109966 A1 | 5/2010 | Mateychuk et al. |
| 2010/0114233 A1 | 5/2010 | Von Arx et al. |
| 2010/0114245 A1 | 5/2010 | Yamamoto et al. |
| 2010/0114246 A1 | 5/2010 | Yamamoto et al. |
| 2010/0115606 A1 | 5/2010 | Samovskiy et al. |
| 2010/0121169 A1 | 5/2010 | Petisce et al. |
| 2010/0121705 A1 | 5/2010 | Ramer et al. |
| 2010/0131027 A1 | 5/2010 | Sathaye et al. |
| 2010/0131618 A1 | 5/2010 | Brewis et al. |
| 2010/0131619 A1 | 5/2010 | Brewis et al. |
| 2010/0131622 A1 | 5/2010 | Brewis et al. |
| 2010/0131652 A1 | 5/2010 | Brewis et al. |
| 2010/0132040 A1 | 5/2010 | Bhagwat et al. |
| 2010/0138293 A1 | 6/2010 | Ramer et al. |
| 2010/0138296 A1 | 6/2010 | Ramer et al. |
| 2010/0138908 A1 | 6/2010 | Vennelakanti et al. |
| 2010/0138926 A1 | 6/2010 | Kashchenko et al. |
| 2010/0139672 A1 | 6/2010 | Kroll et al. |
| 2010/0142410 A1 | 6/2010 | Huynh Van et al. |
| 2010/0143871 A1 | 6/2010 | Berger |
| 2010/0144641 A1 | 6/2010 | Popel et al. |
| 2010/0145337 A1 | 6/2010 | Janna et al. |
| 2010/0145804 A1 | 6/2010 | Ramer et al. |
| 2010/0146146 A1 | 6/2010 | Welts et al. |
| 2010/0149042 A1 | 6/2010 | Utsi et al. |
| 2010/0150170 A1 | 6/2010 | Lee et al. |
| 2010/0151113 A1 | 6/2010 | Shelton |
| 2010/0152573 A1 | 6/2010 | Ritchey et al. |
| 2010/0152816 A1 | 6/2010 | Von Arx et al. |
| 2010/0153208 A1 | 6/2010 | Ramer et al. |
| 2010/0153211 A1 | 6/2010 | Ramer et al. |
| 2010/0160760 A1 | 6/2010 | Shults et al. |

(56)  References Cited

U.S. PATENT DOCUMENTS

| | | |
|---|---|---|
| 2010/0160997 A1 | 6/2010 | Johnson et al. |
| 2010/0161004 A1 | 6/2010 | Najafi et al. |
| 2010/0164488 A1 | 7/2010 | Lowe et al. |
| 2010/0165593 A1 | 7/2010 | Townsend et al. |
| 2010/0168817 A1 | 7/2010 | Yamamoto et al. |
| 2010/0168818 A1 | 7/2010 | Barror et al. |
| 2010/0168821 A1 | 7/2010 | Johnson et al. |
| 2010/0169179 A1 | 7/2010 | Ramer et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174240 A1 | 7/2010 | Wells et al. |
| 2010/0174349 A1 | 7/2010 | Stevenson et al. |
| 2010/0179404 A1 | 7/2010 | Kamath et al. |
| 2010/0179408 A1 | 7/2010 | Kamath et al. |
| 2010/0185055 A1 | 7/2010 | Robertson et al. |
| 2010/0185069 A1 | 7/2010 | Brister et al. |
| 2010/0185075 A1 | 7/2010 | Brister et al. |
| 2010/0185249 A1 | 7/2010 | Wingeier et al. |
| 2010/0186078 A1 | 7/2010 | Napoli et al. |
| 2010/0188975 A1 | 7/2010 | Raleigh |
| 2010/0188990 A1 | 7/2010 | Raleigh |
| 2010/0188991 A1 | 7/2010 | Raleigh |
| 2010/0188992 A1 | 7/2010 | Raleigh |
| 2010/0188993 A1 | 7/2010 | Raleigh |
| 2010/0188994 A1 | 7/2010 | Raleigh |
| 2010/0188995 A1 | 7/2010 | Raleigh |
| 2010/0190470 A1 | 7/2010 | Raleigh |
| 2010/0191082 A1 | 7/2010 | Brister et al. |
| 2010/0191236 A1 | 7/2010 | Johnson et al. |
| 2010/0191306 A1 | 7/2010 | Stevenson et al. |
| 2010/0191575 A1 | 7/2010 | Raleigh |
| 2010/0191576 A1 | 7/2010 | Raleigh |
| 2010/0191604 A1 | 7/2010 | Raleigh |
| 2010/0191612 A1 | 7/2010 | Raleigh |
| 2010/0191613 A1 | 7/2010 | Raleigh |
| 2010/0191846 A1 | 7/2010 | Raleigh |
| 2010/0191847 A1 | 7/2010 | Raleigh |
| 2010/0192120 A1 | 7/2010 | Raleigh |
| 2010/0192170 A1 | 7/2010 | Raleigh |
| 2010/0192207 A1 | 7/2010 | Raleigh |
| 2010/0192212 A1 | 7/2010 | Raleigh |
| 2010/0192220 A1 | 7/2010 | Heizmann et al. |
| 2010/0197266 A1 | 8/2010 | Raleigh |
| 2010/0197268 A1 | 8/2010 | Raleigh |
| 2010/0198034 A1 | 8/2010 | Thomas et al. |
| 2010/0198039 A1 | 8/2010 | Towe |
| 2010/0198681 A1 | 8/2010 | Ramer et al. |
| 2010/0204759 A1 | 8/2010 | Christman et al. |
| 2010/0204802 A1 | 8/2010 | Wilson et al. |
| 2010/0208397 A1 | 8/2010 | Johnson et al. |
| 2010/0208631 A1 | 8/2010 | Zhang et al. |
| 2010/0209298 A1 | 8/2010 | Kalra et al. |
| 2010/0211124 A1 | 8/2010 | Ni et al. |
| 2010/0211458 A1 | 8/2010 | Ramer et al. |
| 2010/0211645 A1 | 8/2010 | Wang et al. |
| 2010/0212583 A1 | 8/2010 | Brister et al. |
| 2010/0216175 A1 | 8/2010 | Melker et al. |
| 2010/0217239 A1 | 8/2010 | Mann et al. |
| 2010/0217240 A1 | 8/2010 | Mann et al. |
| 2010/0217241 A1 | 8/2010 | Mann et al. |
| 2010/0217242 A1 | 8/2010 | Mann et al. |
| 2010/0217243 A1 | 8/2010 | Mann |
| 2010/0217244 A1 | 8/2010 | Mann et al. |
| 2010/0217298 A1 | 8/2010 | Bardy |
| 2010/0217301 A1 | 8/2010 | Bardy |
| 2010/0217662 A1 | 8/2010 | Ramer et al. |
| 2010/0217663 A1 | 8/2010 | Ramer et al. |
| 2010/0222686 A1 | 9/2010 | Fisher et al. |
| 2010/0222802 A1 | 9/2010 | Gillespie, Jr. et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228141 A1 | 9/2010 | Kountotsis |
| 2010/0228497 A1 | 9/2010 | Kamath et al. |
| 2010/0231481 A1* | 9/2010 | Chiang .................. H01Q 9/42 |
| | | 343/702 |
| 2010/0235285 A1 | 9/2010 | Hoffberg |
| 2010/0235879 A1 | 9/2010 | Burnside et al. |
| 2010/0241195 A1 | 9/2010 | Meadows et al. |
| 2010/0249696 A1 | 9/2010 | Bardy |
| 2010/0250497 A1 | 9/2010 | Redlich et al. |
| 2010/0261526 A1 | 10/2010 | Anderson et al. |
| 2010/0262036 A1 | 10/2010 | Najafi et al. |
| 2010/0269146 A1 | 10/2010 | Britt |
| 2010/0274121 A1 | 10/2010 | Ritchey et al. |
| 2010/0274141 A1 | 10/2010 | Patangay et al. |
| 2010/0274147 A1 | 10/2010 | Patangay et al. |
| 2010/0275250 A1 | 10/2010 | Devadoss et al. |
| 2010/0281364 A1 | 11/2010 | Sidman |
| 2010/0282005 A1 | 11/2010 | Kwon |
| 2010/0285082 A1 | 11/2010 | Fernandez |
| 2010/0286739 A1 | 11/2010 | Yost et al. |
| 2010/0293051 A1 | 11/2010 | Ramer et al. |
| 2010/0293221 A1 | 11/2010 | Sidman et al. |
| 2010/0298895 A1 | 11/2010 | Ghaffari et al. |
| 2010/0299522 A1 | 11/2010 | Khambete |
| 2010/0299763 A1 | 11/2010 | Marcus et al. |
| 2010/0304737 A1 | 12/2010 | Jain et al. |
| 2010/0305476 A1 | 12/2010 | Thornton et al. |
| 2010/0305664 A1 | 12/2010 | Wingeier et al. |
| 2010/0305869 A1 | 12/2010 | Brauker et al. |
| 2010/0308974 A1 | 12/2010 | Rowland et al. |
| 2010/0311640 A1 | 12/2010 | Genove et al. |
| 2010/0312081 A1 | 12/2010 | Benaron et al. |
| 2010/0312309 A1 | 12/2010 | Harding |
| 2010/0317420 A1 | 12/2010 | Hoffberg |
| 2010/0317955 A1 | 12/2010 | Madsen et al. |
| 2010/0318160 A1 | 12/2010 | Stevenson et al. |
| 2010/0321163 A1 | 12/2010 | Stevenson |
| 2010/0324403 A1 | 12/2010 | Brister et al. |
| 2010/0324578 A1 | 12/2010 | Bardy |
| 2010/0324579 A1 | 12/2010 | Bardy |
| 2010/0324639 A1 | 12/2010 | Stevenson et al. |
| 2010/0328049 A1 | 12/2010 | Frysz et al. |
| 2010/0331644 A1 | 12/2010 | Neale et al. |
| 2010/0331663 A1 | 12/2010 | Stein |
| 2010/0331868 A1 | 12/2010 | Bardy |
| 2010/0331874 A1 | 12/2010 | Bardy |
| 2010/0331894 A1 | 12/2010 | Stein |
| 2010/0331921 A1 | 12/2010 | Bornzin et al. |
| 2010/0331932 A1 | 12/2010 | Stevenson et al. |
| 2011/0004277 A1 | 1/2011 | Johnson et al. |
| 2011/0004513 A1 | 1/2011 | Hoffberg |
| 2011/0015993 A1 | 1/2011 | Ramer et al. |
| 2011/0015994 A1 | 1/2011 | Ramer et al. |
| 2011/0019627 A1 | 1/2011 | Krishnaswamy et al. |
| 2011/0021934 A1 | 1/2011 | Kim et al. |
| 2011/0022025 A1* | 1/2011 | Savoie ................ H04B 13/005 |
| | | 604/151 |
| 2011/0022140 A1 | 1/2011 | Stevenson et al. |
| 2011/0023343 A1 | 2/2011 | Turner et al. |
| 2011/0029043 A1 | 2/2011 | Frysz et al. |
| 2011/0029378 A1 | 2/2011 | Ramer et al. |
| 2011/0029387 A1 | 2/2011 | Ramer et al. |
| 2011/0034812 A1 | 2/2011 | Patangay et al. |
| 2011/0034912 A1 | 2/2011 | de Graff et al. |
| 2011/0040343 A1 | 2/2011 | Johnson et al. |
| 2011/0043297 A1 | 2/2011 | Stevenson et al. |
| 2011/0047062 A1 | 2/2011 | Kerschner et al. |
| 2011/0057037 A1 | 3/2011 | Frysz et al. |
| 2011/0063088 A1 | 3/2011 | Stevenson et al. |
| 2011/0066079 A1 | 3/2011 | Otto et al. |
| 2011/0066211 A1 | 3/2011 | Von Arx et al. |
| 2011/0066212 A1 | 3/2011 | Stevenson et al. |
| 2011/0074349 A1 | 3/2011 | Ghovanloo |
| 2011/0077706 A1 | 3/2011 | Ellingson et al. |
| 2011/0082523 A1 | 4/2011 | Nghiem et al. |
| 2011/0093040 A1 | 4/2011 | Ellingson et al. |
| 2011/0093046 A1 | 4/2011 | Ellingson et al. |

(56)　　　　References Cited

U.S. PATENT DOCUMENTS

| | | |
|---|---|---|
| 2011/0098576 A1 | 4/2011 | Hollstien |
| 2011/0098788 A1 | 4/2011 | Quiles |
| 2011/0106204 A1 | 5/2011 | Yoon et al. |
| 2011/0106212 A1 | 5/2011 | Ellingson et al. |
| 2011/0106614 A1 | 5/2011 | Ramer et al. |
| 2011/0118813 A1 | 5/2011 | Yang et al. |
| 2011/0124983 A1 | 5/2011 | Kroll et al. |
| 2011/0125063 A1 | 5/2011 | Shalon et al. |
| 2011/0130636 A1 | 6/2011 | Daniel et al. |
| 2011/0144465 A1 | 6/2011 | Shults et al. |
| 2011/0145076 A1 | 6/2011 | Ramer et al. |
| 2011/0152673 A1 | 6/2011 | Doerr et al. |
| 2011/0152756 A1 | 6/2011 | Drew |
| 2011/0152971 A1 | 6/2011 | Nghiem et al. |
| 2011/0159519 A1 | 6/2011 | Schmidt et al. |
| 2011/0159902 A1 | 6/2011 | Ramer et al. |
| 2011/0160791 A1 | 6/2011 | Ellingson et al. |
| 2011/0167474 A1 | 7/2011 | Sinha et al. |
| 2011/0171905 A1 | 7/2011 | Roberts et al. |
| 2011/0172741 A1 | 7/2011 | Roberts et al. |
| 2011/0177955 A1 | 7/2011 | Burzio et al. |
| 2011/0178378 A1 | 7/2011 | Brister et al. |
| 2011/0178577 A1 | 7/2011 | Li et al. |
| 2011/0190614 A1 | 8/2011 | Brister et al. |
| 2011/0194698 A1 | 8/2011 | Asano et al. |
| 2011/0196447 A1 | 8/2011 | McClure et al. |
| 2011/0196450 A1 | 8/2011 | McClure et al. |
| 2011/0197067 A1 | 8/2011 | Corndorf |
| 2011/0200194 A1 | 8/2011 | Goscha et al. |
| 2011/0201911 A1 | 8/2011 | Johnson et al. |
| 2011/0201912 A1 | 8/2011 | Stevenson et al. |
| 2011/0202874 A1 | 8/2011 | Ramer et al. |
| 2011/0208030 A1 | 8/2011 | Stevenson et al. |
| 2011/0208031 A1 | 8/2011 | Wolfe et al. |
| 2011/0213225 A1 | 9/2011 | Bernstein et al. |
| 2011/0213232 A1 | 9/2011 | Stevenson et al. |
| 2011/0213233 A1 | 9/2011 | Stevenson et al. |
| 2011/0216674 A1 | 9/2011 | McDonald et al. |
| 2011/0217966 A1 | 9/2011 | McDonald et al. |
| 2011/0218414 A1 | 9/2011 | Kamath et al. |
| 2011/0219234 A1 | 9/2011 | Bogner |
| 2011/0219419 A1 | 9/2011 | Reisman |
| 2011/0230268 A1 | 9/2011 | Williams |
| 2011/0231107 A1 | 9/2011 | Brauker et al. |
| 2011/0231936 A1 | 9/2011 | Williams et al. |
| 2011/0237861 A1 | 9/2011 | Pool et al. |
| 2011/0245644 A1 | 10/2011 | Stevenson et al. |
| 2011/0246766 A1 | 10/2011 | Orsini et al. |
| 2011/0249381 A1 | 10/2011 | Diebold |
| 2011/0251516 A1 | 10/2011 | Doerr |
| 2011/0257895 A1 | 10/2011 | Brauker et al. |
| 2011/0258046 A1 | 10/2011 | Ramer et al. |
| 2011/0262963 A1 | 10/2011 | Geierstanger et al. |
| 2011/0264058 A1 | 10/2011 | Linden et al. |
| 2011/0270369 A1 | 11/2011 | Tekmen et al. |
| 2011/0273287 A1 | 11/2011 | LaLonde et al. |
| 2011/0273568 A1 | 11/2011 | Lagassey |
| 2011/0275393 A1 | 11/2011 | Ramer et al. |
| 2011/0275911 A1 | 11/2011 | Mosesov |
| 2011/0275930 A1 | 11/2011 | Jho et al. |
| 2011/0276673 A1 | 11/2011 | Piazza et al. |
| 2011/0277028 A1 | 11/2011 | Piazza et al. |
| 2011/0288600 A1 | 11/2011 | Ritchey et al. |
| 2011/0289308 A1 | 11/2011 | Sobko et al. |
| 2011/0289314 A1 | 11/2011 | Whitcomb |
| 2011/0290645 A1 | 12/2011 | Brister et al. |
| 2011/0302408 A1 | 12/2011 | McDermott et al. |
| 2011/0305672 A1 | 12/2011 | Dalton et al. |
| 2011/0307274 A1 | 12/2011 | Thompson et al. |
| 2011/0307710 A1 | 12/2011 | McGuire et al. |
| 2011/0312310 A1 | 12/2011 | Ramer et al. |
| 2011/0313862 A1 | 12/2011 | Ramer et al. |
| 2011/0319785 A1 | 12/2011 | Snyder et al. |
| 2011/0320142 A1 | 12/2011 | Surman et al. |
| 2011/0320264 A1 | 12/2011 | Ramer et al. |
| 2011/0320265 A1 | 12/2011 | Ramer et al. |
| 2011/0320266 A1 | 12/2011 | Ramer et al. |
| 2011/0320267 A1 | 12/2011 | Ramer et al. |
| 2011/0320268 A1 | 12/2011 | Ramer et al. |
| 2011/0320269 A1 | 12/2011 | Ramer et al. |
| 2011/0320270 A1 | 12/2011 | Ramer et al. |
| 2011/0320271 A1 | 12/2011 | Ramer et al. |
| 2011/0320279 A1 | 12/2011 | Ramer et al. |
| 2011/0320280 A1 | 12/2011 | Ramer et al. |
| 2011/0320281 A1 | 12/2011 | Ramer et al. |
| 2011/0320282 A1 | 12/2011 | Ramer et al. |
| 2011/0321127 A1 | 12/2011 | Pitroda et al. |
| 2012/0004984 A1 | 1/2012 | Ramer et al. |
| 2012/0004985 A1 | 1/2012 | Ramer et al. |
| 2012/0004986 A1 | 1/2012 | Ramer et al. |
| 2012/0004987 A1 | 1/2012 | Ramer et al. |
| 2012/0004988 A1 | 1/2012 | Ramer et al. |
| 2012/0004989 A1 | 1/2012 | Ramer et al. |
| 2012/0004990 A1 | 1/2012 | Ramer et al. |
| 2012/0004991 A1 | 1/2012 | Ramer et al. |
| 2012/0004992 A1 | 1/2012 | Ramer et al. |
| 2012/0004993 A1 | 1/2012 | Ramer et al. |
| 2012/0004994 A1 | 1/2012 | Ramer et al. |
| 2012/0004995 A1 | 1/2012 | Ramer et al. |
| 2012/0004996 A1 | 1/2012 | Ramer et al. |
| 2012/0004997 A1 | 1/2012 | Ramer et al. |
| 2012/0004998 A1 | 1/2012 | Ramer et al. |
| 2012/0004999 A1 | 1/2012 | Ramer et al. |
| 2012/0005000 A1 | 1/2012 | Ramer et al. |
| 2012/0005001 A1 | 1/2012 | Ramer et al. |
| 2012/0005002 A1 | 1/2012 | Ramer et al. |
| 2012/0005003 A1 | 1/2012 | Ramer et al. |
| 2012/0005004 A1 | 1/2012 | Ramer et al. |
| 2012/0005005 A1 | 1/2012 | Ramer et al. |
| 2012/0005006 A1 | 1/2012 | Ramer et al. |
| 2012/0005007 A1 | 1/2012 | Ramer et al. |
| 2012/0005008 A1 | 1/2012 | Ramer et al. |
| 2012/0005009 A1 | 1/2012 | Ramer et al. |
| 2012/0005010 A1 | 1/2012 | Ramer et al. |
| 2012/0005011 A1 | 1/2012 | Ramer et al. |
| 2012/0005012 A1 | 1/2012 | Ramer et al. |
| 2012/0005013 A1 | 1/2012 | Ramer et al. |
| 2012/0005014 A1 | 1/2012 | Ramer et al. |
| 2012/0005020 A1 | 1/2012 | Ramer et al. |
| 2012/0005077 A1 | 1/2012 | Pitroda et al. |
| 2012/0005078 A1 | 1/2012 | Pitroda et al. |
| 2012/0005079 A1 | 1/2012 | Pitroda et al. |
| 2012/0005080 A1 | 1/2012 | Pitroda et al. |
| 2012/0005081 A1 | 1/2012 | Pitroda et al. |
| 2012/0005082 A1 | 1/2012 | Pitroda et al. |
| 2012/0005083 A1 | 1/2012 | Pitroda et al. |
| 2012/0005084 A1 | 1/2012 | Pitroda et al. |
| 2012/0005085 A1 | 1/2012 | Pitroda et al. |
| 2012/0005086 A1 | 1/2012 | Pitroda et al. |
| 2012/0005087 A1 | 1/2012 | Pitroda et al. |
| 2012/0005088 A1 | 1/2012 | Pitroda et al. |
| 2012/0005089 A1 | 1/2012 | Pitroda et al. |
| 2012/0005090 A1 | 1/2012 | Pitroda et al. |
| 2012/0005091 A1 | 1/2012 | Pitroda et al. |
| 2012/0005092 A1 | 1/2012 | Pitroda et al. |
| 2012/0005725 A1 | 1/2012 | Pitroda et al. |
| 2012/0005726 A1 | 1/2012 | Pitroda et al. |
| 2012/0008714 A1 | 1/2012 | Rizwan |
| 2012/0010562 A1 | 1/2012 | Hill et al. |
| 2012/0010945 A1 | 1/2012 | Ramer et al. |
| 2012/0010946 A1 | 1/2012 | Ramer et al. |
| 2012/0010947 A1 | 1/2012 | Ramer et al. |
| 2012/0010948 A1 | 1/2012 | Ramer et al. |
| 2012/0010949 A1 | 1/2012 | Ramer et al. |
| 2012/0010950 A1 | 1/2012 | Ramer et al. |
| 2012/0010951 A1 | 1/2012 | Ramer et al. |
| 2012/0010952 A1 | 1/2012 | Ramer et al. |
| 2012/0010953 A1 | 1/2012 | Ramer et al. |
| 2012/0010954 A1 | 1/2012 | Ramer et al. |
| 2012/0010955 A1 | 1/2012 | Ramer et al. |
| 2012/0010956 A1 | 1/2012 | Ramer et al. |
| 2012/0010957 A1 | 1/2012 | Ramer et al. |
| 2012/0010958 A1 | 1/2012 | Ramer et al. |
| 2012/0010959 A1 | 1/2012 | Ramer et al. |

(56) References Cited

U.S. PATENT DOCUMENTS

| | | |
|---|---|---|
| 2012/0010960 A1 | 1/2012 | Ramer et al. |
| 2012/0010961 A1 | 1/2012 | Ramer et al. |
| 2012/0010962 A1 | 1/2012 | Ramer et al. |
| 2012/0010963 A1 | 1/2012 | Ramer et al. |
| 2012/0010964 A1 | 1/2012 | Ramer et al. |
| 2012/0010965 A1 | 1/2012 | Ramer et al. |
| 2012/0010966 A1 | 1/2012 | Ramer et al. |
| 2012/0010967 A1 | 1/2012 | Ramer et al. |
| 2012/0010968 A1 | 1/2012 | Ramer et al. |
| 2012/0010969 A1 | 1/2012 | Ramer et al. |
| 2012/0010970 A1 | 1/2012 | Ramer et al. |
| 2012/0010971 A1 | 1/2012 | Ramer et al. |
| 2012/0010972 A1 | 1/2012 | Ramer et al. |
| 2012/0010973 A1 | 1/2012 | Ramer et al. |
| 2012/0010974 A1 | 1/2012 | Ramer et al. |
| 2012/0010975 A1 | 1/2012 | Ramer et al. |
| 2012/0010976 A1 | 1/2012 | Ramer et al. |
| 2012/0010977 A1 | 1/2012 | Ramer et al. |
| 2012/0010978 A1 | 1/2012 | Ramer et al. |
| 2012/0010979 A1 | 1/2012 | Ramer et al. |
| 2012/0011058 A1 | 1/2012 | Pitroda et al. |
| 2012/0015644 A1 | 1/2012 | Danford et al. |
| 2012/0016925 A1 | 1/2012 | Brown et al. |
| 2012/0027001 A1 | 2/2012 | Krishnaswamy et al. |
| 2012/0029323 A1 | 2/2012 | Zhao |
| 2012/0030470 A1 | 2/2012 | Jdanov et al. |
| 2012/0032945 A1 | 2/2012 | Dare et al. |
| 2012/0035434 A1 | 2/2012 | Ferren et al. |
| 2012/0035437 A1 | 2/2012 | Ferren et al. |
| 2012/0035438 A1 | 2/2012 | Ferren et al. |
| 2012/0035439 A1 | 2/2012 | Ferren et al. |
| 2012/0035440 A1 | 2/2012 | Ferren et al. |
| 2012/0035540 A1 | 2/2012 | Ferren et al. |
| 2012/0035951 A1 | 2/2012 | Goetz et al. |
| 2012/0036010 A1 | 2/2012 | Ramer et al. |
| 2012/0036220 A1 | 2/2012 | Dare et al. |
| 2012/0036245 A1 | 2/2012 | Dare et al. |
| 2012/0036440 A1 | 2/2012 | Dare et al. |
| 2012/0036442 A1 | 2/2012 | Dare et al. |
| 2012/0036552 A1 | 2/2012 | Dare et al. |
| 2012/0038477 A1 | 2/2012 | Torgerson et al. |
| 2012/0041291 A1 | 2/2012 | Ferren et al. |
| 2012/0041819 A1 | 2/2012 | Ramer et al. |
| 2012/0046197 A1 | 2/2012 | Glezer et al. |
| 2012/0046564 A1 | 2/2012 | Koh et al. |
| 2012/0051976 A1 | 3/2012 | Lu et al. |
| 2012/0053585 A1 | 3/2012 | Nycz et al. |
| 2012/0054848 A1 | 3/2012 | Salowey et al. |
| 2012/0058012 A1 | 3/2012 | Silver et al. |
| 2012/0058106 A1 | 3/2012 | Chahal et al. |
| 2012/0059238 A1 | 3/2012 | Wolf |
| 2012/0059434 A1 | 3/2012 | Nycz |
| 2012/0059711 A1 | 3/2012 | Ramer et al. |
| 2012/0059718 A1 | 3/2012 | Ramer et al. |
| 2012/0065696 A1 | 3/2012 | Bocek et al. |
| 2012/0066057 A1 | 3/2012 | Ramer et al. |
| 2012/0066065 A1 | 3/2012 | Switzer |
| 2012/0066198 A1 | 3/2012 | Ramer et al. |
| 2012/0066199 A1 | 3/2012 | Ramer et al. |
| 2012/0069131 A1 | 3/2012 | Abelow |
| 2012/0084544 A1 | 4/2012 | Farina et al. |
| 2012/0084545 A1 | 4/2012 | Farina et al. |
| 2012/0084562 A1 | 4/2012 | Farina et al. |
| 2012/0084566 A1 | 4/2012 | Chin et al. |
| 2012/0084838 A1 | 4/2012 | Inforzato et al. |
| 2012/0086345 A1 | 4/2012 | Tran |
| 2012/0087319 A1 | 4/2012 | Raleigh et al. |
| 2012/0088470 A1 | 4/2012 | Raleigh |
| 2012/0089699 A1 | 4/2012 | Cholas |
| 2012/0089845 A1 | 4/2012 | Raleigh |
| 2012/0094769 A1 | 4/2012 | Nguyen et al. |
| 2012/0096513 A1 | 4/2012 | Raleigh et al. |
| 2012/0101831 A1 | 4/2012 | Pitroda et al. |
| 2012/0101832 A1 | 4/2012 | Pitroda et al. |
| 2012/0101833 A1 | 4/2012 | Pitroda et al. |
| 2012/0101834 A1 | 4/2012 | Pitroda et al. |
| 2012/0101835 A1 | 4/2012 | Pitroda et al. |
| 2012/0101836 A1 | 4/2012 | Pitroda et al. |
| 2012/0102143 A1 | 4/2012 | Mandre |
| 2012/0105199 A1 | 5/2012 | Sanders |
| 2012/0105201 A1 | 5/2012 | Sanders |
| 2012/0105214 A1 | 5/2012 | Sanders |
| 2012/0109256 A1 | 5/2012 | Meskins et al. |
| 2012/0109667 A1 | 5/2012 | Pitroda et al. |
| 2012/0109668 A1 | 5/2012 | Pitroda et al. |
| 2012/0109669 A1 | 5/2012 | Pitroda et al. |
| 2012/0109670 A1 | 5/2012 | Pitroda et al. |
| 2012/0109671 A1 | 5/2012 | Pitroda et al. |
| 2012/0109672 A1 | 5/2012 | Pitroda et al. |
| 2012/0109673 A1 | 5/2012 | Pitroda et al. |
| 2012/0109674 A1 | 5/2012 | Pitroda et al. |
| 2012/0109851 A1 | 5/2012 | Sanders |
| 2012/0110602 A1 | 5/2012 | Sanders |
| 2012/0116790 A1 | 5/2012 | Pitroda et al. |
| 2012/0116959 A1 | 5/2012 | Pitroda et al. |
| 2012/0118947 A1 | 5/2012 | Lyons et al. |
| 2012/0122528 A1 | 5/2012 | Lyons et al. |
| 2012/0122529 A1 | 5/2012 | Lyons |
| 2012/0122558 A1 | 5/2012 | Lyons et al. |
| 2012/0123221 A1 | 5/2012 | Windolf |
| 2012/0129503 A1 | 5/2012 | Lindeman et al. |
| 2012/0130214 A1 | 5/2012 | Brister et al. |
| 2012/0130811 A1 | 5/2012 | Ramer et al. |
| 2012/0130812 A1 | 5/2012 | Ramer et al. |
| 2012/0131685 A1 | 5/2012 | Broch et al. |
| 2012/0134291 A1 | 5/2012 | Raleigh |
| 2012/0135531 A1 | 5/2012 | Silver |
| 2012/0150629 A1 | 6/2012 | Ramer et al. |
| 2012/0158607 A1 | 6/2012 | Burns et al. |
| 2012/0159438 A1 | 6/2012 | Plate |
| 2012/0159578 A1 | 6/2012 | Chawla et al. |
| 2012/0161901 A1 | 6/2012 | Stevenson et al. |
| 2012/0165684 A1 | 6/2012 | Sholder |
| 2012/0169468 A1 | 7/2012 | Butler et al. |
| 2012/0169469 A1 | 7/2012 | Butler et al. |
| 2012/0169474 A1 | 7/2012 | Butler et al. |
| 2012/0172691 A1 | 7/2012 | Brauker et al. |
| 2012/0179014 A1 | 7/2012 | Shults et al. |
| 2012/0179057 A1 | 7/2012 | Kim et al. |
| 2012/0180731 A1 | 7/2012 | Garner et al. |
| 2012/0182123 A1 | 7/2012 | Butler et al. |
| 2012/0185390 A1 | 7/2012 | Palnitkar et al. |
| 2012/0190386 A1 | 7/2012 | Anderson |
| 2012/0191860 A1 | 7/2012 | Traversat et al. |
| 2012/0192249 A1 | 7/2012 | Raleigh |
| 2012/0195206 A1 | 8/2012 | Raleigh |
| 2012/0195222 A1 | 8/2012 | Raleigh |
| 2012/0195223 A1 | 8/2012 | Raleigh |
| 2012/0196565 A1 | 8/2012 | Raleigh |
| 2012/0197347 A1 | 8/2012 | Olson et al. |
| 2012/0197348 A1 | 8/2012 | Bornhoft et al. |
| 2012/0197351 A1 | 8/2012 | Olson et al. |
| 2012/0197709 A1 | 8/2012 | Kendall et al. |
| 2012/0197724 A1 | 8/2012 | Kendall |
| 2012/0197792 A1 | 8/2012 | Raleigh |
| 2012/0201133 A1 | 8/2012 | Raleigh |
| 2012/0203079 A1 | 8/2012 | McLaughlin |
| 2012/0203677 A1 | 8/2012 | Raleigh |
| 2012/0204245 A1 | 8/2012 | Ting et al. |
| 2012/0206243 A1 | 8/2012 | Butler et al. |
| 2012/0208496 A1 | 8/2012 | Raleigh |
| 2012/0209353 A1 | 8/2012 | Bange et al. |
| 2012/0209750 A1 | 8/2012 | Raleigh |
| 2012/0210130 A1 | 8/2012 | Buer et al. |
| 2012/0210391 A1 | 8/2012 | Raleigh |
| 2012/0210401 A1 | 8/2012 | Pepin et al. |
| 2012/0214441 A1 | 8/2012 | Raleigh |
| 2012/0215831 A1 | 8/2012 | Urbach |
| 2012/0216225 A1 | 8/2012 | Britt |
| 2012/0220849 A1 | 8/2012 | Brockway et al. |
| 2012/0220986 A1 | 8/2012 | Wolff et al. |
| 2012/0222123 A1 | 8/2012 | Williams et al. |
| 2012/0223705 A1 | 9/2012 | Lowery et al. |
| 2012/0226118 A1 | 9/2012 | Delbeke et al. |

(56)                References Cited

U.S. PATENT DOCUMENTS

| 2012/0226130 A1 | 9/2012 | De Graff et al. |
| 2012/0232012 A1 | 9/2012 | Popel et al. |
| 2012/0232945 A1 | 9/2012 | Tong |
| 2012/0232970 A1 | 9/2012 | Kara |
| 2012/0234433 A1 | 9/2012 | Shih et al. |
| 2012/0238255 A1 | 9/2012 | Ramer et al. |
| 2012/0240183 A1 | 9/2012 | Sinha |
| 2012/0240196 A1 | 9/2012 | Bhagwat et al. |
| 2012/0240236 A1 | 9/2012 | Wyatt et al. |
| 2012/0254474 A1 | 10/2012 | Brown et al. |
| 2012/0259981 A1 | 10/2012 | Lewinski et al. |
| 2012/0260323 A1* | 10/2012 | San Vicente ....... A61B 5/14532 |
|  |  | 455/66.1 |
| 2012/0271380 A1 | 10/2012 | Roberts et al. |
| 2012/0277562 A1 | 11/2012 | Brister et al. |
| 2012/0277859 A1 | 11/2012 | Govil et al. |
| 2012/0283543 A1 | 11/2012 | Brauker et al. |
| 2012/0284416 A1 | 11/2012 | Li et al. |
| 2012/0289757 A1 | 11/2012 | Boyden et al. |
| 2012/0289758 A1 | 11/2012 | Boyden et al. |
| 2012/0289761 A1 | 11/2012 | Boyden et al. |
| 2012/0289763 A1 | 11/2012 | Boyden et al. |
| 2012/0290023 A1 | 11/2012 | Boyden et al. |
| 2012/0290051 A1 | 11/2012 | Boyden et al. |
| 2012/0293324 A1 | 11/2012 | Rao et al. |
| 2012/0294195 A1 | 11/2012 | Raleigh |
| 2012/0296271 A1 | 11/2012 | Yomtov et al. |
| 2012/0296399 A1 | 11/2012 | Cauller et al. |
| 2012/0297464 A1 | 11/2012 | Busch et al. |
| 2012/0299175 A1 | 11/2012 | Tran |
| 2012/0302874 A1 | 11/2012 | Hollstien |
| 2012/0319823 A1 | 12/2012 | Butler et al. |
| 2012/0323717 A1 | 12/2012 | Kirsch |
| 2012/0323786 A1 | 12/2012 | Kirsch |
| 2012/0324067 A1 | 12/2012 | Hari et al. |
| 2012/0324242 A1 | 12/2012 | Kirsch |
| 2012/0324562 A1 | 12/2012 | Bansal et al. |
| 2012/0326886 A1 | 12/2012 | Herman et al. |
| 2012/0329986 A1 | 12/2012 | Bolduc et al. |
| 2012/0330372 A1 | 12/2012 | Sathaye et al. |
| 2012/0330380 A1 | 12/2012 | Corndorf |
| 2012/0330829 A1 | 12/2012 | Raleigh |
| 2013/0002448 A1 | 1/2013 | Makdissi |
| 2013/0002496 A1 | 1/2013 | Utsi et al. |
| 2013/0003613 A1 | 1/2013 | Raleigh |
| 2013/0005299 A1 | 1/2013 | Raleigh |
| 2013/0005322 A1 | 1/2013 | Raleigh |
| 2013/0006729 A1 | 1/2013 | Raleigh |
| 2013/0006780 A1 | 1/2013 | Raleigh |
| 2013/0007837 A1 | 1/2013 | King |
| 2013/0009786 A1 | 1/2013 | Mosesov et al. |
| 2013/0009838 A1 | 1/2013 | Nghiem et al. |
| 2013/0009839 A1 | 1/2013 | Nghiem et al. |
| 2013/0010945 A1 | 1/2013 | McDonald et al. |
| 2013/0012178 A1 | 1/2013 | Ramer et al. |
| 2013/0012798 A1 | 1/2013 | Brister et al. |
| 2013/0012800 A1 | 1/2013 | Brockway et al. |
| 2013/0014263 A1 | 1/2013 | Porcello et al. |
| 2013/0016636 A1 | 1/2013 | Berger et al. |
| 2013/0023954 A1 | 1/2013 | Meskens |
| 2013/0024254 A1 | 1/2013 | Libenson et al. |
| 2013/0024257 A1 | 1/2013 | Libenson et al. |
| 2013/0024262 A1 | 1/2013 | Libenson et al. |
| 2013/0024267 A1 | 1/2013 | Libenson et al. |
| 2013/0024364 A1 | 1/2013 | Shrivastava et al. |
| 2013/0024371 A1 | 1/2013 | Hariramani et al. |
| 2013/0030255 A1 | 1/2013 | Ben |
| 2013/0034230 A1 | 2/2013 | Takahashi |
| 2013/0035544 A1 | 2/2013 | Pool et al. |
| 2013/0035577 A1 | 2/2013 | Wolf |
| 2013/0040703 A1 | 2/2013 | Raleigh |
| 2013/0041251 A1 | 2/2013 | Bailey et al. |
| 2013/0043974 A1 | 2/2013 | Hyde et al. |
| 2013/0043975 A1 | 2/2013 | Hyde et al. |
| 2013/0043991 A1 | 2/2013 | Hyde et al. |
| 2013/0043993 A1 | 2/2013 | Hyde et al. |
| 2013/0045710 A1 | 2/2013 | Raleigh |
| 2013/0046152 A1 | 2/2013 | Najafi et al. |
| 2013/0046153 A1 | 2/2013 | Hyde et al. |
| 2013/0046477 A1 | 2/2013 | Hyde et al. |
| 2013/0053665 A1 | 2/2013 | Hughes et al. |
| 2013/0053666 A1 | 2/2013 | Hughes et al. |
| 2013/0053711 A1 | 2/2013 | Kotlanka et al. |
| 2013/0053713 A1 | 2/2013 | Albu |
| 2013/0053908 A1 | 2/2013 | Smith et al. |
| 2013/0054820 A1 | 2/2013 | Reisman |
| 2013/0054962 A1 | 2/2013 | Chawla et al. |
| 2013/0055315 A1 | 2/2013 | Reisman |
| 2013/0055347 A1 | 2/2013 | Chawla et al. |
| 2013/0059396 A1 | 3/2013 | LeBoeuf et al. |
| 2013/0061264 A1 | 3/2013 | Reisman |
| 2013/0061273 A1 | 3/2013 | Reisman |
| 2013/0065551 A1 | 3/2013 | Raleigh et al. |
| 2013/0066723 A1 | 3/2013 | Ramer et al. |
| 2013/0067023 A1 | 3/2013 | Joy et al. |
| 2013/0067526 A1 | 3/2013 | Reisman |
| 2013/0070387 A1 | 3/2013 | Stevenson et al. |
| 2013/0072770 A1 | 3/2013 | Rao et al. |
| 2013/0078244 A1 | 3/2013 | Christiano et al. |
| 2013/0085408 A1 | 4/2013 | Pool |
| 2013/0090534 A1* | 4/2013 | Burns .................... G16H 10/60 |
|  |  | 600/398 |
| 2013/0092564 A1 | 4/2013 | Doherty |
| 2013/0116664 A1 | 5/2013 | Tai et al. |
| 2013/0116665 A1 | 5/2013 | Humayun et al. |
| 2013/0116666 A1 | 5/2013 | Shih et al. |
| 2013/0116667 A1 | 5/2013 | Ricotti et al. |
| 2013/0116740 A1 | 5/2013 | Bornzin et al. |
| 2013/0123882 A1 | 5/2013 | Towe |
| 2013/0131679 A1 | 5/2013 | Janna et al. |
| 2013/0131752 A1 | 5/2013 | Rawat et al. |
| 2013/0144179 A1 | 6/2013 | Mosesov |
| 2013/0147622 A1 | 6/2013 | LaLonde et al. |
| 2013/0154851 A1 | 6/2013 | Gaskill et al. |
| 2013/0157729 A1 | 6/2013 | Tabe |
| 2013/0165996 A1 | 6/2013 | Meadows et al. |
| 2013/0173284 A1 | 7/2013 | Hyde et al. |
| 2013/0173285 A1 | 7/2013 | Hyde et al. |
| 2013/0173293 A1 | 7/2013 | Hyde et al. |
| 2013/0173294 A1 | 7/2013 | Hyde et al. |
| 2013/0173295 A1 | 7/2013 | Hyde et al. |
| 2013/0173296 A1 | 7/2013 | Hyde et al. |
| 2013/0173297 A1 | 7/2013 | Hyde et al. |
| 2013/0173298 A1 | 7/2013 | Hyde et al. |
| 2013/0173299 A1 | 7/2013 | Hyde et al. |
| 2013/0173300 A1 | 7/2013 | Hyde et al. |
| 2013/0173301 A1 | 7/2013 | Hyde et al. |
| 2013/0173302 A1 | 7/2013 | Hyde et al. |
| 2013/0173303 A1 | 7/2013 | Hyde et al. |
| 2013/0173304 A1 | 7/2013 | Hyde et al. |
| 2013/0173305 A1 | 7/2013 | Hyde et al. |
| 2013/0178751 A1 | 7/2013 | Min |
| 2013/0179188 A1 | 7/2013 | Hyde et al. |
| 2013/0195806 A1 | 8/2013 | Gay et al. |
| 2013/0197380 A1 | 8/2013 | Oral et al. |
| 2013/0198463 A1 | 8/2013 | Hintz |
| 2013/0202721 A1 | 8/2013 | Silver |
| 2013/0226104 A1 | 8/2013 | Hyde et al. |
| 2013/0226217 A1 | 8/2013 | Hyde et al. |
| 2013/0226221 A1 | 8/2013 | Hyde et al. |
| 2013/0233324 A1 | 9/2013 | Witt et al. |
| 2013/0238056 A1 | 9/2013 | Poore et al. |
| 2013/0243799 A1 | 9/2013 | Chahal et al. |
| 2013/0245401 A1 | 9/2013 | Estes et al. |
| 2013/0245981 A1 | 9/2013 | Estes et al. |
| 2013/0253297 A1 | 9/2013 | Johnson et al. |
| 2013/0253660 A1 | 9/2013 | Nycz et al. |
| 2013/0255570 A1 | 10/2013 | Brister et al. |
| 2013/0257656 A1 | 10/2013 | Parker et al. |
| 2013/0267808 A1 | 10/2013 | Brister et al. |
| 2013/0267809 A1 | 10/2013 | Brister et al. |
| 2013/0268029 A1 | 10/2013 | Cauller et al. |
| 2013/0274563 A1 | 10/2013 | Duesterhoft et al. |
| 2013/0289529 A1 | 10/2013 | Caira et al. |

(56) References Cited

U.S. PATENT DOCUMENTS

| | | | |
|---|---|---|---|
| 2013/0289666 A1 | 10/2013 | Johnson et al. | |
| 2013/0310666 A1 | 11/2013 | Shults et al. | |
| 2013/0310896 A1 | 11/2013 | Mass | |
| 2013/0317584 A1 | 11/2013 | Stevenson et al. | |
| 2013/0338494 A1 | 12/2013 | Wiley et al. | |
| 2013/0338768 A1 | 12/2013 | Boyden et al. | |
| 2013/0338769 A1 | 12/2013 | Boyden et al. | |
| 2013/0338770 A1 | 12/2013 | Boyden et al. | |
| 2013/0338771 A1 | 12/2013 | Boyden et al. | |
| 2013/0338772 A1 | 12/2013 | Boyden et al. | |
| 2013/0338773 A1 | 12/2013 | Boyden et al. | |
| 2013/0343585 A1* | 12/2013 | Bennett | H04W 4/80 |
| | | | 381/317 |
| 2013/0345561 A1 | 12/2013 | Quigley | |
| 2014/0012111 A1 | 1/2014 | Snyder et al. | |
| 2014/0012122 A1 | 1/2014 | Sadek et al. | |
| 2014/0012341 A1 | 1/2014 | Von Arx et al. | |
| 2014/0018644 A1 | 1/2014 | Colvin, Jr. et al. | |
| 2014/0039290 A1 | 2/2014 | De Graff et al. | |
| 2014/0045757 A1 | 2/2014 | Popel et al. | |
| 2014/0046690 A1 | 2/2014 | Gunderson et al. | |
| 2014/0051965 A1 | 2/2014 | Zdeblick et al. | |
| 2014/0058235 A1 | 2/2014 | Li et al. | |
| 2014/0062717 A1 | 3/2014 | Mudumbai et al. | |
| 2014/0062718 A1 | 3/2014 | LaLonde et al. | |
| 2014/0065153 A1 | 3/2014 | Christiano et al. | |
| 2014/0073704 A1 | 3/2014 | Ju et al. | |
| 2014/0073839 A1 | 3/2014 | Yomtov et al. | |
| 2014/0081076 A1 | 3/2014 | Schutt et al. | |
| 2014/0085104 A1 | 3/2014 | Rao et al. | |
| 2014/0088391 A1 | 3/2014 | Leach et al. | |
| 2014/0091811 A1 | 4/2014 | Potyrailo et al. | |
| 2014/0091940 A1 | 4/2014 | Johnson et al. | |
| 2014/0091941 A1 | 4/2014 | Johnson et al. | |
| 2014/0094673 A1 | 4/2014 | Johnson et al. | |
| 2014/0094891 A1 | 4/2014 | Pare et al. | |
| 2014/0095102 A1 | 4/2014 | Potyrailo et al. | |
| 2014/0113828 A1 | 4/2014 | Gilbert et al. | |
| 2014/0114158 A1 | 4/2014 | Brister et al. | |
| 2014/0120841 A1 | 5/2014 | Roberts et al. | |
| 2014/0121989 A1 | 5/2014 | Kamath et al. | |
| 2014/0127822 A1 | 5/2014 | Arora et al. | |
| 2014/0135597 A1 | 5/2014 | Wolf | |
| 2014/0135647 A1 | 5/2014 | Wolf | |
| 2014/0141985 A1 | 5/2014 | Glezer et al. | |
| 2014/0142405 A1 | 5/2014 | Brister et al. | |
| 2014/0142648 A1 | 5/2014 | Smith et al. | |
| 2014/0142661 A1 | 5/2014 | Chiu et al. | |
| 2014/0148676 A1 | 5/2014 | Stein et al. | |
| 2014/0163338 A1 | 6/2014 | Roesicke | |
| 2014/0163644 A1 | 6/2014 | Scott et al. | |
| 2014/0163648 A1 | 6/2014 | Olson et al. | |
| 2014/0172060 A1 | 6/2014 | Bornzin et al. | |
| 2014/0193830 A1 | 7/2014 | Schmidt et al. | |
| 2014/0214104 A1 | 7/2014 | Greenhut et al. | |
| 2014/0221732 A1 | 8/2014 | Dayton et al. | |
| 2014/0221767 A1 | 8/2014 | Olson et al. | |
| 2014/0228904 A1 | 8/2014 | Rao et al. | |
| 2014/0236105 A1 | 8/2014 | Hanson et al. | |
| 2014/0239528 A1 | 8/2014 | Govil et al. | |
| 2014/0245783 A1 | 9/2014 | Proud et al. | |
| 2014/0245784 A1 | 9/2014 | Proud et al. | |
| 2014/0245785 A1 | 9/2014 | Proud et al. | |
| 2014/0245786 A1 | 9/2014 | Proud et al. | |
| 2014/0245787 A1 | 9/2014 | Proud et al. | |
| 2014/0245788 A1 | 9/2014 | Proud et al. | |
| 2014/0245789 A1 | 9/2014 | Proud et al. | |
| 2014/0245790 A1 | 9/2014 | Proud et al. | |
| 2014/0245791 A1 | 9/2014 | Proud et al. | |
| 2014/0246497 A1 | 9/2014 | Proud et al. | |
| 2014/0246498 A1 | 9/2014 | Proud et al. | |
| 2014/0246499 A1 | 9/2014 | Proud et al. | |
| 2014/0246500 A1 | 9/2014 | Proud et al. | |
| 2014/0246501 A1 | 9/2014 | Proud et al. | |
| 2014/0246502 A1 | 9/2014 | Proud et al. | |
| 2014/0246917 A1 | 9/2014 | Proud et al. | |
| 2014/0247136 A1 | 9/2014 | Proud et al. | |
| 2014/0247137 A1 | 9/2014 | Proud et al. | |
| 2014/0247142 A1 | 9/2014 | Proud | |
| 2014/0247143 A1 | 9/2014 | Proud | |
| 2014/0247144 A1 | 9/2014 | Proud | |
| 2014/0247146 A1 | 9/2014 | Proud | |
| 2014/0247147 A1 | 9/2014 | Proud | |
| 2014/0247149 A1 | 9/2014 | Proud | |
| 2014/0247150 A1 | 9/2014 | Proud | |
| 2014/0247151 A1 | 9/2014 | Proud et al. | |
| 2014/0247154 A1 | 9/2014 | Proud | |
| 2014/0247155 A1 | 9/2014 | Proud | |
| 2014/0247156 A1 | 9/2014 | Proud | |
| 2014/0249379 A1 | 9/2014 | Proud | |
| 2014/0249557 A1* | 9/2014 | Koch, Jr. | A61B 17/32002 |
| | | | 606/170 |
| 2014/0249760 A1 | 9/2014 | Proud et al. | |
| 2014/0249853 A1 | 9/2014 | Proud et al. | |
| 2014/0257065 A1 | 9/2014 | Brister et al. | |
| 2014/0266933 A1 | 9/2014 | Andersen et al. | |
| 2014/0273824 A1* | 9/2014 | Fenner | H04L 63/0823 |
| | | | 455/41.1 |
| 2014/0275727 A1 | 9/2014 | Bonde et al. | |
| 2014/0277277 A1 | 9/2014 | Gordon et al. | |
| 2014/0278189 A1 | 9/2014 | Vanslyke et al. | |
| 2014/0285396 A1 | 9/2014 | Lee et al. | |
| 2014/0288402 A1 | 9/2014 | Brister et al. | |
| 2014/0288403 A1 | 9/2014 | Brister et al. | |
| 2014/0288619 A1 | 9/2014 | Johnson et al. | |
| 2014/0288647 A1 | 9/2014 | Boyden et al. | |
| 2014/0292490 A1 | 10/2014 | Butler et al. | |
| 2014/0296663 A1 | 10/2014 | Boyden et al. | |
| 2014/0296687 A1 | 10/2014 | Irazoqui et al. | |
| 2014/0296978 A1 | 10/2014 | Boyden et al. | |
| 2014/0300490 A1 | 10/2014 | Kotz et al. | |
| 2014/0302553 A1 | 10/2014 | Geierstanger et al. | |
| 2014/0303452 A1 | 10/2014 | Ghaffari | |
| 2014/0306807 A1 | 10/2014 | Rowland et al. | |
| 2014/0324138 A1 | 10/2014 | Wentz et al. | |
| 2014/0328517 A1 | 11/2014 | Gluncic | |
| 2014/0330244 A1 | 11/2014 | Hyde et al. | |
| 2014/0330256 A1 | 11/2014 | Hyde et al. | |
| 2014/0330257 A1 | 11/2014 | Hyde et al. | |
| 2014/0330347 A1 | 11/2014 | Simms, Jr. | |
| 2014/0330357 A1 | 11/2014 | Stevenson et al. | |
| 2014/0343691 A1 | 11/2014 | Guillory et al. | |
| 2014/0358196 A1 | 12/2014 | Mashiach | |
| 2014/0358197 A1 | 12/2014 | Mashiach et al. | |
| 2014/0368601 A1 | 12/2014 | deCharms | |
| 2014/0371821 A1 | 12/2014 | Mashiach et al. | |
| 2014/0371824 A1 | 12/2014 | Mashiach et al. | |
| 2014/0376336 A1 | 12/2014 | Steckner et al. | |
| 2014/0379090 A1 | 12/2014 | Diomidis et al. | |
| 2015/0011860 A1 | 1/2015 | Pool et al. | |
| 2015/0025478 A1 | 1/2015 | Hibdon et al. | |
| 2015/0039041 A1 | 2/2015 | Smith et al. | |
| 2015/0051465 A1 | 2/2015 | Robertson et al. | |
| 2015/0057595 A1 | 2/2015 | Gunn et al. | |
| 2015/0061840 A1 | 3/2015 | Butler et al. | |
| 2015/0066124 A1 | 3/2015 | Stevenson et al. | |
| 2015/0071934 A1 | 3/2015 | Christiano | |
| 2015/0073498 A1 | 3/2015 | Kothandaraman | |
| 2015/0073499 A1 | 3/2015 | Kothandaraman | |
| 2015/0073500 A1 | 3/2015 | Kothandaraman et al. | |
| 2015/0077050 A1 | 3/2015 | Van Funderburk | |
| 2015/0080982 A1 | 3/2015 | Van Funderburk | |
| 2015/0080992 A1 | 3/2015 | Drnek et al. | |
| 2015/0086565 A1 | 3/2015 | Hynes et al. | |
| 2015/0087935 A1 | 3/2015 | Davis et al. | |
| 2015/0087942 A1 | 3/2015 | Brauker et al. | |
| 2015/0087943 A1 | 3/2015 | Shults et al. | |
| 2015/0088226 A1 | 3/2015 | Tourrel et al. | |
| 2015/0088227 A1 | 3/2015 | Shishilla et al. | |
| 2015/0094547 A1 | 4/2015 | Mickle et al. | |
| 2015/0094790 A1 | 4/2015 | Shishilla et al. | |
| 2015/0099959 A1 | 4/2015 | Bonmassar et al. | |
| 2015/0099976 A1 | 4/2015 | Ghaffari et al. | |
| 2015/0100106 A1 | 4/2015 | Shishilla et al. | |

(56) References Cited

U.S. PATENT DOCUMENTS

| | | |
|---|---|---|
| 2015/0100108 A1 | 4/2015 | Vansickle et al. |
| 2015/0100109 A1 | 4/2015 | Feldman et al. |
| 2015/0116053 A1 | 4/2015 | Stevenson et al. |
| 2015/0117645 A1 | 4/2015 | Carlson et al. |
| 2015/0119666 A1 | 4/2015 | Brister et al. |
| 2015/0127068 A1 | 5/2015 | Simon et al. |
| 2015/0129664 A1 | 5/2015 | Brar |
| 2015/0134026 A1 | 5/2015 | Kaula et al. |
| 2015/0134027 A1 | 5/2015 | Kaula et al. |
| 2015/0134028 A1 | 5/2015 | Kaula et al. |
| 2015/0141770 A1 | 5/2015 | Rastogi et al. |
| 2015/0147573 A1 | 5/2015 | Zhang et al. |
| 2015/0148638 A1 | 5/2015 | Simpson et al. |
| 2015/0148868 A1 | 5/2015 | Shahandeh et al. |
| 2015/0150892 A1 | 6/2015 | Jacks et al. |
| 2015/0153319 A1 | 6/2015 | Shapiro et al. |
| 2015/0171905 A1 | 6/2015 | Makdissi |
| 2015/0174296 A1 | 6/2015 | Ju et al. |
| 2015/0179038 A1 | 6/2015 | Daniel et al. |
| 2015/0182115 A1 | 7/2015 | DeHennis |
| 2015/0183828 A1 | 7/2015 | Genove et al. |
| 2015/0190638 A1 | 7/2015 | Smith et al. |
| 2015/0194052 A1 | 7/2015 | Sagan et al. |
| 2015/0196378 A1 | 7/2015 | Mayer et al. |
| 2015/0196409 A1 | 7/2015 | Pool et al. |
| 2015/0202456 A1 | 7/2015 | Andersen et al. |
| 2015/0206408 A1 | 7/2015 | LaLonde et al. |
| 2015/0209588 A1 | 7/2015 | Christensen |
| 2015/0218645 A1 | 8/2015 | Feldser et al. |
| 2015/0221208 A1 | 8/2015 | Knighton et al. |
| 2015/0229139 A1 | 8/2015 | Greene |
| 2015/0230742 A1 | 8/2015 | Silver |
| 2015/0231402 A1 | 8/2015 | Aghassian |
| 2015/0238277 A1 | 8/2015 | Ritchey et al. |
| 2015/0246242 A1 | 9/2015 | Delp et al. |
| 2015/0253334 A1 | 9/2015 | Johnson et al. |
| 2015/0257670 A1 | 9/2015 | Ortega et al. |
| 2015/0258345 A1 | 9/2015 | Smith et al. |
| 2015/0260618 A1 | 9/2015 | Kalra |
| 2015/0265458 A1 | 9/2015 | Andersen et al. |
| 2015/0265459 A1 | 9/2015 | Andersen et al. |
| 2015/0265843 A1 | 9/2015 | Wu et al. |
| 2015/0269624 A1 | 9/2015 | Cheng et al. |
| 2015/0282711 A1 | 10/2015 | Thomas et al. |
| 2015/0282741 A1 | 10/2015 | Brister et al. |
| 2015/0283397 A1 | 10/2015 | Andersen et al. |
| 2015/0283398 A1 | 10/2015 | Andersen et al. |
| 2015/0289911 A1 | 10/2015 | Beyar et al. |
| 2015/0297103 A1 | 10/2015 | Hu et al. |
| 2015/0297905 A1 | 10/2015 | Greenhut et al. |
| 2015/0302178 A1 | 10/2015 | Patel et al. |
| 2015/0308018 A1 | 10/2015 | Zhang et al. |
| 2015/0309050 A1 | 10/2015 | May |
| 2015/0321011 A1 | 11/2015 | Carney et al. |
| 2015/0321012 A1 | 11/2015 | Cinbis et al. |
| 2015/0321016 A1 | 11/2015 | O'Brien et al. |
| 2015/0327896 A1 | 11/2015 | Bottlang et al. |
| 2015/0327989 A1 | 11/2015 | Boyden et al. |
| 2015/0328455 A1 | 11/2015 | Meadows et al. |
| 2015/0343144 A1 | 12/2015 | Altschul et al. |
| 2015/0351674 A1 | 12/2015 | Thomas et al. |
| 2015/0356524 A1 | 12/2015 | Pennanen |
| 2015/0356555 A1 | 12/2015 | Pennanen |
| 2015/0360038 A1 | 12/2015 | Zottola et al. |
| 2015/0360049 A1 | 12/2015 | Kaplitt et al. |
| 2015/0360050 A1 | 12/2015 | Kaplitt et al. |
| 2015/0365738 A1 | 12/2015 | Purvis et al. |
| 2015/0366915 A1 | 12/2015 | Gay et al. |
| 2015/0367144 A1 | 12/2015 | Flynn et al. |
| 2015/0374270 A1 | 12/2015 | Shults et al. |
| 2015/0374541 A1 | 12/2015 | de Juan, Jr. et al. |
| 2016/0008029 A1 | 1/2016 | Brister et al. |
| 2016/0012465 A1 | 1/2016 | Sharp |
| 2016/0015267 A1 | 1/2016 | Bernstein et al. |
| 2016/0015268 A1 | 1/2016 | Bernstein et al. |
| 2016/0015303 A1 | 1/2016 | Bernstein et al. |
| 2016/0015984 A1 | 1/2016 | Demmer et al. |
| 2016/0015985 A1 | 1/2016 | Cho et al. |
| 2016/0023007 A1 | 1/2016 | Stouffer et al. |
| 2016/0029998 A1 | 2/2016 | Brister et al. |
| 2016/0030650 A1 | 2/2016 | Yomtov et al. |
| 2016/0030756 A1 | 2/2016 | Dronov |
| 2016/0030765 A1 | 2/2016 | Towne et al. |
| 2016/0038324 A1 | 2/2016 | Pool et al. |
| 2016/0038744 A1 | 2/2016 | Ellingson et al. |
| 2016/0038755 A1 | 2/2016 | Lundmark et al. |
| 2016/0038756 A1 | 2/2016 | Andersen et al. |
| 2016/0038757 A1 | 2/2016 | Stahler et al. |
| 2016/0038758 A1 | 2/2016 | Stahler et al. |
| 2016/0038759 A1 | 2/2016 | Andersen et al. |
| 2016/0038765 A1 | 2/2016 | Delp et al. |
| 2016/0045145 A1 | 2/2016 | Brister et al. |
| 2016/0045162 A1 | 2/2016 | De Graff et al. |
| 2016/0045764 A1 | 2/2016 | Delp et al. |
| 2016/0045765 A1 | 2/2016 | Lundmark et al. |
| 2016/0051173 A1 | 2/2016 | Brister et al. |
| 2016/0051825 A1 | 2/2016 | Ter-Petrosyan et al. |
| 2016/0051828 A1 | 2/2016 | Stahler et al. |
| 2016/0051830 A1 | 2/2016 | Andersen et al. |
| 2016/0051831 A1 | 2/2016 | Lundmark et al. |
| 2016/0051836 A1 | 2/2016 | Lundmark et al. |
| 2016/0051837 A1 | 2/2016 | Delp et al. |
| 2016/0051838 A1 | 2/2016 | Stahler et al. |
| 2016/0058322 A1 | 3/2016 | Brister et al. |
| 2016/0058324 A1 | 3/2016 | Cao |
| 2016/0059030 A1 | 3/2016 | Huang et al. |
| 2016/0066803 A1 | 3/2016 | Hu et al. |
| 2016/0066850 A1 | 3/2016 | Brockway et al. |
| 2016/0067487 A1 | 3/2016 | Demmer et al. |
| 2016/0067500 A1 | 3/2016 | Demmer et al. |
| 2016/0069913 A1 | 3/2016 | Bakhru et al. |
| 2016/0082279 A1 | 3/2016 | Andersen et al. |
| 2016/0083872 A1 | 3/2016 | Zhang et al. |
| 2016/0096034 A1 | 4/2016 | Lundmark et al. |
| 2016/0096035 A1 | 4/2016 | Lundmark et al. |
| 2016/0098723 A1 | 4/2016 | Feeney |
| 2016/0098730 A1 | 4/2016 | Feeney |
| 2016/0100807 A1 | 4/2016 | Johnson et al. |
| 2016/0103604 A1 | 4/2016 | Johnson et al. |
| 2016/0114162 A1 | 4/2016 | Sheldon et al. |
| 2016/0114168 A1 | 4/2016 | Demmer et al. |
| 2016/0114169 A1 | 4/2016 | Sheldon et al. |
| 2016/0144180 A1 | 5/2016 | Simon et al. |
| 2016/0151553 A1 | 6/2016 | Bonde |
| 2016/0164337 A1 | 6/2016 | Olson et al. |
| 2016/0170996 A1 | 6/2016 | Frank et al. |
| 2016/0183842 A1 | 6/2016 | Najafi et al. |
| 2016/0183855 A1 | 6/2016 | Vanslyke et al. |
| 2016/0186140 A1 | 6/2016 | Dalton et al. |
| 2016/0189174 A1 | 6/2016 | Heath |
| 2016/0191120 A1 | 6/2016 | Dobyns et al. |
| 2016/0192166 A1 | 6/2016 | deCharms |
| 2016/0203522 A1 | 7/2016 | Shiffert et al. |
| 2016/0203572 A1 | 7/2016 | Mcconaghy et al. |
| 2016/0206892 A1 | 7/2016 | Demmer |
| 2016/0210084 A1 | 7/2016 | Butler et al. |
| 2016/0213270 A1 | 7/2016 | Cao et al. |
| 2016/0216768 A1 | 7/2016 | Goetz et al. |
| 2016/0216769 A1 | 7/2016 | Goetz et al. |
| 2016/0220198 A1 | 8/2016 | Proud |
| 2016/0224803 A1 | 8/2016 | Frank et al. |
| 2016/0228034 A1 | 8/2016 | Gluncic |
| 2016/0228052 A1 | 8/2016 | Proud |
| 2016/0235317 A1 | 8/2016 | Sarkar et al. |
| 2016/0235318 A1 | 8/2016 | Sarkar |
| 2016/0236000 A1 | 8/2016 | Smith et al. |
| 2016/0245759 A1 | 8/2016 | Popp |
| 2016/0250478 A1 | 9/2016 | Greenhut et al. |
| 2016/0251778 A1 | 9/2016 | Zhang et al. |
| 2016/0253657 A1* | 9/2016 | Sohn ..................... G06Q 20/40 705/44 |
| 2016/0256697 A1 | 9/2016 | Shahandeh et al. |
| 2016/0273133 A1 | 9/2016 | Zhang et al. |
| 2016/0274752 A1 | 9/2016 | Zhu et al. |

(56)　　　　References Cited

U.S. PATENT DOCUMENTS

| | | |
|---|---|---|
| 2016/0278638 A1 | 9/2016 | Schwartz et al. |
| 2016/0278662 A1 | 9/2016 | Brister et al. |
| 2016/0279388 A1 | 9/2016 | Barrish et al. |
| 2016/0282352 A1 | 9/2016 | Martino et al. |
| 2016/0287380 A1 | 10/2016 | Shi et al. |
| 2016/0294225 A1 | 10/2016 | Blum et al. |
| 2016/0296754 A1 | 10/2016 | Kaula et al. |
| 2016/0300252 A1 | 10/2016 | Frank et al. |
| 2016/0302686 A1 | 10/2016 | Einarsson et al. |
| 2016/0302692 A1 | 10/2016 | Demmer |
| 2016/0303313 A1 | 10/2016 | Burke et al. |
| 2016/0310031 A1 | 10/2016 | Sarkar |
| 2016/0310048 A1 | 10/2016 | Pang et al. |
| 2016/0310051 A1 | 10/2016 | Brister et al. |
| 2016/0310077 A1* | 10/2016 | Hunter .................. G16H 40/60 |
| 2016/0310733 A1 | 10/2016 | Sheldon et al. |
| 2016/0310737 A1 | 10/2016 | Tourrel et al. |
| 2016/0310743 A1 | 10/2016 | Carcieri et al. |
| 2016/0312387 A1 | 10/2016 | Zhang et al. |
| 2016/0313101 A1 | 10/2016 | Parker |
| 2016/0317095 A1 | 11/2016 | Berger et al. |
| 2016/0317797 A1 | 11/2016 | Smith et al. |
| 2016/0317822 A1 | 11/2016 | Rao et al. |
| 2016/0321654 A1 | 11/2016 | Lesavich et al. |
| 2016/0324450 A1 | 11/2016 | Estes et al. |
| 2016/0324478 A1 | 11/2016 | Goldstein |
| 2016/0325083 A1 | 11/2016 | Linden et al. |
| 2016/0325084 A1 | 11/2016 | Linden et al. |
| 2016/0325097 A1 | 11/2016 | Ortega et al. |
| 2016/0331518 A1 | 11/2016 | Cable, II et al. |
| 2016/0335632 A1 | 11/2016 | Proud et al. |
| 2016/0339250 A1 | 11/2016 | Kaula et al. |
| 2016/0339260 A1 | 11/2016 | Rasmussen et al. |
| 2016/0342882 A1 | 11/2016 | Proud et al. |
| 2016/0358063 A1 | 12/2016 | Proud et al. |
| 2016/0358155 A1 | 12/2016 | Proud et al. |
| 2016/0358156 A1 | 12/2016 | Proud et al. |
| 2016/0359222 A1 | 12/2016 | Li et al. |
| 2016/0361009 A1 | 12/2016 | Proud et al. |
| 2016/0361543 A1 | 12/2016 | Kaula et al. |
| 2016/0361545 A1 | 12/2016 | Kaula et al. |
| 2016/0361551 A1 | 12/2016 | Kaula et al. |
| 2016/0361552 A1 | 12/2016 | Kaula et al. |
| 2016/0361553 A1 | 12/2016 | Kaula et al. |
| 2016/0361554 A1 | 12/2016 | Kaula et al. |
| 2016/0374556 A1 | 12/2016 | Colvin, Jr. et al. |
| 2016/0374597 A1 | 12/2016 | Stahmann |
| 2016/0379312 A1 | 12/2016 | Arjomand et al. |
| 2017/0001866 A1 | 1/2017 | Zhang et al. |
| 2017/0007420 A1 | 1/2017 | Stevenson et al. |
| 2017/0017936 A1 | 1/2017 | Bisikalo et al. |
| 2017/0017954 A1 | 1/2017 | McDonough et al. |
| 2017/0017955 A1 | 1/2017 | Stern et al. |
| 2017/0020241 A1 | 1/2017 | Proud et al. |
| 2017/0020402 A1* | 1/2017 | Rogers ................. A61B 5/0031 |
| 2017/0020415 A1 | 1/2017 | Scherer et al. |
| 2017/0020416 A1 | 1/2017 | Scherer et al. |
| 2017/0020418 A1 | 1/2017 | Shults et al. |
| 2017/0021132 A1 | 1/2017 | Laby et al. |
| 2017/0027168 A1 | 2/2017 | Heath |
| 2017/0027424 A1 | 2/2017 | Ferren et al. |
| 2017/0028185 A1 | 2/2017 | Wiley et al. |
| 2017/0028203 A1 | 2/2017 | Ghosh |
| 2017/0028622 A1 | 2/2017 | Westlind et al. |
| 2017/0031874 A1 | 2/2017 | Boudville |
| 2017/0033932 A1 | 2/2017 | Truu et al. |
| 2017/0042487 A1 | 2/2017 | Johnson et al. |
| 2017/0043174 A1 | 2/2017 | Greenhut et al. |
| 2017/0046652 A1 | 2/2017 | Haldenby et al. |
| 2017/0046689 A1 | 2/2017 | Lohe et al. |
| 2017/0046694 A1 | 2/2017 | Chow et al. |
| 2017/0046799 A1 | 2/2017 | Chan et al. |
| 2017/0046806 A1 | 2/2017 | Haldenby et al. |
| 2017/0048209 A1 | 2/2017 | Lohe et al. |
| 2017/0048234 A1 | 2/2017 | Lohe et al. |
| 2017/0048235 A1 | 2/2017 | Lohe et al. |
| 2017/0051073 A1 | 2/2017 | Hynes et al. |
| 2017/0056677 A1 | 3/2017 | Zhang et al. |
| 2017/0065820 A1 | 3/2017 | Kaula et al. |
| 2017/0071510 A1 | 3/2017 | Delbeke et al. |
| 2017/0071511 A1 | 3/2017 | Garcia et al. |
| 2017/0071512 A1 | 3/2017 | Garcia et al. |
| 2017/0072121 A1 | 3/2017 | Yomtov et al. |
| 2017/0074757 A1 | 3/2017 | Garcia et al. |
| 2017/0074857 A1 | 3/2017 | Dennis et al. |
| 2017/0083907 A1 | 3/2017 | McDonough et al. |
| 2017/0085545 A1 | 3/2017 | Lohe et al. |
| 2017/0085555 A1 | 3/2017 | Bisikalo et al. |
| 2017/0086683 A1 | 3/2017 | Bailey et al. |
| 2017/0086697 A1 | 3/2017 | Bellock et al. |
| 2017/0091756 A1 | 3/2017 | Stern et al. |
| 2017/0095210 A1 | 4/2017 | Najafi et al. |
| 2017/0096750 A1 | 4/2017 | Zhang et al. |
| 2017/0097359 A1 | 4/2017 | Verdine et al. |
| 2017/0100056 A1 | 4/2017 | Zhu et al. |
| 2017/0100214 A1 | 4/2017 | Wen |
| 2017/0106178 A1 | 4/2017 | Altschul et al. |
| 2017/0106196 A1 | 4/2017 | Ter-Petrosyan et al. |
| 2017/0109735 A1 | 4/2017 | Sheng et al. |
| 2017/0112671 A1 | 4/2017 | Goldstein |
| 2017/0113046 A1 | 4/2017 | Fried et al. |
| 2017/0117739 A1 | 4/2017 | Tuseth et al. |
| 2017/0127196 A1 | 5/2017 | Blum et al. |
| 2017/0127929 A1 | 5/2017 | Schutt et al. |
| 2017/0127941 A1 | 5/2017 | Ostermeier et al. |
| 2017/0127975 A1* | 5/2017 | Bozkurt .............. A01K 29/005 |
| 2017/0132615 A1 | 5/2017 | Castinado et al. |
| 2017/0132630 A1 | 5/2017 | Castinado et al. |
| 2017/0136244 A1 | 5/2017 | Bonde et al. |
| 2017/0137290 A1 | 5/2017 | Zhang et al. |
| 2017/0140121 A1 | 5/2017 | Schulhauser et al. |
| 2017/0140127 A1 | 5/2017 | Schulhauser et al. |
| 2017/0140408 A1 | 5/2017 | Wuehler |
| 2017/0143206 A1 | 5/2017 | Kotz et al. |
| 2017/0152486 A1 | 6/2017 | Shen et al. |
| 2017/0157411 A1 | 6/2017 | Shahandeh et al. |
| 2017/0161517 A1 | 6/2017 | Shah |
| 2017/0173216 A1 | 6/2017 | Ju et al. |
| 2017/0173262 A1 | 6/2017 | Veltz |
| 2017/0182191 A1 | 6/2017 | Towne et al. |
| 2017/0188902 A1 | 7/2017 | Wang et al. |
| 2017/0188905 A1 | 7/2017 | Lee et al. |
| 2017/0188906 A1 | 7/2017 | Ma et al. |
| 2017/0188907 A1 | 7/2017 | Ma et al. |
| 2017/0188916 A1 | 7/2017 | Wang et al. |
| 2017/0188921 A1 | 7/2017 | Wang et al. |
| 2017/0188922 A1 | 7/2017 | Lee et al. |
| 2017/0188923 A1 | 7/2017 | Zou et al. |
| 2017/0188942 A1 | 7/2017 | Ghaffari et al. |
| 2017/0191955 A1 | 7/2017 | Zou et al. |
| 2017/0196491 A1 | 7/2017 | Brister et al. |
| 2017/0197028 A1 | 7/2017 | Goldsmith |
| 2017/0197072 A1 | 7/2017 | Linden et al. |
| 2017/0199970 A1 | 7/2017 | Stahmann et al. |
| 2017/0206532 A1 | 7/2017 | Choi |
| 2017/0207535 A1* | 7/2017 | Tsukuda .................. H01Q 1/24 |
| 2017/0209666 A1 | 7/2017 | Quigley |
| 2017/0209705 A1 | 7/2017 | Faltys et al. |
| 2017/0212913 A1 | 7/2017 | Kurse |
| 2017/0215815 A1 | 8/2017 | Rastogi et al. |
| 2017/0216610 A1 | 8/2017 | Yoder et al. |
| 2017/0216611 A1 | 8/2017 | Yoder et al. |
| 2017/0221032 A1 | 8/2017 | Mazed |
| 2017/0221052 A1 | 8/2017 | Sheng et al. |
| 2017/0224248 A1 | 8/2017 | Zou et al. |
| 2017/0225008 A1 | 8/2017 | Stahler et al. |
| 2017/0225009 A1 | 8/2017 | Delp et al. |
| 2017/0225013 A1 | 8/2017 | Delp et al. |
| 2017/0228510 A1 | 8/2017 | Zottola |
| 2017/0228627 A1* | 8/2017 | Geissler ........... G06K 19/07773 |
| 2017/0228706 A1 | 8/2017 | Parziale et al. |
| 2017/0228731 A1 | 8/2017 | Sheng et al. |
| 2017/0228734 A1 | 8/2017 | Kurian |
| 2017/0230084 A1 | 8/2017 | Zhu et al. |

(56) References Cited

U.S. PATENT DOCUMENTS

| | | |
|---|---|---|
| 2017/0231497 A1 | 8/2017 | Brister et al. |
| 2017/0231738 A1 | 8/2017 | Severson |
| 2017/0231812 A1 | 8/2017 | Boyden et al. |
| 2017/0232256 A1 | 8/2017 | Meskens |
| 2017/0232300 A1 | 8/2017 | Tran et al. |
| 2017/0236177 A1 | 8/2017 | Sebastian et al. |
| 2017/0236196 A1 | 8/2017 | Isaacson et al. |
| 2017/0237569 A1 | 8/2017 | Vandervort |
| 2017/0237570 A1 | 8/2017 | Vandervort |
| 2017/0239488 A1 | 8/2017 | Stahler et al. |
| 2017/0243177 A1 | 8/2017 | Johnsrud et al. |
| 2017/0243208 A1 | 8/2017 | Kurian et al. |
| 2017/0243209 A1 | 8/2017 | Johnsrud et al. |
| 2017/0243212 A1 | 8/2017 | Castinado et al. |
| 2017/0243213 A1 | 8/2017 | Castinado et al. |
| 2017/0243214 A1 | 8/2017 | Johnsrud et al. |
| 2017/0243217 A1 | 8/2017 | Johnsrud et al. |
| 2017/0243222 A1 | 8/2017 | Balasubramanian |
| 2017/0243286 A1 | 8/2017 | Castinado et al. |
| 2017/0243287 A1 | 8/2017 | Johnsrud et al. |
| 2017/0244707 A1 | 8/2017 | Johnsrud et al. |
| 2017/0244721 A1 | 8/2017 | Kurian et al. |
| 2017/0250796 A1 | 8/2017 | Samid |
| 2017/0256000 A1 | 9/2017 | Isaacson et al. |
| 2017/0256001 A1 | 9/2017 | Isaacson et al. |
| 2017/0256003 A1 | 9/2017 | Isaacson et al. |
| 2017/0258363 A1 | 9/2017 | Towe |
| 2017/0258585 A1 | 9/2017 | Marquez et al. |
| 2017/0259050 A1 | 9/2017 | Altschul et al. |
| 2017/0259061 A1 | 9/2017 | Simon et al. |
| 2017/0259072 A1 | 9/2017 | Newham et al. |
| 2017/0262862 A1 | 9/2017 | Aljawhari |
| 2017/0266437 A1 | 9/2017 | Kaula et al. |
| 2017/0266455 A1 | 9/2017 | Steinke |
| 2017/0269052 A1 | 9/2017 | Adams et al. |
| 2017/0270721 A1 | 9/2017 | Graafstra |
| 2017/0272123 A1 | 9/2017 | Zhu et al. |
| 2017/0272316 A1 | 9/2017 | Johnson et al. |
| 2017/0273589 A1 | 9/2017 | Sarkar et al. |
| 2017/0273606 A1 | 9/2017 | Estes et al. |
| 2017/0274200 A1 | 9/2017 | Towe |
| 2017/0274213 A1 | 9/2017 | Ghosh et al. |
| 2017/0281033 A1 | 10/2017 | Higgins et al. |
| 2017/0281034 A1 | 10/2017 | Higgins et al. |
| 2017/0281092 A1 | 10/2017 | Burnette et al. |
| 2017/0281927 A1 | 10/2017 | Orinski |
| 2017/0281928 A1 | 10/2017 | Orinski |
| 2017/0281957 A1 | 10/2017 | Howard |
| 2017/0283384 A1 | 10/2017 | Pomper et al. |
| 2017/0296093 A1 | 10/2017 | Ravid et al. |
| 2017/0296827 A1 | 10/2017 | Yoon et al. |
| 2017/0296834 A1 | 10/2017 | Kothandaraman et al. |
| 2017/0296835 A1 | 10/2017 | Yoon et al. |
| 2017/0300905 A1 | 10/2017 | Withrow et al. |
| 2017/0300910 A1 | 10/2017 | Bethke et al. |
| 2017/0300946 A1 | 10/2017 | Wilkinson et al. |
| 2017/0304635 A1 | 10/2017 | Aghassian |
| 2017/0312502 A1 | 11/2017 | Yoon et al. |
| 2017/0312530 A1 | 11/2017 | Schilling et al. |
| 2017/0316487 A1 | 11/2017 | Mazed |
| 2017/0317518 A1 | 11/2017 | Olson et al. |
| 2017/0320960 A1 | 11/2017 | Williams et al. |
| 2017/0325726 A1 | 11/2017 | Shults et al. |
| 2017/0327377 A1 | 11/2017 | Zhang et al. |
| 2017/0333080 A1 | 11/2017 | Roschak et al. |
| 2017/0333716 A1 | 11/2017 | Ortega et al. |
| 2017/0340254 A1 | 11/2017 | Davis et al. |
| 2017/0340872 A1 | 11/2017 | Hanson et al. |
| 2017/0343553 A9 | 11/2017 | Hynes et al. |
| 2017/0343561 A1 | 11/2017 | May et al. |
| 2017/0345105 A1 | 11/2017 | Isaacson et al. |
| 2017/0348146 A1 | 12/2017 | Drnek et al. |
| 2017/0358041 A1 | 12/2017 | Forbes, Jr. et al. |
| 2017/0361104 A1 | 12/2017 | Carcieri et al. |
| 2017/0364860 A1 | 12/2017 | Wilkinson et al. |
| 2017/0367627 A1 | 12/2017 | Brister et al. |
| 2017/0368158 A1 | 12/2017 | Vescovi et al. |
| 2017/0368330 A1 | 12/2017 | Silay et al. |
| 2017/0373849 A1 | 12/2017 | Donner et al. |
| 2018/0001018 A1 | 1/2018 | Burke et al. |
| 2018/0001184 A1 | 1/2018 | Tran et al. |
| 2018/0006990 A1 | 1/2018 | Munemann |
| 2018/0008185 A1 | 1/2018 | Ramu et al. |
| 2018/0008834 A1 | 1/2018 | Kaula et al. |
| 2018/0009767 A9 | 1/2018 | Pomper et al. |
| 2018/0012311 A1 | 1/2018 | Small et al. |
| 2018/0013815 A1 | 1/2018 | Gold |
| 2018/0014762 A1 | 1/2018 | Brister et al. |
| 2018/0019984 A1 | 1/2018 | Isaacson et al. |
| 2018/0021235 A1 | 1/2018 | Christiano et al. |
| 2018/0021498 A1 | 1/2018 | Yomtov et al. |
| 2018/0021510 A1 | 1/2018 | Burke et al. |
| 2018/0028086 A1 | 2/2018 | Cao et al. |
| 2018/0028275 A1 | 2/2018 | Bradley et al. |
| 2018/0028814 A1 | 2/2018 | Ghosh |
| 2018/0028827 A1* | 2/2018 | Schilling ............ A61N 1/37223 |
| 2018/0028832 A1 | 2/2018 | Lundmark et al. |
| 2018/0035888 A1 | 2/2018 | Irazoqui et al. |
| 2018/0036053 A1 | 2/2018 | Toscano et al. |
| 2018/0036115 A1 | 2/2018 | Smirnov |
| 2018/0038672 A1 | 2/2018 | Parker |
| 2018/0039512 A1 | 2/2018 | Almasan et al. |
| 2018/0040944 A1 | 2/2018 | Andersen et al. |
| 2018/0041345 A1 | 2/2018 | Maim |
| 2018/0042553 A1 | 2/2018 | Min et al. |
| 2018/0042583 A1 | 2/2018 | Pringle et al. |
| 2018/0047555 A1 | 2/2018 | Pringle et al. |
| 2018/0049682 A1 | 2/2018 | Brister et al. |
| 2018/0050189 A1 | 2/2018 | Rump et al. |
| 2018/0050214 A1 | 2/2018 | Rump |
| 2018/0055361 A1 | 3/2018 | Brister et al. |
| 2018/0055500 A1 | 3/2018 | Scott et al. |
| 2018/0056085 A1 | 3/2018 | Lundmark et al. |
| 2018/0059126 A1 | 3/2018 | Jones et al. |
| 2018/0060520 A1 | 3/2018 | Degen et al. |
| 2018/0069899 A1 | 3/2018 | Lang et al. |
| 2018/0070876 A1 | 3/2018 | Brockway et al. |
| 2018/0071789 A1 | 3/2018 | Kingston et al. |
| 2018/0072415 A1 | 3/2018 | Cantrell et al. |
| 2018/0072416 A1 | 3/2018 | Cantrell et al. |
| 2018/0074481 A1 | 3/2018 | Kingston et al. |
| 2018/0074488 A1 | 3/2018 | Cantrell et al. |
| 2018/0074521 A1 | 3/2018 | Cantrell et al. |
| 2018/0074522 A1 | 3/2018 | Cantrell et al. |
| 2018/0074523 A1 | 3/2018 | Cantrell et al. |
| 2018/0075386 A1 | 3/2018 | Kingston et al. |
| 2018/0075406 A1 | 3/2018 | Kingston et al. |
| 2018/0076336 A1 | 3/2018 | De Graff et al. |
| 2018/0076670 A1 | 3/2018 | O'Driscoll et al. |
| 2018/0078747 A1 | 3/2018 | Altschul et al. |
| 2018/0078748 A1 | 3/2018 | Altschul et al. |
| 2018/0078843 A1 | 3/2018 | Tran et al. |
| 2018/0081787 A1 | 3/2018 | Riddick et al. |
| 2018/0081955 A1 | 3/2018 | Gupta et al. |
| 2018/0082043 A1 | 3/2018 | Witchey et al. |
| 2018/0082295 A1 | 3/2018 | Boucard |
| 2018/0083786 A1 | 3/2018 | Dierks et al. |
| 2018/0085038 A1 | 3/2018 | Chen et al. |
| 2018/0085506 A1 | 3/2018 | Yomtov et al. |
| 2018/0085559 A1 | 3/2018 | Laby et al. |
| 2018/0085588 A1 | 3/2018 | Splett et al. |
| 2018/0085589 A1 | 3/2018 | Splett et al. |
| 2018/0085592 A1 | 3/2018 | Yoder et al. |
| 2018/0085605 A1* | 3/2018 | Maharbiz ............... A61B 5/076 |
| 2018/0088108 A1 | 3/2018 | Glezer et al. |
| 2018/0089627 A1 | 3/2018 | Liss |
| 2018/0089641 A1 | 3/2018 | Chan et al. |
| 2018/0089669 A1 | 3/2018 | Singh |
| 2018/0094953 A1 | 4/2018 | Colson et al. |
| 2018/0096121 A1 | 4/2018 | Goeringer et al. |
| 2018/0096175 A1 | 4/2018 | Schmeling et al. |
| 2018/0103863 A1 | 4/2018 | Hu et al. |
| 2018/0103879 A1 | 4/2018 | Masciotti et al. |
| 2018/0103935 A1 | 4/2018 | Pringle et al. |

(56) References Cited

U.S. PATENT DOCUMENTS

| | | |
|---|---|---|
| 2018/0108024 A1 | 4/2018 | Greco et al. |
| 2018/0115600 A1 | 4/2018 | Almasan et al. |
| 2018/0117337 A1 | 5/2018 | Demmer et al. |
| 2018/0117446 A1 | 5/2018 | Tran et al. |
| 2018/0117447 A1 | 5/2018 | Tran et al. |
| 2018/0120225 A1 | 5/2018 | Ditterich |
| 2018/0123804 A1 | 5/2018 | Smith et al. |
| 2018/0125364 A1 | 5/2018 | DeHennis |
| 2018/0126053 A1 | 5/2018 | Zilbershlag |
| 2018/0126133 A1 | 5/2018 | Cully et al. |
| 2018/0126168 A1 | 5/2018 | Kaula et al. |
| 2018/0128820 A1 | 5/2018 | Huang et al. |
| 2018/0130034 A1 | 5/2018 | Taylor et al. |
| 2018/0130050 A1 | 5/2018 | Taylor et al. |
| 2018/0130158 A1 | 5/2018 | Atkinson et al. |
| 2018/0131415 A1 | 5/2018 | Bashirullah |
| 2018/0131765 A1 | 5/2018 | Puleston et al. |
| 2018/0133474 A1 | 5/2018 | Meadows et al. |
| 2018/0133501 A1 | 5/2018 | Stahler et al. |
| 2018/0133583 A1 | 5/2018 | Tran et al. |
| 2018/0136633 A1 | 5/2018 | Small et al. |
| 2018/0137461 A1 | 5/2018 | Wilkinson et al. |
| 2018/0137506 A1 | 5/2018 | Kel et al. |
| 2018/0137512 A1 | 5/2018 | Georgiadis et al. |
| 2018/0138022 A1 | 5/2018 | Lam et al. |
| 2018/0139057 A1 | 5/2018 | Truu et al. |
| 2018/0140236 A1 | 5/2018 | Brister et al. |
| 2018/0140862 A1 | 5/2018 | Stahler et al. |
| 2018/0144298 A1 | 5/2018 | Rankin |
| 2018/0144342 A1 | 5/2018 | Borandi |
| 2018/0147413 A1 | 5/2018 | Ter-Petrosyan et al. |
| 2018/0150816 A1 | 5/2018 | Liu et al. |
| 2018/0154075 A1 | 6/2018 | Jho et al. |
| 2018/0154154 A1 | 6/2018 | Sheldon et al. |
| 2018/0158036 A1 | 6/2018 | Zhou et al. |
| 2018/0160949 A1 | 6/2018 | Brister et al. |
| 2018/0161580 A1 | 6/2018 | Demmer et al. |
| 2018/0164276 A1 | 6/2018 | Shapiro et al. |
| 2018/0165738 A1 | 6/2018 | Chilukuri et al. |
| 2018/0167394 A1 | 6/2018 | High et al. |
| 2018/0168811 A1 | 6/2018 | Ranganathan et al. |
| 2018/0173906 A1 | 6/2018 | Rodriguez et al. |
| 2018/0174097 A1 | 6/2018 | Liu et al. |
| 2018/0174188 A1 | 6/2018 | Wilkinson et al. |
| 2018/0176017 A1 | 6/2018 | Rodriguez et al. |
| 2018/0181806 A1 | 6/2018 | Chandrashekar et al. |
| 2018/0181909 A1 | 6/2018 | Wilkinson et al. |
| 2018/0181964 A1 | 6/2018 | Zagarese et al. |
| 2018/0182140 A1 | 6/2018 | Biradar et al. |
| 2018/0183796 A1 | 6/2018 | Smith et al. |
| 2018/0184944 A1 | 7/2018 | Bodewes et al. |
| 2018/0188704 A1 | 7/2018 | Cella et al. |
| 2018/0188714 A1 | 7/2018 | Cella et al. |
| 2018/0188715 A1 | 7/2018 | Cella et al. |
| 2018/0189528 A1 | 7/2018 | Hanis et al. |
| 2018/0189854 A1 | 7/2018 | Gabriele et al. |
| 2018/0191503 A1 | 7/2018 | Alwar et al. |
| 2018/0192909 A1 | 7/2018 | Einarsson et al. |
| 2018/0192926 A1 | 7/2018 | Shults et al. |
| 2018/0192941 A1 | 7/2018 | Annoni et al. |
| 2018/0192942 A1 | 7/2018 | Clark et al. |
| 2018/0192943 A1 | 7/2018 | Annoni et al. |
| 2018/0192952 A1 | 7/2018 | Rogers et al. |
| 2018/0193644 A1 | 7/2018 | Annoni et al. |
| 2018/0193650 A1 | 7/2018 | Srivastava et al. |
| 2018/0193651 A1 | 7/2018 | Annoni et al. |
| 2018/0193652 A1 | 7/2018 | Srivastava et al. |
| 2018/0198617 A1 | 7/2018 | Drouin et al. |
| 2018/0198876 A1 | 7/2018 | Ma et al. |
| 2018/0199873 A1 | 7/2018 | Wang et al. |
| 2018/0200003 A1 | 7/2018 | Olson |
| 2018/0200185 A1 | 7/2018 | Labib et al. |
| 2018/0200525 A1 | 7/2018 | Schilling et al. |
| 2018/0203755 A1 | 7/2018 | Das et al. |
| 2018/0204034 A1 | 7/2018 | Tonnelier |
| 2018/0204111 A1 | 7/2018 | Zadeh et al. |
| 2018/0205764 A1* | 7/2018 | Jeon ..................... H04W 88/10 |
| 2018/0210425 A1 | 7/2018 | Cella et al. |
| 2018/0210426 A1 | 7/2018 | Cella et al. |
| 2018/0210427 A1 | 7/2018 | Cella et al. |
| 2018/0211213 A1 | 7/2018 | Vivier |
| 2018/0211718 A1 | 7/2018 | Heath |
| 2018/0214690 A1 | 8/2018 | Hodgson-Zingman et al. |
| 2018/0214694 A1 | 8/2018 | Parramon |
| 2018/0214711 A1 | 8/2018 | Stahler et al. |
| 2018/0218003 A1 | 8/2018 | Banga et al. |
| 2018/0218354 A1 | 8/2018 | Kumar et al. |
| 2018/0221663 A1 | 8/2018 | Saini |
| 2018/0225649 A1 | 8/2018 | Babar et al. |
| 2018/0227354 A1 | 8/2018 | Gold |
| 2018/0231513 A1 | 8/2018 | Lim et al. |
| 2018/0232693 A1 | 8/2018 | Gillen et al. |
| 2018/0232730 A1 | 8/2018 | Harbour et al. |
| 2018/0232817 A1 | 8/2018 | Isaacson et al. |
| 2018/0233016 A1 | 8/2018 | Daniel et al. |
| 2018/0242864 A1 | 8/2018 | Hu et al. |
| 2018/0243435 A1 | 8/2018 | Dylla et al. |
| 2018/0243567 A1 | 8/2018 | St. Martin et al. |
| 2018/0243573 A1* | 8/2018 | Yoder ..................... H04W 4/80 |
| 2018/0243577 A1 | 8/2018 | Kivi et al. |
| 2018/0252726 A1 | 9/2018 | Verdine et al. |
| 2018/0252734 A1 | 9/2018 | Bakhru et al. |
| 2018/0253073 A1 | 9/2018 | Cella et al. |
| 2018/0253074 A1 | 9/2018 | Cella et al. |
| 2018/0253075 A1 | 9/2018 | Cella et al. |
| 2018/0253430 A1 | 9/2018 | Grigorescu et al. |
| 2018/0253805 A1 | 9/2018 | Kelly et al. |
| 2018/0255374 A1 | 9/2018 | Cella et al. |
| 2018/0255375 A1 | 9/2018 | Cella et al. |
| 2018/0255376 A1 | 9/2018 | Cella et al. |
| 2018/0255377 A1 | 9/2018 | Cella et al. |
| 2018/0255378 A1 | 9/2018 | Cella et al. |
| 2018/0255379 A1 | 9/2018 | Cella et al. |
| 2018/0255380 A1 | 9/2018 | Cella et al. |
| 2018/0255381 A1 | 9/2018 | Cella et al. |
| 2018/0255382 A1 | 9/2018 | Cella et al. |
| 2018/0255383 A1 | 9/2018 | Cella et al. |
| 2018/0256208 A1 | 9/2018 | Altschul et al. |
| 2018/0256909 A1 | 9/2018 | Smith et al. |
| 2018/0257306 A1 | 9/2018 | Mattingly et al. |
| 2018/0259535 A1 | 9/2018 | Verdine et al. |
| 2018/0259976 A1 | 9/2018 | Williams et al. |
| 2018/0261307 A1 | 9/2018 | Couse et al. |
| 2018/0262493 A1 | 9/2018 | Andrade |
| 2018/0264347 A1 | 9/2018 | Tran et al. |
| 2018/0268360 A1 | 9/2018 | Millhouse et al. |
| 2018/0268418 A1 | 9/2018 | Tanksali |
| 2018/0268479 A1 | 9/2018 | Dowling et al. |
| 2018/0268483 A1 | 9/2018 | Jayaram et al. |
| 2018/0271450 A1 | 9/2018 | Kamath et al. |
| 2018/0271980 A1 | 9/2018 | Altschul et al. |
| 2018/0272142 A1 | 9/2018 | Zhang et al. |
| 2018/0277938 A1 | 9/2018 | Andersen et al. |
| 2018/0280694 A1 | 10/2018 | Mashiach et al. |
| 2018/0280716 A1 | 10/2018 | Stahler et al. |
| 2018/0284093 A1 | 10/2018 | Brown et al. |
| 2018/0284735 A1 | 10/2018 | Cella et al. |
| 2018/0284736 A1 | 10/2018 | Cella et al. |
| 2018/0284737 A1 | 10/2018 | Cella et al. |
| 2018/0284741 A1 | 10/2018 | Cella et al. |
| 2018/0284742 A1 | 10/2018 | Cella et al. |
| 2018/0284743 A1 | 10/2018 | Cella et al. |
| 2018/0284744 A1 | 10/2018 | Cella et al. |
| 2018/0284745 A1 | 10/2018 | Cella et al. |
| 2018/0284746 A1 | 10/2018 | Cella et al. |
| 2018/0284747 A1 | 10/2018 | Cella et al. |
| 2018/0284749 A1 | 10/2018 | Cella et al. |
| 2018/0284752 A1 | 10/2018 | Cella et al. |
| 2018/0284753 A1 | 10/2018 | Cella et al. |
| 2018/0284754 A1 | 10/2018 | Cella et al. |
| 2018/0284755 A1 | 10/2018 | Cella et al. |
| 2018/0284756 A1 | 10/2018 | Cella et al. |
| 2018/0284757 A1 | 10/2018 | Cella et al. |
| 2018/0284758 A1 | 10/2018 | Cella et al. |

(56) References Cited

U.S. PATENT DOCUMENTS

| | | |
|---|---|---|
| 2018/0285709 A1 | 10/2018 | Braunstein |
| 2018/0289971 A1 | 10/2018 | Yeh et al. |
| 2018/0293577 A1 | 10/2018 | Kim et al. |
| 2018/0296143 A1 | 10/2018 | Anderson et al. |
| 2018/0299878 A1 | 10/2018 | Cella et al. |
| 2018/0300772 A1 | 10/2018 | Bushong, Jr. |
| 2018/0307854 A1 | 10/2018 | Bernau et al. |
| 2018/0307859 A1 | 10/2018 | LaFever et al. |
| 2018/0307959 A1 | 10/2018 | Pigott et al. |
| 2018/0310824 A1 | 11/2018 | Windolf |
| 2018/0310964 A1 | 11/2018 | Stevenson et al. |
| 2018/0311504 A1 | 11/2018 | Cao et al. |
| 2018/0314868 A1 | 11/2018 | Raynesford |
| 2018/0315141 A1 | 11/2018 | Hunn et al. |
| 2018/0315509 A1 | 11/2018 | Zhang et al. |
| 2018/0321666 A1 | 11/2018 | Cella et al. |
| 2018/0321667 A1 | 11/2018 | Cella et al. |
| 2018/0321672 A1 | 11/2018 | Cella et al. |
| 2018/0322164 A1 | 11/2018 | Dasari et al. |
| 2018/0322445 A1 | 11/2018 | Sayles et al. |
| 2018/0324407 A1 | 11/2018 | Peeters et al. |
| 2018/0325402 A1 | 11/2018 | Thakur et al. |
| 2018/0325437 A1 | 11/2018 | Li et al. |
| 2018/0326220 A1 | 11/2018 | Kaula et al. |
| 2018/0326291 A1 | 11/2018 | Tran et al. |
| 2018/0327506 A1 | 11/2018 | Karsunky et al. |
| 2018/0330369 A1 | 11/2018 | Warner |
| 2018/0333086 A1 | 11/2018 | Gupta |
| 2018/0333578 A1 | 11/2018 | Mock et al. |
| 2018/0336515 A1 | 11/2018 | Mehring et al. |
| 2018/0336970 A1 | 11/2018 | Sherwood et al. |
| 2018/0338699 A1 | 11/2018 | Higgins et al. |
| 2018/0344212 A1 | 12/2018 | An et al. |
| 2018/0345027 A1 | 12/2018 | Kaula et al. |
| 2018/0345033 A1 | 12/2018 | Lundmark et al. |
| 2018/0349893 A1 | 12/2018 | Tsai |
| 2018/0353219 A1 | 12/2018 | Beyar et al. |
| 2018/0357603 A1 | 12/2018 | Wilkinson et al. |
| 2018/0357725 A1 | 12/2018 | Roth et al. |
| 2018/0360355 A1 | 12/2018 | Chavan et al. |
| 2018/0361150 A1 | 12/2018 | Ternes et al. |
| 2018/0361160 A1 | 12/2018 | Sheldon et al. |
| 2018/0361161 A1 | 12/2018 | Ternes et al. |
| 2018/0361162 A1 | 12/2018 | Ternes et al. |
| 2018/0361169 A1 | 12/2018 | Delp et al. |
| 2018/0365633 A1 | 12/2018 | Hanis et al. |
| 2018/0368685 A1 | 12/2018 | DeHennis |
| 2018/0369437 A1 | 12/2018 | Grossman et al. |
| 2018/0369438 A1 | 12/2018 | Grossman et al. |
| 2018/0369573 A1 | 12/2018 | Cholette et al. |
| 2018/0372720 A1 | 12/2018 | Wildburger et al. |
| 2018/0374037 A1 | 12/2018 | Nazzari et al. |
| 2018/0375750 A1 | 12/2018 | Moeller |
| 2018/0376336 A1 | 12/2018 | Turner et al. |
| 2019/0000656 A1 | 1/2019 | Pool et al. |
| 2019/0000969 A1 | 1/2019 | Mcknight et al. |
| 2019/0002283 A1 | 1/2019 | Zhang et al. |
| 2019/0005507 A1 | 1/2019 | Rodoni et al. |
| 2019/0005566 A1 | 1/2019 | Black |
| 2019/0007381 A1 | 1/2019 | Isaacson et al. |
| 2019/0008117 A1 | 1/2019 | Dijkstra et al. |
| 2019/0009095 A1 | 1/2019 | Sheldon et al. |
| 2019/0012637 A1 | 1/2019 | Gillen |
| 2019/0015020 A1 | 1/2019 | Brister et al. |
| 2019/0015669 A1 | 1/2019 | Muessig et al. |
| 2019/0015677 A1 | 1/2019 | Stahler et al. |
| 2019/0016812 A1 | 1/2019 | Bernstein et al. |
| 2019/0019144 A1 | 1/2019 | Gillen |
| 2019/0019171 A1 | 1/2019 | Silvestre |
| 2019/0021596 A1 | 1/2019 | Brister et al. |
| 2019/0022242 A1 | 1/2019 | Roy et al. |
| 2019/0022397 A1 | 1/2019 | Srivastava et al. |
| 2019/0022428 A1 | 1/2019 | Maharbiz et al. |
| 2019/0025805 A1 | 1/2019 | Cella et al. |
| 2019/0025806 A1 | 1/2019 | Cella et al. |
| 2019/0025812 A1 | 1/2019 | Cella et al. |
| 2019/0025813 A1 | 1/2019 | Cella et al. |
| 2019/0026690 A1 | 1/2019 | Wappler et al. |
| 2019/0029567 A1 | 1/2019 | Stahmann et al. |
| 2019/0030348 A1 | 1/2019 | Bornhoft et al. |
| 2019/0033845 A1 | 1/2019 | Cella et al. |
| 2019/0033846 A1 | 1/2019 | Cella et al. |
| 2019/0033847 A1 | 1/2019 | Cella et al. |
| 2019/0033848 A1 | 1/2019 | Cella et al. |
| 2019/0033849 A1 | 1/2019 | Cella et al. |
| 2019/0034536 A1 | 1/2019 | Papp et al. |
| 2019/0034605 A1 | 1/2019 | Wang et al. |
| 2019/0034808 A1 | 1/2019 | Palanichamy |
| 2019/0034888 A1 | 1/2019 | Grassadonia et al. |
| 2019/0034889 A1 | 1/2019 | Brock et al. |
| 2019/0034923 A1 | 1/2019 | Greco et al. |
| 2019/0035499 A1 | 1/2019 | Daya |
| 2019/0036887 A1 | 1/2019 | Miller |
| 2019/0038214 A1 | 2/2019 | Mikhail et al. |
| 2019/0038496 A1 | 2/2019 | Levesque et al. |
| 2019/0038791 A1 | 2/2019 | Gerrans et al. |
| 2019/0038908 A1 | 2/2019 | Lundmark et al. |
| 2019/0041835 A1 | 2/2019 | Cella et al. |
| 2019/0041836 A1 | 2/2019 | Cella et al. |
| 2019/0041840 A1 | 2/2019 | Cella et al. |
| 2019/0041841 A1 | 2/2019 | Cella et al. |
| 2019/0041842 A1 | 2/2019 | Cella et al. |
| 2019/0041843 A1 | 2/2019 | Cella et al. |
| 2019/0041844 A1 | 2/2019 | Cella et al. |
| 2019/0041845 A1 | 2/2019 | Cella et al. |
| 2019/0041846 A1 | 2/2019 | Cella et al. |
| 2019/0043008 A1 | 2/2019 | Vivier |
| 2019/0043010 A1 | 2/2019 | Smith et al. |
| 2019/0044736 A1 | 2/2019 | Vandervort |
| 2019/0046032 A1 | 2/2019 | Stahmann et al. |
| 2019/0046035 A1 | 2/2019 | Nyquist |
| 2019/0046800 A1 | 2/2019 | Doan et al. |
| 2019/0046863 A1 | 2/2019 | Eurlings et al. |
| 2019/0049931 A1 | 2/2019 | Tschirschnitz et al. |
| 2019/0050888 A1 | 2/2019 | Elder et al. |
| 2019/0053470 A1 | 2/2019 | Singh et al. |
| 2019/0053712 A1 | 2/2019 | Rogers et al. |
| 2019/0053915 A1 | 2/2019 | Macke et al. |
| 2019/0054284 A1 | 2/2019 | Smith et al. |
| 2019/0054301 A1 | 2/2019 | Kaula et al. |
| 2019/0056726 A1 | 2/2019 | Weldemariam et al. |
| 2019/0057454 A1 | 2/2019 | Komenda et al. |
| 2019/0058242 A1 | 2/2019 | Tabe |
| 2019/0059062 A1 | 2/2019 | Mulligan |
| 2019/0059730 A1 | 2/2019 | Brister et al. |
| 2019/0059792 A1 | 2/2019 | Kane et al. |
| 2019/0064791 A1 | 2/2019 | Cella et al. |
| 2019/0064792 A1 | 2/2019 | Cella et al. |
| 2019/0065733 A1 | 2/2019 | Forehand |
| 2019/0066063 A1 | 2/2019 | Jessamine |
| 2019/0069815 A1 | 3/2019 | Burnes et al. |
| 2019/0069817 A1 | 3/2019 | Brister et al. |
| 2019/0070350 A1 | 3/2019 | Yomtov et al. |
| 2019/0072922 A1 | 3/2019 | Cella et al. |
| 2019/0072923 A1 | 3/2019 | Cella et al. |
| 2019/0072924 A1 | 3/2019 | Cella et al. |
| 2019/0072925 A1 | 3/2019 | Cella et al. |
| 2019/0072926 A1 | 3/2019 | Cella et al. |
| 2019/0072928 A1 | 3/2019 | Cella et al. |
| 2019/0140358 A1* | 5/2019 | Antonetti ............... H01Q 13/10 |
| 2019/0336054 A1* | 11/2019 | Shah ...................... A61B 5/681 |
| 2020/0205735 A1* | 7/2020 | Narayanan .............. G06F 3/017 |
| 2020/0275866 A1* | 9/2020 | Klemm .................. A61B 5/076 |
| 2021/0236735 A1* | 8/2021 | Love .................... A61M 5/315 |
| 2021/0401418 A1* | 12/2021 | Dang .................. A61B 5/0215 |

OTHER PUBLICATIONS

Woolley, Martin. Exploring Bluetooth 5 -Going the Distance. Bluetooth® Technology Website, Feb. 13, 2017, www.bluetooth. com/blog/exploring-bluetooth-5-going-the-distance/. Accessed Apr. 6, 2024. (Year: 2017).*

(56) References Cited

OTHER PUBLICATIONS

ISO/IEC 18092:2013. ISO, 2013, www.iso.org/standard/56692. html#:~: text=Abstract,for%20interconnection%20of%20computer% 20peripherals. Accessed Apr. 6, 2024. (Year: 2013).*

Most Powerful Millimeter-Scale Energy Harvester Generates Electricity from Vibrations.a University of Michigan News, Apr. 25, 2011 , news.umich.edu/most-powerful-millimeter-scale-energy-harvester-generates-electricity-from-vibrations/. Accessed Apr. 6, 2024. (Year: 2011).*

Radio Spectrum Allocation. Federal Communications Commission, www.fcc.gov/engineering-technology/policy-and-rules-division/ general/radio-spectrum-allocation. Accessed Apr. 6, 2024. (Year: 2018).*

Abdelhamid, Mohamed R., Ruicong Chen, Joonhyuk Cho, Anantha p. Chandrakasan, and Fadel Adib. "Self-reconfigurable micro-implants for cross-tissue wireless and batteryless connectivity." In Proceedings of the 26th Annual International Conference on Mobile Computing and Networking, pp. 1-14. 2020.

Bayasi, Nourhan, Temesghen Tekeste, Hani Saleh, Baker Mohammad, Ahsan Khandoker, and Mohammed Ismail. "Low-power ECG-based processor for predicting ventricular arrhythmia." IEEE Transactions on Very Large Scale Integration (VLSI) Systems 24, No. 5 (2015): 1962-1974.

Bluetooth SIG, Bluetooth Core Specification 5.1 (2019).

Bluetooth.com, Enhancing Bluetooth Location Services with Direction Finding (2019).

Bourzac, Katherine. "Speck-size computers: Now with deep learning [news]." IEEE Spectrum 54, No. 4 (2017): 13-15.

Braintree Scientific, Inc. 2019 Catalog, p. 42.

Chen, Yen-Po, Dongsuk Jeon, Yoonmyung Lee, Yejoong Kim, Zhiyoong Foo, Inhee Lee, Nicholas B. Langhals et al. "An injectable 64 nW ECG mixed-signal SoC in 65 nm for arrhythmia monitoring." IEEE Journal of Solid-State Circuits 50, No. 1 (2014): 375-390.

Chip Scale Review, Jul.-Aug. 2019, Semiconductor-on-Polymer™ chip-scale packaging (SoP CSP) By Douglas Hackler, Dale Wilson [American Semiconductor] and Edward Prack [MASIP LLC].

EaglePicher medical Power, Contego 3 mAh Battery D-00122 (2018).

EM Microelectronic—marin S.A. EM4205-EM4305 specifications (2013).

Fair-Rite Products Corp Catalog (2013).

Future Technology Magazine, Issue 1706 Analog Sensing (2017).

Jang, Taekwang, Gyouho Kim, Benjamin Kempke, Michael B. Henry, Nikolaos Chiotellis, Carl Pfeiffer, Dongkwun Kim et al. "Circuit and system designs of ultra-low power sensor nodes with illustration in a miniaturized GNSS logger for position tracking: Part I-Analog circuit techniques." IEEE Transactions on Circuits and Systems I: Regular Papers 64, No. 9 (2017): 2237-2249.

Jang, Taekwang, Gyouho Kim, Benjamin Kempke, Michael B. Henry, Nikolaos Chiotellis, Carl Pfeiffer, Dongkwun Kim et al. "Circuit and system designs of ultra-low power sensor nodes with illustration in a miniaturized GNSS logger for position tracking: Part II-Data communication, energy harvesting, power management, and digital circuits." IEEE Transactions on Circuits and Systems I: Regular Papers 64, No. 9 (2017): 2250-2262.

Jeon, Dongsuk, Yen-Po Chen, Yoonmyung Lee, Yejoong Kim, Zhiyoong Foo, Grant Kruger, Hakan Oral et al. "24.3 An implant-able 64nW ECG-monitoring mixed-signal SoC for arrhythmia diagnosis." In 2014 IEEE International Solid-State Circuits Conference Digest of Technical Papers (ISSCC), pp. 416-417. IEEE, 2014.

Jeong, Junwon, Seokhyeon Jeong, Dennis Sylvester, David Blaauw, and Chulwoo Kim. "A 42 n.J/conversion on-demand state-of-charge indicator for miniature IoT li-ion batteries." IEEE Journal of Solid-State Circuits 54, No. 2 (2018): 524-537.

Jeong, Seokhyeon, Yu Chen, Taekwang Jang, Julius Ming-Lin Tsai, David Blaauw, Hun-Seok Kim, and Dennis Sylvester. "Always-on 12-nW acoustic sensing and object recognition microsystem for unattended ground sensor nodes." IEEE Journal of Solid-State Circuits 53, No. 1 (2017): 261-274.

Kosari, Avish, Jacob Breiholz, NingXi Liu, Benton H. Calhoun, and David D. Wentzloff. "A 0.5 v 68 nw ecg monitoring analog front-end for arrhythmia diagnosis." Journal of Low Power Electronics and Applications 8, No. 3 (2018): 27.

Lee, Jae-Ho, and Dong-Wook Seo. "Development of ECG monitoring system and implantable device with wireless charging." Micromachines 10, No. 1 (2019): 38.

Lifechip flyer (2008).

NXP B.V. "NXP low-frequency HITAG-μ ICs" (2010).

NXP B.V. "NXP NFC tag ICs NTAG21x" (2013).

NXP B.V. NHS3100 Temperature Logger specifications (2018).

NXP B.V. NHS3152 Therapy Adherence Resistive Monitor specifications (2018).

NXP B.V. NTAG® SmartSensor Portfolio Brochure (2017).

NXP B.V. NTAG213/215/216 NFC Forum Type 2 Tag Compliant IC with 144/504/888 Bytes user memory specifications (2012).

NXP B.V. QN9080-001-M17 Ultra Low-Power Bluetooth Smart 5.0 SIP specifications (2018).

NXP B.V. SL3S4011_4021 UCODE I2C Product Data Sheet, Version 3.5—Sep. 10, 2018.

NXP B.V. SOT902-3 Plastic Extremely Thin Quad Flat Package, No. leads, 8 terminals, Jul. 21, 2016.

Oh, Sechang, Yoonmyung Lee, Jingcheng Wang, Zhiyoong Foo, Yejoong Kim, Wanyeong Jung, Ziyun Li, David Blaauw, and Dennis Sylvester. "A dual-slope capacitance-to-digital converter integrated in an implantable pressure-sensing system." IEEE Journal of Solid-State Circuits 50, No. 7 (2015): 1581-1591.

Sandy Mahfouz, "Kernel-based Machine Learning for Tracking and Environmental Monitoring in Wireless Sensor Networks", Ph.D Thesis (2015), Universite De Technologie De Troyes.

Shi, Bojing, Zhou Li, and Yubo Fan. "Implantable energy-harvesting devices." Advanced Materials 30, No. 44 (2018): 1801511.

ST Microelectronics IMP34DT05 specifications (2019).

ST Microelectronics, STM32WB5MMG Datasheet, Bluetooth® Low Energy 5.0 and 802.15.4 module DS13252 Rev. Nov. 1, 2020.

Texas Instruments Tag-it HF-I Plus Transponder IC Reference Guide (2007).

THOR-NFC/Multiprotocol data logger IC Including on-chip temperature sensor, Delta. Aisc.madebydelta.com (2016).

UNO RFID Transponders and Readers (2013).

Yasin, Muhammad, Temesghen Tekeste, Hani Saleh, Baker Mohammad, Ozgur Sinanoglu, and Mohammed Ismail. "Ultra-low power, secure IoT platform for predicting cardiovascular diseases." IEEE Transactions on Circuits and Systems I: Regular Papers 64, No. 9 (2017): 2624-2637.

* cited by examiner

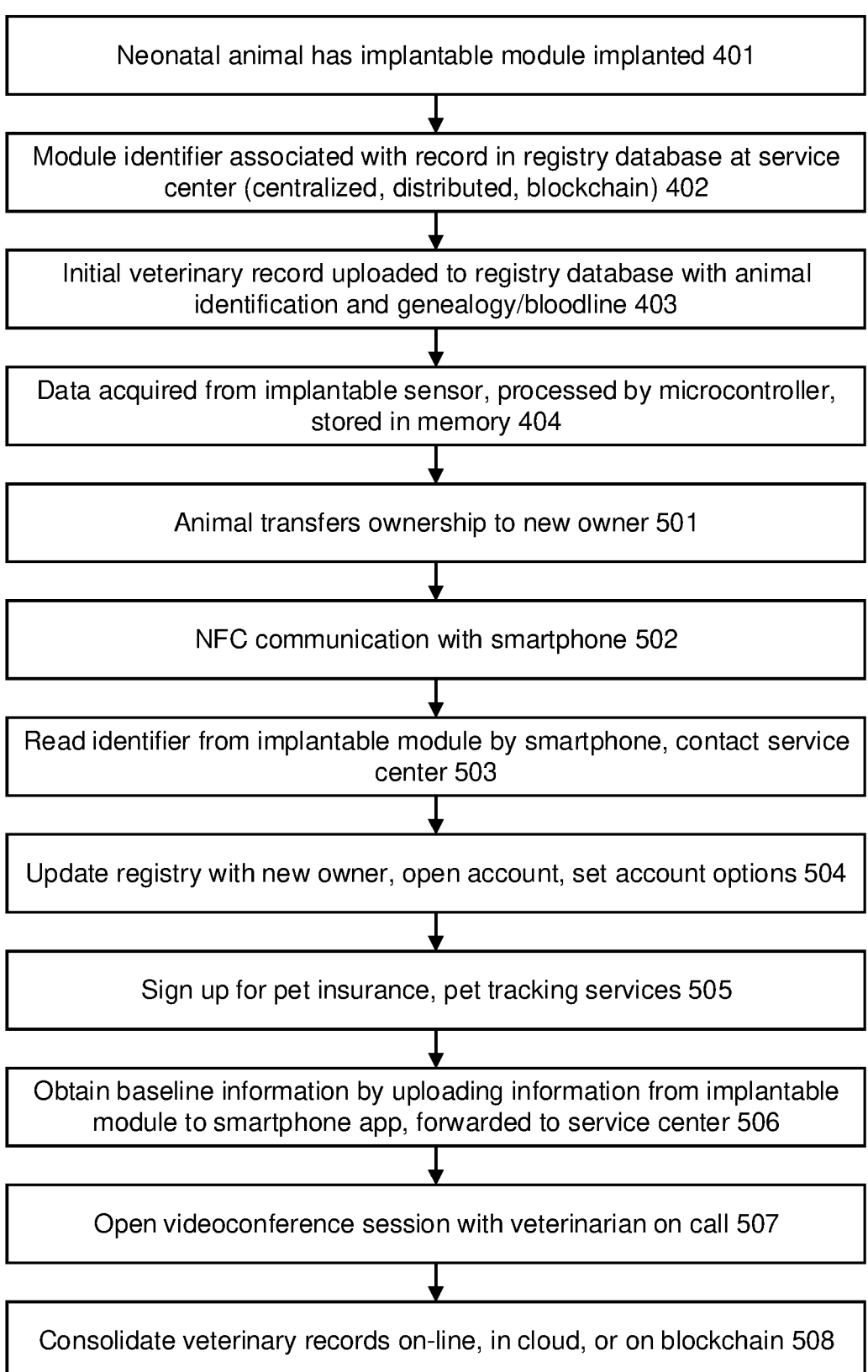

Neonatal animal has implantable module implanted 401

Module identifier associated with record in registry database at service center (centralized, distributed, blockchain) 402

Initial veterinary record uploaded to registry database with animal identification and genealogy/bloodline 403

Data acquired from implantable sensor, processed by microcontroller, stored in memory 404

Animal transfers ownership to new owner 501

NFC communication with smartphone 502

Read identifier from implantable module by smartphone, contact service center 503

Update registry with new owner, open account, set account options 504

Sign up for pet insurance, pet tracking services 505

Obtain baseline information by uploading information from implantable module to smartphone app, forwarded to service center 506

Open videoconference session with veterinarian on call 507

Consolidate veterinary records on-line, in cloud, or on blockchain 508

Fig. 5

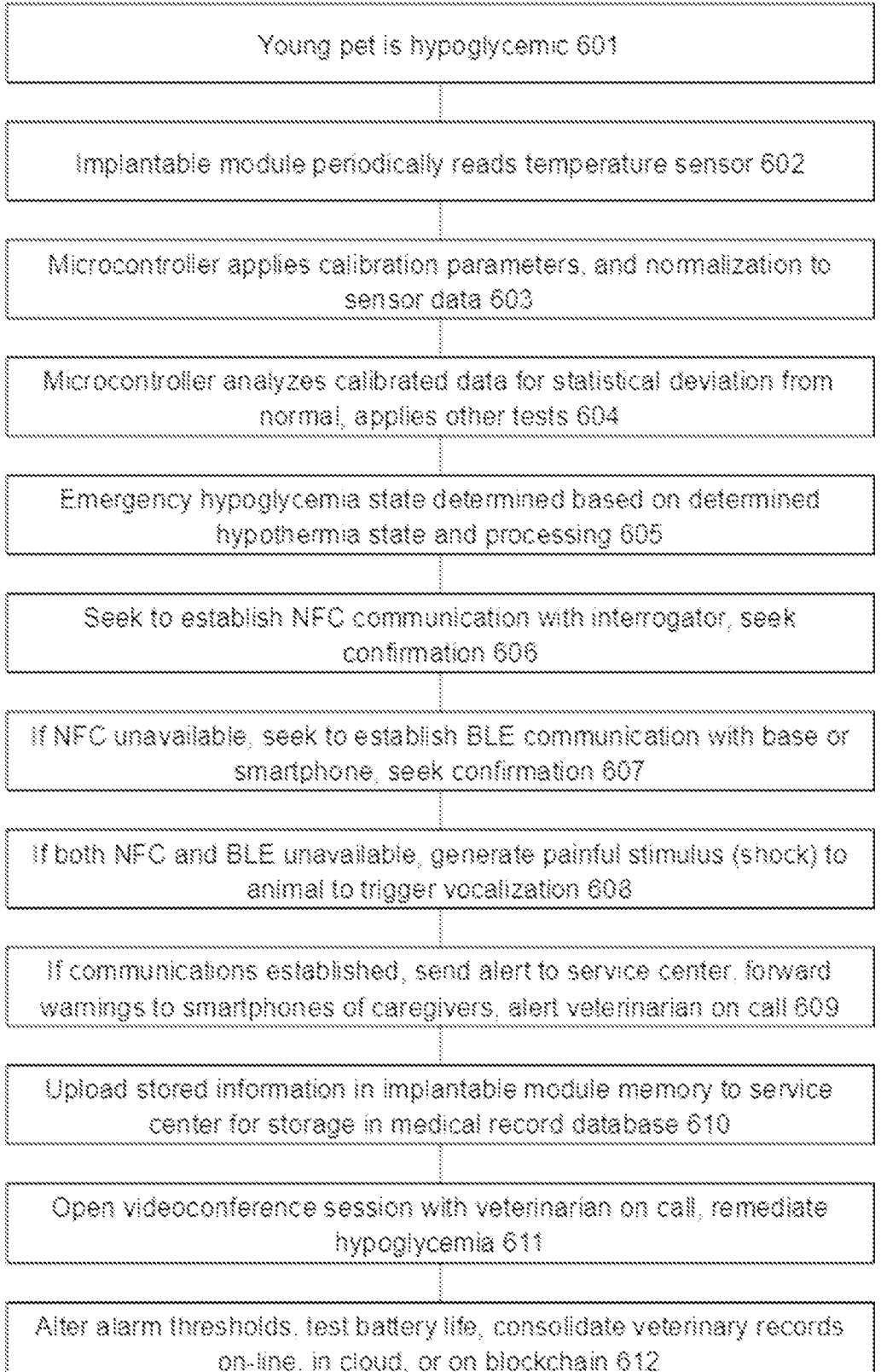

Young pet is hypoglycemic 601

Implantable module periodically reads temperature sensor 602

Microcontroller applies calibration parameters, and normalization to sensor data 603

Microcontroller analyzes calibrated data for statistical deviation from normal, applies other tests 604

Emergency hypoglycemia state determined based on determined hypothermia state and processing 605

Seek to establish NFC communication with interrogator, seek confirmation 606

If NFC unavailable, seek to establish BLE communication with base or smartphone, seek confirmation 607

If both NFC and BLE unavailable, generate painful stimulus (shock) to animal to trigger vocalization 608

If communications established, send alert to service center, forward warnings to smartphones of caregivers, alert veterinarian on call 609

Upload stored information in implantable module memory to service center for storage in medical record database 610

Open videoconference session with veterinarian on call, remediate hypoglycemia 611

Alter alarm thresholds, test battery life, consolidate veterinary records on-line, in cloud, or on blockchain 612

Fig. 6

TELEMETRY IMPLANTS

CROSS REFERENCE TO RELATED APPLICATIONS

The present application is a non-provisional of, and claims benefit of priority under 35 U.S.C. § 119(e) from, U.S. Provisional Patent Application No. 62/821,013 filed Mar. 20, 2019, the entirety of which is expressly incorporated herein by reference.

FIELD OF THE INVENTION

The present invention relates to implantable devices for sensing and reporting physiological conditions in an animal or human subject.

BACKGROUND OF THE INVENTION

The references, standards, and patent documents referenced in this disclosure are each expressly incorporated herein by reference in their entirety.

Implantable modules are commonly used to identify animals and in some cases humans. These modules often comply with RFID standards. Two standard in particular were developed and deployed for animal tracking, e.g., ISO 11784 and 11785. However, these operate at a frequency of 125 kHz or 134.2 kHz, which is incompatible with NFC standards implemented in smartphones, which support operation at 13.56 MHz. Further, the typical implantable animal identification tag does not support data logging of biological signals, especially when interrogator excitation is unavailable.

Implantable identification tags typically have limited use, such as purely identification, which in the case of pets comes into play when the pet becomes lost, and in the case of livestock may be used for management. In the case of pets, a business model has evolved for maintaining a registry database to permit finders of lost pets to identify the animal based on the RFID tag identification code. While in some cases the tag may be rewritable and capable of storing limited information, in many cases, an on-line database record referenced by the tag is preferred.

Implantable tags are also employed in research, and such ISO 11784 and 11785 compliant tags may have thermal sensors. See, U.S. Pat. No. 7,015,826; www.surepetcare-.com/en-gb/bio-thermo; www.implantable-device.com/2016/01/19/destron-fearing-bio-thermo-pet-id-temperature-sensor-implantable-tag/.

NFC compatible implantable tags are known. The reference design from Sensionics does not have a persistent power source, and requires NFC interrogation fields for power.

DeHennis, Andrew, Stefan Getzlaff, David Grice, and Marko Mailand. "An NFC-enabled CMOS IC for a wireless fully implantable glucose sensor." IEEE journal of biomedical and health informatics 20, no. 1 (2015): 18-28; www.medicaldesignbriefs.com/component/content/article/mdb/features/applications/17695; ieeexplore.ieee.org/abstract/document/6688255;

Tankiewicz, Szymon, Joshua Schaefer, and Andrew DeHennis. "A co-planar, near field communication telemetry link for a fully-implantable glucose sensor using high permeability ferrites." In SENSORS, 2013 IEEE, pp. 1-4. IEEE, 2013;

Chen, Xiaoxiao Oliver, Suresh Addaguduru, Colleen Mdingi, Ravi Rastogi, and Andrew DeHennis. "Usability, Safety, And Benefits Of Multiple Sensor Use Of A Long-Term Implantable Continuous Glucose Monitoring System." In Diabetes Technology & Therapeutics, Vol. 20, Pp. A42-A42. 140 Huguenot Street, 3rd Fl, New Rochelle, Ny 10801 Usa: Mary Ann Liebert, Inc., 2018;

Choudhary, Pratik, J. Hans DeVries, Jort Kropff, Sankalpa Neupane, Steve C. Bain, Christoph Kapitza, Thomas Forst, Manuela Link, Ravi Rastogi, and Xiaoxiao Oliver Chen. "Glycemic Benefits of a Long-Term Implantable Glucose Sensor in the PRECISE Study." Screening 55, no. 7.5 (2016): 1-1;

Rajaraman, S., X. Chen, X. Wang, A. DeHennis, and T. Whitehurst. "A Calibration Algorithm For Compensating Errors in Reference Glucose Measurements For A Fluorescence-Based, Fully Implantable Continuous Glucose Sensor." Senseonics, Incorporated Germantown, Maryland 20876, USA;

DeHennis, A., X. Wang, C. Mdingi, O. Tymchyshyn, T. Whitehurst, and S. Rajaraman. "Differences in Upper Arm versus Wrist Insertion Sites with Fluorescence-based Continuous Glucose Sensor.", Senseonics (formerly Sensors for Medicine and Science, Inc.), Germantown, Maryland USA;

Christiansen, Mark P., Leslie J. Klaff, Timothy S. Bailey, Ronald Brazg, Grace Carlson, and Katherine S. Tweden. "A prospective multicenter evaluation of the accuracy and safety of an implanted continuous glucose sensor: the PRECISION study." Diabetes technology & therapeutics 21, no. 5 (2019): 231-237;

Deiss, Dorothee, Concetta Irace, Grace Carlson, Katherine S. Tweden, and Francine R. Kaufman. "Real-world safety of an implantable continuous glucose sensor over multiple cycles of use: a post-market registry study." Diabetes technology & therapeutics 22, no. 1 (2020): 48-52;

Sanchez, Patricia, Samanwoy Ghosh-Dastidar, Katherine S. Tweden, and Francine R. Kaufman. "Real-world data from the first US commercial Users of an implantable continuous glucose sensor." Diabetes Technology & Therapeutics 21, no. 12 (2019): 677-681;

Saadatfard, O., M. Muzny, and E. Arsand. "Wearable technologies and Sensors.", Fact Sheet No. 4/2016 ISSN: 2535-277, ehealthresearch.no;

Barnard, Katharine, Colleen Mdingi, and Pratik Choudhary. "Usability Feedback of the 90-Day Implantable Glucose Sensor in the PRECISE Study." In Diabetes, vol. 65, pp. A229-A229. 1701 N Beauregard St, Alexandria, VA 22311-1717 USA: Amer Diabetes Assoc, 2016;

Irace, Concetta, Antonio Cutruzzola, Annamaria Nuzzi, Roberta Assaloni, Barbara Brunato, Dario Pitocco, Linda Tartaglione et al. "Clinical Use of a 180-Day Implantable Glucose Sensor Improves Glycated Hemoglobin and Time in Range in Patients with Type 1 Diabetes." Diabetes, Obesity and Metabolism (2020);

Karvonen, Heikki, Juha Petajajarvi, Ville Niemela, Matti Hamalainen, Jari Iinatti, and Ryuji Kohno. "Energy efficient UWB-WUR dual-radio solution for WBANs." In 2017 11th International Symposium on Medical Information and Communication Technology (IS-MICT), pp. 64-68. IEEE, 2017.

Another design employs a photovoltaic cell to provide power to an implantable device.

Lim, Wootaek, Inhee Lee, Dennis Sylvester, and David Blaauw. "8.2 Batteryless Sub-nW Cortex-M0+ processor with dynamic leakage-suppression logic." In 2015

IEEE International Solid-State Circuits Conference-(ISSCC) Digest of Technical Papers, pp. 1-3. IEEE, 2015.

Paul, Somnath, Vinayak Honkote, Ryan Gary Kim, Turbo Majumder, Paolo A. Aseron, Vaughn Grossnickle, Robert Sankman et al. "A sub-cm 3 energy-harvesting stacked wireless sensor node featuring a near-threshold voltage IA-32 microcontroller in 14-nm tri-gate CMOS for always-ON always-sensing applications." IEEE Journal of Solid-State Circuits 52, no. 4 (2017): 961-971.

Kim, Soaram, Itmenon Towfeeq, Yongchang Dong, Sean Gorman, Apparao M. Rao, and Goutam Koley. "P (VDF-TrFE) film on PDMS substrate for energy harvesting applications." Applied Sciences 8, no. 2 (2018): 213.

A further design for an implantable device employs a photovoltaic energy harvesting system and a thin film lithium ion battery.

Chen, Gregory, Matthew Fojtik, Daeyeon Kim, David Fick, Junsun Park, Mingoo Seok, Mao-Ter Chen, Zhiyoong Foo, Dennis Sylvester, and David Blaauw. "Millimeter-scale nearly perpetual sensor system with stacked battery and solar cells." In 2010 IEEE International Solid-State Circuits Conference-(ISSCC), pp. 288-289. IEEE, 2010.

Fojtik, Matthew, Daeyeon Kim, Gregory Chen, Yu-Shiang Lin, David Fick, Junsun Park, Mingoo Seok et al. "A millimeter-scale energy-autonomous sensor system with stacked battery and solar cells." IEEE Journal of Solid-State Circuits 48, no. 3 (2013): 801-813.

Lee, Inhee, Suyoung Bang, Yoonmyung Lee, Yejoong Kim, Gyouho Kim, Dennis Sylvester, and David Blaauw. "A 635 pW battery voltage supervisory circuit for miniature sensor nodes." In 2012 Symposium on VLSI Circuits (VLSIC), pp. 202-203. IEEE, 2012.

Lee, Yoonmyung, Suyoung Bang, Inhee Lee, Yejoong Kim, Gyouho Kim, Mohammad Hassan Ghaed, Pat Pannuto, Prabal Dutta, Dennis Sylvester, and David Blaauw. "A modular 1 mm^die-stacked sensing platform with low power I^2C inter-die communication and multi-modal energy harvesting." IEEE Journal of Solid-State Circuits 48, no. 1 (2012): 229-243.

Oh, Sechang, Minchang Cho, Xiao Wu, Yejoong Kim, Li-Xuan Chuo, Wootaek Lim, Pat Pannuto et al. "IoT 2—the Internet of Tiny Things: Realizing mm-Scale Sensors through 3D Die Stacking." In 2019 Design, Automation & Test in Europe Conference & Exhibition (DATE), pp. 686-691. IEEE, 2019.

Kang, Taewook, Inhee Lee, Sechang Oh, Taekwang Jang, Yejoong Kim, Hyochan Ahn, Gyouho Kim et al. "A 1.74. 12 mm 3 Fully Integrated pH Sensor for Implantable Applications using Differential Sensing and Drift-Compensation." In 2019 Symposium on VLSI Circuits, pp. C310-C311. IEEE, 2019.

Wu, Xiao, David Theodore Blaauw, and Dennis Michael Chen Sylvester. "Energy harvester." U.S. Pat. No. 10,476,382, issued Nov. 12, 2019.

Bollella, Paolo, Inhee Lee, David Blaauw, and Evgeny Katz. "A Microelectronic Sensor Device Powered by a Small Implantable Biofuel Cell." ChemPhysChem 21, no. 1 (2020): 120-128.

El Alaoui, Mustapha, Fouad Farah, Karim El Khadiri, Hassan Qjidaa, Abdellah Aarab, Ahmed Lakhssassi, and Ahmed Tahiri. "Design and Analysis of New Level Shifter With Gate Driver for Li-Ion Battery Charger in 180 nm CMOS Technology." Iranian Journal of Electrical and Electronic Engineering 15, no. 4 (2019): 477-484.

Park, Jeongpyo, Min-Gyu Jeong, Jin-Gyu Kang, and Changsik Yoo. "A Solar Energy Harvesting Buck-Boost Converter with Battery-Charging and Battery-Assisted Modes." IEEE Transactions on Industrial Electronics (2020).

Radfar, Mohsen, Amir Nakhlestani, Hoang Le Viet, and Aniruddha Desai. "Battery Management Technique to reduce Standby Energy Consumption in Ultra-Low Power IoT and Sensory Applications." IEEE Transactions on Circuits and Systems I: Regular Papers (2019).

Sharma, Sukesha, Preeti Singh, Oshin Garg, and Pooja Tuteja. "Indoor light energy harvesting using infrared LED." International Journal of Environmental Analytical Chemistry (2020): 1-11.

Choi, Myungjoon, Dennis Sylvester, and David T. Blaauw. "Environmental sensor." U.S. Pat. No. 10,254, 173, issued Apr. 9, 2019.

Energy harvesting toward powering Bluetooth transceivers has been considered.

Shaik, Mahammad Firose, and M. Monica Subashini. "Implementation of wearable glucose sensor node with energy harvesting for Wireless Body Area Network." In 2019 5th International Conference on Advanced Computing & Communication Systems (ICACCS), pp. 624-627. IEEE, 2019.

Kruiskamp, Wim. "From Bluetooth Low-Energy to Bluetooth No-Energy: System and Circuit Aspects of Energy Harvesting for IoT Applications." In Low-Power Analog Techniques, Sensors for Mobile Devices, and Energy Efficient Amplifiers, pp. 13-30. Springer, Cham, 2019.

Brunecker, Oliver, and Michele Magno. "TinyBird: An Energy Neutral Acoustic Bluetooth-Low-Energy Sensor Node with RF Energy Harvesting." In Proceedings of the 7th International Workshop on Energy Harvesting & Energy-Neutral Sensing Systems, pp. 1-7. 2019.

Mouris, Boules A., Wael Elshennawy, Panagiotis Petridis, Yuan Ding, and Spyridon N. Daskalakis. "Rectenna for Bluetooth Low Energy Applications." In Wireless Power Week 2019. 2019.

Zhang, Hao, Yong-Xin Guo, Zheng Zhong, and Wen Wu. "Cooperative integration of RF energy harvesting and dedicated WPT for wireless sensor networks." IEEE Microwave and Wireless Components Letters 29, no. 4 (2019): 291-293.

Gummeson, Jeremy. "Energy Harvesting is Charging Up." GetMobile: Mobile Computing and Communications 22, no. 4 (2019): 22-24.

Soonsawad, Perm, Kang Eun Jeon, James She, Ching Hong Lam, and Pai Chet Ng. "Maximizing Energy Harvesting with Adjustable Solar Panel for BLE Beacon." In 2019 International Conference on Internet of Things (iThings) and IEEE Green Computing and Communications (GreenCom) and IEEE Cyber, Physical and Social Computing (CPSCom) and IEEE Smart Data (SmartData), pp. 229-234. IEEE, 2019.

Fraternali, Francesco, Bharathan Balaji, Yuvraj Agarwal, and Rajesh K. Gupta. "ACES—Automatic Configuration of Energy Harvesting Sensors with Reinforcement Learning." arXiv preprint arXiv:1909.01968 (2019).

Yang, Shiheng, Jun Yin, Haidong Yi, Wei-Han Yu, Pui-In Mak, and Rui P. Martins. "A 0.2-V Energy-Harvesting BLE Transmitter With a Micropower Manager Achieving 25% System Efficiency at 0-dBm Output and

5

5.2-nW Sleep Power in 28-nm CMOS." IEEE Journal of Solid-State Circuits 54, no. 5 (2019): 1351-1362.

Magno, Michele, Xiaying Wang, Manuel Eggimann, Lukas Cavigelli, and Luca Benini. "InfiniWolf: Energy Efficient Smart Bracelet for Edge Computing with Dual Source Energy Harvesting." arXiv preprint arXiv: 2003.00041 (2020).

Various types of implantable electronic technologies have been devised. Some of these provide a means of extracorporeal communication, such as radio frequency communications. In this realm, there are generally two subcategories of communication: active transmission, and passive backscatter (RFID). Active transmission requires an internal power source to provide the energy for transmitting the radio waves, while passive backscatter modulates an incident radio frequency (RF) field, without supplying significant RF power itself. Passive backscatter RF technologies typically have very limited range, and must therefore be proximate to an interrogator to supply the incident exciting RF field. In a typical implementation, an energy harvesting scheme draws some of the incident RF power to run the modulator. Examples of these technologies are known as RFID and NFC.

The International Organization for Standardization (ISO) has created standards for tracking cattle with RFID. ISO 11784 defines how data is structured on the tag. ISO 11785 defines the air interface protocol. ISO has created a standard for the air interface protocol for RFID tags used in payment systems and contactless smart cards (ISO 14443) and in vicinity cards (ISO 15693). ISO/IEC 10536 covers Close Coupling Cards. It also has established standards for testing the conformance of RFID tags and readers to a standard (ISO 18047), and for testing the performance of RFID tags and readers (ISO 18046). ISO has developed RFID standards for automatic identification and item management. This standard, known as the ISO 18000 series, covers the air interface protocol for systems likely to be used to track goods in the supply chain. They cover the major frequencies used in RFID systems around the world. The seven parts are: 18000-1: Generic parameters for air interfaces for globally accepted frequencies; 18000-2: Air interface for 135 KHz; 18000-3: Air interface for 13.56 MHz; 18000-4: Air interface for 2.45 GHz; 18000-5: Air interface for 5.8 GHz; 18000-6: Air interface for 860 MHz to 930 MHz; and 18000-7: Air interface at 433.92 MHz. EPCglobal's UHF Generation 2 air interface protocol was incorporated into the ISO/IEC 18000-6 Amendment 1 as Type C. ISO/IEC 15693 systems operate at the 13.56 MHz frequency, and offer maximum read distance of 1-1.5 meters. As the vicinity cards have to operate at a greater distance, the necessary magnetic field is less (0.15 to 5 A/m) than that for a proximity card (1.5 to 7.5 A/m).

The NFC interface protocol standard (ISO/IEC 18092/ NFCIP-1) uses components from the RFID standards ISO/ IEC 14443 (Type A) and JIS X 6319-4. This essentially merges the technologies MIFARE (by NXP) and FeliCa (by Sony). In addition, ISO/IEC 21481 (NFCIP-2) defines compatibility/coexistence mechanisms between NFC and other HF-RFID standards (such as ISO/IEC 15693). NFCIP-1 defines two communication modes: active and passive NFC peer-to-peer mode at three different communication speeds (106 kbps, 212 kbps and 424 kbps). Passive P2P mode at 106 kbps uses the same modulation, coding, framing, and anticollision primitives as ISO/IEC 14443A. One side (one device) operates in a mode that is similar to a ISO/IEC 14443A reader and the other side (other device) operates in a mode that is similar to a ISO/IEC 14443A card. Passive P2P mode at 212 kbps and 424 kbps uses the same modulation, coding, framing, and anticollision primitives as JIS X 6319-4. One side (one device) operates in a mode that is similar to a JIS X 6319-4 reader and the other side (other device) operates in a mode that is similar to a JIS X 6319-4 card. Active P2P mode at 106 kbps uses the same modulation, coding, and framing as the reader-side of ISO/IEC 14443A. Active P2P mode at 212 kbps and 424 kbps uses the same modulation, coding, and framing as the reader-side of JIS X 6319-4. This means that NFC devices that support passive P2P mode also support all the protocol primitives to operate as ISO/IEC 14443A and JIS X 6319-4 readers as well as cards. In fact, an NFC device that waits to be activated by another NFC device in passive peer-to-peer mode will also be detectable by an HF-RFID reader (that polls for tags of the respective standard).

Android NFC phones can typically detect and read at least transponders that implement the anti-collision and activation of ISO/IEC 14443-3 (though there are some limitations with Type B), Topaz (a variation of ISO/IEC 14443A), FeliCa (JIS X 6319-4) cards, and ISO/IEC 15693 transponders. Some also support MIFARE Classic cards (which use a protocol similar to ISO/IEC 14443-3A) and B' (a variation of ISO/IEC 14443B). Recent Android NFC devices are also capable of emulating smartcards based on ISO/IEC 14443-4 (typically Type A).

A previously known "neural dust" system includes small, implantable devices (referred to as "neural dust" or "motes"), an implantable ultrasound transceiver that communicates with each of the motes using ultrasound transmissions and backscatter transmissions reflected from the motes, and an external transceiver that communicates wirelessly with the implantable ultrasound transceiver. See Seo et al., Neural dust: an ultrasonic, low power solution for chronic brain-machine interfaces, arXiv: 1307.2196v1 (Jul. 8, 2013); Seo et al., Model validation of untethered, ultrasonic neural dust motes for cortical recording, Journal of Neuroscience Methods, vol. 224, pp. 114-122; and Bertrand et al., Beamforming approaches for untethered, ultrasonic neural dust motes for cortical recording: a simulation study, IEEE EMBC (August 2014); iota.bio/technology/. The neural dust system described in these papers is used for cortical recording (i.e., the recording of brain electrical signals). In that application as shown in the papers, the motes are implanted in the brain tissue (cortex), the ultrasound transceiver (i.e., an "interrogator") is implanted below the dura, on the cortex, and the external transceiver is placed against the head of the patient proximate to where the subdural ultrasound transceiver is implanted. See also United States Patent Application 20190022428.

Careful monitoring of certain physiological conditions in a subject can allow for a better understanding of health and disease prognosis. For example, blood sugar monitoring is used to monitor the health of a diabetic patient, and blood oxygenation levels are useful in monitoring compartment syndrome, cancer or metastases monitoring, or organ transplants. U.S. 20170281092 discloses an implantable glucose sensor module. Continuous detection and/or quantification of blood glucose values can be accomplished using a continuous glucose monitor (CGM), one example of a continuous analyte sensor. In particular, the continuous analyte sensor measures the concentration of a given analyte within the host, e.g., glucose, and a raw signal is generated by electronics (sometimes referred to as a sensor electronics module) associated with the continuous analyte sensor. The sensor electronics module can be physically connected to the continuous analyte sensor and includes electronics/sensor measurement circuitry configured to process a data stream associated with the analyte concentration measured by the continuous analyte sensor in order to generate sensor information that includes the raw signal/raw sensor data, transformed sensor data, and/or any other sensor data or data derived therefrom, e.g., predictive or trend data. The sensor electronics module may further be configured to generate sensor information that is customized for respective display devices, such that different display devices may receive different sensor information for presentation to the host, a host care taker, etc. The sensor electronics module includes one or more communication modules, such as wireless radio transmitters for transmitting the sensor information to the display devices. The display devices may include one or more communication modules for transmitting sensor information or other data, such as fault or error information (described in greater detail below) to a remote server or database. A reliable and true raw signal is generally presumed to have been received by the sensor electronics module. However, in some cases, faults or errors may occur and the raw signal is no longer reliable and true. These faults or errors may be detectable by analysis of the signal, analysis of the clinical context, or both. Discrimination can therefore be performed to distinguish the same from actual measured signal behavior, as well as for responsive signal processing, which can vary according to the fault.

Faults or errors may be caused in a number of ways, whether they're associated with a physiological activity in the host, e.g., metabolic responses, and/or associated with an in vivo portion of the continuous analyte sensor as the same settles into the host environment, during use over time, etc. They may also be associated with transient events within the control of a patient or with the external environment surrounding continuous analyte sensor. Accordingly, various proposals provide fault or error detection in a continuous analyte sensor system, and the implementation of one or more corrective/compensatory actions in response to the detected fault or error so that a user of the analyte sensor system is provided with accurate analyte measurement data. For example, an anomalous or abnormal change or fluctuation in a signal indicative of an analyte concentration in a host can be detected. Once detected, the cause(s) of the change in the signal can be determined, and the change in the signal can be accounted for such that the analyte concentration is the host is represented accurately.

Systems were proposed for continuous measurement of an analyte in a host that includes: a continuous analyte sensor configured to continuously measure a concentration of the analyte in the host; and a sensor electronics module physically connected to the continuous analyte sensor to receive the analyte concentration measurements and communicate them to display devices. In particular, the sensor electronics module includes electronics configured to process a data stream associated with an analyte concentration measured by the continuous analyte sensor in order to generate sensor information that includes raw sensor data, transformed sensor data, and/or any other sensor data or data derived therefrom, e.g., predictive or trend data. The sensor electronics module may further be configured to generate sensor information that is customized for respective display devices, such that different display devices may receive different sensor information for presentation to the host, a host care taker, etc. Further still, the sensor electronics module includes one or more communication modules, such as wireless radio transmitters for transmitting the sensor information to the display devices.

The sensor electronics module may be configured to search for and/or attempt to wirelessly communicate with a display device. The search for and/or attempted wireless communication with the display device can occur in a predetermined and/or programmable order (e.g., grading and/or escalating). The sensor electronics module is not necessarily tied to a single display device. Rather the sensor electronics module is configured to communicate with a plurality of different display devices directly, systematically, simultaneously (e.g., via broadcasting), regularly, periodically, randomly, on-demand, in response to a query, based on alerts or alarms, and/or the like.

The sensor electronics module may receive sensor information from the continuous analyte sensor. This sensor information may be raw data which the display device receives and processes, e.g., in accordance with one or more algorithms, for generating and/or displaying estimated analyte values. In the context of continuous glucose monitoring, the estimated analyte values may be estimated glucose value data. Some display devices include software including display instructions (software programming comprising instructions configured to display the sensor information and optionally query the sensor electronics module to obtain the displayable sensor information) configured to enable display of the displayable sensor information thereon.

The processing of the raw data may be performed at the sensor electronics module. That is, the requisite algorithms, software, and/or other processing functionality for transforming the raw data into estimated analyte value data may be implemented at the sensor electronics module rather than at the display device. Transforming the raw data at the sensor electronics module may avoid the possibility for inconsistent estimated analyte value data, e.g., due to inconsistent calibration between two or more display devices. Moreover, implementing this functionality at the sensor electronics module may discourage third party display device/medicament delivery device providers from tampering or otherwise altering the processing algorithms and software.

Certain display devices may be in direct wireless communication with the sensor electronics module, although intermediate network hardware, firmware, and/or software can be included within the direct wireless communication. A repeater (e.g., a Bluetooth repeater) can be used to re-transmit the transmitted sensor information to a location farther away than the immediate range of the telemetry module of the sensor electronics module. A receiver (e.g., Bluetooth receiver) can be used to re-transmit the transmitted sensor information to a display device, e.g., a TV screen, possibly in a different format, such as in a text message.

One or more display devices may be configured to query the sensor electronics module for sensor information, where the display device requests sensor information from the sensor electronics module in an "on-demand" fashion, for example, in response to a query. The sensor electronics module may be configured for periodic, systematic, regular, or irregular or aperiodic transmission of sensor information to one or more display devices (for example, every one, two, five, or ten minutes or more). The sensor electronics module may be configured to transmit data packages associated with a triggered alert (e.g., triggered by one or more alert conditions).

The glucose sensor may be a continuous device, for example a subcutaneous, transdermal, transcutaneous, non-invasive, intraocular and/or intravascular (e.g., intravenous) device. Alternately, a plurality of intermittent blood samples can be analyzed. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

The analyte sensor may be an implantable glucose sensor, such as described with reference to U.S. Pat. No. 6,001,067 and U.S. Patent Publication No. 2005/0027463; a transcutaneous glucose sensor, see, U.S. Patent Publication No. 2006/0020187. The sensor may be configured to be implanted in a host vessel or extracorporeally, e.g., U.S. Patent Publication Nos. 2007/0027385; 2008/0119703; 2008/0108942, and 2007/0197890. The continuous glucose sensor may comprise a transcutaneous sensor such as described in U.S. Pat. No. 6,565,509 for example; a subcutaneous sensor, e.g., U.S. Pat. Nos. 6,579,690; 6,484,046; 6,512,939; 6,477,395; or 6,424,847. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, each of which are incorporated herein by reference in their entirety for all purposes.

Generally, a continuous analyte sensor may be an implantable analyte (e.g., glucose) sensor that utilizes amperometric electrochemical sensor technology to measure glucose concentration. Electrodes comprising continuous analyte sensor may include a working electrode, a counter electrode, and a reference electrode. The counter electrode may be provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate. The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$) and one oxygen molecule ($O_2$).

Additional electrodes can be included within the assembly, for example, a three-electrode system (working, reference, and counter electrodes) and an additional working electrode (e.g., an electrode which can be used to generate oxygen, which is configured as a baseline subtracting electrode, or which is configured for measuring additional analytes). U.S. Pat. No. 7,081,195, U.S. Patent Publication Nos. 2005/0143635 and 2007/0027385, each of which are incorporated herein by reference, describe some systems and methods for implementing and using additional working, counter, and reference electrodes. Two or more working electrodes may be provided, wherein the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Patent Publication Nos. 2005/0143635; 2007/0027385; 2007/0213611; and 2008/0083617, which are incorporated herein by reference in their entirety.

The sensor electronics module can include an application-specific integrated circuit (ASIC), a user interface, temperature sensor, motion sensor, body sensor, and clock. ASIC can also be coupled to a communication port and a battery. Further, the ASIC can include one or more additional features of sensor electronics module, such as telemetry module, potentiostat, offset/calibration module, data storage memory, and clock—can be separate from the ASIC. A potentiostat (one example of an analog front end (AFE)) is coupled to continuous analyte sensor via data line, for example, in order to receive sensor information obtained/measured by continuous analyte sensor. The potentiostat may provide a voltage to continuous analyte sensor via data line in order to bias continuous analyte sensor to enable measurement of a current value indicative of the analyte concentration in the host (also referred to as the analog portion). The potentiostat can have one channel or multiple channels (and a corresponding one or multiple data lines), depending on the number of working electrodes, for example. The potentiostat may include a resistor that translates current into voltage. A current to frequency converter may be provided that is configured to continuously integrate the measured current, for example, using a charge counting device. An A/D converter may digitize the analog signal. The raw data stream can be directly related to the current measured by the potentiostat.

A processor may control the processing of the sensor electronics module. The processor typically provides a program memory, which provides semi-permanent storage of data, for example, storing data such as sensor identifier (ID) and programming to process data streams (for example, filtering, calibration, fail-safe checking, and the like). The processor can additionally be used for the cache memory of continuous analyte monitoring system, for example for temporarily storing recent sensor data. The processor may comprise memory storage components such as ROM, RAM, dynamic-RAM, static-RAM, non-static RAM, EEPROM, rewritable ROMs, flash memory, and the like. RAM can be used for the continuous analyte monitoring system cache memory, for example for temporarily storing recent sensor information. The processor may comprise a digital filter, for example, an infinite or finite impulse response (IIR or FIR) filter, configured to smooth the raw data stream from the A/D converter. Generally, digital filters are programmed to filter data sampled at a predetermined time interval (also referred to as a sample rate). The potentiostat can be configured to measure the analyte at discrete time intervals, and these time intervals determine the sample rate of the digital filter. When the potentiostat is configured to continuously measure an analyte, for example, using a current-to-frequency converter, the processor can be programmed to request a digital value from an integrator at a predetermined time interval, also referred to as the acquisition time. The values obtained by the processor can be averaged over the acquisition time due the continuity of the current measurement. Accordingly, the acquisition time determines the sample rate of the digital filter.

The processor may be configured to generate data packages for transmission to one or more display devices. Furthermore, processor generate data packets for transmission to these outside sources, e.g., via telemetry. The data packages may be customizable for each display device, for example, and may include any available data, such as sensor information having customized sensor data and/or transformed sensor data, sensor/sensor electronics module ID code, raw data, filtered data, calibrated data, rate of change information, trend information, error detection or correction, and/or the like.

A data storage memory may be operably connected to processor and configured to store a variety of sensor information. The data storage memory may store, for example, 0.25, 0.33, 0.5, 0.66, 0.75, 1, 2, 5, 7, 9, 14, 15, 20, 30 or more days of continuous analyte sensor data, or statistics representing that data. The data storage memory may store sensor information such as raw sensor data (one or more raw analyte concentration values), calibrated data, filtered data, transformed sensor data, and/or any other displayable sensor information.

A telemetry module may be operably connected to the processor module and provide the hardware, firmware, and/or software that enable wireless communication between the sensor electronics module and one or more display devices. A variety of wireless communication technologies that can be implemented in the telemetry module include radio frequency (RF), infrared (IR), Bluetooth, Bluetooth Low Energy (BLE), spread spectrum communication, frequency hopping communication, ZigBee, IEEE 802.11/802.16, wireless (e.g., cellular) telecommunication, paging network communication, near-field communication (NFC), radio frequency ID (RFID) magnetic induction, satellite data communication, GPRS, ANT, and/or the like. the telemetry module may comprise a Bluetooth chip. Bluetooth technology may be implemented in a combination of the telemetry module and processor.

A battery may be is operatively connected to the processor (and possibly other components of the sensor electronics module) and provide the necessary power for the sensor electronics module. The battery may be rechargeable. A battery charger and/or regulator may be configured to receive energy from an internal and/or external charger. A battery regulator (or balancer) may regulate the recharging process by bleeding off excess charge current to allow all cells or batteries in the sensor electronics module to be fully charged without overcharging other cells or batteries. The battery (or batteries) is configured to be charged via an inductive and/or wireless charging pad. Batteries may be charged by a variety of methods, including wired (cable/plug), wireless, energy harvesting, electrochemical, etc. methods. Each type or model or set of batteries may have their own unique battery performance characteristics or battery profile. This can include, but is not limited to operating characteristics such as voltage range, continuous current rating, pulse current rating, voltage thresholds, etc. In order to be able to predict when a given battery is going to run out of charge/how long a battery will last in sensor electronics module, such battery parameters are used in calculations performed by the firmware/processor in sensor electronics module over the course of the life of sensor electronics module. As discussed below, one or more battery operating parameters (e.g., for different types of batteries) may be transmitted from a server to the sensor electronics module (e.g., via one of the display devices).

Bounds can be used to determine potential battery issues if operating parameters are incorrectly input. One or more operating parameters indicative of a battery profile are received by sensor electronics module. These operating parameters, examples of which are described above, can be used by the firmware of sensor electronics module to characterize the battery profile. Additionally, bounds are input based upon the one or more operating parameters at operation. These bounds can refer to minimum/maximum expected performance characteristics relative to the one or more operating parameters associated with a particular battery. During operation, the sensor electronics module determines whether the one more operating parameters exceed the permissible bounds, and if so, appropriate action taken. That is, if the determination is performed during manufacturing, sensor electronics module can go into a sleep or low power storage mode until powered on by the user. If the determination is performed when sensor electronics module is already operational, it can continue operating. If, however, sensor electronics module determines that the one or more operating parameters that were received exceed the bounds input, processor can instruct user interface or display devices to display a notification, trip an alarm or otherwise alert the user or manufacturing personnel that the operating parameters require updating at operation. The sensor electronics module may determine when to provide alert notification (e.g., for low battery) based on one of the reconfigurable battery operating parameters (e.g., voltage threshold) for the different types of batteries.

A charge pump or voltage converter may be implemented in the analyte sensor system that may increase (e.g., double) the battery voltage of a single battery to carry out power intensive operations. As such, additional batteries may not be needed, thus advantageously saving physical space of the analyte sensor system (i.e., by not installing extra batteries). The charge pump may be internally coupled to the ASIC.

Implementations can switch between a wireless charging mode and a normal, battery-powered mode. In particular sensor electronics module may have an energy harvesting circuit and a charging circuit implemented as part of, e.g., ASIC. In this way, during a first mode (e.g., during manufacturing, when proximate to an inductive power transfer coil), a wireless charger may be used to wirelessly power sensor electronics module thereby avoiding draining battery. The energy harvesting circuit may harvest power from the wireless charger. In a second mode (e.g., during normal use, remote from inductive power transfer coil), the ASIC can draw power from the battery. A mode selector circuit can be used to alternate from the first mode to the second mode. The battery may be a rechargeable battery or a primary battery, optionally with a rechargeable battery or supercapacitor can be used as an additional power source.

Environmental sensors may also be utilized. For example, a temperature sensor, e.g., temperature sensor, can be used to gauge the temperature of the host and/or sensor electronics module. A motion sensor can sense or determine movement of the host. A pressure sensor can be used to detect a pressure on an analyte sensor and/or on neighboring tissue. Other sensors include electrophysiological sensors, various analyte sensors, accelerometers, magnetometers, gyroscope (angular rotation) sensors, altimeters, heart rate sensors, microphones, etc.

A clock can regulate the rate at which processor executes instructions. The speed of clock can be configured as needed. An offset/calibration module can include circuitry or logical component(s) used to provide an offset current to shift a received signal at the potentiostat when measuring current/counts, as well as to calibrate the potentiostat for that additional offset current. The offset current can also be calibrated by offset/calibration module.

In conventional continuous analyte sensor systems in a split-system architecture, the on-skin portion of the sensor electronics is generally simplified to minimize complexity and/or size of on-skin electronics, for example, providing only raw, calibrated, and/or filtered data to a display device configured to run calibration and other algorithms required for displaying sensor information received from the on-skin portion. In contrast, an implantable sensor electronics module may execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor information, set modes of operation, evaluate the data for aberrancies, and/or the like, which are described in more detail in U.S. Pat. and Pub. Appl. Nos. U.S. Pat. Nos. 7,310,544, 6,931, 327, 2005/0043598, 2007/0032706, 2007/0016381, 2008/0033254, 2005/0203360, 2005/0154271, 2005/0192557, 2006/0222566, 2007/0203966 and 2007/0208245, each of which is incorporated herein by reference in its entirety. Furthermore, the sensor electronics module may be configured to store the transformed sensor data (e.g., estimated analyte values, trend information) and to communicate the sensor information to a plurality of different display devices. The display devices may be configured to display the sensor information as received from sensor electronics module, without any additional sensor data processing.

The analyte sensor system may include an implantable continuous analyte sensor coupled to a sensor measurement circuit for processing and managing sensor data. The sensor measurement circuit may be coupled to a processor. The processor may perform part or all of the functions of the sensor measurement circuit for obtaining and processing sensor measurement values from the implantable continuous sensor. The processor may be further coupled to a radio unit or transceiver for sending sensor information to and receiving requests and commands from an external device, such as display device, which is used to display or otherwise present the sensor information to a user. The radio unit or transceiver can wirelessly transmit and/or receive data. The transmission and receipt of such data further includes utilization of an antenna. It should be noted that more than one antenna may be utilized in the analyte sensor system. The analyte sensor system may further include a memory and a real time clock (RTC) for storing and tracking sensor information. The analyte sensor system further may include near field communication (NFC) capability. An NFC tag communication module may be implemented/integrated into the electronics in analyte sensor system.

Detection of abnormal fluctuations or changes can be accomplished by discriminating between abnormal or anomalous analyte concentration levels and "normal" or expected analyte concentration levels. Discriminating can include determining if the received signal or the received data matches or meets a predetermined criterion or performing a comparison between clinical context information corresponding to user data that excludes analyte concentration level/measurements. The discriminating may include analyzing the signal using a time-based technique, a frequency-based technique, or a wavelet-based technique. The discriminating may include raw signal analysis, residualized signal analysis, pattern analysis, and/or slow versus fast sampling. The discriminating may include projecting the received signal onto a plurality of templates, each template corresponding to a fault mode. The discriminating may include variability analysis or fuzzy logic analysis. The received clinical context data may be selected from the group consisting of: age, anthropometric data, drugs currently operating on the patient, temperature as compared to a criteria, a fault history of the patient, activity level of the patient, exercise level of the patient, a patient level of interaction with a glucose monitor, patterns of glucose signal values, clinical glucose value and its derivatives, a range of patient glucose levels over a time period, a duration over which patient glucose levels are maintained in a range, a patient glucose state, a glycemic urgency index, time of day, or pressure. The clinical context data may include time since implant, the clinical context criteria may include a range of times since implant in which dip and recover faults are likely. The clinical context data may also include a clinical glucose value and a datum selected from the group consisting of: age, anthropometric data, activity, exercise, clinical use of data, or patient interaction with an analyte monitor. Example systems and methods of discrimination are described in U.S. Pat. No. 10,238,322.

The user interface may include a variety of interfaces, such as one or more buttons, a liquid crystal display (LCD), a vibrator, an audio transducer (e.g., speaker), a backlight (not shown), and/or the like. The components that comprise user interface may provide controls to interact with the user (e.g., the host). One or more buttons may allow, for example, toggle, menu selection, option selection, status selection, yes/no response to on-screen questions, a "turn off" function (e.g., for an alarm), an "acknowledged" function (e.g., for an alarm), a reset, and/or the like. An LCD may provide the user with, for example, visual data output. An audio transducer (e.g., a speaker) may provide audible signals in response to triggering of certain alerts, such as present and/or predicted hyperglycemic and hypoglycemic conditions.

A display device may be used for alerting and providing sensor information to a user, such as host, and may include a processor for processing and managing sensor information. Display device may include a display, a memory, and a real time clock for displaying, storing and tracking sensor information, respectively. Display device may further include a radio unit or transceiver for receiving sensor information and for sending requests, instructions, and data to the analyte sensor system. The transceiver may further employ a wireless communication protocol. The memory may also be used for storing an operating system and/or a custom (e.g., proprietary) application designed for wireless data communication between a transceiver, e.g., transceiver and display device. The memory may be a single memory device or multiple memory devices and may be a volatile or non-volatile memory for storing data and/or instructions for software programs and applications. The instructions may be executed by the processor to control and manage the transceiver.

Wireless communication protocols may be used to transmit and receive data between analyte sensor system and display device. The wireless communication protocol used may be designed for use in a wireless sensor network that is optimized for periodic and small data transmissions (that may be transmitted at low rates if necessary) to and from multiple devices in a close range (e.g., a personal area network (PAN), e.g., IEEE-802.15.1, IEEE-802.15.4). For example, the wireless communication protocol may be optimized for periodic data transfers where transceivers may be configured to transmit data for short intervals and then enter low power modes for long intervals. The wireless communication protocol may have low overhead requirements both for normal data transmissions and for initially setting up communication channels (e.g., by reducing header overhead) to reduce power consumption. Burst broadcasting schemes (e.g., one-way communication) may be used. This may eliminate overhead required for acknowledgement signals and allow for periodic transmissions that consume little power.

The wireless communication protocol may further be configured to establish communication channels with multiple display devices, e.g., two or more of display devices, while implementing interference avoidance schemes. The wireless communication protocol may make use of adaptive isochronous network topologies that define various time slots and frequency bands for communication with several ones of display devices. The wireless communication protocol may thus modify transmission windows and frequencies in response to interference and to support communication with multiple ones of display devices. Accordingly, the wireless protocol may use time and frequency division multiplexing (TDMA) based schemes. The wireless communication protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth (4.0, 4.1, 4.2, 5.0, 5.1, 5.2, etc.), Bluetooth Low Energy (BLE), and ANT. The wireless communication protocol may operate in various frequency bands such as an open ISM band such as 2.4 GHz. Furthermore, to reduce power usage, the wireless communication protocol may adaptively configure data rates according to power consumption. Like the antenna of analyte sensor system, a corresponding antenna is utilized in display device for transmission/receipt of data to/from analyte sensor system. Again, one or more antennas in addition to antenna may be used to allow for the various aforementioned communication protocols to operate at their requisite frequencies/frequency ranges.

When a standardized communication protocol is used, commercially available transceiver circuits may be utilized that incorporate processing circuitry to handle low level data communication functions such as the management of data encoding, transmission frequencies, handshake protocols, and the like. The processors do not need to manage these activities, but rather provide desired data values for transmission, and manage high-level functions such as power up or down, set a rate at which messages are transmitted, and the like. Instructions and data values for performing these high level functions can be provided to the transceiver circuits, respectively, via a data bus and transfer protocol established by the manufacturer of the transceiver circuits.

A motion sensor may be an accelerometer, such as a 3-axis accelerometer for detecting user activity/motion. The motion sensor could also be used for orientation detection, e.g., sensing that sensor electronics module is in an inverted position. Analysis by processor of this sensor data (distinguished from sensor information related to analyte concentration and measured or determined by continuous analyte sensor) can result in processor determining that the user is laying on sensor electronics module. The processor may then take steps to discriminate (described in greater detail below) as sensor electronics module may give false readings of measured analyte concentration due to lack of oxygen, e.g., the user's tissue area near sensor electronics module gets pushed or pinched. The motion sensor may further comprise a 3-axis compass that can be used in conjunction with the 3-axis accelerometer to better determine the activity level of the user. An angular rotation sensor, such as a 3-axis gyroscope may also be included.

Still other external factors, such as sensor drift can result in signal fluctuations. For example, sensor drift can be experienced by continuous analyte sensor. Sensor drift can refer to a phenomenon where the sensitivity information (e.g., the relationship between measured current and the glucose level per unit time) may be affected due to changes in temperature. Because temperature can affect the metabolization of glucose, any changes in temperature (whether experienced by the user or analyte sensor system) can alter the sensitivity of continuous analyte sensor such that inaccurate glucose measurements or levels may be presented to the user.

Variations in temperature can be due to external factors (e.g., change in the body temperature of the user) and/or internal factors (e.g., change in temperature in the circuitry comprising sensor electronics module or continuous analyte sensor itself). Accordingly, temperature sensor can be used to detect whether sensor drift may be causing faults or fluctuations. In particular, pre-determined knowledge regarding a particular amount of drift associated with a particular temperature or temperature range can be used as a basis for compensating (discussed in greater detail below) for any fluctuation(s) or noise(s) upon detecting the existence or occurrence of that particular temperature or temperature range.

Continuous analyte sensors is generally configured to operate at very low currents (e.g., in the nanoamp (nA) to pico-Ampere (pA) range). Noise levels introduced by internal noise sources, such as circuitry and/or the aforementioned triboelectric effect can far exceed that of the glucose signal level, and may also drive the glucose signal level below zero. In a case where the sensor electronics module is configured to only measure positive signal values, any noise that drives the glucose signal levels below zero is not seen, and would not be compensated for. A filtering mechanism may be employed to average the measured signal.

A temperature sensor can measure the skin temperature of a host, the tissue neighboring the implantation site of continuous analyte sensor, etc. The temperature sensor can be implemented in a variety of ways and/or can refer to an array of sensors. Any sensor itself or data storage memory unit can store sensor manufacturing and calibration information (whether it be temperature sensor or another sensor(s), e.g., motion sensor, pressure sensor, etc.). Such stored sensor manufacturing and calibration information can include, but is not limited to factory-default calibration settings or information, sensor identification information, etc. Such information can be stored and used for comparison purposes or as, e.g., a baseline or threshold on which sensor electronics module can base a determination(s) of sensor and/or temperature drift, a determination of noise, faults, fluctuations, etc. Further still, temperature sensor can be implemented as a subcutaneous temperature sensor for sensing temperature near or at the tip of continuous analyte sensor. The various aforementioned temperature sensors may also be utilized to measure the temperature of other sensors and used for fluctuation-cause correlation and compensation efforts.

An implant has security issues quite distinct from other devices. The implant cannot be readily replaced or rendered obsolete by external factors. Thus, on one hand, the implant needs to be secure, while on the other hand requires some flexibility in communications to tolerate changes after implantation.

U.S. Pat. No. 9,942,051 discloses implantable and programmable personal medical devices are becoming common. In some cases, these represent applications ("apps") for smartphones. In other cases, regulated medical devices communicate through commercial off the shelf technologies. In both these cases, it is possible for provide communications to be intercepted, revealing potentially personal or confidential information. Further, it may be possible to modify communications, leading to misdiagnosis, improper treatment, or other harm.

For example, a smartphone app or the platform on which a smartphone app executes may include security vulnerabilities, even if the app is digitally signed. For example, of the medical device is a defibrillator, this could be reprogrammed to fail to generate a required discharge, or to discharge in a harmful or lethal pattern.

Oyvind Borthus and Tomas Mikael Engh, "Privacy protection in a mobile Biomedical Information Collection Service", (Master's Thesis), Agder University College, Grimstad Norway (May 2005), expressly incorporated herein in its entirety, discusses a persistent problem: How does one secure the communication from the patient to a provider, and from the provider to the patient, where the data communicated is private, and corruption of that data may be life-threatening? Borthus and Engh do not consider security of the "handheld device" as an issue to be addressed.

The use of a mobile wireless sensor gives the patient the possibility of being at home and doing his or her normal daily activities while being monitored, but it also creates the need for new mechanisms for privacy protection. Fensli, R., E. Gunnarson, and T. Gundersen (2005) "A Wearable ECG-recording System for Continuous Arrhythmia Monitoring in a Wireless Tele-Home-Care Situation," presented at The 18th IEEE International Symposium on Computer-Based Medical Systems, Dublin, Ireland. For the patient to stay in his normal environment gives several benefits for both the patient and the quality of the monitoring. The patient will be more relaxed and the recordings will not be affected by the stressful situation at a hospital.

A mobile wireless sensor is a compact electronic electrode attached to a patient that can measure different biomedical signals. In this scenario we are using a sensor for electrocardiogram (ECG) recordings as an example. This sensor will continuously measure and wirelessly transmit sampled ECG-recordings using a built-in RF-radio transmitter. The RF-radio receiver converts the ECG-samples by the use of a microcontroller before transmitting the ECG-samples to a standard personal digital assistant (PDA). The sensor measures ECG-signals with a sampling frequency up to 1000 samples per second. Crawford, M. H. et al. (1999) "ACC/AHA Guidelines for Ambulatory Electrocardiography: Executive summary and Recommendations" American College of Cardiology. The signal is digitalized with 10-bit resolution, requiring up to 10 kb/s of bandwidth plus overhead to transmit to the PDA. The range of the RF-radio signal is up to 10 meters. The transmitter chip used by the sensor described in Fensli et al. is a RF-transmitter CC1050 from ChipCon, operating at 869.700 MHz, with a bit rate of up to 76.8 kbit/s. The sensor will transmit continuously, and will be attached to the patient for 3 days to a week at a time. The sensor is a disposable unit, and will only be used once.

A PDA is used to receive the information from the sensor of Fensli et al. and will often have 400 to 600 MHz processor, 64 to 128 MB of internal memory and a memory card with capacity of more than 2 GB for storing data. The PDA has both a short range wireless RF-radio device and a GPRS card installed. (Current smartphones are more powerful, with 3 GHz multicore processors, GPUs, 4-16 GB RAM, 64-1024 GB flash memory, 5G, 4G, LTE, etc. cellular communications, IEEE-802.11, 802.15, etc. LAN and PAN specifications, etc.). The PDA is an "intelligent" unit, using automatic arrhythmia detection algorithms for analyzing the signals from the sensor and decides if the recordings are within normal values. As long as the signals are within normal values the PDA will regularly send an extract of the recordings to an electronic health register (EHR) connected to the Internet by the use of cellular communication. If an abnormal ECG activity is encountered, the PDA will store a period of the ECG recordings and then transmit the recordings to the EHR server.

There are several security and privacy threats relevant to this scenario. From a medical standpoint it is very important that the PDA only receives data from the correct sensor, and not from other devices in the same area. Keeping the integrity of the data is also very important to avoid false alarms or incorrect normal signals. The data must also be protected in such a way that possible attackers cannot get access to personal information about the patient.

For the transmission of data from the PDA to the EHR, and between users in the national health network many of the same threats applies. Integrity, security and privacy must be protected when sending electronic messages containing sensitive medical and personal information. The electronic messages contain a lot more sensitive information than the data packets sent from the sensor and thus require a higher level of security protection. Non repudiation is especially important when sending messages regarding medication and diagnosis.

Bluetooth is a short range radio standard designed for low power consumption. Bluetooth operates in the unlicensed industrial, scientific and medical (ISM) band at 2.4 to 2.485 GHz, using a spread spectrum, frequency hopping, full-duplex signal at a nominal rate of 1600 hops/sec. Bluetooth SIG (2004) "Specification of the Bluetooth System". See, en.wikipedia.org/wiki/Bluetooth_Low_Energy; en.wikipedia.org/wiki/Bluetooth. Bluetooth devices can be paired to establish a trusted connection. By user input (a pin code) they can learn a shared secret key known as a "passkey". A device can then cryptographically authenticate the identity of another device. With some devices, like wireless earphones, it is impossible for the user to enter a pin code, and the device has a fixed pin code, which can be entered into the peer device. Trusted devices can also encrypt information they transmit so no one can "listen in". The encryption can be turned off, and the passkey is stored in the device's memory, and not in the Bluetooth chip itself. The trusted connection can be canceled by either device at any time. Devices will generally require pairing or user input before it allows a remote device to use its services.

In order to communicate with other Bluetooth devices a device must be able to interpret certain Bluetooth profiles. These profiles define the possible applications. 24 profiles are defined and adopted by the Bluetooth SIG, for example: Generic Access Profile (GAP) which provides the basis for all other profiles. This profile describes which features must be implemented in all Bluetooth devices, generic procedures for discovering and linking to devices, and basic user-interface terminology; Basic Imaging Profile (BIP). This profile is designed for sending images between devices and includes the ability to resize, and convert images to make them suitable for the receiving device; and Human Interface Device Profile (HID) provides support for devices such as mice, joysticks, keyboards, etc.; Advanced Audio Distribution Profile (A2DP). Also referred to as the AV profile, it is designed to transfer a stereo audio stream like music from an MP3 player to a headset or car radio.

On the link layer Bluetooth uses the SAFER+ algorithm for authentication and key generation, and E0 stream cipher for encrypting packets. The link layer security is independent of possible application layer security. The SAFER+ (Secure and Fast Encryption Routine) algorithm is a block cipher with block size of 128 bits, and a default key size of 128 bits. Wikipedia.org "SAFER" en.wikipedia.org/wiki/ SAFER. The cipher uses 8 rounds with 4 stages; a key-mixing stage, a substitution layer, another key-mixing stage, and finally a diffusion layer. The E0 is a stream cipher. Wikipedia.org "E0 (cipher)" en.wikipedia.org/wiki/E0_(cipher). It generates a sequence of pseudorandom numbers and combines it with the data using a XOR operator. The key length is usually 128 bits, but may vary. For each iteration E0 generates a bit using 4 shift registers of different length (25, 31, 33, 39 bits), and two internal states, each 2 bits long. For each clock cycle, the registers are shifted and the two states are updated with the current state, the previous state and the values in the shift registers. Four bits are then extracted from the shift registers and added together. Then the algorithm XORs that sum with the value in the 2-bit register. The first bit of the result is output for the encoding. E0 is divided in three parts: 1. Payload key generation; 2. Key stream generation; and 3. Encoding.

The setup of the initial state in Bluetooth uses the same structure as the random bit stream generator. We are thus dealing with two combined E0 algorithms. Using the 128-bit key, Bluetooth address on 48 bits and the 26-bit master counter an initial 132-bit state is produced at the first stage. The output is then processed by a polynomial operation and the resulting key goes through the second stage, which generates the stream used for encoding. The key is a multiple of 2 varying from 8 to 128 bits length. 128 bit keys are generally used. These are stored into the second stage's shift registers. 200 pseudorandom bits are then produced, and the last 128 bits are inserted into the shift registers. It is the stream generator's initial state.

ZigBee focuses on low powered devices with a need for security and sending small amounts of data. The most common devices that use ZigBee are industrial automation, remote metering, embedded sensors, medical devices, smoke and intruder alarms, interactive toys, building automation and home automation. ZigBee operates in the European 868 MHz ISM band with one channel, the American and Australian 915 MHz ISM band with 10 channels or the 2.4 GHz ISM band with 16 channels. The data rate is 250 kbit/s in the 2.4 GHz band, 40 kbit/s in the 915 MHz band, and 20 kbit/s in the 868 MHz band. ZigBee Alliance (2004) "ZigBee Specification v1.0"; Kinney, P. (2003) "ZigBee Technology: Wireless Control that Simply Works", Kinney Consulting LLC, Chair of IEEE 802.15.4 Task Group, Secretary of ZigBee BoD, Chair of ZigBee Building Automation Profile WG. Transmission range is typical between 10 and 75 meters. The ZigBee protocol supports up to 65,536 nodes. It has handshaking for transfer reliability.

The ZigBee stack architecture is based on the standard Open Systems Interconnection (OSI) seven-layer model but defines only those layers relevant to achieving functionality in the intended market space. The IEEE 802.15.4-2003 standard defines two lower layers: the physical (PHY) layer and the medium access control (MAC) sub-layer. The ZigBee Alliance builds on this foundation by providing the network (NWK) layer and the framework for the application layer. The application layer framework is comprised of the application support sub-layer (APS), the ZigBee device objects (ZDO) and the manufacturer-defined application objects. The protocol is called CSMA-CA. The MAC layer also transmits beacon frames, synchronization, and provides reliable transmission mechanisms. The network layer has 3 main functions: join and leave networks, apply security, and route frames to their destinations. In a coordinator device, the network layer has the responsibility to start a new network and discover what kind of application services nearby devices. It also assigns addresses to newly assigned devices. The network layer supports star, cluster three and mesh topology. As mentioned above, the APL layer consists of Application Support sub-layer (APS), ZigBee Device Object (ZDO) and manufacturer-defined applications. The APS is responsible for maintaining the tables for binding i.e. the ability to match two devices and forward the messages between two devices. The ZDO define the role of a device in the network (network coordinator, coordinator, or end device), initiate and/or respond to binding requests, and establish a secure connection.

ZigBee has several different security mechanisms (ZigBee Alliance (2005) "ZigBee Security specification overview"), and are found in the MAC layer, NWK layer and the APS layer. Among them are freshness, integrity, authentication, and encryption. The freshness checks prevent replay attacks. It uses incoming and outgoing freshness counters that are reset every time a new key is created. The integrity checks prevent anyone from modifying the message, and supports up to 128 bit message integrity. Authentication is handled either in the network level or the device level. The network level authentication is achieved when using a common network key. This will prevent attacks from outsiders, and it has very little memory cost. The device level authentication is achieved when using unique link keys between pair of devices. This prevents attacks from both outsiders and insiders, but has a higher memory cost. ZigBee supports 128 bit AES encryption. This encryption can be used either at network level or device level, and is handled the same way as authentication. The encryption can be turned on or off without impacting the freshness, integrity or authentication. ZigBee can also add security to frames. ZigBee Security can add headers to the data frames at the MAC, NWK, and APS layers. ZigBee supports 3 types of topologies: Star, Cluster tree and Mesh.

In a star topology the network is controlled by a PAN coordinator (network controller). All end devices can only talk to the coordinator. The coordinator is almost always in a listening mode, except when new end devices are trying to connect. The star topology supports up to 65,536 end devices. It is a very simple layout and has low latency. Oyen, G. E. (2006) "ZigBee and IEEE 802.15.4: A brief introduction". In a cluster tree topology the tree structure is rooted at the PAN coordinator. The coordinator initiates the network, and the children (end devices) routes through parents in a hierarchy. It uses a multi-hop topology to increase the network range. The cluster tree topology is not ideal for network devices that require low latency. The idea with mesh topology is that messages can be routed from any source to any destination. The way this is done is that every PAN coordinator (FFD) is functioning as a router for all its neighbors. Like cluster tree topology, the mesh topology uses multi-hop topology to increase the network range. It has high reliability, since the messages can go many routes. If one or more of FFD disconnects, the messages still gets to the destination, but uses another route than it normally does. This way it is self-configuring. Since this topology depends on the routers, it may not be ideal for battery driven networks, as the routers will have relatively large power consumption.

Only one Zigbee coordinator (ZC) is required in each ZigBee network. It is the most capable device in the network, and initiates the formation. It is the root of the network tree, and might bridge to other networks. It acts as a PAN coordinator (FFD) and as a router when the network is formed. The ZC also acts as a repository for security keys. The coordinator is also assumed to be the trust center, which is responsible for allowing new devices into the network and for distributing keys. It is possible for the trust center to be a dedicated device. The Zigbee Router (ZR) is an optional component in a ZigBee network. The routers associate with the ZC or with other previously associated ZR. The ZR acts as a coordinator (FFD) and is used as a local address allocation/de-allocation device. It is used in multi-hop routing of messages. The ZR also looks after its own Zigbee End Device (ZED). The ZED contains very little functionality. It is limited to communicate with its coordinator. The ZED is not allowed to associate or participate in routing. It requires the least amount of memory and is therefore cheaper than ZC or ZR. It has low power consumption since its parent puts it to sleep.

When a new device is installed in the network, it will initiate queries to discover already active ZigBee devices in the network. The request is either an IEEE address request, which is unicast, or a NWK address request, which is broadcast. When the unicast request is sent, it assumes the NWK address is known. When the broadcast request is sent, it carries the known IEEE address as payload. The response on these queries is dependent on the three device types mentioned above: ZED, ZR and ZC. The ZED responds to the query by sending its own IEEE or NWK address. The ZR responds to the query by sending its own IEEE or NWK as well as the IEEE and NWK address of all the other devices connected to the ZR. The ZC responds to the query by sending its own IEEE or NWK as well as the IEEE and NWK address of all the other devices connected to the ZC.

There are 3 different key types used in ZigBee; master key, link key and network key. The master key is used as basis for long term communication between devices, and can be either factory installed or be set up over the air or using out-of-band mechanisms. The link key is used for security between two devices. The link key is also used to authenticate devices to the coordinator device. The network key is used for security in a network. The link and network keys can be factory installed, be set up using a symmetric key-key exchange handshake or be sent from the trust center.

GSM offers several security services (Schiller, J. (2003) Mobile Communications, second edition, Addison-Wesley, pages 93-156), and they are found either in the SIM card or the AuC (authentication center, a separate system in the network that contains the algorithms for authentication and the keys for encryption). The SIM card stores personal data and a secret key Ki, and is only accessed with a four-digit PIN number. After MS authenticates itself, the MS and BTS (base transceiver station) encrypts all voice and data. There are 3 types of algorithms: A3 for authentication, A5 for encryption and A8 for generation of the cipher key. The algorithms are very weak, but it is possible for the network providers to use stronger algorithms for encryption or user can provide stronger end-to-end encryption. To encrypt the messages, a key Kc is created by using the individual key Ki and a random number by generated by the A8 algorithm. The Kc key is calculated both in the MS (SIM) and the network, and is not transmitted over the air interface.

Hash functions are the most versatile of all cryptographic primitives. Bishop, M. (2003) Computer Security Art and Science, Addison-Wesley. It can be used for encryption, authentication, and a simple digital signature. The typical use of a hash function is digital signatures. The idea behind hashing is to take a long string of bits (or bytes) as input, run a hash function, and produce a fixed length hash sum. Mao, W. (2004) Modern Cryptography Theory & Practice, Bristol, Prentice Hall. If you have a message (m) and a hash (h), you are signing h(m) instead of signing m. The reason for signing h(m) is that the message (m) are usually very large, up to millions of bits, but the hash function is usually between 128 and 256 bits, thus making it much faster and more effective. One of the practical problems with selecting a hash function, is that there's only a couple methods to choose from Wikipedia.org "Cryptographic Hash Function" en.wikipedia.org/wiki/Cryptographic_hash_function (current Apr. 25, 2006); the SHA family and MD5. There are a couple of alternatives, but they have not been tested thoroughly enough to trust them. A typical hash function is shown below. MD5 is a cryptographic hash function used to verify data integrity. Rivest, R. (1992), MIT laboratory for Computer Science and RSA Data security, inc. April 1992. It was developed by Ronald Rivest in 1991 to replace MD4, because MD4 proved to have some security weakness. When using MD5, the message is split into blocks of 512 bits. Answers.com "MD5" www.answers.com/topic/md5#after_ad1 (online May 25, 2006). The last block is padded, and includes the length of the message. MD5 has 128-bit hash value that is split into four words of 32 bits, each with a compression function h' with four rounds. Each round mix the message block and the state, with a combination of addition, XOR, AND, OR and rotation operations on 32-bit words. This way each message word is used four times. After the four rounds of the h' function, the input state and the result are added together to produce the output of h'. The structure of operating 32-bits words is very efficient on 32-bits CPUs.

One of the basic ideas behind hash functions is that it is collision resistant. SHA (Secure Hash Algorithm, Wikipedia.org "SHA Hash functions" en.wikipedia.org/wiki/SHA (current May 6, 2006)) is a set of cryptographic hash functions. SHA-1 (National Institute of Standards and Technology (1995) "Secure Hash Standard" www.itl.nist.gov/fipspubs/fip180-1.htm. en.wikipedia.org/wiki/SHA. SHA is used in a wide area of security applications, like TLS, SSL, PGP, SSH, S/MIME, and IPSec. SHA-0 and SHA-1 is based on the same principles as MD4 and MD5, and produces a 160-bit message digest with a maximum size of 264 bits. SHA-1 has a 160-bit state consisting of five 32-bit words. It uses four rounds that consist of a mixture of 32-bit operations. SHA-1 uses a linear recurrence to stretch the 16 words of a message block to the 80 words it needs, to ensure that each message bit affects the mixing function at least a dozen times. See, Schneier, B. (2005) "New Cryptanalytic Results Against SHA-1" www.schneier.com/blog/archives/2005/08/new_cryptanalyt.html (current Aug. 17, 2005).

Advanced Encryption Standard (AES, Wikipedia.org "Advanced Encryption Standard" en.wikipedia.org/wiki/Advanced_Encryption_Standard, also known as Rijndael, is a block cipher. In 2000 the National Institute of Standards and Technology (NIST), chose Rijndael as the new encryption standard for the US government. Rijndael is a block cipher.

Public Key Infrastructure (PKI) is a policy to establish a secure method for information exchange. Bishop, M. (2003) Computer Security Art and Science, Addison-Wesley. It is also a set of integrated services and administrative tools to create and manage applications based on public keys. This includes cryptographic methods, the use of digital certificates, certification authorities, and the system to manage the process. There are two key elements in PKI: Public Key Cryptography and Certification Authorities (CA). Public Key Cryptography is a form of cryptography and uses a pair of cryptographic keys designed as a private key and a public key, which are related mathematically. The private key is kept secret by the user and the public key may be widely distributed. Generally, if user Bob shall send a message to user Alice, Bob will contact Alice and ask for her public key. Alice sends Bob her public key, and Bob uses it to encrypt his message. Bob will then send Alice the message, encrypted with Alice's public key, and the only way to decrypt the message is to use Alice's private key. Borthus, B and Tomas, E. (2005) "Public Key Infrastructure for Windows Server 2003". Some examples of public key techniques are: Diffie-Hellmann, DSS, ElGamal, RSA, and various Elliptic Curve techniques. Wikipedia.org "Public Key Infrastructure" (current May 26, 2006).

A CA is responsible for establishing and vouching for the identity of certificate holders. A CA also revokes certificates if they are no longer valid and publishes certificate revocation lists (CRLs) to be used by certification verifiers. The certificates are issued by a CA based on information provided in the certification request and settings contained in a certification template. A certification template is the set of rules and settings that are applied against incoming certificate requests. The most common digital certificates in PKI use the X.509 Digital Certificate format and usually contain the following: The user's public key; The user's identity, such as name and e-mail address; The validity period of the certificate; The digital signature of the issuer, which attest to the validity of the binding between the user's public key and the user's identifier information. There are different levels of certificates based on the need for functions. As a general rule, the higher level of the certificate, the stricter are the policies for verifying. PKI supports hashing to keep the integrity of the data.

Smart cards are pocket sized plastic cards with embedded integrated circuits. There are 2 broad categories of cards; memory cards and microprocessor cards. c. The standardization of smart card systems is an ongoing process. One of the standards most referred to is the ISO-7816 standard. A memory card contains non-volatile memory that can store information and perhaps some specific non-programmable security logic. An example of a memory card is a prepaid phone card. They can also be used as a high security alternative to magnetic stripe cards. Memory cards can only perform fixed operations. Microprocessor cards contain memory and microprocessor components. These cards can process data on the card and can used for a variety of applications. Microprocessor cards can provide secure access to networks, be used as SIM card in mobile phones and as electronic wallets. Smart cards are engineered to be tamper resistant and are very suitable to hold personal digital signatures that can be used as authentication to grant access to secure networks. Hong Kong University of Science & Technology (1998) "Guide to Smart Card Technology".

The definition of VPN is "A virtual private network (VPN) is a private data network that makes use of the public telecommunication infrastructure, maintaining privacy through the use of a tunneling protocol and security procedures". VPN Consortium (2006) "VPN Technologies: Definitions and Requirements" www.vpnc.org/vpn-technologies.html. A VPN makes it possible to share resources in a secure way over an insecure public network like the Internet. There are 3 important VPN technologies used: secure, trusted and hybrid VPN. Only secure VPN is relevant to our scenario. Secure VPN uses an encrypted secure "tunnel" to transport data over a public network. Tunneling is generally done by encapsulating the private network data and protocol information within the public network transmission units so that the private network protocol information appears to the public network as data. Tunneling allows the use of the Internet, to convey data on behalf of a private network in a secure way. There are several secure VPN protocols, like IPsec, SSL and PPTP. A properly chosen, implemented, and used secure VPN protocol can provide secure communications over unsecured networks, and provide protection of confidentiality and integrity, and sender authentication to ensure privacy. Secure authentication is very important when using a VPN solution. Authentication mechanisms can make use of what you know (pin code, password), what you have (smart card) or what you are (fingerprint, retinal scan). Wikipedia.org "Virtual private network" en.wikipedia.org/wiki/Virtual_Private_Network. The use of one of the above will give weak authentication, but the use of two will give a much stronger authentication.

See, U.S. Patent and Pub. App. Nos. U.S. Pat. Nos. 5,129,394; 5,899,929; 6,052,621; 6,141,592; 6,230,059; 6,375,612; 6,381,494; 6,428,484; 6,477,424; 6,569,092; 6,579,235; 6,735,479; 6,889,079; 6,944,502; 6,959,212; 6,965,816; 6,985,773; 6,993,393; 7,025,727; 7,047,076; 7,072,718; 7,085,599; 7,097,662; 7,177,699; 7,187,974; 7,209,790; 7,218,967; 7,256,695; 7,260,432; 7,270,633; 7,310,544; 7,319,901; 7,337,776; 7,347,822; 7,392,092; 7,414,534; 7,426,411; 7,445,605; 7,478,108; 7,494,465; 7,497,827; 7,577,479; 7,583,998; 7,593,776; 7,610,065; 7,613,522; 7,620,452; 7,623,922; 7,640,048; 7,651,596; 7,654,956; 7,657,314; 7,668,596; 7,681,572; 7,702,387; 7,705,736; 7,713,574; 7,720,535; 7,720,544; 7,725,195; 7,729,776; 7,736,330; 7,738,964; 7,761,159; 7,771,352; 7,774,145; 7,786,867; 7,792,588; 7,801,612; 7,818,056; 7,848,813; 7,853,324; 7,857,760; 7,860,574; 7,876,228; 7,877,145; 7,885,697; 7,890,180; 7,899,511; 7,901,354; 7,904,169; 7,904,170; 7,905,833; 7,912,544; 7,914,468; 7,917,226; 7,925,356; 7,930,543; 7,937,159; 7,940,933; 7,945,322; 7,946,984; 7,949,381; 7,955,258; 7,962,209; 7,966,075; 7,967,751; 7,970,734; 7,978,062; 7,981,025; 8,000,901; 8,032,486; 8,041,432; 8,046,080; 8,050,771; 8,057,401; 8,057,472; 8,070,768; 8,090,443; 8,092,549; 8,097,926; 8,102,999; 8,109,920; 8,114,021; 8,115,618; 8,116,862; 8,123,687; 8,133,178; 8,145,295; 8,145,301; 8,160,669; 8,160,680; 8,165,684; 8,165,691; 8,170,667; 8,170,680; 8,170,803; 8,180,436; 8,180,438; 8,180,448; 8,182,435; 8,183,998; 8,185,195; 8,185,204; 8,190,256; 8,190,900; 8,195,305; 8,200,328; 8,216,135; 8,219,204; 8,224,443; 8,229,534; 8,231,531; 8,233,959; 8,238,975; 8,242,907; 8,242,908; 8,248,238; 8,248,239; 8,251,946; 8,253,567; 8,257,295; 8,260,422; 8,265,738; 8,265,754; 8,267,863; 8,269,630; 8,269,635; 8,269,636; 8,271,087; 8,275,437; 8,275,438; 8,277,713; 8,279,065; 8,280,475; 8,280,499; 8,281,408; 8,284,055; 8,285,387; 8,287,453; 8,290,560; 8,294,579; 8,298,142; 8,299,899; 8,301,110; 8,301,243; 8,301,254; 8,303,573; 8,311,628; 8,311,749;

8,313,434; 8,317,776; 8,321,149; 8,322,346; 8,323,232;
8,325,011; 8,325,031; 8,332,024; 8,333,754; 8,337,482;
8,343,068; 8,348,882; 8,352,044; 8,353,896; 8,360,069;
8,361,013; 8,366,633; 8,369,950; 8,369,959; 8,369,961;
8,373,556; 8,382,756; 8,386,043; 8,388,553; 8,391,981;
8,391,990; 8,395,498; 8,403,881; 8,415,837; 8,419,673;
8,419,734; 8,421,630; 8,435,208; 8,442,631; 8,447,376;
8,447,389; 8,447,414; 8,449,464; 8,452,368; 8,454,552;
8,457,708; 8,457,757; 8,457,760; 8,463,350; 8,463,375;
8,474,397; 8,475,373; 8,478,377; 8,483,791; 8,483,838;
8,483,840; 8,486,070; 8,493,187; 8,494,647; 8,497,804;
8,502,675; 8,509,911; 8,509,913; 8,512,219; 8,514,067;
8,515,516; 8,515,519; 8,515,547; 8,517,013; 8,536,667;
8,538,528; 8,540,632; 8,540,644; 8,545,402; 8,545,431;
8,545,436; 8,547,248; 8,548,551; 8,558,563; 8,558,699;
8,562,528; 8,565,848; 8,565,849; 8,565,891; 8,570,187;
8,571,625; 8,574,164; 8,577,453; 8,577,464; 8,577,465;
8,577,466; 8,577,467; 8,577,468; 8,577,472; 8,577,478;
8,579,848; 8,583,210; 8,583,231; 8,585,631; 8,587,427;
8,588,924; 8,588,941; 8,599,009; 8,603,024; 8,608,310;
8,615,282; 8,626,257; 8,626,310; 8,634,927; 8,636,670;
8,644,957; 8,649,757; 8,649,857; 8,649,859; 8,653,966;
8,657,747; 8,660,642; 8,660,659; 8,663,109; 8,663,202;
8,672,845; 8,674,825; 8,681,000; 8,682,446; 8,690,775;
8,690,929; 8,694,092; 8,700,181; 8,700,183; 8,704,124;
8,706,208; 8,706,226; 8,707,964; 8,712,541; 8,715,159;
8,715,269; 8,718,193; 8,718,776; 8,718,787; 8,721,545;
8,721,580; 8,721,643; 8,723,640; 8,730,032; 8,731,630;
8,731,668; 8,736,441; 8,738,139; 8,744,572; 8,744,581;
8,750,955; 8,751,013; 8,753,305; 8,781,581; 8,784,332;
8,788,007; 8,788,057; 8,789,536; 8,792,953; 8,792,954;
8,792,955; 8,792,983; 8,798,773; 8,801,611; 8,808,163;
8,808,224; 8,808,271; 8,808,276; 8,811,926; 8,816,814;
8,818,522; 8,825,127; 8,838,254; 8,840,578; 8,845,536;
8,847,766; 8,855,785; 8,858,432; 8,858,434; 8,868,201;
8,870,813; 8,884,779; 8,886,272; 8,886,273; 8,886,300;
8,886,334; 8,903,500; 8,914,131; 8,915,849; 8,929,999;
8,932,221; 8,933,848; 8,936,629; 8,941,470; 8,945,005;
8,947,233; 8,947,301; 8,951,203; 8,956,288; 8,961,412;
8,963,737; 8,968,198; 8,970,392; 8,983,618; 8,986,209;
8,989,833; 8,989,867; 8,989,868; 8,989,870; 8,995,949;
9,002,467; 9,002,471; 9,011,329; 9,014,815; 9,031,658;
9,037,258; 9,042,999; 9,044,199; 9,044,612; 9,055,901;
9,060,742; 9,061,139; 9,061,151; 9,067,073; 9,072,588;
9,072,914; 9,078,613; 9,078,626; 9,083,424; 9,083,589;
9,119,533; 9,119,554; 9,126,031; 9,149,423; 9,149,577;
9,155,496; 9,166,655; 9,168,005; 9,168,380; 9,173,837;
9,174,058; 9,179,960; 9,185,087; 9,186,060; 9,198,563;
9,198,591; 9,205,258; 9,205,268; 9,220,917; 9,226,851;
9,242,103; 9,242,113; 9,247,900; 9,248,291; 9,265,949;
9,269,251; 9,270,025; 9,270,137; 9,271,781; 9,271,857;
9,283,115; 9,288,614; 9,289,614; 9,289,619; 9,291,636;
9,302,093; 9,314,613; 9,316,469; 9,318,916; 9,320,455;
9,320,908; 9,326,726; 9,333,365; 9,352,164; 9,358,392;
9,390,362; 9,392,949; 9,393,424; 9,393,434; 9,399,139;
9,399,143; 9,402,583; 9,402,994; 9,403,009; 9,408,530;
9,409,013; 9,414,777; 9,415,215; 9,415,216; 9,421,372;
9,427,584; 9,433,371; 9,433,376; 9,433,790; 9,444,503;
9,445,720; 9,451,910; 9,465,559; 9,468,766; 9,468,772;
9,492,656; 9,492,671; 9,492,677; 9,492,678; 9,496,733;
9,497,928; 9,504,830; 9,522,282; 9,526,650; 9,528,633;
9,533,165; 9,550,064; 9,561,381; 9,572,992; 9,592,010;
9,592,392; 9,595,187; 9,596,988; 9,597,513; 9,603,557;
9,610,031; 9,610,450; 9,615,970; 9,616,237; 9,629,586;
9,636,509; 9,649,493; 9,649,503; 9,655,777; 9,656,074;
9,656,087; 9,659,423; 9,662,069; 9,662,508; 9,668,677;
9,668,682; 9,669,217; 9,669,224; 9,669,227; 9,675,261;

9,675,270; 9,675,809; 9,681,842; 9,687,654; 9,693,708;
9,693,813; 9,700,253; 9,700,712; 9,707,405; 9,717,916;
9,724,028; 9,729,001; 9,748,986; 9,750,939; 9,750,946;
9,756,549; 9,757,061; 9,757,200; 9,764,139; 9,770,189;
9,775,543; 9,788,756; 9,789,236; 9,789,317; 9,801,527;
9,801,572; 9,801,989; 9,814,389; 9,814,414; 9,814,900;
9,821,166; 9,821,170; 9,823,737; 9,826,963; 9,833,143;
9,833,176; 9,833,628; 9,837,704; 9,848,775; 9,848,789;
9,849,288; 9,855,433; 9,872,988; 9,878,159; 9,878,168;
9,883,815; 9,884,191; 9,895,532; 9,895,540; 9,901,269;
9,913,989; 9,915,641; 9,919,088; 9,919,158; 9,936,877;
9,943,686; 9,958,515; 9,960,916; 9,964,384; 9,974,492;
9,974,965; 9,981,135; 9,993,173; 9,993,654; 9,996,669;
9,999,774; 9,999,775; 10,003,862; 10,014,571; 10,015,720;
10,016,135; 10,022,552; 10,022,553; 10,039,469; 10,039,
661; 10,045,697; 10,045,710; 10,045,764; 10,052,055;
10,052,490; 10,065,042; 10,070,905; 10,080,897; 10,080,
900; 10,080,903; 10,092,363; 10,105,550; 10,118,037;
10,118,054; 10,119,798; 10,123,882; 10,124,171; 10,130,
282; 10,159,847; 10,177,609; 10,185,513; 10,186,546;
10,188,870; 10,193,217; 10,194,802; 10,207,116; 10,213,
617; 10,219,229; 10,220,217; 20020024450; 20020049482;
20020095194; 20030028226; 20030040780; 20030114897;
20030114898; 20030130702; 20030149459; 20030195572;
20040082973; 20040106967; 20040129270; 20040133092;
20040167587; 20040199221; 20040215240; 20040230229;
20040260346; 20050004615; 20050028816; 20050070962;
20050070968; 20050107839; 20050181018; 20050256417;
20050283196; 20060016700; 20060019327; 20060020186;
20060020187; 20060020188; 20060020189; 20060020190;
20060020191; 20060020192; 20060025834; 20060030904;
20060036139; 20060036140; 20060036141; 20060036142;
20060036143; 20060036144; 20060036145; 20060047283;
20060064037; 20060116744; 20060122863; 20060122864;
20060142651; 20060142820; 20060155180; 20060161225;
20060183984; 20060183985; 20060194615; 20060195029;
20060195161; 20060200020; 20060200970; 20060212080;
20060212084; 20060212085; 20060217621; 20060222566;
20060224206; 20060224207; 20060229512; 20060235285;
20060247711; 20060265018; 20060287685; 20060293714;
20060293717; 20070016381; 20070032749; 20070038044;
20070049976; 20070055324; 20070059196; 20070066873;
20070067004; 20070068523; 20070100385; 20070106138;
20070106346; 20070112398; 20070135803; 20070163880;
20070167867; 20070173708; 20070173709; 20070173710;
20070179549; 20070179558; 20070197889; 20070203966;
20070208244; 20070208245; 20070208246; 20070210923;
20070232879; 20070249992; 20070250020; 20070265515;
20070282634; 20070288065; 20070288066; 20070288069;
20070299386; 20070299420; 20080004671; 20080015494;
20080015655; 20080015656; 20080021522; 20080021524;
20080039904; 20080044014; 20080044025; 20080046037;
20080046038; 20080046039; 20080046057; 20080049376;
20080071156; 20080071313; 20080071328; 20080129465;
20080140154; 20080140160; 20080157928; 20080161886;
20080164975; 20080164977; 20080167600; 20080180249;
20080183072; 20080183247; 20080186137; 20080186138;
20080186139; 20080186180; 20080188731; 20080194935;
20080195180; 20080208025; 20080211630; 20080214915;
20080234599; 20080234784; 20080242961; 20080242976;
20080243200; 20080252459; 20080269573; 20080275312;
20080275313; 20080281371; 20080288027; 20080296155;
20080300658; 20080306359; 20080319280; 20090005656;
20090036910; 20090043347; 20090044804; 20090058635;
20090058636; 20090062887; 20090063193; 20090065001;
20090071474; 20090071475; 20090071476; 20090071481;
20090076360; 20090076361; 20090088609; 20090102682;

20090104250; 20090105561; 20090105694; 20090110714; 20090112048; 20090112189; 20090112190; 20090112191; 20090112523; 20090118597; 20090124879; 20090131768; 20090131769; 20090131776; 20090131777; 20090137866; 20090137886; 20090137887; 20090143659; 20090143660; 20090143696; 20090156919; 20090156988; 20090157056; 20090157057; 20090157058; 20090157141; 20090163790; 20090163791; 20090163894; 20090163980; 20090163981; 20090178459; 20090182217; 20090192381; 20090192449; 20090192574; 20090192724; 20090203980; 20090216103; 20090228075; 20090228076; 20090248112; 20090270948; 20090281589; 20090284378; 20090287093; 20090287094; 20090287101; 20090287109; 20090287110; 20090287120; 20090287191; 20090292212; 20090292213; 20090292214; 20090292222; 20090299156; 20090299438; 20100004500; 20100004523; 20100016925; 20100036209; 20100036263; 20100036268; 20100036269; 20100036463; 20100045480; 20100069987; 20100081908; 20100082080; 20100085160; 20100100157; 20100106224; 20100109958; 20100109966; 20100114233; 20100114245; 20100114246; 20100121169; 20100131027; 20100139672; 20100145337; 20100149042; 20100151113; 20100152816; 20100160997; 20100161004; 20100165593; 20100168817; 20100168818; 20100168821; 20100174157; 20100174158; 20100174163; 20100174164; 20100174165; 20100174166; 20100179404; 20100179408; 20100185055; 20100185069; 20100185075; 20100185249; 20100191082; 20100191236; 20100198039; 20100204759; 20100204802; 20100208397; 20100208631; 20100211124; 20100212583; 20100217298; 20100217301; 20100223013; 20100223022; 20100223023; 20100228109; 20100228497; 20100241195; 20100249696; 20100262036; 20100274141; 20100274147; 20100286739; 20100298895; 20100305476; 20100305664; 20100305869; 20100308974; 20100312309; 20100318160; 20100324403; 20100324578; 20100324579; 20100328049; 20100331644; 20100331663; 20100331868; 20100331874; 20100331894; 20100331921; 20110004277; 20110021934; 20110034812; 20110034912; 20110040343; 20110043297; 20110066211; 20110066212; 20110077706; 20110082523; 20110093040; 20110093046; 20110098788; 20110106204; 20110106212; 20110118813; 20110124983; 20110125063; 20110144465; 20110152673; 20110152971; 20110160791; 20110171905; 20110172741; 20110178378; 20110178577; 20110190614; 20110196447; 20110196450; 20110197067; 20110200194; 20110201912; 20110208030; 20110213232; 20110213233; 20110218414; 20110231107; 20110245644; 20110257895; 20110270369; 20110273287; 20110275911; 20110290645; 20110307274; 20120029323; 20120035951; 20120038477; 20120046564; 20120059238; 20120065696; 20120109256; 20120123221; 20120130214; 20120161901; 20120165684; 20120169468; 20120169469; 20120169474; 20120172691; 20120179057; 20120180731; 20120182123; 20120197347; 20120197348; 20120197351; 20120206243; 20120209353; 20120220849; 20120220986; 20120226130; 20120271380; 20120277562; 20120283543; 20120293324; 20120296271; 20120319823; 20120326886; 20120330372; 20120330380; 20130002448; 20130002496; 20130009786; 20130009838; 20130009839; 20130012798; 20130012800; 20130035577; 20130043974; 20130043975; 20130043991; 20130043993; 20130046152; 20130046153; 20130046477; 20130053713; 20130053908; 20130072770; 20130116740; 20130123882; 20130131752; 20130144179; 20130147622; 20130154851; 20130165996; 20130173284; 20130173285; 20130173293; 20130173294; 20130173295; 20130173296; 20130173297; 20130173298; 20130173299; 20130173300; 20130173301; 20130173302; 20130173303; 20130173304; 20130173305; 20130178751; 20130179188; 20130198463; 20130238056; 20130245401; 20130245981;

20130253297; 20130255570; 20130257656; 20130267808; 20130267809; 20130274563; 20130289666; 20130310896; 20130317584; 20140012341; 20140039290; 20140046690; 20140051965; 20140058235; 20140062718; 20140085104; 20140088391; 20140094891; 20140114158; 20140120841; 20140121989; 20140135597; 20140135647; 20140142405; 20140142648; 20140142661; 20140148676; 20140163338; 20140163644; 20140163648; 20140172060; 20140214104; 20140221767; 20140228904; 20140257065; 20140266933; 20140275727; 20140278189; 20140288402; 20140288403; 20140288619; 20140292490; 20140296687; 20140300490; 20140303452; 20140306807; 20140324138; 20140330347; 20140330357; 20140376336; 20150039041; 20150051465; 20150061840; 20150077050; 20150080982; 20150087942; 20150088227; 20150094790; 20150099976; 20150100106; 20150116053; 20150117645; 20150119666; 20150127068; 20150134026; 20150134027; 20150134028; 20150141770; 20150148638; 20150148868; 20150153319; 20150171905; 20150182115; 20150190638; 20150202456; 20150206408; 20150209588; 20150229139; 20150246242; 20150257670; 20150258345; 20150265458; 20150265459; 20150265843; 20150282741; 20150283397; 20150283398; 20150297103; 20150297905; 20150302178; 20150321011; 20150321012; 20150321016; 20150327896; 20150328455; 20150360049; 20150360050; 20150374270; 20160008029; 20160015984; 20160015985; 20160029998; 20160030765; 20160038744; 20160038755; 20160038756; 20160038757; 20160038758; 20160038759; 20160038765; 20160045145; 20160045162; 20160045764; 20160045765; 20160051173; 20160051828; 20160051830; 20160051831; 20160051836; 20160051837; 20160051838; 20160058322; 20160058324; 20160059030; 20160066803; 20160066850; 20160067487; 20160067500; 20160082279; 20160096034; 20160096035; 20160114162; 20160114168; 20160114169; 20160144180; 20160151553; 20160164337; 20160183842; 20160183855; 20160189174; 20160206892; 20160210084; 20160213270; 20160216768; 20160216769; 20160236000; 20160250478; 20160256697; 20160278662; 20160279388; 20160294225; 20160296754; 20160302686; 20160302692; 20160310031; 20160310051; 20160310733; 20160310743; 20160313101; 20160317822; 20160324450; 20160325097; 20160339250; 20160339260; 20160361543; 20160361545; 20160361551; 20160361552; 20160361553; 20160361554; 20170020415; 20170020416; 20170021132; 20170028203; 20170043174; 20170065820; 20170071511; 20170071512; 20170074757; 20170086697; 20170095210; 20170113046; 20170127196; 20170127941; 20170127975; 20170136244; 20170140121; 20170140127; 20170143206; 20170157411; 20170182191; 20170188906; 20170188907; 20170188942; 20170196491; 20170197028; 20170199970; 20170212913; 20170215815; 20170216611; 20170224248; 20170225008; 20170225009; 20170225013; 20170228510; 20170231497; 20170239488; 20170258363; 20170259061; 20170259072; 20170266437; 20170266455; 20170272123; 20170273589; 20170273606; 20170274200; 20170274213; 20170281033; 20170281034; 20170281092; 20170296093; 20170296827; 20170296835; 20170312502; 20170312530; 20170317518; 20170325726; 20170333716; 20170361104; 20170367627; 20170368330; 20180008834; 20180014762; 20180028086; 20180028814; 20180028832; 20180035888; 20180038672; 20180040944; 20180042553; 20180049682; 20180050189; 20180055361; 20180055500; 20180056085; 20180070876; 20180076336; 20180076670; 20180085506; 20180085559; 20180085588; 20180085589; 20180085592; 20180103863; 20180117337; 20180125364; 20180126168; 20180131415; 20180133474; 20180133501; 20180140236; 20180140862; 20180154154; 20180160949; 20180161580; 20180164276; 20180192909; 20180192941;

20180192942; 20180192943; 20180193644; 20180193650; 20180193651; 20180193652; 20180199873; 20180200525; 20180211718; 20180214711; 20180242864; 20180256909; 20180271450; 20180272142; 20180277938; 20180280716; 20180289971; 20180310824; 20180311504; 20180315509; 20180322445; 20180325402; 20180325437; 20180326220; 20180333578; 20180336970; 20180338699; 20180344212; 20180345027; 20180345033; 20180360355; 20180361150; 20180361160; 20180361161; 20180361162; 20180361169; 20180368685; 20180369573; 20190009095; 20190015020; 20190015669; 20190015677; 20190021596; 20190022397; 20190030348; 20190038908; 20190046035; 20190046800; 20190054301; 20190059062; 20190059730; 20190069815; and 20190069817.

There are therefore many known technologies of use in implementing an implantable device.

SUMMARY OF THE INVENTION

Details of one or more implementations of the subject matter described in this specification are set forth in the accompanying drawings and the description below. Other features, aspects, and advantages will become apparent from the description, the drawings, and the claims.

The present technology provides an implantable device for use in, e.g., veterinary or medical applications, which acquires physiological data as a set of time samples, internally processes those samples, e.g., to compress the data, perform an analysis of the data, and store the data and/or processed data in a memory, preferably being operable even when an interrogator or other external energy source is not present. The implant communicates with an external interrogator using e.g., near field communications (NFC), e.g., radio frequency backscatter at 13.56 MHz, according to e.g., ISO 14443A, which can be read by an NFC equipped smartphone. The implant preferably supports both passive radio frequency backscatter communications, as well as an active transmit mode. The implant further preferably provides continuous monitoring, whether in range of an interrogator or not, and preferably processes physiological data in real time for alarm or action threshold determination, and optionally data compression and storage.

Implantable devices may include identification/data storage functions, sensor functions, or actuator functions such as stimulation, drug delivery, mechanical changes, etc. All three functions may be present alone or in subcombination.

The implant may support a beacon mode, to transmit a message, such as when the physiological data warrants, and the implant is not in range of an active interrogator. The implant may also support an active receive mode in which the implant monitors a radio frequency communication channel for messages directed to it, and to process those messages. The implant may have an associated actuator or effector output, responsive to the internal processor and its sources of information and algorithms, e.g., memory, received instructions, sensor signals, etc.

The implant has an associated power source, e.g., supercapacitor or battery, to provide power, and the power source in some cases may be recharged using an energy harvesting technique, such as RF, illumination (photovoltaic), thermo-electric, muscular (kinetic), and/or other kinetic energy. In some cases, a nuclear battery is possible, though the hazards may make this unjustified.

The implant is preferably nanopower class, and as such, employs various power minimization techniques, especially when operating in active modes. In passive communication modes, the implant preferably employs energy harvesting, and therefore is constrained to operate within the power envelope of the available energy source, which is typically in excess of its minimum requirements. The implant may employ thin film transistors (TFTs), e.g., on a flexible substrate, and may have integrated optoelectronics (e.g., organic light emitting diodes (oLEDs), laser diodes, photo-receptors, etc.), piezoelectronics, ion sensitive field effect transistors (isFETs), etc.

The implant preferably has one or more integral sensors, which may include temperature, blood oxygen, pH, glucose, sodium, potassium, electrical signals, bioelectric signal inputs, motion or activity, sound, etc. The implant preferably samples the physiological data at a physiologically relevant data rate, process the data for various criteria (e.g., alarm, alert, normal), which may be threshold, rate, variability, etc., and optionally compresses the data for storage in a local memory. The stored data may also be uncompressed, or a statistical model of the physiological data.

The implant preferably has a useful life of at least 1 month, and preferably at least 3 months, and more preferably at least two years or five years. If a consumable battery is employed, the device may revert to a mode in which operation is available only when an interrogation field is available. Typically, the limiting factors in useful life are electrochemical sensors and power source, with the former typically being a more critical limitation. The implant may have redundant sensors, which are protected from exposure and degradation before activation, and thus permit prolongation of useful life of the implant.

The implant may be designed to detect temperature, glucose concentration, and electromyographic or electrocardiographic signals. The glucose sensor has a limited life, but the implant has continued utility after the glucose sensor is inoperative, based on the other sensors, and the use of the implant as an RFID tag which stores information. The glucose sensor after exhaustion of glucose oxidase, for example, may still provide pH readings.

The implant may be a multi-component system, in which at least one sensor is a separate module from the main implant controller. The sensor module communicates with the main implant controller using a short range communication technology (subcutaneous), and may be provided in a dissolvable or erodible design. For example, a glucose sensor implant may be provided which has a life of 15 days, and which bioerodes within 45 days. The glucose sensor implant may have an active power source, such as a primary battery, which powers it for its useful life. The glucose sensor module transmits, e.g., periodically, its output to an adjacent implant controller module, which is persistent, and includes a processor and memory. After the sensor lifetime is passed, another sensor may be implanted, if the need remains. The sensor module need not be implanted in the same tissue compartment as the controller, though physical proximity facilitates reliable low power communications. In some cases, the sensor module is a passive, and employs backscatter communications, in which case the controller may serve as an intermittent interrogator.

A bioerodible sensor module typically comprises a bio-erodible substrate, pattern(s) on the substrate with a non-toxic metal or other conductor, a thin film transistor implementation of sensing and control electronics, and optionally a thin film battery which is non-toxic and erodible. Alternately, a silicon integrated circuit, which may be less than 1 $mm^3$, is included in the implant, which would typically not cause a substantial acute foreign body reaction or itself slowly erode.

A preferred design is less than 3 mm diameter, and less than 3 cm long, and is implantable with a needle or trochar. The implant may have a glass shell, with optional exposed sensor elements.

Advantageously, during an initial implant, associated modules may be implanted in a single procedure, while subsequent implants of sensor or other accessory modules implanted nearby. For example, one module may support external communications, while the other modules communicate with the communication module using a nanopower technology, such as backscatter, glucose oxidase battery, etc.

The implant may provide RFID capability, and may be used to automatically distinguish between different animals. For example, a pet food bowl may be keyed to recognize a particular animal, and limit access by other animals. The consumption by each animal may be monitored and recorded, and optionally reported back to the NFC/RFID implant, for storage in local memory. A door or passage may be locked or unlocked based on which animals are present. An implant may also be located in or near the animal's ear, and provide an acoustic or neurostimulatory output perceptible by the animal, to provide instructions, or messages, e.g., "come home".

In some cases, a geolocation system is provided within the implant, which may be based on inertial parameters (direction, acceleration, rotation), GPS/Glonass/Galileo/etc., assisted GPS, ground station triangulation, etc. This may be used to provide location-based services and/or geofencing functions.

The implant may have compatibility with cellular communications, e.g., 5G, and especially may participate in a passive backscatter communication mode. It is noted that, with emergence of MIMO communications, typical receivers are sensitive to scattered communications, and 5G may permit it to communicate with passive devices.

The implant preferably implements industry-standard security protocols, which prevent spurious write to memory, and block reading of private information. In addition, less standard or proprietary protocols and techniques may be used. Depending on the hazards and risks of rogue communications with the device, various levels of encryption may be employed. One technique provides a Boolean state machine in a memory, dependent on prior memory contents, to encrypt a message. This requires low computational complexity, but requires synchronization of transmitter and receiver, which itself presents a security risk due to the possibility of interception or eavesdropping during key exchange.

The implant may also implement or rely on a form of blockchain/distributed ledger technology, which permits consensus authentication of a token, such as an access token. The implant itself, outside of an interrogator powered environment, typically cannot perform complex cryptographic calculations, but may authenticate a token, especially where external power is available. Thus, the implant may support limited Internet access, through a gateway device. The implants may have a mode in which they may communicate with each other, and may coordinate their processing, especially for shared or common tasks or for mesh networking. For example, an implant that has near zero reserve power may request another nearby implant to broadcast an alert for it. They may form a wireless body area network (WBAN), which may be an ad hoc network.

The present invention provides a medical or veterinary device, which may be an implantable device, having a low power communication transceiver with limited communication range, either passive or active. The device includes its own processor configured to establish and communicate preferably through an encrypted secure channel which tunnels over a network connection, especially where sensitive information is involved. For example, a virtual private network (VPN) is provided. This VPN then communicates with a predetermined endpoint through potentially insecure public channels and infrastructure. For non-sensitive information, such as a patient or animal identifier, a non-encrypted or promiscuous endpoint communication may be appropriate.

The technology provides, for example, an implantable device, comprising: a self-contained power source (e.g., a battery, supercapacitor, fuel cell, nuclear cell, electrochemical cell, energy harvesting system, etc.); at least one programmable automated electronic processor; a wireless radio frequency digital communication radio transmitter or transceiver; a digital memory; and a physiological interface adapted to at least one of receive a physiological signal, produce a physiological stimulation, produce a motion or displacement, infuse a drug, and acquire a biological sample, wherein the at least one programmable automated electronic processor is configured to communicate with a relay device, and through the relay device establish communication with a remoter server, e.g., on a public network The system may further provide that the implant respond to a request for opening a communication channel with a respective remote endpoint based on a received message. The system preferably is not homed to single remote server, and rather permits updating of a preferred server, while maintaining secure communications capability with an authenticated server. The security infrastructure may employ certificates, certificate registrars, certificate revocation lists, etc., in a private key infrastructure, with various options being implemented to ensure a desired degree of security.

Electronic implantable devices may include cardiac monitors, pacemakers, defibrillators, neurological stimulators, pain control devices, artificial or assistive sensory technologies (hearing aids, optic stimulators to restore vision, etc.), insulin and other drug infusion pumps, bladder control stimulators, etc. The electronic device may also include various types of sensors.

The implantable device may support an IEEE-802.11x and/or IEEE-802.15x protocol, or other types of LAN or PAN protocol; however, these tend to be power consuming, and often have excess communication bandwidth and capabilities not required for an implantable device. The device may have a strictly limited power budget, making such communications imprudent. However, in certain circumstances, an 802.11b or 802.11g communications might be appropriate. Further, in some configurations, external power might be available during communications.

A Bluetooth protocol, IEEE 802.15.1 may be used, with Class 1 or Class 2 power (100 mW or 10 mW). See, Bluetooth Core Specification 5.1, Jan. 21, 2019, Bluetooth Core Specification 5.2, Dec. 31, 2019. Bluetooth employs a 2.4 GHz band (2400-2480 MHz). in a frequency hopping spread spectrum protocol having 79 channels each with a bandwidth of 1 MHz. The protocol uses Gaussian frequency-shift keying (GFSK) modulation (Bluetooth 1.0), $\pi/4$-DQPSK and 8DPSK (Bluetooth 2.0+EDR) modulation supporting 1, 2 or 3 Mbits/sec communications. While Bluetooth communications employ security, this typically is only between paired communication partners or small subnets.

Other protocols may be employed; however, it is important that the protocol comprise error detection and correction, tunneling encryption, and low power. Because implantable electronics may endure for many years, it may be important that the endpoint of the tunneling encryption be updatable in a secure manner.

Therefore, each implantable device has its own digital certificate (or equivalent), and only through a key exchange process will the device open a communications channel. Typically, VPN's are locked to particular endpoints. However, this potentially limits availability of access to the device in emergencies, and permits a central point of failure. Meanwhile, providing a special "administrative access" mode which bypasses the VPN with a lower security level effectively reduces the net security of the device to that lower level plus any vulnerabilities in the VPN implementation. While there are advantages in having a fully standards-based IP-SEC VPN mode of operation, the purpose of the encrypted communication is to provide privacy and security, and any vulnerability leads to a reduction in these.

In an emergency, such as a central point of failure, bankruptcy or government action to interrupt services, IP filtering, or the like, it is desirable to provide a secure and private mode of access to the device which permits both downloading of information from the device and uploading operational parameters and commands to the device. An implantable device typically has only a rudimentary local interface, which may involve a magnetic field, mechanical pressure, acoustic/ultrasonic, other physical effect, but preferably there is no required local user interface at all, and remote communications through an interrogator device using a local interface to the interrogator, or a remote server, provided all interface interaction.

A smartphone or other internet or network-connected device may serve as a local endpoint or relay. According to one premise, these relay devices are not themselves required to be secure and reliable (but for their immediate use) devices, and may include vulnerabilities and therefore should not be presumed secure in all aspects. For example, requiring the user to input a personal identification number (PIN) or password through a smartphone to authorize access to the device might lead to release of the PIN or password by a keystroke logger or other malicious software on the phone, or if the phone must further communicate the PIN or password, it could be intercepted in transmission. It is possible for the device to authenticate the relay device based on an authentication protocol, independent of the formation of the VPN channel to a remote endpoint, but some relay infrastructure, such as wireless access points, do not support customized apps or such authentication, and indeed, these may be in fact truly insecure and security-compromised.

Therefore, the device operates by periodically polling its environment for available communications relays, and may in fact operate in a multiprotocol manner. If it finds a suitable partner, it then selects a "best" partner (or may indeed select multiple partners), and establishes a communication link. Typically, the device will seek to establish the lowest power consumption reliable link available. Various ad hoc networking technologies may be employed to balance link reliability and power consumption.

After a link is established, the device then communicates through the link, which acts as a router, to an Internet connected resource or other resource available through the link. In order to ensure compatibility, preferably IPv4 and/or IPv6 communications protocols are employed, generally with TCP. The device seeks to communicate with a registration server or distributed registration server, in which the device authenticates the server, and the server identifies and authenticates the device. Once the handshake authentication, which may employ a Kerberos-type cryptographic protocol, is complete, a message stored in the server is processed by the server, and/or is communicated to the device, representing a request for communication. That is, for example, a service provider may have a pending request to download a data file from the device. That request identifies the service provider and other parameters of the request. The device then seeks to form a communication channel, through the link, with the identified service provider based on the identification. A token may be communicated from the registration server to the device, which is then used as part of a protocol to establish the communication channel; however, it is preferred that the mutual authentication of the device and the service provider be conducted directly through these two communication partners. The device seeks to authenticate the service provider to ensure privacy of the communication, etc. The service provider, however, seeks to authenticate the device in order to avoid uploading malicious data that may incur costs and/or lead to changes in functioning of the device that is party to the communication, or another device that is being spoofed.

Once the device and service provider establish a communication link, which will generally be encrypted and secure, e.g., a VPN, communications, up to and including a full exchange of information, may be conducted, depending on various security rules and administrative limits. A certificate exchange protocol is provided to mutually authenticate the device and service provider. The device stores a set of certificates for a set of authorized communications partners. An emergency override is provided only upon physical access to the device, such as by activating a magnetic reed switch, or generating a unique pseudo-physiological signal that can be recognized by an internal controller. The authorized communications partners may be, for example, the manufacturer (which itself may serve as a root certificate authority), the patient's caregiver, the hospital, an on-line service which maintains the device, etc. In some cases, multiple authorized communications partners may be required to concur on a change to be made to the device operational parameters. This serves to limit mistakes, and also increases control system security.

For example, an implantable pacemaker-defibrillator device maintains an EKG record for the patient for an extended duration, e.g., 1 month, as well as various events and determinations. After some period of time, for example 3 weeks, the device seeks to download its archive to free storage space and permit medical monitoring and analysis. The implantable device therefore enters a mode where it seeks suitable communications relays, and may produce a signal perceptible by the patient for the patient to make a relay available. The device may use an NFC protocol to communicate with an NFC compatible device configured to accept the relay communication.

For example, the user has a smartphone that has an application installed that interacts with NFC devices. If the device fails to find a compatible device, over an acceptable period of time, it may shift to a different protocol, for example Bluetooth, Zigbee or 802.11b/g/n/ac/ad/ax. Use of an 802.11ac or ad protocol, for example, incurs high power consumption, but may permit communications over a longer range and with shorter duration. After finding a suitable relay, the device handshakes to establish a link, but does not necessarily require a secure or reliable link. The device then uses the relay to commence negotiation of a virtual private network with at least one of its predetermined endpoints. The link is established based on both an address of the endpoint (i.e., IPv4 of IPv6 address), and secret information which acts as a cryptographic key, wherein the secret itself is not communicated between the partners. The authentication is mutual.

In some cases, after an analysis of the data, a medical professional or automated device may determine that the parameters of operation of the device require updating. In that case, both the treating physician/cardiologist and manufacturer (or authorized service provider) may be required to concur on the proposed changes. Typically, the dual authorization is ensured by the device, and the authorization does not rely on one party to offer proof of authorization by the other. Therefore, the device uploads the proposed changes to the parameters, and then communicates with the other authorizing party the proposed changes. This dual communication paradigm may incur higher energy consumption or inconvenience, but limits the risk of collusion or breach of security. Once the parameters are updated and dual-authorized, the device may then adopt and use the new parameters. In some cases, it is the certificates maintained in the device that require updating. In that case, the device typically uses a public key infrastructure key hierarchy management system, to manage key importing, expiration, revocation, and use.

Since the relay device, e.g., smartphone is generally near to the subject, in some cases, there is significant incentive to trust that device and therefore increase communications and power efficiency. One way to achieve trusted operation is for the smartphone to enter a mode where the existence of malware or unpatched vulnerabilities are detectable, and therefore that in an absence of either, the local processor can be permitted access to private information and/or control over sensitive parameters. For example, the execution of a program by the smartphone can be checkpointed and compared against a set of known-good checkpoints for the same code, or the code interspersed with "generic" sequences that are also executed remotely on a reference platform, and the results compared. In this case, the results to be analyzed are not necessarily the regular output of the program, but memory pages, executing timing, and other indicia of the nature of the software environment. If unauthorized software is concurrently executing, its presence will be made known by changes in timing of execution, content or hash signatures of memory pages, etc.

The present technology seeks to exploit the known state of the art in virtual private networks. The following references are therefore cited and expressly incorporated by reference in their entirety: Pulkkis, Goran, et al. "Security of Symbian Based Mobile Devices." Advances in Enterprise Information Technology Security (2007): 31. Koponen, Pekka, et al. "Interfaces of consumption metering infrastructures with the energy consumers." VTT Research Notes 2542 (2010). Ross, David Andrew. "Securing IEEE 802.11 wireless LANs." (2010). Ph.D. Thesis Queensland University (2010). Fischer, Martin. "Enhancing the ReMoteCare prototype by adding an SNMP proxy and video surveillance." (2008). University of Techn., Sydney. Pankakoski, Veikko. "Experimental design for a next generation residential gateway." (2010). M.S. Thesis Aalto University (2010).

See also, U.S. Pat. Nos. 5,246,008; 6,292,659; 6,643,650; 6,700,535; 6,721,542; 6,744,753; 6,772,331; 6,789,077; 6,789,126; 6,792,466; 6,810,363; 6,813,501; 6,845,097; 6,850,979; 6,862,594; 6,868,447; 6,879,574; 6,885,388; 6,886,095; 6,898,445; 6,898,618; 6,908,391; 6,912,657; 6,916,247; 6,917,976; 6,918,084; 6,922,725; 6,925,562; 6,945,870; 6,947,995; 6,948,066; 6,950,875; 6,950,946; 6,961,541; 6,965,868; 6,968,453; 6,970,869; 6,973,493; 6,975,205; 6,980,660; 6,990,444; 7,010,573; 7,016,966;

7,028,184; 7,031,945; 7,042,988; 7,065,574; 7,065,579; 7,072,967; 7,080,078; 7,082,200; 7,084,736; 7,089,089; 7,089,298; 7,096,137; 7,103,313; 7,110,372; 7,116,661; 7,120,667; 7,121,639; 7,136,927; 7,146,307; 7,152,942; 7,155,518; 7,162,454; 7,165,107; 7,165,824; 7,167,892; 7,167,920; 7,171,323; 7,181,572; 7,181,614; 7,185,199; 7,188,251; 7,188,282; 7,197,565; 7,200,848; 7,203,665; 7,203,753; 7,206,841; 7,206,934; 7,213,047; 7,215,775; 7,216,109; 7,216,231; 7,216,365; 7,222,187; 7,243,356; 7,249,182; 7,251,331; 7,254,608; 7,260,538; 7,260,543; 7,262,709; 7,263,560; 7,263,612; 7,275,102; 7,275,156; 7,278,034; 7,278,697; 7,280,975; 7,283,803; 7,290,132; 7,293,047; 7,295,119; 7,297,062; 7,299,007; 7,302,592; 7,308,496; 7,312,721; 7,318,049; 7,318,086; 7,328,243; 7,339,914; 7,340,214; 7,340,438; 7,340,500; 7,340,770; 7,343,350; 7,346,167; 7,348,895; 7,356,329; 7,366,901; 7,370,091; 7,377,608; 7,379,891; 7,379,913; 7,383,433; 7,386,517; 7,392,375; 7,392,387; 7,395,333; 7,395,536; 7,398,533; 7,399,043; 7,401,152; 7,401,153; 7,409,434; 7,409,569; 7,412,518; 7,415,424; 7,415,439; 7,415,537; 7,418,593; 7,420,956; 7,421,411; 7,424,285; 7,426,271; 7,426,721; 7,433,649; 7,433,773; 7,444,644; 7,454,542; 7,454,619; 7,458,082; 7,461,172; 7,475,244; 7,477,873; 7,484,225; 7,487,509; 7,500,104; 7,509,387; 7,512,649; 7,516,325; 7,522,549; 7,523,111; 7,529,713; 7,533,141; 7,533,161; 7,533,172; 7,536,177; 7,536,723; 7,545,941; 7,546,254; 7,548,946; 7,549,056; 7,562,028; 7,562,051; 7,565,328; 7,565,529; 7,570,943; 7,571,346; 7,573,855; 7,574,523; 7,577,575; 7,577,619; 7,577,620; 7,577,834; 7,581,096; 7,584,360; 7,587,196; 7,590,589; 7,592,829; 7,596,227; 7,597,250; 7,599,305; 7,600,252; 7,606,242; 7,606,570; 7,607,012; 7,613,881; 7,617,159; 7,624,143; 7,630,941; 7,634,230; 7,649,872; 7,657,255; 7,657,597; 7,660,990; 7,660,998; 7,672,662; 7,680,133; 7,684,374; 7,689,508; 7,697,894; 7,698,393; 7,701,912; 7,702,821; 7,703,073; 7,707,415; 7,707,621; 7,708,194; 7,712,111; 7,712,777; 7,715,351; 7,716,492; 7,724,717; 7,730,482; 7,733,804; 7,743,074; 7,747,980; 7,748,618; 7,757,076; 7,760,654; 7,761,863; 7,761,885; 7,761,910; 7,762,470; 7,770,008; 7,774,495; 7,778,927; 7,783,041; 7,783,777; 7,783,886; 7,787,865; 7,788,663; 7,801,058; 7,801,781; 7,804,807; 7,818,519; 7,818,811; 7,822,863; 7,823,772; 7,831,238; 7,831,752; 7,831,827; 7,844,834; 7,848,746; 7,849,140; 7,853,255; 7,853,780; 7,860,922; 7,860,923; 7,864,673; 7,869,601; 7,870,097; 7,881,667; 7,886,962; 7,899,187; 7,899,915; 7,904,074; 7,907,935; 7,916,861; 7,920,518; 7,920,534; 7,920,851; 7,937,089; 7,944,577; 7,945,959; 7,950,047; 7,953,818; 7,962,164; 7,970,894; 7,974,234; 7,974,296; 7,975,002; 7,975,051; 7,978,062; 7,979,692; 7,983,615; 7,983,835; 7,986,704; 7,987,491; 7,990,947; 7,991,764; 8,000,314; 8,001,232; 8,005,476; 8,009,608; 8,013,732; 8,014,722; 8,019,352; 8,023,425; 8,028,329; 8,031,650; 8,032,939; 8,036,195; 8,037,202; 8,038,239; 8,046,328; 8,046,504; 8,050,405; 8,064,412; 8,064,879; 8,064,926; 8,068,831; 8,073,839; 8,082,491; 8,090,399; 8,103,691; 8,103,718; 8,108,455; 8,116,734; 8,117,547; 8,127,039; 8,130,146; 8,131,645; 8,135,796; 8,136,149; 8,139,588; 8,144,725; 8,145,219; 8,149,848; 8,150,312; 8,150,372; 8,150,416; 8,151,336; 8,156,337; 8,159,985; 8,160,077; 8,161,172; 8,165,142; 8,166,296; 8,166,551; 8,171,136; 8,171,292; 8,175,528; 8,179,911; 8,182,340; 8,185,119; 8,193,930; 8,195,233; 8,195,934; 8,200,195; 8,200,700; 8,204,522; 8,204,992; 8,212,667; 8,213,907; 8,214,228; 8,214,645; 8,223,010; 8,224,893; 8,225,094; 8,225,380; 8,226,474; 8,228,861; 8,229,785; 8,229,812; 8,229,813; 8,229,888; 8,233,471; 8,234,387; 8,245,315; 8,249,028; 8,249,559; 8,250,207; 8,250,628;

8,260,274; 8,260,320; 8,261,338; 8,266,212; 8,266,438;
8,266,676; 8,270,310; 8,270,952; 8,271,800; 8,271,802;
8,275,395; 8,275,672; 8,279,067; 8,280,359; 8,281,169;
8,284,748; 8,289,886; 8,290,498; 8,296,825; 8,301,784;
8,302,167; 8,305,935; 8,305,936; 8,305,980; 8,311,214;
8,311,939; 8,316,091; 8,316,438; 8,320,879; 8,321,330;
8,321,526; 8,321,534; 8,322,607; 8,326,958; 8,327,131;
8,331,901; 8,335,222; 8,335,304; 8,341,141; 8,341,291;
8,341,292; 8,345,881; 8,346,248; 8,347,088; 8,347,093;
8,351,898; 8,352,342; 8,352,636; 8,353,052; 8,355,337;
8,359,016; 8,359,397; 8,364,961; 8,369,830; 8,370,236;
8,373,556; 8,375,202; 8,379,564; 8,380,982; 8,381,262;
8,385,240; 8,385,916; 8,386,394; 8,392,289; 8,395,498;
8,396,458; RE42725; RE42871; 20020069278;
20020072975; 20020075844; 20020133534; 20020143655;
20020143855; 20020143944; 20020147771; 20020147810;
20020152299; 20020161476; 20020184310; 20020184311;
20020184357; 20020184358; 20020188657; 20030002521;
20030041141; 20030065525; 20030087629; 20030093691;
20030100369; 20030100370; 20030100371; 20030100372;
20030229900; 20040019807; 20040030743; 20040030794;
20040031038; 20040031058; 20040044727; 20040064512;
20040064568; 20040064693; 20040073795; 20040088347;
20040088348; 20040088369; 20040088646; 20040098447;
20040133640; 20040148326; 20040162871; 20040198220;
20050086300; 20050109841; 20050129240; 20050141706;
20050144437; 20050233811; 20050259611; 20050261970;
20050273850; 20060002331; 20060010251; 20060010485;
20060040248; 20060041445; 20060041446; 20060041460;
20060041891; 20060062206; 20060092043; 20060095199;
20060156054; 20060167784; 20060174017; 20060208066;
20060219776; 20060234678; 20060282662; 20060291455;
20070004436; 20070022474; 20070022479; 20070025245;
20070025265; 20070060099; 20070060109; 20070060114;
20070060129; 20070060136; 20070060173; 20070061197;
20070061198; 20070061211; 20070061229; 20070061242;
20070061243; 20070061244; 20070061245; 20070061246;
20070061247; 20070061300; 20070061301; 20070061302;
20070061303; 20070061317; 20070061328; 20070061331;
20070061332; 20070061333; 20070061334; 20070061335;
20070061336; 20070061363; 20070073717; 20070073718;
20070073719; 20070073722; 20070073723; 20070087756;
20070094042; 20070097885; 20070100650; 20070100651;
20070100652; 20070100653; 20070100805; 20070100806;
20070118533; 20070136817; 20070143629; 20070143827;
20070143851; 20070156895; 20070168354; 20070169184;
20070171885; 20070192294; 20070192318; 20070198432;
20070198485; 20070239724; 20070260635; 20070263783;
20070288427; 20070293323; 20080009268; 20080032801;
20080033869; 20080041937; 20080052769; 20080063201;
20080076572; 20080092181; 20080095180; 20080097858;
20080098212; 20080109879; 20080141360; 20080167954;
20080183853; 20080222715; 20080229402; 20080234047;
20080242279; 20080252485; 20080256618; 20090013380;
20090016529; 20090036111; 20090046591; 20090046598;
20090046644; 20090046676; 20090046861; 20090047930;
20090047966; 20090049158; 20090060201; 20090073943;
20090088133; 20090119741; 20090119776; 20090168990;
20090199009; 20090204805; 20090204964; 20090254572;
20090254646; 20090275403; 20090281872; 20090319672;
20090320073; 20090322510; 20090327729; 20100057801;
20100076845; 20100082430; 20100082431; 20100094981;
20100095077; 20100099396; 20100100930; 20100115606;
20100121705; 20100131618; 20100131619; 20100131622;
20100131652; 20100132040; 20100138293; 20100138296;
20100138908; 20100138926; 20100142410; 20100145804;
20100146146; 20100150170; 20100153208; 20100153211;

20100169179; 20100186078; 20100188975; 20100188990;
20100188991; 20100188992; 20100188993; 20100188994;
20100188995; 20100190470; 20100191575; 20100191576;
20100191604; 20100191612; 20100191613; 20100191846;
20100191847; 20100192120; 20100192170; 20100192207;
20100192212; 20100192220; 20100197266; 20100197268;
20100198681; 20100211458; 20100211645; 20100217662;
20100217663; 20100235285; 20100235879; 20100250497;
20100269146; 20100275250; 20100281364; 20100293051;
20100293221; 20100299522; 20100299763; 20100304737;
20100317420; 20110004513; 20110015993; 20110015994;
20110019627; 20110029378; 20110029387; 20110047062;
20110106614; 20110145076; 20110159902; 20110167474;
20110194698; 20110202874; 20110216674; 20110217966;
20110219234; 20110219419; 20110230268; 20110231936;
20110246766; 20110258046; 20110273568; 20110275393;
20110276673; 20110277028; 20110289308; 20110289314;
20110302408; 20110307710; 20110312310; 20110313862;
20110320264; 20110320265; 20110320266; 20110320267;
20110320268; 20110320269; 20110320270; 20110320271;
20110320279; 20110320280; 20110320281; 20110320282;
20110321127; 20120004984; 20120004985; 20120004986;
20120004987; 20120004988; 20120004989; 20120004990;
20120004991; 20120004992; 20120004993; 20120004994;
20120004995; 20120004996; 20120004997; 20120004998;
20120004999; 20120005000; 20120005001; 20120005002;
20120005003; 20120005004; 20120005005; 20120005006;
20120005007; 20120005008; 20120005009; 20120005010;
20120005011; 20120005012; 20120005013; 20120005014;
20120005020; 20120005077; 20120005078; 20120005079;
20120005080; 20120005081; 20120005082; 20120005083;
20120005084; 20120005085; 20120005086; 20120005087;
20120005088; 20120005089; 20120005090; 20120005091;
20120005092; 20120005725; 20120005726; 20120010945;
20120010946; 20120010947; 20120010948; 20120010949;
20120010950; 20120010951; 20120010952; 20120010953;
20120010954; 20120010955; 20120010956; 20120010957;
20120010958; 20120010959; 20120010960; 20120010961;
20120010962; 20120010963; 20120010964; 20120010965;
20120010966; 20120010967; 20120010968; 20120010969;
20120010970; 20120010971; 20120010972; 20120010973;
20120010974; 20120010975; 20120010976; 20120010977;
20120010978; 20120010979; 20120011058; 20120015644;
20120016925; 20120027001; 20120030470; 20120032945;
20120036010; 20120036220; 20120036245; 20120036440;
20120036442; 20120036552; 20120041819; 20120054848;
20120059711; 20120059718; 20120066057; 20120066065;
20120066198; 20120066199; 20120069131; 20120084544;
20120084545; 20120084562; 20120084566; 20120084838;
20120086345; 20120087319; 20120088470; 20120089699;
20120089845; 20120094769; 20120096513; 20120101831;
20120101832; 20120101833; 20120101834; 20120101835;
20120101836; 20120102143; 20120105199; 20120105201;
20120105214; 20120109667; 20120109668; 20120109669;
20120109670; 20120109671; 20120109672; 20120109673;
20120109674; 20120109851; 20120110602; 20120116790;
20120116959; 20120118947; 20120122528; 20120122529;
20120122558; 20120129503; 20120130811; 20120130812;
20120131685; 20120134291; 20120150629; 20120158607;
20120159438; 20120159578; 20120185390; 20120190386;
20120191860; 20120192249; 20120195206; 20120195222;
20120195223; 20120196565; 20120197709; 20120197724;
20120197792; 20120201133; 20120203677; 20120204245;
20120208496; 20120209750; 20120210130; 20120210391;
20120210401; 20120214441; 20120215831; 20120216225;
20120222123; 20120232945; 20120232970; 20120238255;
20120240183; 20120240196; 20120240236; 20120254474;

20120259981; 20120284416; 20120294195; 20120297464; 20120323717; 20120323786; 20120324067; 20120324242; 20120324562; 20120330829; 20130003613; 20130005299; 20130005322; 20130006729; 20130006780; 20130007837; 20130010945; 20130012178; 20130014263; 20130016636; 20130024254; 20130024257; 20130024262; 20130024267; 20130024364; 20130024371; 20130034230; 20130040703; 20130045710; 20130054820; 20130054962; 20130055315; 20130055347; 20130061264; 20130061273; 20130065551; 20130066723; 20130067023; and 20130067526.

If several different applications or data need to be secured between the devices, it often makes sense to apply a suitable VPN (Virtual Private Network) technology. VPN can protect the data communication interfaces from malicious attacks by dropping all inadequate data traffic, and also provides the secure tunneling for insecure protocols and data to traverse securely over various networks. A useful information and comparison of various VPN protocols is available e.g. in NIST SP 800-77 "Guide to IPSec VPNs", Chapter 5.

Transport Layer Security (TLS)—IETF RFC5246 can cryptographically protect the information that the OSI transport layer 4 delivers. It can provide adequate security with: Payload data authentication, integrity verification and encryption; Replay protection; and Public key certificate based mutual authentication of the peers. The strength of the algorithms and key lengths are negotiated in the beginning of a secure TLS session, using a special handshake protocol. The handshakes can utilize public key certificates and cryptography (e.g. DSS, RSA) also for mutual authentication (server+client certificates), when necessary. The cryptographic key and policy negotiation messaging is rather well secured in TLS specification and most implementations. Also the strength of the strongest user data "Cipher-Suites" are very good (AES, 3DES, etc. are supported with long keys). Also, the Datagram Transport Layer Security (DTLS)—IETF RFC4347 is a protocol that travels within the transport layer PDU. So, both TLS and DTLS can traverse NATs and provide easy and secure device data exchanges without securing the transport layer or lower layers. This allows for example any client/server applications to communicate in straightforward way. DTLS over the Datagram Congestion Control Protocol (DCCP)—IETF RFC5238 is also one possible protocol to be considered.

Security Architecture for the Internet Protocol—IPSec (IETF RFC4301-4309) is a family of protocols (of which AH and ESP are implemented at TCP/IP stack's network layer, or at least under transport layer). IPSec can provide adequate security in flexible ways using: IP header and payload data authentication, integrity verification and encryption (only ESP); Replay protection; and Public key certificate or shared secrets based mutual authentication of the peers. The IPsec architecture consists of a number of specifications: Security Architecture for the Internet Protocol (IETF RFC4301); IP Authentication Header (AH) (IETF RFC4302); IP Encapsulating Security Payload (ESP) (IETF RFC4303); Internet Key Exchange (IKEv2) Protocol (IETF RFC4306); Cryptographic Algorithms for Use in the Internet Key Exchange Version 2 (IKEv2) (IETF RFC4307); Cryptographic Suites for IPsec (IETF RFC4308); Using Advanced Encryption Standard (AES) CCM Mode with IPsec Encapsulating Security Payload (ESP) (IETF RFC4309); Cryptographic Algorithm Implementation Requirements for ESP and AH (IETF RFC4835). The tunnel mode ESP (and IKE) are used in the construction of IPSec based Virtual Private Networks (VPNs). However, IKE is a rather resource consuming protocol for secure connection establishment with its complex ISAKMP message exchanges, but it is a scalable way to establish the secure connections between different parties of the infrastructure.

An alternative approach is to utilize even stronger, lower-layer security protocol to provide the security services for SNMP. For example, RFC5590 defines an extension which allows an "external" security protocol to be used with SNMP engines. Potential external protocols include TLS and SSH (RFC4251).

A transport layer Stream Control Transmission Protocol (SCTP)—IETF RFC4960 is quite a recent, reliable protocol providing for independent message streams: May use TLS/SSL or run over IPsec; Congestion avoidance behavior; Protection against flooding attacks (lightweight mutual authentication). Delivery mechanisms include: Sequential non-duplicated delivery of messages for each independent stream and Immediate delivery (bypassing the sequential delivery). The Secure Real-time Transport Protocol (SRTP)—IETF RFC3711 defines a RTP (Real-time Transport Protocol) profile which provides for unicast and multicast RTP data security to be used as a stream cipher: Segmented Integer Counter Mode: AES with 128-bit key as default; f8-mode: AES with 128-bit key as default; Authentication, integrity and replay protection: HMAC-SHA1 as truncated to 80 or 32-bits size; Hashing over the payload and the header including sequence number. There are several possible choices that can be used for the negotiation and derivation of cryptographic keys that SRTP will need. Alternatives include: MIKEY (RFC3830: Multimedia Internet KEYing); SDES (RFC4568: Session Description Protocol (SDP) Security Descriptions for Media Streams); ZRTP (IETF Draft: Media Path Key Agreement for Secure RTP).

Bluetooth provides a secure way to connect and exchange information between devices such as faxes, mobile phones, telephones, laptops, personal computers, printers, Global Positioning System (GPS) receivers, digital cameras, and video game consoles. It was principally designed as a low-bandwidth technology. A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone will necessarily begin as master, as initiator of the connection; but may subsequently prefer to be slave).

The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode). The master chooses which slave device to address; typically, it switches rapidly from one device to another in a round-robin fashion. Since it is the master that chooses which slave to address, whereas a slave is (in theory) supposed to listen in each receive slot, being a master is a lighter burden than being a slave. Being a master of seven slaves is possible; being a slave of more than one master is difficult. The specification is vague as to required behavior in scatternets.

The effective range varies due to propagation conditions, material coverage, production sample variations, antenna configurations and battery conditions. In most cases the effective range of Class 2 devices is extended if they connect to a Class 1 transceiver, compared to a pure Class 2 network. This is accomplished by the higher sensitivity and transmission power of Class 1 devices.

To use Bluetooth wireless technology, a device has to be able to interpret certain Bluetooth profiles, which are definitions of possible applications and specify general behaviors that Bluetooth enabled devices use to communicate with other Bluetooth devices. These profiles include settings to parametrize and to control the communication from start. Adherence to profiles saves the time for transmitting the parameters anew before the bi-directional link becomes effective. There are a wide range of Bluetooth profiles that describe many different types of applications or use cases for devices.

Wi-Fi is a wireless version of a common wired Ethernet network, and requires configuration to set up shared resources, transmit files, and to set up audio links (for example, headsets and hands-free devices). Wi-Fi uses the same radio frequencies as Bluetooth, but with higher power, resulting in higher bit rates and better range from the base station. The nearest equivalents in Bluetooth are the DUN profile, which allows devices to act as modem interfaces, and the PAN profile, which allows for ad-hoc networking. Bluetooth v2.1+EDR has a data rate of about 3 Mbit/s, although the practical data transfer rate is 2.1 Mbit/s. EDR uses a combination of GFSK and Phase Shift Keying modulation (PSK) with two variants, π/4-DQPSK and 8DPSK. EDR can provide a lower power consumption through a reduced duty cycle. Bluetooth v3.0+HS provides theoretical data transfer speeds of up to 24 Mbit/s, though not over the Bluetooth link itself. Instead, the Bluetooth link is used for negotiation and establishment, and the high data rate traffic is carried over a collocated 802.11 link. The main new feature is AMP (Alternate MAC/PHY), the addition of 802.11 as a high speed transport. Bluetooth Core Specification version 4.0 includes Classic Bluetooth, Bluetooth high speed and Bluetooth low energy protocols. Bluetooth high speed is based on Wi-Fi, and Classic Bluetooth consists of legacy Bluetooth protocols. Bluetooth low energy (BLE), previously known as WiBree, is a subset to Bluetooth v4.0 with an entirely new protocol stack for rapid build-up of simple links. As an alternative to the Bluetooth standard protocols that were introduced in Bluetooth v1.0 to v3.0, it is aimed at very low power applications running off a coin cell. Chip designs allow for two types of implementation, dual-mode, single-mode and enhanced past versions. General improvements in version 4.0 include the changes necessary to facilitate BLE modes, as well the Generic Attribute Profile (GATT) and Security Manager (SM) services with AES Encryption.

Many of the services offered over Bluetooth can expose private data or allow the connecting party to control the Bluetooth device. For security reasons it is necessary to be able to recognize specific devices and thus enable control over which devices are allowed to connect to a given Bluetooth device. At the same time, it is useful for Bluetooth devices to be able to establish a connection without user intervention (for example, as soon as they are in range).

To resolve this conflict, Bluetooth uses a process called bonding, and a bond is created through a process called pairing. The pairing process is triggered either by a specific request from a user to create a bond (for example, the user explicitly requests to "Add a Bluetooth device"), or it is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices. When desired, the bonding relationship can later be removed by the user.

During the pairing process, the two devices involved establish a relationship by creating a shared secret known as a link key. If a link key is stored by both devices, they are said to be paired or bonded. A device that wants to communicate only with a bonded device can cryptographically authenticate the identity of the other device, and so be sure that it is the same device it previously paired with. Once a link key has been generated, an authenticated Asynchronous Connection-Less (ACL) link between the devices may be encrypted so that the data that they exchange over the airwaves is protected against eavesdropping. Link keys can be deleted at any time by either device. If done by either device this will implicitly remove the bonding between the devices; so it is possible for one of the devices to have a link key stored but not be aware that it is no longer bonded to the device associated with the given link key. Bluetooth services generally require either encryption or authentication, and as such require pairing before they allow a remote device to use the given service. Some services, such as the Object Push Profile, elect not to explicitly require authentication or encryption so that pairing does not interfere with the user experience associated with the service use-cases.

Bluetooth implements confidentiality, authentication and key derivation with custom algorithms based on the SAFER+block cipher. Bluetooth key generation is generally based on a Bluetooth PIN, which must be entered into both devices. This procedure might be modified if one of the devices has a fixed PIN (e.g., for headsets or similar devices with a restricted user interface). During pairing, an initialization key or master key is generated, using the E22 algorithm. The E0 stream cipher is used for encrypting packets, granting confidentiality, and is based on a shared cryptographic secret, namely a previously generated link key or master key. Those keys, used for subsequent encryption of data sent via the air interface, rely on the Bluetooth PIN, which has been entered into one or both devices.

Bluetooth is susceptible to denial-of-service attacks, eavesdropping, man-in-the-middle attacks, message modification, and resource misappropriation. The present technology addresses these security limitations (except for denial-of-service attacks) by providing a security layer which tunnels through the Bluetooth link, and therefore does not rely on the Bluetooth security protocols.

A virtual private network (VPN) extends a private network and the resources contained in the network across public networks like the Internet. It enables a host computer to send and receive data across shared or public networks as if it were a private network with all the functionality, security and management policies of the private network. This is done by establishing a virtual point-to-point connection through the use of dedicated connections, encryption, or a combination of the two. The VPN connection across the Internet is technically a wide area network (WAN) link between the sites but appears to the user as a private network link—hence the name "virtual private network".

VPNs can be either remote-access (connecting an individual computer to a network) or site-to-site (connecting two networks together). In a corporate setting, remote-access VPNs allow employees to access their company's intranet from home or while traveling outside the office, and site-to-site VPNs allow employees in geographically separated offices to share one cohesive virtual network. A VPN can also be used to interconnect two similar networks over a dissimilar middle network; for example, two IPv6 networks over an IPv4 network.

VPNs typically require remote access to be authenticated and make use of encryption techniques to prevent disclosure of private information. VPNs provide security through tunneling protocols and security procedures such as encryption. Their security model provides: Confidentiality such that even if traffic is sniffed, an attacker would only see encrypted data which they cannot understand; (see Packet analyzer and Deep packet inspection); Allowing Sender authentication to prevent unauthorized users from accessing the VPN; Message integrity to detect any instances of transmitted messages having been tampered with.

Secure VPN protocols include the following: IPSec (Internet Protocol Security); Transport Layer Security (SSL/TLS); Datagram Transport Layer Security (DTLS); Microsoft Point-to-Point Encryption (MPPE); Microsoft's Secure Socket Tunneling Protocol (SSTP); MPVPN (Multi Path Virtual Private Network); and Secure Shell (SSH).

Tunnel endpoints must authenticate before secure VPN tunnels can be established. User-created remote access VPNs may use passwords, biometrics, two-factor authentication or other cryptographic methods. Network-to-network tunnels often use passwords or digital certificates, as they permanently store the key to allow the tunnel to establish automatically and without intervention from the user. Tunneling protocols can operate in a point-to-point network topology that would theoretically not be considered a VPN, because a VPN by definition is expected to support arbitrary and changing sets of network nodes. But since most router implementations support a software-defined tunnel interface, customer-provisioned VPNs often are simply defined tunnels running conventional routing protocols. According to the present technology, support for arbitrary and changing sets of network nodes is preferably, but not mandatorily, provided.

Depending on whether the PPVPN (Provider Provisioned VPN) runs in layer 2 or layer 3, the building blocks described below may be L2 only, L3 only, or combine them both. Multiprotocol label switching (MPLS) functionality blurs the L2-L3 identity. RFC 4026 generalized the following terms to cover L2 and L3 VPNs, but they were introduced in RFC 2547. Mobile VPNs are used in a setting where an endpoint of the VPN is not fixed to a single IP address, but instead roams across various networks such as data networks from cellular carriers or between multiple Wi-Fi access points. The mobile VPN software handles the necessary network authentication and maintains the network sessions in a manner transparent to the application and the user. The Host Identity Protocol (HIP), under study by the Internet Engineering Task Force, is designed to support mobility of hosts by separating the role of IP addresses for host identification from their locator functionality in an IP network. With HIP a mobile host maintains its logical connections established via the host identity identifier while associating with different IP addresses when roaming between access networks. See: OpenBSD ssh manual page, VPN section; Unix Toolbox section on SSH VPN E. Rosen & Y. Rekhter (March 1999). "RFC 2547 BGP/MPLS VPNs". Internet Engineering Task Force (IETF). www.ietforg/rfc/rfc2547.txt.

Secure Shell (SSH) is a cryptographic network protocol for secure data communication, remote shell services or command execution and other secure network services between two networked computers that connects, via a secure channel over an insecure network, a server and a client (running SSH server and SSH client programs, respectively). The protocol specification distinguishes between two major versions that are referred to as SSH-1 and SSH-2. SSH uses public-key cryptography to authenticate the remote computer and allow it to authenticate the user, if necessary. Anyone can produce a matching pair of different keys (public and private). The public key is placed on all computers that must allow access to the owner of the matching private key (the owner keeps the private key secret). While authentication is based on the private key, the key itself is never transferred through the network during authentication. SSH only verifies whether the same person offering the public key also owns the matching private key. Hence, in all versions of SSH it is important to verify unknown public keys, i.e. associate the public keys with identities, before accepting them as valid. Accepting an attacker's public key without validation will authorize an unauthorized attacker as a valid user.

SSH also supports password-based authentication that is encrypted by automatically generated keys. In this case the attacker could imitate the legitimate side, ask for the password and obtain it (man-in-the-middle attack). However, this is only possible if the two sides have never authenticated before, as SSH remembers the key that the remote side once used. Password authentication can be disabled. SSH is important in cloud computing to solve connectivity problems, avoiding the security issues of exposing a cloud-based virtual machine directly on the Internet. An SSH tunnel can provide a secure path over the Internet, through a firewall to a virtual machine.

The following RFC publications by the IETF "secsh" working group document SSH-2 as a proposed Internet standard: RFC 4250, The Secure Shell (SSH) Protocol Assigned Numbers; RFC 4251, The Secure Shell (SSH) Protocol Architecture; RFC 4252, The Secure Shell (SSH) Authentication Protocol; RFC 4253, The Secure Shell (SSH) Transport Layer Protocol; RFC 4254, The Secure Shell (SSH) Connection Protocol; RFC 4255, Using DNS to Securely Publish Secure Shell (SSH) Key Fingerprints; RFC 4256, Generic Message Exchange Authentication for the Secure Shell Protocol (SSH); RFC 4335, The Secure Shell (SSH) Session Channel Break Extension; RFC 4344, The Secure Shell (SSH) Transport Layer Encryption Modes; RFC 4345, Improved Arcfour Modes for the Secure Shell (SSH) Transport Layer Protocol; RFC 4419, Diffie-Hellman Group Exchange for the Secure Shell (SSH) Transport Layer Protocol (March 2006); RFC 4432, RSA Key Exchange for the Secure Shell (SSH) Transport Layer Protocol (March 2006); RFC 4462, Generic Security Service Application Program Interface (GSS-API) Authentication and Key Exchange for the Secure Shell (SSH) Protocol (May 2006); RFC 4716, The Secure Shell (SSH) Public Key File Format (November 2006); RFC 5656, Elliptic Curve Algorithm Integration in the Secure Shell Transport Layer (December 2009).

The SSH-2 protocol has an internal architecture (defined in RFC 4251) with well-separated layers. These are: The transport layer (RFC 4253). This layer handles initial key exchange as well as server authentication, and sets up encryption, compression and integrity verification. It exposes to the upper layer an interface for sending and receiving plaintext packets with sizes of up to 32,768 bytes each (more can be allowed by the implementation). The transport layer also arranges for key re-exchange, usually after 1 GB of data has been transferred or after 1 hour has passed, whichever is sooner. The user authentication layer (RFC 4252). This layer handles client authentication and provides a number of authentication methods. Authentication is client-driven: when one is prompted for a password, it may be the SSH client prompting, not the server. The server merely responds to the client's authentication requests. Widely used user authentication methods include the following: password: a method for straightforward password authentication, including a facility allowing a password to be changed. This method is not implemented by all programs; publickey: a method for public key-based authentication, usually supporting at least DSA or RSA keypairs, with other implementations also supporting X.509 certificates. keyboard-interactive (RFC 4256) is a versatile method where the server sends one or more prompts to enter information and the client displays them and sends back responses keyed-in by the user. Used to provide one-time password authentication such as S/Key or SecurID. Used by some OpenSSH configurations when PAM is the underlying host authentication provider to effectively provide password authentication, sometimes leading to inability to log in with a client that supports just the plain password authentication method. GSSAPI authentication methods which provide an extensible scheme to perform SSH authentication using external mechanisms such as Kerberos 5 or NTLM, providing single sign on capability to SSH sessions. These methods are usually implemented by commercial SSH implementations for use in organizations, though OpenSSH does have a working GSSAPI implementation.

The connection layer (RFC 4254). This layer defines the concept of channels, channel requests and global requests using which SSH services are provided. A single SSH connection can host multiple channels simultaneously, each transferring data in both directions. Channel requests are used to relay out-of-band channel specific data, such as the changed size of a terminal window or the exit code of a server-side process. The SSH client requests a server-side port to be forwarded using a global request. The SSHFP DNS record (RFC 4255) provides the public host key fingerprints in order to aid in verifying the authenticity of the host.

This open architecture provides considerable flexibility, allowing SSH to be used for a variety of purposes beyond a secure shell. The functionality of the transport layer alone is comparable to Transport Layer Security (TLS); the user authentication layer is highly extensible with custom authentication methods; and the connection layer provides the ability to multiplex many secondary sessions into a single SSH connection, a feature comparable to BEEP and not available in TLS. These are intended for performance enhancements of SSH products: SSH-over-SCTP: support for SCTP rather than TCP as the connection oriented transport layer protocol; ECDSA: support for elliptic curve DSA rather than DSA or RSA for signing; ECDH: support for elliptic curve Diffie-Hellman rather than plain Diffie-Hellman for encryption key exchange; and UMAC: support for UMAC rather than HMAC for MAC/integrity.

The implantable medical device is controlled by at least one programmable automated electronic processor, having a memory, configured to:

(a) communicate through the wireless radio frequency digital communication radio transceiver over a wireless communication channel to an interrogator device, which may be smartphone, and optionally through the smartphone to establish a connection with a remote endpoint, in a manner which may be cryptographically secure using a tunneling protocol. The endpoint may be unique or one of many authorized or that could be authorized. Each endpoint preferable has a respective associated endpoint security certificate to implement a public key infrastructure;

(b) respond to a request for an identification, and after completing a communication initiation protocol, transmitting stored data and permitting the stored data to be overwritten; and (c) provide an emergency beacon signal independent of an interrogator electromagnetic field. The interrogator may excite communications in the low frequency (30 kHz-300 kHz), medium frequency (300 kHz-3 Mhz), high frequency (3-30 MHz), very high frequency (30 MHz-300 Mhz), or ultra-high frequency (300 MHz-3 Ghz), for example. Preferably, the communication from the implant is on a frequency, and using a protocol available on a common smartphone. The smartphone may be configured to execute a smartphone app to provide a local user interface with the at least one programmable automated electronic processor.

The at least one programmable automated electronic processor may initiate a request to a respective one of the plurality of different endpoints to open a cryptographically secure tunneling protocol communication session according to the public key infrastructure, by sending a message over the insecure physical channel, which may be, e.g., a short range communication protocol such as NFC. The at least one programmable automated electronic processor may encrypt information according to the Advanced_Encryption_Standard (AES). The at least one programmable automated electronic processor may request the certificate revocation list from a certificate server at a certification authority through the insecure physical channel with the relay device, and through the relay device (smartphone) to the certification server through cellular communication channel and communication network channel according to a public key infrastructure hierarchy management system. The cryptographically secure tunneling protocol communication may be a virtual private network (VPN).

It is noted that the implant need not implement a proprietary security scheme, and may in fact implement a known NFC security scheme, such as developed for payment protocols.

The implantable medical device may include a power supply and a rewritable memory storing computer readable instructions for controlling the at least one programmable automated electronic processor to implement the public key infrastructure stored in the rewritable memory, which are securely updatable through the physical channel. The power supply may be a primary Lithium ion battery, such as a 3 mm diameter 8-10 mm long cell, or a rechargeable battery with similar dimensions. The battery, if rechargeable, may be charged from a current supplied by an energy conversion circuit driven from the energy harvesting circuit that derives power from the interrogation field. Alternately, a supercapacitor may be used, though these generally have lower power density than a battery of similar dimensions.

The implantable device has various modes of operation. In a normal state, a wakeup timer activates the processor to read the sensor periodically, store a value in memory, process the value to determine an adverse event, and return to a sleep mode. If an adverse event occurs, further processing or changing of sensor sampling period is implemented. If the adverse event is an emergency, the implantable device is triggered to enter an emergency alert mode, wherein the implantable device consumes its power reserve to contact an external device. That external device may be a Bluetooth, ANT, or WiFi device. The implantable device may also alert the host, such as by generating an electrical shock, mechanical vibration, or audibly. In this emergency mode, the internal power is consumed as necessary to generate the alert. Another mode provides occurs when the implantable device is within range of an authenticated interrogator, which provides external power and communications. When in this mode, the processor generally is not in a sleep mode, and the contents of memory are transferred, and the sensor may be calibrated, for example. The interrogator may update processing and sampling parameters of the implantable device.

The smartphone need not be merely a conduit, and may have software that interacts with the implant. The software may be present at a bootloader level, root level, or user space (app) or other implementation. The software handles interaction with the implant, including any security protocols, interfacing with phone hardware and software, and remote communication with a remote server or caregiver endpoint. Typically, the cellphone software provides user interface, downloading implant memory and clearing memory space, secure reprogramming of embedded code in the implant, and other local management tasks.

The remote endpoint may be a server, which receives data from many implants, through respective smartphones, and analyzes the data individually and in statistical aggregate. The server may manage thresholds/alarm limits, trend analysis, remote reprogramming, appointment management with health care professionals, etc.

Biocompatible implants are well known. See, U.S. Pat. Nos. 5,764,518; 6,379,669; 6,567,259; 7,097,662; 7,333, 013; 7,371,825; 7,414,534; 7,713,923; 7,727,143; 7,765, 005; 7,780,590; 7,787,958; 7,813,778; 7,842,092; 7,876, 228; 7,916,013; 7,932,825; 7,956,162; 7,966,075; 7,981, 025; 7,983,435; 7,983,763; 8,000,801; 8,036,736; 8,078, 282; 8,079,518; 8,081,925; 8,093,991; 8,114,345; 8,114, 964; 8,192,406; 8,197,454; 8,200,342; 8,202,260; 8,207, 316; 8,246,533; 8,251,946; 8,257,729; 8,269,635; 8,269, 636; 8,301,243; 8,321,032; 8,323,232; 8,326,435; 8,348, 882; 8,374,697; 8,389,286; 8,444,653; 8,454,552; 8,457, 757; 8,457,760; 8,478,378; 8,483,840; 8,486,070; 8,496, 657; 8,509,913; 8,543,199; 8,557,772; 8,574,146; 8,577, 453; 8,577,465; 8,577,468; 8,577,478; 8,623,023; 8,639, 524; 8,644,957; 8,666,471; 8,673,194; 8,707,040; 8,715, 159; 8,718,776; 8,721,520; 8,721,643; 8,751,013; 8,784, 425; 8,788,057; 8,790,400; 8,795,260; 8,795,359; 8,798, 773; 8,805,478; 8,805,530; 8,808,163; 8,808,373; 8,814, 868; 8,838,249; 8,849,368; 8,855,785; 8,875,714; 8,901, 084; 8,911,486; 8,926,573; 8,929,999; 8,946,390; 8,975, 372; 8,989,867; 8,989,870; 9,002,471; 9,011,361; 9,017, 380; 9,026,792; 9,031,637; 9,044,209; 9,044,612; 9,055, 791; 9,061,139; 9,061,151; 9,067,073; 9,072,560; 9,113, 844; 9,125,981; 9,126,825; 9,144,488; 9,144,489; 9,149, 189; 9,159,223; 9,161,693; 9,187,539; 9,198,911; 9,204, 798; 9,211,185; 9,237,012; 9,248,291; 9,248,302; 9,251, 960; 9,271,857; 9,288,614; 9,308,381; 9,317,920; 9,326, 720; 9,326,730; 9,327,061; 9,333,071; 9,339,188; 9,339, 372; 9,345,404; 9,356,473; 9,357,922; 9,358,378; 9,358, 392; 9,361,572; 9,367,793; 9,370,618; 9,370,619; 9,386, 360; 9,392,939; 9,398,854; 9,403,009; 9,403,021; 9,409, 018; 9,414,651; 9,414,775; 9,415,163; 9,420,856; 9,420, 857; 9,421,388; 9,424,508; 9,427,053; 9,427,160; 9,427, 189; 9,427,190; 9,436,903; 9,445,651; 9,445,730; 9,462, 856; 9,462,962; 9,463,012; 9,474,461; 9,474,888; 9,486, 168; 9,492,656; 9,492,678; 9,498,195; 9,501,735; 9,514, 338; 9,517,023; 9,522,282; 9,526,422; 9,526,650; 9,530, 089; 9,532,716; 9,532,738; 9,539,037; 9,542,685; 9,545, 506; 9,553,486; 9,564,777; 9,569,719; 9,569,720; 9,576, 236; 9,579,422; 9,579,510; 9,582,748; 9,582,749; 9,585, 722; 9,603,997; 9,610,391; 9,634,921; 9,636,509; 9,655, 558; 9,662,015; 9,672,393; 9,675,273; 9,675,809; 9,693, 777; 9,700,234; 9,704,209; 9,723,898; 9,724,098; 9,724, 183; 9,731,104; 9,732,322; 9,757,124; 9,804,672; 9,826, 963; 9,833,353; 9,839,422; 9,839,423; 9,854,370; 9,874, 923; 9,876,537; 9,878,159; 9,884,150; 9,884,456; 9,895, 301; 9,901,276; 9,918,716; 9,919,099; 9,936,890; 9,943, 697; 9,950,166; 9,974,705; 9,986,924; 10,028,659; 10,028, 743; 10,034,743; 10,039,661; 10,045,764; 10,045,798; 10,064,624; 10,066,203; 10,070,992; 10,105,081; 10,117, 621; 10,124,182; 10,130,476; 10,164,685; 10,176,412; 10,179,065; 10,182,819; 10,186,760; 10,188,394; 10,194, 802; 10,196,596; 10,220,217; 20020001588; 20030053284; 20050181973; 20050197677; 20050247319; 20060047283; 20060212096; 20070027371; 20070120683; 20070154030; 20070179562; 20070219639; 20070265704; 20070282196; 20080004642; 20080020012; 20080048855; 20080049376; 20080065181; 20080097496; 20080102096; 20080106419; 20080180242; 20080207983; 20080208010; 20080234598; 20080288027; 20080303728; 20090012372; 20090024161; 20090028957; 20090062825; 20090069869; 20090099626; 20090118683; 20090148496; 20090155900; 20090157147; 20090157151; 20090163980; 20090163981; 20090198293; 20090202387; 20090206087; 20090227862; 20090254179; 20090274737; 20090281597; 20090305972; 20100015201; 20100063347; 20100082102; 20100094654; 20100139672; 20100143871; 20100144641; 20100145337; 20100152573; 20100160997; 20100161004; 20100168821; 20100174240; 20100174349; 20100191236; 20100191306; 20100217239; 20100217240; 20100217241; 20100217242; 20100217243; 20100217244; 20100222686; 20100222802; 20100261526; 20100274121; 20100311640; 20100312081; 20100317955; 20100318160; 20100321163; 20100324578; 20100324579; 20100324639; 20100331868; 20100331874; 20100331932; 20110022140; 20110023343; 20110029043; 20110040343; 20110043297; 20110057037; 20110063088; 20110066079; 20110074349; 20110098576; 20110124983; 20110130636; 20110152756; 20110237861; 20110249381; 20110251516; 20110264058; 20110275930; 20110288600; 20110305672; 20110319785; 20120008714; 20120053585; 20120058106; 20120059434; 20120123221; 20120161901; 20120190386; 20120203079; 20120223705; 20120226118; 20120232012; 20120234433; 20120277859; 20120296399; 20120302874; 20130023954; 20130030255; 20130035544; 20130053711; 20130070387; 20130078244; 20130085408; 20130092564; 20130116664; 20130116665; 20130116666; 20130116667; 20130131679; 20130195806; 20130198463; 20130233324; 20130238056; 20130243799; 20130253297; 20130253660; 20130268029; 20130289529; 20130317584; 20130338494; 20130338768; 20130338769; 20130338770; 20130338771; 20130338772; 20130338773; 20130345561; 20140012111; 20140018644; 20140045757; 20140062717; 20140065153; 20140073704; 20140073839; 20140081076; 20140163644; 20140221732; 20140236105; 20140239528; 20140245783; 20140245784; 20140245785; 20140245786; 20140245787; 20140245788; 20140245789; 20140245790; 20140245791; 20140246497; 20140246498; 20140246499; 20140246500; 20140246501; 20140246502; 20140246917; 20140247136; 20140247137; 20140247142; 20140247143; 20140247144; 20140247146; 20140247147; 20140247149; 20140247150; 20140247151; 20140247154; 20140247155; 20140247156; 20140249379; 20140249760; 20140249853; 20140273824; 20140277277; 20140285396; 20140288619; 20140288647; 20140296663; 20140296978; 20140328517; 20140330244; 20140330256; 20140330257; 20140330347; 20140330357; 20140343691; 20140358196; 20140358197; 20140371821;

20140371824; 20140376336; 20140379090; 20150011860; 20150025478; 20150057595; 20150066124; 20150071934; 20150073498; 20150073499; 20150073500; 20150077050; 20150080982; 20150080992; 20150088226; 20150094547; 20150099959; 20150100108; 20150100109; 20150116053; 20150129664; 20150174296; 20150179038; 20150183828; 20150194052; 20150196378; 20150196409; 20150221208; 20150231402; 20150238277; 20150289911; 20150327989; 20150360038; 20150365738; 20150366915; 20150367144; 20150374541; 20160023007; 20160030650; 20160030756; 20160038324; 20160051825; 20160058324; 20160186140; 20160191120; 20160220198; 20160228034; 20160228052; 20160235317; 20160235318; 20160274752; 20160278638; 20160287380; 20160303313; 20160310048; 20160310737; 20160317095; 20160317797; 20160325083; 20160325084; 20160331518; 20160335632; 20160342882; 20160358063; 20160358155; 20160358156; 20160359222; 20160361009; 20160374556; 20170007420; 20170020241; 20170020402; 20170028185; 20170056677; 20170071510; 20170072121; 20170100214; 20170106196; 20170117739; 20170127929; 20170152486; 20170173216; 20170197072; 20170209666; 20170209705; 20170216610; 20170216611; 20170228627; 20170230084; 20170231738; 20170232256; 20170258585; 20170259072; 20170270721; 20170272316; 20170281927; 20170281928; 20170281957; 20170296834; 20170304635; 20170312530; 20170316487; 20170333080; 20170340872; 20170348146; 20170368158; 20180001018; 20180008185; 20180021235; 20180021498; 20180021510; 20180028275; 20180028827; 20180036053; 20180036115; 20180050189; 20180050214; 20180055500; 20180059126; 20180060520; 20180085038; 20180085592; 20180103879; 20180126053; 20180126133; 20180138022; 20180147413; 20180154075; 20180168811; 20180184944; 20180188704; 20180188714; 20180188715; 20180192952; 20180200003; 20180200185; 20180210425; 20180210426; 20180210427; 20180214690; 20180214694; 20180221663; 20180233016; 20180243567; 20180243573; 20180243577; 20180253073; 20180253074; 20180253075; 20180255374; 20180255375; 20180255376; 20180255377; 20180255378; 20180255379; 20180255380; 20180255381; 20180255382; 20180255383; 20180280694; 20180284735; 20180284736; 20180284737; 20180284741; 20180284742; 20180284743; 20180284744; 20180284745; 20180284746; 20180284747; 20180284749; 20180284752; 20180284753; 20180284754; 20180284755; 20180284756; 20180284757; 20180284758; 20180299878; 20180310824; 20180310964; 20180321666; 20180321667; 20180321672; 20180322445; 20180353219; 20180360355; 20180372720; 20190000656; 20190025805; 20190025806; 20190025812; 20190025813; 20190033845; 20190033846; 20190033847; 20190033848; 20190033849; 20190038214; 20190038496; 20190041835; 20190041836; 20190041840; 20190041841; 20190041842; 20190041843; 20190041844; 20190041845; 20190041846; 20190053712; 20190053915; 20190054284; 20190064791; 20190064792; 20190070350; 20190072922; 20190072923; 20190072924; 20190072925; 20190072926; 20190072928;

Swarm methods may be used for relay of messages, selection of supernodes for forwarding of messages in an ad hoc network, distributed processing of tasks, etc.

The implant may have functions of other types of RF-ID tags, such as access, control, feeding and consumption management, etc. For example, a pet door, feeder, etc., may receive identification signals from the implant, and selectively authorize or react to the identification.

Various distributed ledger technologies may be employed. See, U.S. Pat. Nos. 9,014,661; 9,351,124; 9,436,923; 9,569, 771; 9,641,342; 9,818,092; 9,820,120; 9,849,364; 9,853, 819; 9,855,785; 9,862,222; 9,922,380; 9,922,381; 9,942, 304; 10,005,564; 10,022,613; 10,022,614; 10,026,118; 10,039,113; 10,046,228; 10,055,715; 10,078,839; 10,080, 498; 10,103,936; 10,108,938; 10,115,068; 10,120,888; 10,121,186; 10,127,247; 10,129,032; 10,135,835; 10,142, 312; 10,147,076; 10,152,756; 10,160,251; 10,163,079; 10,163,080; 10,164,952; 10,168,693; 10,172,409; 10,176, 418; 10,176,481; 10,178,105; 10,178,890; 10,192,198; 10,193,695; 10,195,513; 10,200,199; 10,200,834; 10,204, 160; 10,225,085; 20140368601; 20150269624; 20150356524; 20150356555; 20160012465; 20160098723; 20160098730; 20160170996; 20160192166; 20160203522; 20160203572; 20160224803; 20160300252; 20160321654; 20160379312; 20170017936; 20170017954; 20170017955; 20170028622; 20170031874; 20170033932; 20170046652; 20170046689; 20170046694; 20170046799; 20170046806; 20170048209; 20170048234; 20170048235; 20170083907; 20170085545; 20170085555; 20170091756; 20170109735; 20170132615; 20170132630; 20170140408; 20170161517; 20170173262; 20170206532; 20170221032; 20170221052; 20170228706; 20170228731; 20170228734; 20170232300; 20170236177; 20170236196; 20170237569; 20170237570; 20170243177; 20170243208; 20170243209; 20170243212; 20170243213; 20170243214; 20170243217; 20170243222; 20170243286; 20170243287; 20170244707; 20170244721; 20170250796; 20170256000; 20170256001; 20170256003; 20170262862; 20170300905; 20170300910; 20170300946; 20170316487; 20170345105; 20170358041; 20170364860; 20170373849; 20180001184; 20180006990; 20180012311; 20180013815; 20180019984; 20180039512; 20180041345; 20180069899; 20180071789; 20180072415; 20180072416; 20180074481; 20180074488; 20180074521; 20180074522; 20180074523; 20180075386; 20180075406; 20180078843; 20180081787; 20180081955; 20180082043; 20180082295; 20180083786; 20180089627; 20180089641; 20180089669; 20180094953; 20180096121; 20180096175; 20180108024; 20180115600; 20180117446; 20180117447; 20180120225; 20180123804; 20180130034; 20180130050; 20180130158; 20180131765; 20180133583; 20180136633; 20180137461; 20180137506; 20180137512; 20180139057; 20180144298; 20180144342; 20180150816; 20180158036; 20180165738; 20180167394; 20180173906; 20180174097; 20180174188; 20180176017; 20180181806; 20180181909; 20180181964; 20180182140; 20180183796; 20180189528; 20180189854; 20180191503; 20180198617; 20180198876; 20180203755; 20180204034; 20180204111; 20180211213; 20180211718; 20180218003; 20180218354; 20180225649; 20180227354; 20180232693; 20180232730; 20180232817; 20180253430; 20180253805; 20180257306; 20180259976; 20180261307; 20180262493; 20180264347; 20180268360; 20180268418; 20180268479; 20180268483; 20180284093; 20180285709; 20180293577; 20180300772; 20180307854; 20180307859; 20180307959; 20180314868; 20180315141; 20180322164; 20180324407; 20180326291; 20180330369; 20180336515; 20180349893; 20180357603; 20180357725; 20180365633; 20180369437; 20180369438; 20180374037; 20180375750; 20180376336; 20190005507; 20190005566; 20190007381; 20190008117; 20190012637; 20190019144; 20190019171; 20190026690; 20190034536; 20190034605; 20190034808; 20190034888; 20190034889; 20190034923; 20190035499; 20190036887; 20190038791; 20190043008; 20190043010; 20190044736; 20190046863; 20190049931; 20190050888; 20190053470; 20190056726; 20190057454; 20190065733; 20190066063;

Cubeworks, founded by David T. Blauuw and Dennis Sylvester at the University of Michigan, have advanced subminiature, low power implantable computers. See, Shi, Yao, Myungjoon Choi, Ziyun Li, Zhihong Luo, Gyouho Kim, Zhiyoong Foo, Hun-Seok Kim, David D. Wentzloff, and David Blaauw. "A 10 mm 3 inductive coupling radio for syringe-implantable smart sensor nodes." IEEE Journal of Solid-State Circuits 51, no. 11 (2016): 2570-2583.

Chen, Yen-Po, Dongsuk Jeon, Yoonmyung Lee, Yejoong Kim, Zhiyoong Foo, Inhee Lee, Nicholas B. Langhals et al. "An injectable 64 nW ECG mixed-signal SoC in 65 nm for arrhythmia monitoring." IEEE Journal of Solid-State Circuits 50, no. 1 (2015): 375-390.

To achieve a syringe implantable design according to Blauuw and Sylvester, the entire system must pass through the 14-gauge syringe needle during the implantation. Hence, the device width is limited to 1.5 mm. In contrast, the length is less constrained and the two electrodes attached to either side of the device require 2 cm separation in order to provide sufficient separation to yield an acceptably large potential difference. According to the present technology, the 1.5 mm dimension is relaxed to 3 mm diameter (9 gauge). In contrast to surgically implanted devices such as pacemakers with large batteries, the device is designed for daily wireless recharging, enabling a much smaller battery. While the patient sleeps, a host station could recharge and retrieve the stored data through a wireless channel. The lifetime between recharging is set to be five days to provide a safety margin. Matching battery size to device size allows for a 5 pA hr, 3.7 mm Li battery, which constrains system power consumption to be less than 167 nW. This represents a challenging power constraint given that comparable systems in the literature typically consume 1-30 μW.

A. Shukla and A. B. Curtis, "Avoiding permanent atrial fibrillation: Treatment approaches to prevent disease progression," Dec. 6, 2013. Available: www.ncbi.nlm-.nih.gov/pmc/articles/PMC3872084/

L. S. Y. Wong, S. Hossain, A. Ta, J. Edvinsson, D. H. Rivas, and H. Naas, "A very low-power CMOS mixed-signal IC for implantable pacemaker applications," IEEE J. Solid-State Circuits, vol. 39, no. 12, pp. 2446-2456, December 2004.

A. Berson and H. Pipberger, "Skin-Electrode impedance problems in electrocardiography," J. Amer. Heart, vol. 76, no. 4, pp. 514-525, October 1968.

M. S. Spach, R. C. Barr, J. W. Havstad, and E. C. Long, "Skin-electrode impedance and its effect on recording cardiac potentials," Circulation, vol. 34, pp. 649-656, 1966.

J. Rosell, J. Colominas, P. Riu, R. Pallás-Areny, and J. G. Webster, "Skin impedance from 1 Hz to 1 MHz," IEEE Trans. Biomed. Eng., vol. 35, no. 8, pp. 649-651, August 1988.

C. Zellerhoff, E. Himmrich, D. Nebeling, O. Przibille, B. Nowak, and A. Liebrich, "How can we identify the best implantation site for an ECG event recorder?", Pacing & Clinical Electrophys, pp. 1545-1549, 2000.

X. Zou, X. Xu, L. Yao, and Y. Lian, "A 1-V 450-nW fully integrated programmable biomedical sensor interface chip," IEEE J. Solid-State Circuits, vol. 44, no. 4, p. 1067,1077, April 2009.

R. F. Yazicioglu, K. Sunyoung, T. Torfs, K. Hyejung, and C. VanHoof, "A 30 W analog signal processor ASIC for portable biopotential signal monitoring," IEEE J. Solid-State Circuits, vol. 46, no. 1, pp. 209-223, January 2011.

M. Yip, J. L. Bohorquez, and A. P. Chandrakasan, "A 0.6 V 2.9 W mixed-signal front-end for ECG monitoring," in Proc. Symp. VLSI Circuits, Jun. 13-15, 2012, pp. 66-67.

S.-Y. Hsu, Y. Ho, Y. Tseng, T.-Y. Lin, P.-Y. Chang, J.-W. Lee, J.-H. Hsiao, S.-M. Chuang, T.-Z. Yang, P.-C. Liu, T.-F. Yang, R.-J. Chen, C. Su, and C.-Y. Lee, "A sub-100 W multi-functional cardiac signal processor for mobile health care applications," in Proc. Symp. VLSI Circuits, Jun. 13-15, 2012, pp. 156-157.

S. Kim, Y. Long, S. Mitra, M. Osawa, Y. Harada, K. Tamiya, C. Van Hoof, and R. F. Yazicioglu, "A 20 μW intra-cardiac signal-processing IC with 82 dB bio-impedance measurement dynamic range and analog feature extraction for ventricular fibrillation detection," in IEEE Int. Solid-State Circuits Conf. Dig. Tech. Papers, Feb. 17-21, 2013, pp. 302-303.

X. Liu, J. Zhou, Y. Yang, B. Wang, J. Lan, C. Wang, J. Luo, W. L. Goh, T. T.-H. Kim, and M. Je, "A 457-nW cognitive multi-functional ECG processor," in Proc. IEEE Asian Solid-State Circuits Conf., Nov. 11-13, 2013, pp. 141-144.

C. J. Deepu, X. Zhang, W.-S. Liew, D. L. T. Wong, and Y. Lian, "An ECG-SoC with 535 nW/channel lossless data compression for wearable sensors," in Proc. IEEE Asian Solid-State Circuits Conf., Nov. 11-13, 2013, pp. 145-148.

Y. Long, P. Harpe, M. Osawa, Y. Harada, K. Tamiya, C. Van Hoof, and R. F. Yazicioglu, "A 680 nA fully integrated implantable ECG acquisition IC with analog feature extraction," in IEEE Int. Solid-State Circuits Conf. Dig. Tech. Papers, 2014, pp. 418-419.

D. Jeon, Y.-P. Chen, Y. Lee, Y. Kim, Z. Foo, G. Kruger, H. Oral, O. Berenfeld, Z. Zhang, D. Blaauw, and D. Sylvester, "An implantable 64 nW ECG-monitoring mixed-signal SoC for arrhythmia diagnosis," in IEEE Int. Solid-State Circuits Conf. Dig. Tech. Papers, Feb. 9-13, 2014, pp. 416-417.

Y. Lee, S. Bang; I. Lee, Y. Kim, G. Kim, M. H. Ghaed, P. Pannuto, P. Dutta, D. Sylvester, and D. Blaauw, "A modular 1 mm die-stacked sensing platform with low power IC inter-die communication and multi-modal energy harvesting," IEEE J. Solid-State Circuits, vol. 48, no. 1, p. 229,243, January 2013.

D. Han, Y. Zheng, R. Rajkumar, G. Dawe, and M. Je, "A 0.45 V 100-channel neural-recording IC with sub-W/channel consumption in 0.18 μm CMOS," in IEEE Int. Solid-State Circuits Conf. Dig. Tech. Papers, Feb. 17-21, 2013, pp. 290-291.

J. G. Webster, Medical Instrumentation Application and Design. Hoboken, NJ, USA: Wiley, 2009.

American National Standards for Cardiac Monitors, Hearth Rate Meters and Alarms, ANSI/AAMI-EC13, 2002.

H. Oral, O. Berenfeld, and G. Kruger, "Atrial Fibrillation Classification Using Power Measurement," U.S. Patent 20130197380 A1, Aug. 1, 2013.

C. Enz, "Circuit techniques for reducing the effects of op-amp imperfections: autozeroing, correlated double sampling, and chopper stabilization," Proc. IEEE, vol. 84, no. 11, pp. 1584-1614, November 1996.

Q. Fan, F. Sebastiano, J. H. Huijsing, and K. A. A. Makinwa, "A 1.8 W 60 nV/capacitively-coupled Chopper instrumentation amplifier in 65 nm CMOS for wireless sensor nodes," IEEE J. Solid-State Circuits, vol. 46, no. 7, p. 1534,1543, July 2011.

T. Denison, K. Consoer, A. Kelly, A. Hachenburg, and W. Santa, "A 2.2 W94 nV/Hz, Chopper-stabilized instrumentation amplifier for EEG detection in chronic implants," in IEEE Int. Solid-State Circuits Conf. Dig. Tech. Papers, Feb. 11-15, 2007, p. 162.

J. Holleman and B. Otis, "A sub-microwatt low-noise amplifier for neural recording," in Proc. 29th Annu. Int. Conf. IEEE Eng. Med. Biol. Soc., Aug. 22-26, 2007, pp. 3930-3933.

M. Chae, W. Liu, Z. Yang, T. Chen, J. Kim, M. Sivaprakasam, and M. Yuce, "A 128-Channel 6 mW wireless neural recording IC with on-the-fly spike sorting and UWB transmitter," in Proc. IEEE Int. Solid State Circuits Conf., Feb. 3-7, 2008, pp. 146-603.

A. T. Do, C. K. Lam, Y. S. Tan, K.-S. Yeo, J. H. Cheong, X. Zou, L. Yao, K.-W. Cheng, and M. Je, "A 160 nW 25 kS/s 9-bit SAR ADC for neural signal recording applications," in Proc. IEEE 10th Int. New Circuits and Systems Conf., Jun. 17-20, 2012, pp. 525-528.

D. Zhang, A. Bhide, and A. Alvandpour, "A 53 nW 9.1-ENOB 1 kS/s SAR ADC in 0.13-um CMOS for medical implant devices," IEEE J. Solid-State Circuits, vol. 47, no. 7, pp. 1585-1593, July 2012.

D. Zhang and A. Alvandpour, "A 3-nW 9.1-ENOB SAR ADC at 0.7 V and 1 kS/s," in Proc. ESSCIRC, Sep. 17-21, 2012, pp. 369-372.

P. J. A. Harpe, C. Zhou, Y. Bi, N. P. vander Meijs, X. Wang, K. Philips, G. Dolmans, and H. deGroot, "A 26 μW 8 bit 10 MS/s asynchronous SAR ADC for low energy radios," IEEE J. Solid-State Circuits, vol. 46, no. 7, pp. 1585-1595, July 2011.

T. Wakimoto, H. Li, and K. Murase, "Statistical analysis on the effect of capacitance mismatch in a high-resolution successive-approximation ADC," IEE J Trans. Electr. Electron. Eng., vol. 6, pp. s89-s93, 2011.

H. Zhang, Y. Qin, S. Yang, and Z. Hong, "Design of an ultra-low power SAR ADC for biomedical applications," in Proc. 10[t] IEEE Int. Conf. Solid-State Integr. Circuit Technol., Nov. 1-4, 2010, pp. 460-462.

B. Zhai, S. Hanson, D. Blaauw, and D. Sylvester, "Analysis and mitigation of variability in subthreshold design," in Proc. Int. Symp. Low Power Electron. Design, August 2005, pp. 20-25.

J. Pan and W. J. Tompkins, "A real-time QRS detection algorithm," IEEE Trans. Biomed. Eng., vol. BME-32, no. 3, pp. 230-236, March 1985.

A. Wang and A. Chandrakasan, "A 180-mV subthreshold FFT processor using a minimum energy design methodology," IEEE J. Solid State Circuits, vol. 40, no. 1, pp. 310-319, January 2005.

Y. Zhang, F. Zhang, Y. Shakhsheer, J. D. Silver, A. Klinefelter, M. Nagaraju, J. Boley, J. Pandey, A. Shrivastava, E. J. Carlson, A. Wood, B. H. Calhoun, and B. P. Otis, "A Batteryless 19 WMICS/ISM-band energy harvesting body sensor node SoC for ExG applications," IEEE J. Solid-State Circuits, vol. 48, no. 1, pp. 199-213, January 2013.

Lim, Wootaek, Inhee Lee, Dennis Sylvester, and David Blaauw. "8.2 Batteryless Sub-nW Cortex-M0+ processor with dynamic leakage-suppression logic." In 2015 IEEE International Solid-State Circuits Conference-(ISSCC) Digest of Technical Papers, pp. 1-3. IEEE, 2015.

Recent low-voltage design techniques have enabled dramatic improvements in miniaturization and lifetime of wireless sensor nodes. These systems typically use a secondary battery to provide energy when the sensor is awake and operating; the battery is then recharged from a harvesting source when the sensor is asleep. In these systems, the key requirement is to minimize energy per operation of the sensor. This extends the number of operations on one battery charge and/or reduces the time to recharge the battery between awake cycles. This requirement has driven significant advances in energy efficiency and standby power consumption. Batteries suffer from limited endurance (e.g., $5k$ discharge cycles limiting lifetime to 3.5 months with a 30 min wakeup period) and scalability challenges in the sub-5 mm range due to sealing requirements. A battery-less sensor system may be provided that operates directly from the energy harvesting source. In these systems, power is consumed as it is obtained, and hence the key requirement is to limit the maximum power draw, thereby reducing the size of the required harvesting source. While significant advances have been made in low power systems, the minimum power draw per logic gate remains in the 1-30 pW range, resulting in 10 s of nW consumed by a microcontroller. This in turn requires a relatively large harvesting source, limiting the ability to scale a sensor system to true miniature sizes (e.g., an 4 mm² solar cell @240 lux is needed to produce 30 nW). Note that reducing supply voltage further in these systems is ineffective since they become leakage power dominated. Robustness concerns also often limit voltage scalability. A Cortex M0+ processor implemented in DLS logic, that consumes 295 pW, is available. Autonomous operation when powered by a 0.09 mm² solar cell in room lighting (240 lux).

A. Wang and A. Chandrakasan, "A 180 mV FFT processor using subthreshold circuit techniques," ISSCC, 2004.

S. Hanson, et al., "A Low-Voltage Processor for Sensing Applications With Picowatt Standby Mode," JSSC, April 2009.

Y. Lee, et al., "A Modular 1 mm³ Die-Stacked Sensing Platform with Optical Communication and Multi-Modal Energy Harvesting," ISSCC, 2012.

Cymbet Corp., "EnerChip™ Bare Die Batteries Data Sheet," 2014. R. Hahn, et al., "Development of near hermetic silicon/glass cavities for packaging of integrated lithium micro batteries," MEMS/MOEMS, April 2009.

N. Lotze and Y. Manoli, "A 62 mV 0.13 m CMOS standard-cell-based design technique using Schmitt-trigger logic," ISSCC, 2011.

W. Jung, et al., "A 3 nW fully integrated energy harvester based on self-oscillating switched-capacitor DC-DC converter," ISSCC, 2014.

D. Jeon, et al., "A Super-Pipelined Energy Efficient Subthreshold 240 MS/s FFT Core in 65 nm CMOS" IEEE JSSC, vol. 47, January 2012.

Zhang, Yiqun, Li Xu, Kaiyuan Yang, Qing Dong, Supreet Jeloka, David Blaauw, and Dennis Sylvester. "Recryptor: A reconfigurable in-memory cryptographic Cortex-M0 processor for IoT." In 2017 Symposium on VLSI Circuits, pp. C264-C265. IEEE, 2017.

Lee, Yoonmyung, Gyouho Kim, Suyoung Bang, Yejoong Kim, Inhee Lee, Prabal Dutta, Dennis Sylvester, and David Blaauw. "A modular 1 mm 3 die-stacked sensing platform with optical communication and multi-modal energy harvesting." In 2012 IEEE International Solid-State Circuits Conference, pp. 402-404. IEEE, 2012.

Kim, Gyouho, Yoonmyung Lee, Zhiyoong Foo, Pat Pannuto, Ye-Sheng Kuo, Ben Kempke, Mohammad Hassan Ghaed et al. "A millimeter-scale wireless imaging system with continuous motion detection and energy harvesting." In 2014 Symposium on VLSI Circuits Digest of Technical Papers, pp. 1-2. IEEE, 2014.

Bang, Suyoung, Jingcheng Wang, Ziyun Li, Cao Gao, Yejoong Kim, Qing Dong, Yen-Po Chen et al. "14.7 a 288 pw programmable deep-learning processor with 270 kb on-chip weight storage using non-uniform memory hierarchy for mobile intelligence." In 2017 IEEE International Solid-State Circuits Conference (ISSCC), pp. 250-251. IEEE, 2017.

Jeon, Dongsuk, Yen-Po Chen, Yoonmyung Lee, Yejoong Kim, Zhiyoong Foo, Grant Kruger, Hakan Oral et al. "24.3 An implantable 64 nW ECG-monitoring mixed-signal SoC for arrhythmia diagnosis." In 2014 IEEE International Solid-State Circuits Conference Digest of Technical Papers (ISSCC), pp. 416-417. IEEE, 2014.

Zhang, Yiqun, Li Xu, Qing Dong, Jingcheng Wang, David Blaauw, and Dennis Sylvester. "Recryptor: a reconfigurable cryptographic cortex-M0 processor with in-memory and near-memory computing for IoT security." IEEE Journal of Solid-State Circuits 53, no. 4 (2018): 995-1005.

Kim, Hyeongseok, Gyouho Kim, Yoonmyung Lee, Zhiyoong Foo, Dennis Sylvester, David Blaauw, and David Wentzloff. "A 10.6 mm 3 fully-integrated, wireless sensor node with 8 GHz UWB transmitter." In 2015 Symposium on VLSI Circuits (VLSI Circuits), pp. C202-C203. IEEE, 2015.

Jang, Taekwang, Seokhyeon Jeong, Myungjoon Choi, Wanyeong Jung, Gyouho Kim, Yen-Po Chen, Yejoong Kim, Wootaek Lim, Dennis Sylvester, and David Blaauw. "FOCUS: Key building blocks and integration strategy of a miniaturized wireless sensor node." In ESSCIRC Conference 2015-41st European Solid-State Circuits Conference (ESSCIRC), pp. 257-262. IEEE, 2015.

Pannuto, Pat, Yoonmyung Lee, Ben Kempke, Dennis Sylvester, David Blaauw, and Prabal Dutta. "Ultra-constrained sensor platform interfacing." In 2012 ACM/IEEE 11th International Conference on Information Processing in Sensor Networks (IPSN), pp. 147-148. IEEE, 2012.

Jang, Taekwang, Gyouho Kim, Benjamin Kempke, Michael B. Henry, Nikolaos Chiotellis, Carl Pfeiffer, Dongkwun Kim et al. "Circuit and system designs of ultra-low power sensor nodes with illustration in a miniaturized GNSS logger for position tracking: Part I Analog circuit techniques." IEEE Transactions on Circuits and Systems I: Regular Papers 64, no. 9 (2017): 2237-2249.

Yang, Kaiyuan, David Blaauw, and Dennis Sylvester. "Hardware designs for security in Ultra-Low-Power IoT systems: an overview and survey." IEEE Micro 37, no. 6 (2017): 72-89.

Oh, Sechang, Yao Shi, Gyouho Kim, Yejoong Kim, Taewook Kang, Seokhyeon Jeong, Dennis Sylvester, and David Blaauw. "A 2.5 nJ duty-cycled bridge-to-digital converter integrated in a 13 mm 3 pressure-sensing system." In 2018 IEEE International Solid-State Circuits Conference-(ISSCC), pp. 328-330. IEEE, 2018.

Wu, Xiao, Inhee Lee, Qing Dong, Kaiyuan Yang, Dongkwun Kim, Jingcheng Wang, Yimai Peng et al. "A 0.04 MM 3 16 NW Wireless and Batteryless Sensor System with Integrated Cortex-M0+ Processor and Optical Communication for Cellular Temperature Measurement." In 2018 IEEE Symposium on VLSI Circuits, pp. 191-192. IEEE, 2018.

Reyserhove, Hans, and Wim Dehaene. "A 16.07 pJ/cycle 31 MHz fully differential transmission gate logic ARM Cortex M0 core in 40 nm CMOS." In ESSCIRC Conference 2016: 42nd European Solid-State Circuits Conference, pp. 257-260. IEEE, 2016.

Cho, Minchang, Sechang Oh, Seokhyeon Jeong, Yiqun Zhang, Inhee Lee, Yejoong Kim, Li-Xuan Chuo et al. "A 6×5×4 mm 3 general purpose audio sensor node with a 4.7 W audio processing IC." In 2017 Symposium on VLSI Circuits, pp. C312-C313. IEEE, 2017.

Lee, Inhee, Wanyeong Jung, Hyunsoo Ha, Seokhyeon Jeong, Yejoong Kim, Gyouho Kim, Zhiyoong Foo, Jae-Yoon Sim, Dennis Sylvester, and David Blaauw. "An ultra-low-power biomedical chip for injectable pressure monitor." In 2015 IEEE Biomedical Circuits and Systems Conference (BioCAS), pp. 1-4. IEEE, 2015.

Oh, Sechang, David Blaauw, and Dennis Sylvester. "The Internet of Tiny Things (IoT2): Recent Advances of Millimeter-Scale Computing." IEEE Design & Test (2019).

This system differs from more traditional implants in that it normally operates according to an NFC protocol at 13.56 MHz and not a more traditional livestock RFID protocol at 134 kHz; it harvests energy discretely from interrogation, and also has a battery for continual operation (e.g., data acquisition, emergency beacon); and has a messaging mode which can be used for emergency alerts, such as hypoglycemia, independent of the backscatter communication mode. The messaging mode draws significant power from the battery, and therefore must be used sparingly. The messaging mode may also be used for security purposes, as an out-of-band or second factor for authentication. The messaging mode may be compatible with Bluetooth or WiFi communications, though preferably does not implement a full communication stack. For example, the transmitter may transmit a single packet with a media access control address (MAC address), and a status flag. A receiver is provided to filter received packets for the identifying MAC address, and when received, also captures and processes the status flag.

In further contrast to traditional RFID tags for veterinary purposes, the implant has a processor, e.g., an ARM Cortex M0 core (see, developer.arm.com/docs/ddi0432/c), for controlling the device, compressing the physiological data, and controlling message communication. The implant may optionally receive messages through the messaging mode, though this is typically under controlled conditions, where use of NFC is also permissible, and external power is available to maintain battery charge.

One important use case for the implant is to detect hypoglycemia, a relatively common problem for puppies. Hypoglycemia is characterized by lowered body temperature, reduced activity, altered electrophysiology (EKG, EMG), and of course, lowered blood glucose levels. A direct measurement of blood glucose is difficult, because the implant is not in the vascular space, and implanted glucose sensors tend to lack durability for long term use. However, temperature and activity (movement) are more readily determined, and electrophysiological parameters may also be measured. Because of the small size, and typical dorsal placement of the implant, a proper EKG signal is difficult to acquire. On the other hand, a microphone may serve as a phonocardiogram, a pressure sensor may detect pulse, and an accelerometer may detect a vibrocardiographic signal. On the other hand, an electrophysiological sensor may readily detect local electromyographic (EMG) signals, and in some cases, may perform a stimulus-response test to actively trigger muscle contraction and detect contractile response.

When initial indicia of oncoming hypoglycemia are detected, the system may alter detection strategy to be more sensitive and precise. This alteration may consume more power. If the implant is within range of an active interrogator, the status may be communicated. If the status deteriorates from oncoming hypoglycemia to hypoglycemia, an alert message is transmitted. The system reads the battery level, to determine remaining power, and optimizes use of that power in a series of alerts. If the initial alters is not acted upon, one likely cause is that the message from the implant transponder was not received. An immediate retransmit would likely also not be received, and therefore would needlessly consume limited battery power. The implant may then monitor the band for transmissions from a reader, e.g., a known MAC address. When the reader is detected, the message may then be rebroadcast.

The implant may also provoke a behavioral response from the animal in which it is implanted. For example, it may generate an electric shock, or release a chemical which causes a response, e.g., pain. In the case of hypoglycemia, it may release, for example, powerful glucocorticoid, or other drug the ameliorate the condition.

Described herein are implantable devices for sensing physiological conditions (such as pH, analyte levels, pressure, strain, temperature, bioelectric signals) in a subject, such as a dog, cat, bird, livestock, or even human, and reporting the sensed physiological conditions using telemetry. Further described are systems including one or more implantable devices and an interrogator. Also described are methods for sensing physiological conditions and reporting the sensed physiological conditions.

The implantable device may be about 25 mm or less in length in the longest dimension, 3 mm or less in diameter.

The implantable device may be implanted in a subject. The subject may be a human, an animal or a plant.

The sensor may detect the amount of glucose, or another analyte or pH or oxygen. The sensor may also detect an EMG or EKG signal, or an EEG or MEG signal.

The sensor may be an optical sensor, e.g., a light source and an optical detector. The optical sensor may detect blood pressure, a pulse, or blood oxygen saturation. The optical sensor may comprise a matrix comprising a fluorophore, and wherein fluorescence intensity or fluorescence lifetime of the fluorophore depends on the amount of the analyte. The optical sensor may be configured to perform near-infrared spectroscopy. The sensor may detect glucose. The sensor may be a potentiometric chemical sensor, an amperometric chemical sensor, an oxygen sensor, a pH sensor, a temperature sensor, or a glucose sensor. See www.medicaldesignbriefs.com/component/content/article/mdb/features/applications/17695. A temperature sensor may be a bipolar junction, thermistor, a thermocouple, or a proportional to absolute temperature (PTAT) circuit. The implantable device may comprise a bulk piezoelectric ultrasonic transducer and a thermistor. The sensor may be a pressure sensor or a microelectromechanical system (MEMS) sensor, e.g., a MEMS pressure sensor. The implantable device may be configured to measure blood pressure or a pulse. The sensor may be a strain sensor.

The implantable device may further comprise an integrated circuit, e.g., a power circuit, a driver configured to provide current to the sensor, a front end configured to receive a signal from the sensor, or a digital circuit. The digital circuit may be configured to operate a modulation circuit, transmit a digitized signal to the modulation circuit, wherein the digitized signal is based on the detected amount of the analyte, the temperature, strain, bioelectric signal or the pressure.

The implanted device may be at least partially encapsulated by a biocompatible material or a glass. The implantable device may further comprise a non-responsive reflector. The implantable device may comprise two or more sensors.

Further provided herein is a system comprising one or more implantable devices and an interrogator configured to receive backscatter from the one or more implantable devices. The system may comprise a plurality of implantable devices. The interrogator may be configured to be wearable by a subject.

In one aspect, there is provided a method of detecting an amount of an analyte, a pH, a temperature, strain, bioelectric signal or a pressure. The method may further comprise analyzing a signal at an interrogator to determine the measured amount of the analyte, pH, temperature, strain, bioelectric signal or pressure. The one or more implantable devices may be implanted on, within, or proximal to a blood vessel, an implanted organ, a tumor, or a site of infection. The method may further comprise emitting light and detecting fluorescence intensity or fluorescence lifetime, wherein the fluorescence intensity or fluorescence lifetime depends on the amount of the analyte or the pH. The method may comprise determining a phase shift between oscillating emitted light and detected fluorescence is determined, wherein the phase shift depends on the amount of the analyte or the pH. The method may comprise determining a fluorescent lifetime for the detected fluorescence resulting from pulsed or oscillating emitted light. The method may further comprise determining a location of the one or more implantable devices relative to the interrogator. The method may further comprise detecting movement of the one or more implantable devices. The method may further comprise implanting the implantable device in a subject the subject may be a human, an animal or a plant. The backscatter may encode a digitized signal.

It is an object to provide a method of operating an implantable device, comprising: providing an implantable module, comprising a biocompatible shell, a sensor for detecting a biological state of a host and to produce sensor data, a telemetry system for communicating through radio frequency communications, a memory for storing data, and a microcontroller; harvesting environmental energy from around the implantable module within the host; processing the sensor data for storage as information in the memory; communicating through the telemetry system under control of the microcontroller; powering the microcontroller with the harvested energy in a first mode; powering the microcontroller with a secondary energy source in a second mode, when the harvested energy is insufficient.

The environmental energy may be harvested with a near field communication (NFC) antenna coil, the telemetry system comprises a 13.56 MHz NFC transponder, and the secondary energy source is a battery. The method may further comprise communicating through the transponder with an NFC interrogator; communicating from the NFC interrogator to the Internet; and communicating from the implantable module through a Bluetooth personal area network.

It is also an object to provide a method of communicating with an implantable device, comprising: providing an implantable module, comprising a biocompatible shell, a telemetry system for communicating through radio frequency communications, a memory for storing data, and a microcontroller; harvesting environmental energy from around the implantable module within the host to operate the microcontroller; communicating through the telemetry system under control of the microcontroller with an interrogator; relaying communications from the telemetry system through the interrogator to the Internet; and writing data received from the interrogator into the memory.

It is a still further object to provide an implantable device, comprising: an implantable, biocompatible shell; a sensor configured to detect a biological state of a host and to produce sensor data; a telemetry system configured to communicate by radio frequency communications; an energy harvesting system configured to harvest energy from an environment within the host; a secondary energy source; a memory configured to store sensor data; and a microcontroller, configured to receive sensor data, process the sensor data for storage as information in the memory, and to control communications through the telemetry system, the microcontroller being powered by the energy harvesting system in a first mode and the secondary energy source in a second mode occurring where the energy harvesting system provides insufficient power.

The sensor may comprise an optical sensor comprising a light source and an optical detector, a potentiometric chemical sensor or an amperometric chemical sensor, a microphone, an inertial sensor, a thermometer, a strain sensor, a pressure sensor, a glucose level detector, an ion-specific sensor, a lactic acid detector, a pH sensor, a carbon dioxide detector, an amperometric chemical sensor, an ion-sensitive field effect transistor; an electrochemical reaction sensor; a colorimetric sensor, a fluorometric sensor, a bioelectric activity sensor, an electromyographic detector, an electrocardiographic detector, or an electroencephalographic sensor.

The secondary power source may comprise a rechargeable electrical device configured to receive excess power from the energy harvesting system for recharging the rechargeable electrical device, a lithium ion battery, or a supercapacitor.

The telemetry system may communicate through radio frequency backscatter communications, and may be a radio frequency identification system, e.g., operating at 13.56 MHz. The telemetry system may comprise a near field communication (NFC) system.

The telemetry system may provide power from radio frequency waves to the energy harvesting system. The telemetry system may comprise a coil antenna. The energy harvesting system may also comprise a photovoltaic cell.

The implantable module may further comprised at least one of a local area network (LAN) communication subsystem and a personal area network (PAN) communication subsystem, configured to communicate a warning to a network device selectively dependent on a content of the information.

BRIEF DESCRIPTION OF THE FIGURES

FIG. 5 shows a flowchart of a third method according to the present invention.

FIG. 6 shows a flowchart of a fourth method according to the present invention.

DETAILED DESCRIPTION OF THE INVENTION

Figure 1:
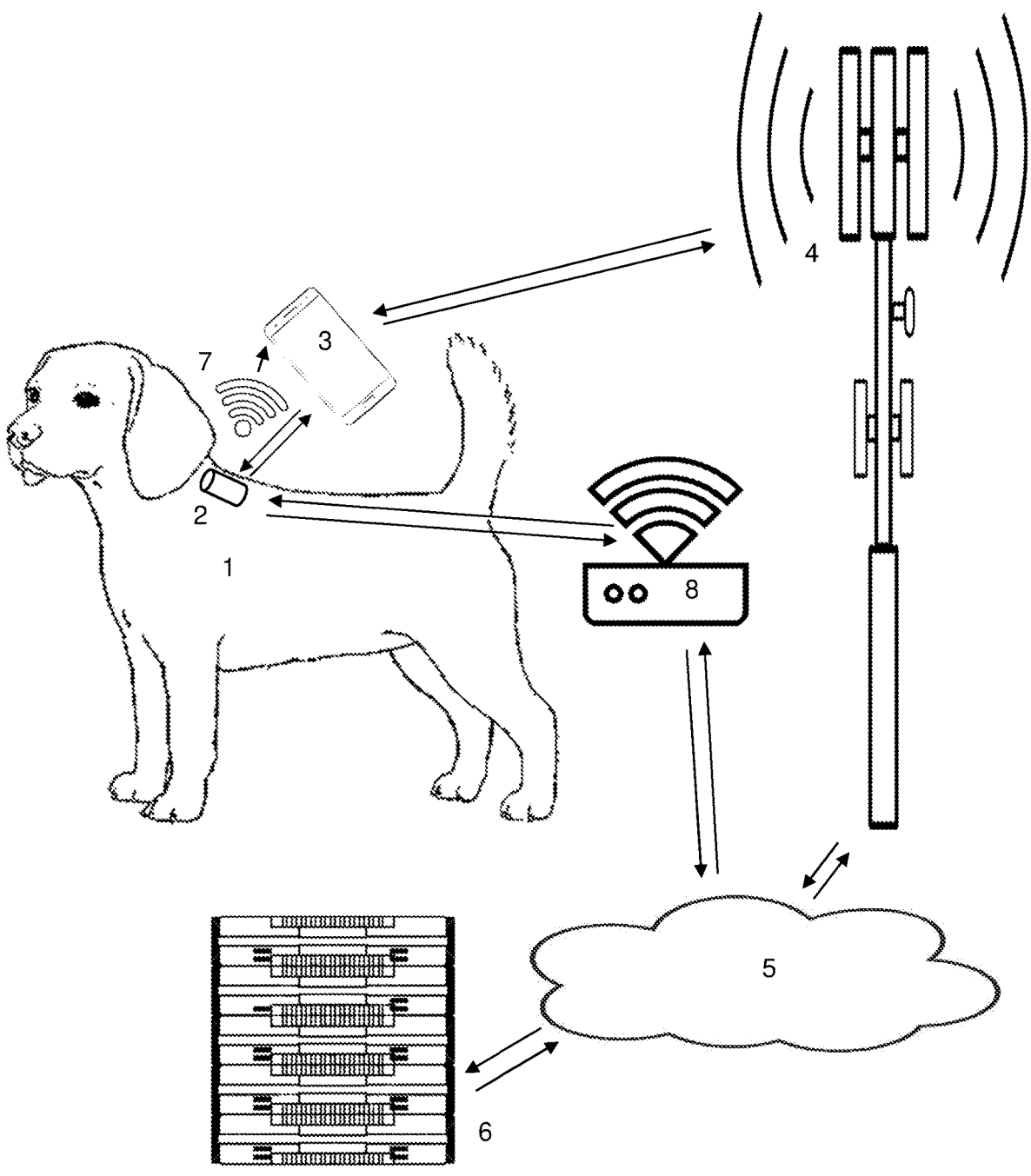
FIG. 1 shows a semi-schematic diagram of a system according to the present invention, in which a transponder/beacon device within an animal communicates using an NFC standard with a proximate smartphone and/or a PAN/LAN/WWAN (personal area network/local area network/wireless wide area network) technology, to provide local processing, and communications relay to a remote server in the cloud, or an alert to the PAN/LAN/WWAN to relay the alert to local user or a remote server.

The following description illustrates some example embodiments of the disclosed technologies in detail. Those of skill in the art will recognize that there are numerous variations and modifications of the disclosed embodiments that are encompassed by its scope. Accordingly, the description of a certain example embodiment should not be deemed to limit the scope of the present disclosure.

Example 1

A significant advantage of the implantable device is the ability to detect one or more physiological conditions in tissue, and to have those physiological conditions wirelessly transmitted to an interrogator, which can be external or relay the information to an external component. Thus, the implantable devices can remain in a subject for an extended period of time without needing to use a wired connection to charge a battery or retrieve information stored on the device.

Electromagnetic (EM) power transfer is known for powering small implantable devices, though suffer power attenuation through tissue and the relatively large apertures (e.g. antennas or coils) required to capture such energy. See, for example, Seo et al., Neural dust: an ultrasonic, low power solution for chronic brain-machine interfaces, arXiv paper (July 2013). Optical power transfer (photovoltaic) is only feasible in the close subcutaneous region. Kinetic energy harvesting may require size and mass. Thermoelectric energy harvesting requires temperature differentials.

The implantable devices can be implanted in or used in a subject (e.g., an animal or human). The subject may be a mammal. Exemplary subjects include a human, rodent (such as a mouse, rat, or guinea pig), cat, dog, chicken, pig, cow, horse, sheep, rabbit, etc. The implantable devices can also be implanted in plants, such as agricultural plants, to measure physiological conditions.

The term "miniaturized" refers to any material or component which comprises a portion of an implantable module, about 25 millimeters or less (such as about 20 mm or less, about 10 mm or less, about 5 mm or less, about 2 mm or less, or about 0.5 mm or less) in the longest dimension.

It is to be understood that one, some or all of the properties of the various embodiments described herein may be combined to form other embodiments of the present invention. The section headings used herein are for organizational purposes only and are not to be construed as limiting the subject matter described. Features and preferences described above in relation to "embodiments" are distinct preferences and are not limited only to that particular embodiment; they may be freely combined with features from other embodiments, where technically feasible, and may form preferred combinations of features.

Interrogator

The interrogator is preferably a smartphone with NFC capability, e.g., compliant with ISO 14443, and related standards. The smartphone is generally standard, though operating software on the smartphone, i.e., an app, or customized operating system or firmware, need not be standard. The smartphone may be a Samsung S20 or Apple iPhone 11 Pro.

The interrogator is preferably external (i.e., not implanted). By way of example, the external interrogator can be a wearable, which may be fixed to the body by a strap or adhesive. In another example, the external interrogator can be a wand, which may be held by a user (such as a healthcare professional). The interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator.

Implantable Device

The implantable device includes a physiological sensor (such as a temperature sensor, an oxygen sensor, a pH sensor, a strain sensor, a pressure sensor, or a glucose sensor). The implantable devices are miniaturized, which allows for comfortable and long-term implantation while limiting tissue inflammation that is often associated with implantable devices. The longest dimension of the device is <35 mm, <30 mm, <25 mm, <20 mm, <15 mm, <14 mm, <13 mm, <12 mm, <11 mm, <10 mm, <9 mm, <8 mm, <7 mm, <6 mm, <5 mm, <4 mm, <3 mm, <2 mm, ~1 mm, or less. The longest dimension of the device may be about 25 mm or longer, about 20 mm or longer, about 15 mm or longer in the longest dimension of the device. The implantable device may have a diameter of 2-3 mm and a length of 15-25 mm. The device is preferably implantable with a hypodermic needle.

The implantable device may be based on an ARM Cortex-M0+, such as an NXP NHS3152 NTAG device. See, www.nxp.com/docs/en/data-sheet/NHS3152.pdf; w www.nxp.com/docs/en/user-guide/UM10876.pdf; ww.nxp-.com/products/rfid-nfc/nfc-hf/ntag/ntag-smartsensor/ntag-smartsensor-with-temperature-sensor-digital-and-analog-ios:NHS3152. NHS3152UK, WLCSP25, wafer level chip-scale package; 25 balls; 2.51×2.51×0.5 mm SOT1401. The antenna is, for example, a coil or wire wound around a soft magnetic core. The battery may be a CR308 or CR313. A Bluetooth beacon may be implemented using an EMM Microelectric EM9304 device, see www.emmicroelectron-ic.com/product/standard-protocols/em9304, or NXP QN908x, see www.nxp.com/docs/en/nxp/data-sheets/QN908x.pdf.

The implantable device may be implanted in a subject. The subject can be for example, an animal, such as a mammal. The subject may be a human, dog, cat, horse, cow, pig, sheep, goat, chicken, monkey, rat, or mouse.

The implantable device or a portion of the implantable device may be encapsulated by a biocompatible material (such as a biocompatible polymer), for example a copolymer of N-vinyl-2-pyrrolidinone (NVP) and n-butylmethacrylate (BMA), polydimethylsiloxane (PDMS), parylene, polyimide, silicon nitride, silicon dioxide, alumina, niobium, hydroxyapatite, or silicon carbide. The silicon carbide can be amorphous silicon carbide or crystalline silicon carbide. The biocompatible material is preferably impermeable to water to avoid damage or interference to electronic circuitry within the device. The implantable device or portion of the implantable device may be encapsulated by a ceramic (for example, alumina or titania) or a metal (for example, steel or titanium).

An integrated circuit in the implantable device may comprise one or more analog and digital circuit which utilizes the electrical power provided by a battery or energy harvesting from an RF source, for example. The circuit may include one or more digital circuits, which can include a memory and one or more circuit blocks or systems for operating the implantable device; these systems can include, for example an onboard microcontroller, a finite state machine implementation or digital circuits capable of executing programs stored on the implant. The digital circuit may include an analog-to-digital converter (ADC), which can convert analog signal from the sensor into a digital signal, and/or a digital-to-analog converter (DAC), which converts a digital signal into an analog signal prior to directing the signal to a modulator.

The digital circuit can operate a modulation circuit (which can also be referred to as the "backscatter circuit"), which connects to a backscatter antenna. The modulation circuit includes a switch, such as an on/off switch or a field-effect transistor (FET). An exemplary FET that can be used with some embodiments of the implantable device is a metal-oxide-semiconductor field-effect transistor (MOSFET). The modulation circuit can alter the impedance presented to the antenna, and the variation in current passing through the antenna encodes signals transmitted by the digital circuit. The digital circuit can also operate one or more amplifiers, which amplifies the current directed to the switch. Where the digital circuit is omitted, the impedance in the modulation circuit can be directly controlled by the sensor.

A driver circuit may provide current to one or more sensors. The driver circuit can be operated by the digital circuit if present. One or more amplifiers may be disposed between the driver circuit and the digital circuit. The circuit may include a front end circuit (such as a CMOS front end), which can receive a signal from the sensor. The signal received by the front end circuit can be relayed to the digital circuit.

Sensors

The implantable device includes one or more sensors. The sensors are configured to detect a physiological condition, such as temperature, oxygen concentration, pH, an analyte (such as glucose), strain, or pressure. Variation in the physiological condition modulates impedance, which in turn modulates current flowing miniaturized ultrasonic transducer on the implantable device. As explained above, this produces ultrasonic backscatter detected by the interrogator; changes in the ultrasonic backscatter waves reflect information about the physiological condition. The system may be configured to detect changes in the physiological system. The system may be configured detect a value or an approximate value of the physiological condition, for example by calibrating the ultrasonic backscatter to known values.

The implantable device may comprise one or more (such as 2, 3, 4, 5 or more) sensors, which may detect the same physiological condition or different physiological conditions. For example, the implantable device may comprise a first sensor configured to detect temperature and a second sensor configured to detect oxygen. Changes in both physiological conditions can be encoded in the ultrasonic backscatter waves, which can be deciphered by an external computing system.

The sensor may include an optical detector. A light source (such as a light emitting diode or vertical cavity surface emitting laser (VCSEL)) emits a light, which is detected by the optical detector. The amount of light detected by the optical detector is indicative of the physiological condition detected. A front end (such as a CMOS front end) can receive a signal from the detector. A digital circuit may receive the signal from the front end circuit and operates a modulation circuit. The light source can be disposed outside of the tissue, implanted within the tissue, or as part of the implantable device itself (which may be controlled by a driver on the ASIC). The light source may emit light in the near infrared range (e.g., a wavelength of about 780 nm to about 2500 nm). A plurality of light sources may be included, which may emit light at different wavelengths. The implantable device may be used for near-infrared spectroscopy, which can be used to detect certain analytes in blood or interstitial tissue, such as glucose. The light source may emit light outside of the infrared range (such as at a wavelength below about 780 nm or above about 2500 nm). Since there is a distance limit when transmitting light through tissue (generally less than about 2 cm), it is generally preferable to include the light source on the implantable device when using the implantable device at depths greater than about 2 cm. The implantable device may be implanted at a depth of about 2 cm or more (such as about 3 cm or more, about 4 cm or more, or about 5 cm or more).

Analyte measurements may also be conducted through means other than NIR spectroscopy. One such example is through the use of optodes for chemical sensing. Scattering should be considered and taken into account when using light outside of the NIR spectral region. The implantable device may include a light detector (not shown), which can receive light from a light source.

Implantable devices with optical sensors can be useful for a variety of purposes. For example, the implantable device can be used to monitor oxygen levels (including blood oxygen levels or interstitial fluid oxygen levels) in a subject, tumor oxygenation monitoring, functional brain imaging, blood analyte measurements, tissue engineering (such as to monitor for anoxia and hypoxia), and pH measurements. The optical sensor may be used for determining a blood pressure, a pulse rate, blood oxygenation (pulse oximeter).

The sensor on the implantable device may be an oxygen sensor or a pH sensor. An implantable device comprising an oxygen sensor or pH sensor can be useful for monitoring physiological oxygen concentration (such as blood oxygen or interstitial fluid oxygen) or physiological pH (such as blood pH or interstitial fluid pH). The oxygen concentration or pH can be localized to the vicinity of the implantable device, or, if a network of devices is used, the measured oxygen concentration or pH can by a systemic physiological measurement. This can be useful, for example, in monitoring hypoxia or acidemia. The implantable device can include a miniaturized ultrasonic transducer (such as a bulk piezoelectric transducer, a PMUT, or a CMUT), an ASIC (which may include a driver and a front end), and an oxygen or pH sensor. The ultrasonic transducer may comprise a surface acoustic wave transducer or bulk acoustic wave (or hybrid mode) transducer than couples directly with the interrogator signal. The substrate may include microcantilevers, or other analyte interactive elements, such that the acoustic waves sense the amount of analyte within an acoustic wave path. See, e.g., U.S. Pat. Nos. 4,698,631; 4,734,698; 4,737,789; 5,095,240; 5,182,570; 5,986,382; 6,060,815; 6,107,910; 6,114,971; 6,208,062; 6,259,991; 6,388,360; 6,424,916; 6,433,671; 6,531,957; 6,580,358; 6,611,224; 6,611,758; 6,633,226; 6,775,616; 6,950,009; 7,023,323; 7,132,778; 7,741,956; 7,916,090; 7,952,528; 8,049,671; 8,059,046; and 8,274,373. See also, U.S. Pat and Pub. App. Nos. U.S. Pat.

Nos. 5,506,420; 5,585,646; 5,967,986; 6,170,318; 6,232,139; 6,287,765; 6,306,598; 6,319,469; 6,383,815; 6,403,944; 6,442,413; 6,444,321; 6,495,892; 6,545,791; 6,567,753; 6,627,154; 6,656,430; 6,684,683; 6,709,869; 6,720,710; 6,746,960; 6,762,025; 6,833,540; 6,846,428; 6,848,295; 6,862,465; 6,867,275; 6,895,265; 6,967,428; 6,986,739; 7,006,858; 7,023,955; 7,033,322; 7,058,243; 7,061,061; 7,136,689; 7,147,695; 7,181,261; 7,205,701; 7,259,019; 7,300,631; 7,332,327; 7,408,147; 7,473,551; 7,504,365; 7,510,882; 7,550,310; 7,598,094; 7,611,908; 7,615,381; 7,629,137; 7,632,638; 7,648,844; 7,666,284; 7,749,445; 7,769,420; 7,826,981; 7,857,756; 7,857,760; 7,896,809; 7,905,833; 7,914,460; 7,920,906; 7,927,274; 7,960,311; 7,972,865; 7,976,492; 7,985,715; 7,989,851; 7,998,071; 8,004,021; 8,005,524; 8,010,174; 8,060,173; 8,073,519; 8,073,520; 8,114,350; 8,128,562; 8,133,178; 8,133,698; 8,143,681; 8,150,488; 8,155,723; 8,160,671; 8,167,801; 8,195,265; 8,206,297; 8,216,139; 8,229,536; 8,233,958; 8,233,959; 8,249,684; 8,251,906; 8,257,259; 8,263,192; 8,265,725; 8,282,549; 8,282,550; 8,287,453; 8,290,559; 8,290,561; 8,292,810; 8,311,749; 8,313,434; 8,321,149; 8,323,193; 8,323,982; 8,336,373; 8,346,338; 8,346,482; 8,364,411; 8,364,413; 8,370,068; 8,370,070; 8,370,071; 8,370,072; 8,370,073; 8,370,078; 8,372,139; 8,374,667; 8,374,796; 8,386,004; 8,394,021; 8,397,762; 8,412,301; 8,417,312; 8,423,298; 8,428,678; 8,435,179; 8,441,081; 8,460,231; 8,469,886; 8,483,793; 8,491,474; 8,527,026; 8,548,553; 8,562,558; 8,609,426; 8,647,861; 8,652,409; 8,657,745; 8,657,747; 8,661,663; 8,663,201; 8,664,364; 8,672,845; 8,680,233; 8,690,934; 8,702,607; 8,747,315; 8,761,856; 8,771,187; 8,774,888; 8,777,853; 8,785,151; 8,788,008; 8,790,260; 8,792,954; 8,795,177; 8,801,610; 8,801,612; 8,808,182; 8,812,073; 8,821,400; 8,843,187; 8,882,741; 8,915,849; 8,920,401; 8,923,947; 8,926,933; 8,968,377; 8,979,885; 8,979,887; 8,986,337; 9,011,330; 9,011,510; 9,041,730; 9,044,182; 9,045,973; 9,050,413; 9,060,742; 9,078,956; 9,107,623; 9,110,836; 9,111,026; 9,135,402; 9,147,144; 9,149,219; 9,149,233; 9,149,234; 9,155,843; 9,192,328; 9,198,563; 9,238,133; 9,247,901; 9,282,925; 9,320,466; 9,339,238; 9,351,668; 9,364,173; 9,389,260; 9,408,530; 9,420,965; 9,420,968; 9,427,183; 9,433,515; 9,433,775; 9,439,589; 9,446,194; 9,448,219; 9,451,908; 9,481,949; 9,498,155; 9,498,164; 9,498,165; 9,504,430; 9,510,780; 9,510,782; 9,512,545; 9,526,800; 9,538,946; 9,549,692; 9,551,635; 9,567,642; 9,585,607; 9,605,363; 9,624,520; 9,631,301; 9,649,069; 9,656,056; 9,662,392; 9,672,393; 9,688,536; 9,688,743; 9,717,449; 9,719,147; 9,724,045; 9,741,139; 9,743,357; 9,750,441; 9,750,460; 9,801,572; 9,815,699; 9,833,199; 9,839,395; 9,845,554; 9,862,607; 9,876,537; 9,878,138; 9,878,139; 9,895,089; 9,901,307; 9,907,497; 9,910,053; 9,931,067; 9,939,449; 9,944,529; 9,989,535; RE44695; 10010703; 10,022,078; 10,022,614; 10,024,860; 10,060,860; 10,136,816; 10,137,288; 10,165,986; 10,168,257; 10,182,751; 10,196,271; 10,200,834; 20010055812; 20020005580; 20020034757; 20020098119; 20020115198; 20020128546; 20020137218; 20020173922; 20020177522; 20020182322; 20030009093; 20030010898; 20030049204; 20030053950; 20030059954; 20030068273; 20030072710; 20030073133; 20030077222; 20030091975; 20030100824; 20030103901; 20030108484; 20030114735; 20030124636; 20030133639; 20030136960; 20030138375; 20030138377; 20030154031; 20030160194; 20030170176; 20030175210; 20030180823; 20030186339; 20030190671; 20030195350; 20030196477; 20040005582; 20040011671; 20040023413; 20040053425; 20040072208; 20040072263; 20040078219; 20040084867; 20040100376; 20040101477; 20040176672; 20040194628;

20040234954; 20040253365; 20050036583; 20050043894; 20050069461; 20050069913; 20050089890; 20050098843; 20050101841; 20050106630; 20050118617; 20050121999; 20050124873; 20050215764; 20050249667; 20050276727; 20060019408; 20060024813; 20060032312; 20060049714; 20060063205; 20060074479; 20060079740; 20060147922; 20060153736; 20060178841; 20060208254; 20060253259; 20070023621; 20070032718; 20070106333; 20070118030; 20070134420; 20070134721; 20070210349; 20070254382; 20070286546; 20080026486; 20080045825; 20080077375; 20080142366; 20080170982; 20080176271; 20080182270; 20080220535; 20080230859; 20090004231; 20090011946; 20090124513; 20090194181; 20090198450; 20090198451; 20090204379; 20090221439; 20090222215; 20090227855; 20090248450; 20090253587; 20090309614; 20100007444; 20100055801; 20100056888; 20100073016; 20100160760; 20100164488; 20100198034; 20100209298; 20100216175; 20100228141; 20100282005; 20100285082; 20100305476; 20110159519; 20110177955; 20110201911; 20110208031; 20110213225; 20110262963; 20110320142; 20120010562; 20120035434; 20120035437; 20120035438; 20120035439; 20120035440; 20120035540; 20120041291; 20120046197; 20120051976; 20120058012; 20120135531; 20120179014; 20120289757; 20120289758; 20120289761; 20120289763; 20120290023; 20120290051; 20120299175; 20120329986; 20130041251; 20130053665; 20130053666; 20130059396; 20130157729; 20130202721; 20130226104; 20130226217; 20130226221; 20130310666; 20140012122; 20140091811; 20140091940; 20140091941; 20140094673; 20140095102; 20140113828; 20140127822; 20140141985; 20140193830; 20140302553; 20150086565; 20150087935; 20150087943; 20150147573; 20150150892; 20150218645; 20150230742; 20150253334; 20150260618; 20150282711; 20150308018; 20150309050; 20150343144; 20150351674; 20160015267; 20160015268; 20160015303; 20160069913; 20160083872; 20160100807; 20160103604; 20160245759; 20160251778; 20160273133; 20160282352; 20160312387; 20160324478; 20160374597; 20170001866; 20170020418; 20170027168; 20170027424; 20170042487; 20170051073; 20170074857; 20170086683; 20170096750; 20170097359; 20170100056; 20170106178; 20170112671; 20170137290; 20170188902; 20170188905; 20170188916; 20170188921; 20170188922; 20170188923; 20170191955; 20170230084; 20170231812; 20170259050; 20170269052; 20170283384; 20170320960; 20170327377; 20170340254; 20170343553; 20170343561; 20180009767; 20180042583; 20180047555; 20180059126; 20180078747; 20180078748; 20180088108; 20180103935; 20180128820; 20180133583; 20180192926; 20180231513; 20180243435; 20180252726; 20180252734; 20180256208; 20180259535; 20180271980; 20180296143; 20180327506; 20180333086; 20190000969; 20190002283; 20190016812; 20190022242; 20190029567; 20190046032; 20190058242; and 20190059792.

The sensor may be an oxygen sensor, e.g., a Clark electrode. A Clark electrode measures oxygen on a catalytic surface (such as a platinum surface) surrounded by a membrane, and can be miniaturized to be included on an implantable device. The Clark electrode can be attached to the ASIC on the implantable device, and variance in the amount of oxygen sensed by the implantable device (which may be blood oxygen or interstitial fluid oxygen) can modulate the ultrasonic backscatter.

The oxygen sensor may include a light source (such as a light emitting diode or vertical cavity surface emitting laser (VCSEL)) and an optical detector (such as a phototransistor or a photovoltaic cell, or an array of phototransistors or photovoltaic cells). A matrix including an oxygen-sensitive fluorophore or a pH-sensitive fluorophore is disposed over the light source and the light detector, or in a position bridging the light source and the light detector, and the amount of light detected by the light source depends on the amount of oxygen in or the pH of the surrounding fluid. Such devices can be referred to as optrodes. The matrix can include, for example, an oxygen-sensitive fluorophore (such as a ruthenium fluorophore) or pH-sensitive fluorophore in a polymer, and increased oxygen or increased or decreased pH (depending on the choice of fluorophore) can cause a faster decay of fluorescence and a decrease in intensity. This oxygen- or pH-dependent change in intensity and fluorescence decay lifetime can be detected by the optical detector. The matrix may be a hydrogel or polydimethylsiloxane (PDMS) polymer containing a ruthenium fluorophore. The ruthenium fluorophore may be bound to silica particles or silica surfaces contained within the matrix (these can be made by sol-gel processes, for example). The matrix protects the fluorophore from components in the extracellular fluid and inhibits adhesion of proteins, cells and other cellular debris that could affect the diffusion of oxygen into the matrix. Further, encapsulation of the ruthenium metal in the matrix reduces potential toxicity of the ruthenium. The light source and/or optical detector can optionally include a filter to limit emitted or detected light to a narrow bandwidth. The ASIC can drive the light source to emit a pulsed or sinusoidal light signal, which causes the light source to emit the light. The light emitted by the light source causes the fluorophore in the matrix to fluoresce. For example, the light source may emit a blue light or a UV light, and the fluorophore can emit an orange or red light. The fluorescence intensity and/or lifetime (decay) of fluorescence is a function of the oxygen concentration or pH of the matrix, which is influenced by the surrounding fluid (e.g., blood or interstitial fluid). From the fluorescence decay, a fluorescent lifetime decay constant can be determined, which can reflect the pH or amount of oxygen.

Use of a light pulse emitted from the light source allows for the observation of fluoresce decay or fluorescence lifetime, which is dependent on pH or oxygen concentration. Thus, the decay of fluorescence (the fluorescence lifetime) following a light pulse from the light source may be used to measure the oxygen concentration or the pH surrounding the sensor.

Use of an oscillating light source allows for the fluorescence emission to be offset from the light source due to the decay of fluorescence (fluorescence lifetime). The phase shift between the light source wave and the fluorescence detection is dependent on the concentration of oxygen or pH. The phase shift of the light source relative to the fluorescence is used to determine pH or oxygen concentration surrounding the sensor. The optical detector detects the light emitted by the fluorophore, which is read by the ASIC. The ASIC may modulate current to the miniaturized ultrasonic transducer as a function of the raw signal (or some portion of the raw signal) from the optical detector, and the miniaturized ultrasonic transducer can emit backscatter ultrasonic waves reflecting the detected signal. The ASIC may modulate the impedance presented to the transducers as a digital representation of the raw or compressed signal. The ASIC itself may calculate the oxygen concentration or pH, and sends a signal to the miniaturized ultrasonic transducer encoding the signal.

The implantable device may include a pH or oxygen sensor. The sensor may include a light source (such as a light emitting diode), a pH-sensitive or oxygen-sensitive matrix, and an optical detector (such as a photovoltaic, a phototransistor, or any other suitable optical detector known in the art). The matrix includes an oxygen sensitive fluorophore (for an oxygen sensor) or a pH sensitive fluorophore (for a pH sensor). Optionally, a filter is disposed between the light source and the matrix. The filter can be configured to allow a narrowband light to be transmitted to the matrix. In addition to or in place of filter, a filter may be disposed between the matrix and the optical detector. The filter can be configured to allow a narrowband light to enter the optical detector. The light source is powered by a driver, and the optical detector transmits a signal received by a front end (such as a CMOS front end). The front end and the driver are connected to a digital circuit. The optical sensor may be used to determine blood pressure or a pulse rate. For example, the optical sensor can include a membrane. Light from the light source is focused on the membrane, and the membrane reflects the light, which is detected by the optical detector. The membrane is deformed by pressure, and the deformations are cause variation in the reflected light.

An implantable device with a temperature sensor may include a miniaturized ultrasonic transducer (such as a bulk piezoelectric transducer, a PMUT, or a CMUT) and a temperature sensor (such as a proportional to absolute temperature (PTAT) circuit, a thermocouple, or a thermistor). The thermistor may be a negative temperature coefficient (NTC) thermistor or a positive temperature coefficient (NTC) thermistor. The implantable device may further comprise an ASIC (which optionally includes a front end, such as a CMOS front end, or a driver), which may be integrated with or distinguishable from the temperature sensor. The ASIC may include a digital circuit, a modulation circuit, or a power circuit; the power circuit derives power from the transducer. The implantable device may include or exclude an ASIC. The impedance presented to the transducer by the temperature sensor depends on the measured temperature, which modulates the current flowing through the ultrasonic transducer. As the current flowing through the ultrasonic transducer produces changes in ultrasonic backscatter detected by the external transceiver, temperature can be measured using the implantable device comprising the temperature sensor.

The implantable device comprising a temperature sensor can be used, for example, to monitor temperature of an organ (such as the liver, stomach, small or large intestine, kidney, pancreas, gallbladder, bladder, ovaries, uterus, spleen, etc.) in a subject, for example during ablation (e.g., radiofrequency ablation, microwave thermotherapy ablation, or cryotherapy ablation) of tissue, such as a cancer. The organ may be a transplanted organ. The implantable device comprising a temperature sensor may be used to monitor the temperature of a site of infection. The implantable device with a temperature sensor may be able to resolve a temperature within about 2° C. or less (such as within about 1° C. or less, within about 0.5° C., or within about 0.1° C., or less).

The sensor may be a pressure sensor. An implantable device comprising a pressure sensor can be used, for example, for monitoring blood pressure, pulse rate, tissue inflammation, vascular constriction, compartment syndrome, gastrointestinal (GI) tract monitoring, wound recovery, intra-ocular pressure, or cranial pressure. The pressure sensor can be, for example, a microelectromechanical system (MEMS), which can modulate current (which may pass through the ASIC, if present) in response to applied pressure.

The sensor may be a glucose sensor. Electrochemical glucose monitoring has been implemented with amperometric measurements using electrodes coated with enzymes such as glucose oxidase (an enzyme) to ensure specificity. Unfortunately, such devices tend to have short device lifetimes. Commercially purchased subcutaneous continuous glucose monitors often only have 3-7 day lifetimes due to the instability of the enzyme layer at body temperatures. To counteract this, non-enzymatic probes have been developed, such as potentiometric chemical sensors. Unfortunately, one of the leading causes for failure of these devices is simply the introduction of foreign bodies into subcutaneous tissue. The issue of foreign body response is similar to the challenge faced in chronic neural interface implantation. Implantable devices coated in SiC provide a solution. The glucose sensor can detect glucose in blood or interstitial fluid, and the current flowing from the sensor can depend on the concentration of glucose detected by the sensor. For example, the glucose sensor can have a first electrode and a second electrode, and a voltage differential can be generated based on the amount of glucose in the sensor. The first electrode may be functionalized by glucose oxidase. The sensor may include a glucose-permeable membrane separating the electrodes from the surrounding tissue.

The sensor may be a strain sensor (or strain gauge). The strain sensor measures how much strain exists in a material (such as a tissue or organ). A strain sensor can include, for example, a thin film conductor or semiconductor that changes resistance as it stretches.

FIG. 1 shows a semi-schematic diagram of a system according to the present invention. An animal, e.g., a dog 1, is implanted with a transponder/beacon module 2, which includes a sensor or sensors, an NFC compatible communication subsystem, an energy harvesting subsystem, a local area network or personal area network interface subsystem, a battery subsystem, a microcontroller subsystem and a memory subsystem. The transponder/beacon module 2 supports two different communication modes. In a first mode, near field communications (NFC) are employed to communicate with a nearby interrogator device, which is conveniently a smartphone 3. NFC supports communications in which the NFC subsystem of the transponder/beacon module 2 communicate by means of backscatter of a radio frequency field emitted by the interrogator, and the transponder/beacon module 2 can further capture and employ power from that field to power the other elements of the transponder/beacon module 2.

A harness or collar (not shown) may be attached to the animal, to externally power the transponder/beacon module 2, and charge the battery subsystem. The smartphone 3 has an app or operating system daemon that communicates with the transponder/beacon module 2, and in some modes passes data to the transponder/beacon module 2, and then processes the received data, which may then be forwarded to a server 6 though the Internet 5, either through a WiFi router 8 or a base station of a cellular network 4. The server 6 accumulates the data, and prepares and transmits reports to the pet owner and/or veterinarian relating to the sensor data.

The transponder/beacon module 2 may include a geographic positioning system (GPS) or other locating technology, or assistive locating technology (e.g., reads identifier such as MAC address from transmitters in its environment) which can be used to locate the dog 2. This location technology may also be used to log activity of the animal, and provide location-based services. The transponder/beacon module 2 has unique identifier, i.e., a serial or index number, that can be used to identify the dog 2.

When the dog 2 is distant from the NFC interrogator, e.g., the smartphone 3, and an emergency arises, the transponder/ beacon module 2 supports a second communication mode, comprising an active broadcast. This may be a WiFi or Bluetooth (e.g., Class 1) packet 7 or set of packets that trigger an emergency response. The active transmission may also be of another type, such as a 928 MHz, 433 Mhz or 315 Mhz emission. In this mode, for example, the 2.4 GHz transponder/beacon module 2 can communicate directly with the WiFi router 8. Note that in some cases, the transponder/beacon module 2 may include a 4G or 5G radio, and communicate directly with the base station 4 of the cellular network.

Figure 2:
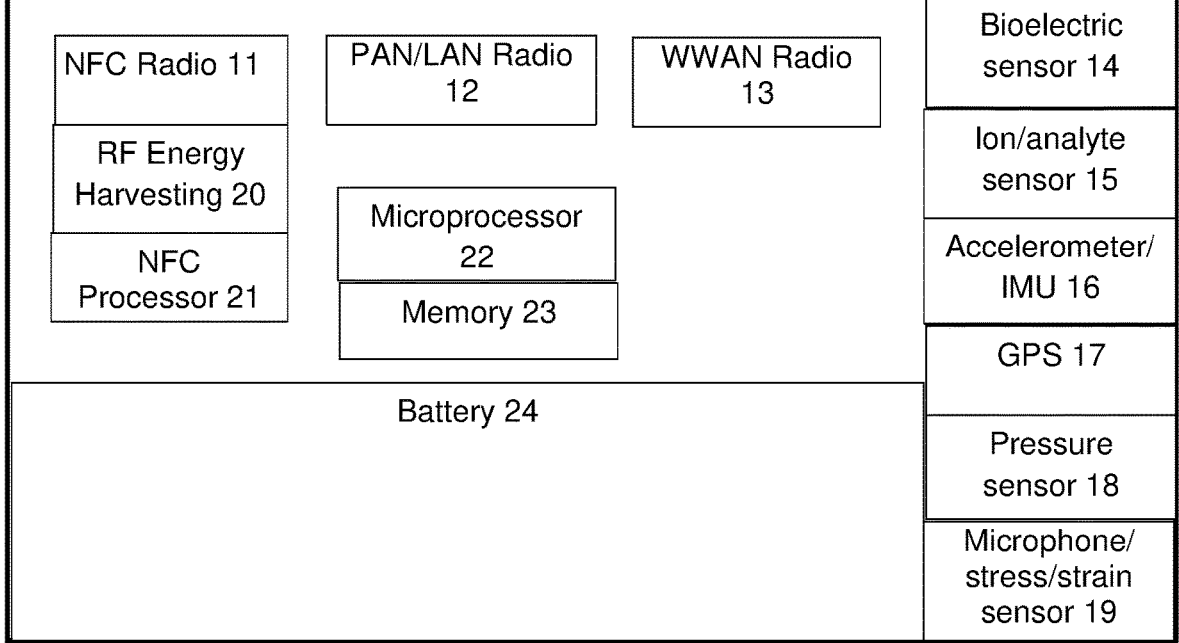
FIG. 2 shows a semi-schematic diagram of a transponder/beacon device according to the present invention.

FIG. 2 shows a semi-schematic drawing of an implantable transponder/beacon module 2. The module includes an NFC radio 11, which has an associated RF energy harvesting module 20, and an NFC processor 21. While the NFC processor 21 is somewhat redundant with the main microprocessor 22, it can reduce power consumption. Note that the NFC radio 11 module, RF energy harvesting module 20, and NFC processor 21 may be integrated in a single integrated circuit, within a multichip module, and therefor may be implemented in a different process than other components. In this case, the NFC processor 21 may have its own memory (not shown), which may act independently of the memory 22 provided for the main microprocessor 22.

In addition, an optional a personal area network (e.g., Bluetooth 5.0, 5.1 or 5.2) and/or local area network (e.g., WiFi n/ac) module, e.g., the PAN/LAN radio 12 is provided, to permit emergency broadcast when the NFC communications are not available. An optional wireless wide area network (e.g., 4G LTE, 5G) module, e.g., WWAN radio 13 is provided, to provide a direct cellular network interface. The PAN/LAN radio 12 and/or WWAN radio 13 require a battery 24 for operation. Likewise, continuous sensing also requires use of a battery (or supercapacitor) if the energy harvesting is unavailable. It is noted that the harvested energy need not be radio frequency, but may also be optical, thermal, acoustic, mechanical/kinetic, or other forms. See, Shi, Bojing, Zhou Li, and Yubo Fan. "Implantable Energy-Harvesting Devices." Advanced Materials 30, no. 44 (2018): 1801511;

Li, Jun, and Xudong Wang. "Research Update: Materials design of implantable nanogenerators for biomechanical energy harvesting." APL materials 5, no. 7 (2017): 073801.

Zheng, Qiang, Hao Zhang, Bojing Shi, Xiang Xue, Zhuo Liu, Yiming Jin, Ye Ma et al. "In vivo self-powered wireless cardiac monitoring via implantable triboelectric nanogenerator." Acs Nano 10, no. 7 (2016): 6510-6518.

Wong, Alan Chi Wai, Mark Dawkins, Gabriele Devita, Nikolaos Kasparidis, Andreas Katsiamis, Oliver King, Franco Lauria, Johannes Schiff, and Alison J. Burdett. "A 1 V 5 mA multimode IEEE 802.15. 6/Bluetooth low-energy WBAN transceiver for biotelemetry applications." IEEE Journal of Solid-State Circuits 48, no. 1 (2013): 186-198.

Ragesh, G. K., and K. Baskaran. "Addressing the Need for Context Awareness and Security Requirements in Wireless Body Area Networks." International Journal of Future Computer and Communication 1, no. 3 (2012): 302.

Che, Tsung-Yen, Yul-Lung Chang, and Shuenn-Yuh Lee. "A Wireless Electrocardiogram System-on-a-Chip with Reed-Solomon Coding and Frequency-Shift-Keying Transmitter for Healthcare Application." In 1st Global Conference on Biomedical Engineering & 9th Asian- Pacific Conference on Medical and Biological Engineering, pp. 209-211. Springer, Chain, 2015.

Feng, Hongqing, Chaochao Zhao, Puchuan Tan, Ruping Liu, Xin Chen, and Zhou Li. "Nanogenerator for biomedical applications." Advanced healthcare materials 7, no. 10 (2018): 1701298.

Ma, Ye, Qiang Zheng, Yang Liu, Bojin Shi, Xiang Xue, Weiping Ji, Zhuo Liu et al. "Self-powered, one-stop, and multifunctional implantable triboelectric active sensor for real-time biomedical monitoring." Nano letters 16, no. 10 (2016): 6042-6051.

Marinkovic, Stevan J., and Emanuel M. Popovici. "Power efficient networking using a novel wake-up radio." In 2011 5th International Conference on Pervasive Computing Technologies for Healthcare (PervasiveHealth) and Workshops, pp. 139-143. IEEE, 2011.

Lundager, Katrine, Behzad Zeinali, Mohammad Tohidi, Jens Madsen, and Farshad Moradi. "Low power design for future wearable and implantable devices." Journal of Low Power Electronics and Applications 6, no. 4 (2016): 20.

Zheng, Qiang, Bojing Shi, Zhou Li, and Zhong Lin Wang. "Recent progress on piezoelectric and triboelectric energy harvesters in biomedical systems." Advanced Science 4, no. 7 (2017): 1700029.

Zamani, Milad, Yasser Rezaeiyan, Omid Shoaei, and Wouter A. Serdijn. "A 1.55 W bio-impedance measurement system for implantable cardiac pacemakers in 0.18 m CMOS." IEEE transactions on biomedical circuits and systems 12, no. 1 (2018): 211-221.

Zhang, Ding, Yuanhao Wang, and Ya Yang. "Design, Performance, and Application of Thermoelectric Nanogenerators." Small (2019): 1805241.

The implantable transponder/beacon module 2 may include various sensors, such as a bioelectric sensor 14, ion/analyze sensor 15, accelerometer/inertial management unit (IMU) 16, GPS 17, pressure sensor 18, MEMS sensor, such as a microphone/stress/strain sensor 19. The implantable transponder/beacon module 2 is housed in a biocompatible shell, e.g., glass, silicon, polyurethane, or the like. The implantable transponder/beacon module 2 is preferably less than 3 mm×3 mm cross section, and less than 25 mm long, and more preferably less than 2 mm diameter and 20 mm long. The battery 24 may be a lithium ion battery.

Figure 3:
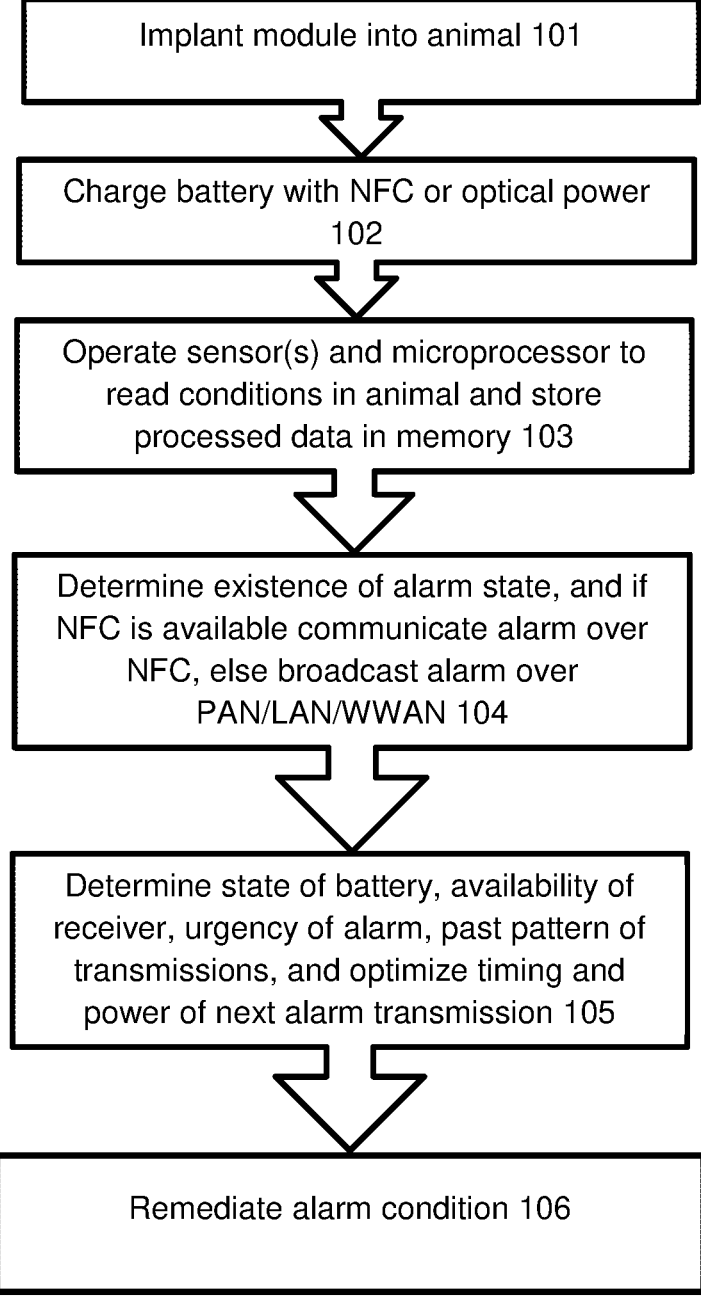
FIG. 3 shows a flowchart of a first method according to the present invention.

FIG. 3 shows a flowchart of a first embodiment of a method according to the present invention. Initially, the module is implanted into an animal 101. A convenient location is under the skin between the scapulae. The implant is operated normally, including charging the battery with NFC or optical power 102. Thus, under normal circumstances, the battery 24 has a power reserve. Also, under normal conditions, the sensors are read by the microprocessor 23, the data processed, and the conditions in animal determined and stored in the memory 103. Using the processed sensor data, the microprocessor determines existence of an alarm state. If NFC is available, the alarm is communicated over NFC. Otherwise, the alarm is broadcast/transmitted over PAN/LAN/WWAN 104. In some cases, no PAN/LAN/WWAN module is available, or the battery is exhausted, in which case attempts to communicate through NFC (RFID) persist. After the initial alarm communication, the microprocessor 24 may adopt an intelligent alarm communication scheme, determining the battery state, and intending to preserve the remaining battery life where possible, but also to communicate the alarm as soon as possible depending on the urgency of the alarm state and a past pattern of transmissions. For example, a transmission frequency may reduce over time, while transmit power increase. Thus, the timing and power of subsequent alarm transmissions is optimized 105.

Determine existence of alarm state, and if NFC is available communicate alarm over NFC, else broadcast alarm over PAN/LAN/WWAN 104. Remediate alarm condition 106.

Example 2

Figure 4:
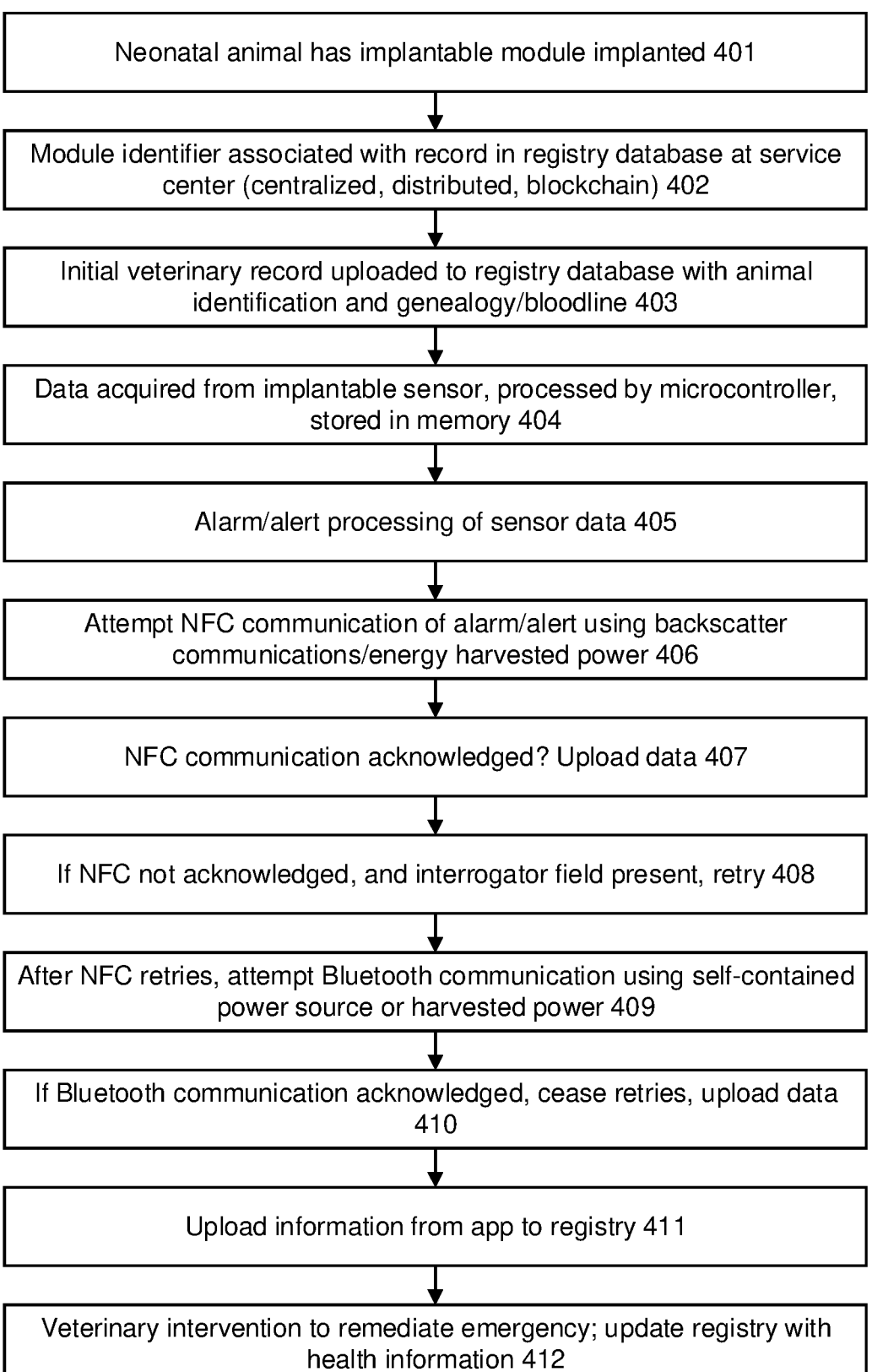
FIG. 4 shows a flowchart of a second method according to the present invention.

FIG. 4 shows a flowchart of a second embodiment of the invention. The implantable module is implanted 401 in a pet during a routine early veterinary visit, before adoption. The module identifier is registered with an online registry database, along with animal specifics 402. The veterinarian may upload clinical information and records for the animal, such as birth and vaccination records, as well as lineage and identification of genetically related animals 403.

Young pet animals may suffer from acute hypoglycemia and other emergencies. These emergencies may be life threatening, and treatable if caught in time. However, the window of opportunity may be hours or minutes.

The implantable module has one or more sensors than sense either a primary defect, such as plasma glucose level, or a biomarker or surrogate for the primary defect. Note that there may be various primary defects, which may be sensed with one or more sensors. The module periodically wakes its processor to acquire a sensor reading 404. The acquired reading is processed for calibration, normalization, and statistical properties, and a determination made whether there is an abnormal condition 405. The calibrated and normalized data is then stored as information in the memory. If there is an abnormal condition indicative of an emergency, the implant module seeks to communicate through the NFC with an interrogator 406. If no interrogator field is present and no acknowledgement received 407, the NFC communication is retried 408, and then the implant uses battery power, from e.g., a CR313 battery, to generate a broadcast alert 409. For example, a Bluetooth Low Energy 5.0 (BLE) communication is sent to a remote Bluetooth radio within range. If the transmission is acknowledged, the implant module ceases attempts at communication through the Bluetooth radio, and if acknowledgement is received, data is uploaded 410 to the smartphone or Bluetooth device, and hence by the app executing in the smartphone to the registry 411 of the service center. If the communication is not acknowledged the implant module will wait 60 seconds, and attempt to communicate over NFC and BLE again. This is repeated while the emergency condition persists, until a low battery alert. In conjunction with a repeated broadcast alert (but typically not the initial attempt), the implant module may charge a capacitor to deliver a painful stimulus to the animal. The normal response of the animal would be a cry, which would potentially alert a nearby human to the condition.

When a low battery condition occurs, the implant module may space the attempted emergency alerts further apart, such as every 10 minutes. In conjunction, the broadcast power may be increased.

If the alert is received, an app in the receiving device triggers an alarm for the user, and potentially to remote users through a cellular network or local area network either locally or through the Internet. The user is prompted to approach the animal suffering the emergency, and when within range for NFC communications, will then download the memory and provide prompts for emergency action, based on an automated assessment of the condition of the animal.

For example, in event of hypoglycemia, the remedy may be administering glucose or fructose. The implant device sensor may be monitored to assess success of the remediation. For example, the sensor is a thermal sensor, and the indication of hypoglycemia is hypothermia. Therefore, successful administration of the sugar should result in remediation of the hypoglycemia, and normothermia. If the sensor is an electrophysiological sensor, the reading may represent changes in muscle fiber twitch spectrum, and also ECG alterations. If the sensor is a stimulus-response electrophysiological sensor, it may additionally be able to assess changes in response latency, amplitude, and duration, for example. The sensor may also be a glucometer, for direct measurement of interstitial glucose, which will correspond to plasma glucose with some delay.

When an emergency alert is generated and received, the app will contact a service center, which will recall the animal health record based on the registry database, and will in turn contact a veterinarian or skilled caretaker to address the problem. For example, the veterinarian may be placed in a video conference with the user to help address the problem 412. The veterinarian on call is provided with the animal health record, and the sensor data. The video conference on the user's cellphone or other device also allows observation of the animal in question.

A record of the emergency event is added to the animal health record.

If the implant module battery is weak or consumed, the implant is replaced or deactivated and a new one implanted.

The typical window of risk for animals is within the first 3 months of life, so the battery in the module for emergency purposes need only last about 100 days. After this initial window, if the battery still has life, the periodic logging function may be deactivated, and the battery preserved for later use, for example to be activated if the animal later becomes ill and needs temporary monitoring.

Example 3

When the animal is adopted, the new owners are provided provide with documents relating to the implant module, and are invited to register with the online registry.

FIG. 5 shows a third embodiment of a method according to the preset invention. The new owners download an app on a smartphone 501, which then interfaces with the implant module using NFC 502. The smartphone app reads the identifier of the implant module, and contacts the service center for the registry database 503, and provides a user interface for updating ownership and location of the animal, as well as registering for various services for the animal and animal owner 504, such as pet insurance, pet tracking service registration 505, veterinary record management, etc.

The service center then uploads sensor data from the implantable tag to the smartphone app, which is then forwarded to the service center 506. The sensor data is processed by the service center or the app to update alarm/alert processing parameters based on current conditions, to improve sensitivity and selectivity of the alarm/alert process. The implantable module may also be updated to show the animal's owner's address in a message available through a smartphone app and NFC of a non-owner, i.e., without strong security, so that a stray animal may be returned. Alternately, the non-owner app contacts the service center which will authenticate the non-owner and mediate return of the animal without release of confidential information.

Optionally, a video conference session may be opened with an on-call veterinarian with the new owners, to provide a well animal care checkup 507.

The implant module is writable, and the app, under control of the service center, updates the locally stored information to reflect changes made during the session, including any veterinarian notes 508.

Example 4

When the pet is near an NFC interrogation device, such as near a water bowl or pet bed, the implant module is activated, and data may be acquired and the information stored in the memory. Typically, there is no need to monitor data when out of range of an interrogator. The interrogator may report directly to the app in the smartphone, or through the service center. Communications are encrypted, and in some cases, the implant module tunnels through the app so that the implant module is isolated from security defects of the smartphone and its app. Likewise, the interrogators need not be secure if the implant implements a tunneling secure protocol.

Such routine monitoring allows acquisition of a baseline, and also to detect excursion of the animal's condition from the baseline potentially indicative of disease.

If the animal's health is impaired, as detected by the sensor, the condition is conveyed to the service center, which then sends an alert to the user's smartphone. The user may then initiate a video conference or other session with the on call veterinarian. The veterinarian is provided with the animal health record, and updates the record as a result of the interaction.

For example, as shown in FIG. 6, which shows a fourth embodiment of a method according to the present invention, a young pet may become hypoglycemic 601, which, among other symptoms, causes hypothermia. The implantable module periodically reads a temperature sensor 602 located in the implantable module. The microcontroller in the implantable module applies calibration parameters, and normalizes the sensor data 603. The microcontroller analyzed calibrated data for statistical deviation from normal, and applies other tests 604. The existence of an emergency hypoglycemia state is determined by the microcontroller in the implantable module by analyzing the stored calibrated sensor data 605. In some cases, the processing of the sensor data may be a single process, without generation of intermediate calibrated data.

In case of an emergency, the implantable module initially seeks to communicate with an NFC interrogator 606. Practically, if energy is available from the antenna to power the implantable module, that energy likely comes from an NFC interrogator and communication will likely be successful. If no interrogation field is present, communication will likely be unsuccessful. In some cases, an NFC field will be available to power the implantable module, but communication is not possible or acknowledged. If the NFC is unavailable, i.e., no acknowledgement of the alert is received, then the secondary communication, i.e., Bluetooth low energy 5.0, 5.1, or 5.2 is attempted, and confirmation of communication sought 607.

If neither NFC nor BLE is available, the implantable module may generate a painful stimulus, such as an electrical shock 608 to cause the animal to generate a vocalization.

If communications are established, an alert is sent to the service center, which then forwards warnings through the cellular network, SMS network, email network, or Internet to the caregivers, and also to a veterinarian on call 609. During the communication, data stored in the implantable module is uploaded to the service center for availability in the medical (veterinary) record and further analysis 610. An attempt will be made to open a videoconference (telemedicine conference) with the veterinarian on call, to assist in making efforts to remediate the hypoglycemia 611. As a result of the session, the alarm thresholds for future alarms/alerts may be altered by a download of parameters to the implantable module, the remaining battery life tested (and the module replaced as appropriate), and to consolidate veterinary records 612.

The service center may be consolidated, and represent a competitive service business, wherein alternate service centers are available to animal owners. The implantable module may store the required contact information, which may be, for example, a static IP address. Alternately, there may be a public lookup database which associates animal tag IDs with service centers.

The records may be stored in a centralized database, a fully database, or in a blockchain. The blockchain storage may be linked to exchangeable tokens, and access to records from the blockchain, or storage of records to the blockchain, may incur a token charge. The wallet for the tokens may be in the user's smartphone, or in the implantable module itself. Typically, cryptographic processing is offloaded from the implantable module, though the implantable module may act as a trusted platform module (TPM) for the smartphone app, storing cryptographic keys.

The tokens may also be used to pay for veterinary services, as well as other animal related expenses. The tokens may be replenished by the owner, or in some cases, by an insurance company to reimburse expenses. For example, A pet owner buys pet insurance, which contracts with veterinary providers. The veterinary providers provide services, which are either charged to the customer for post-approval or preapproved and direct reimbursed by the insurance company. In the post-approval case, an insurance company adjuster can review the veterinary record, veterinary service billing, and reimburse for the services by a token transfer.

In some cases, the animal may require an intervention or veterinary device. Use of that device may be coordinated by or in conjunction with the implant module. For example, the veterinary device may have a BLE module, an NFC module, and a WiFi module, to provide communications with the implant module, the service center and the veterinary device. For example, the service center may provide an adaptively controlled therapy based on an identification of the animal, and optionally a biological sensor reading.

The term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. The modules, circuitry, processors, etc. may be affixed to a printed circuit board (PCB), or the like, and may take a variety of forms. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing circuitry capable of carrying out the functionality described with respect thereto. After reading this description, it will become apparent to a person skilled in the relevant art how to implement the application using other computing modules or architectures.

The terms "computer program medium" and "computer usable medium" are used to generally refer to transitory or non-transitory media. These may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module to perform features or functions of the present application as discussed herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting.

As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred,' 'desired,' or 'desirable,' and words of similar meaning should not be understood as implying that certain features are critical, essential, or even important to the structure or function of the present disclosure, but instead as merely intended to highlight alternative or additional features that may or may not be utilized in a particular embodiment. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments. When only a single bound is identified, the other may be constrained by the laws of physics or nature, and that implied limit shall apply.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the present disclosure to the specific embodiments and examples described herein, but rather to also cover all modification and alternatives coming with the true scope and spirit of the present disclosure.

What is claimed is:

1. An implantable device, comprising:

an implantable, biocompatible shell having dimensions of 1.5-3 mm×1.5-3 mm×5-25 mm;

a plurality of sensors configured to produce sensor data corresponding to a biological state of a host, the plurality of sensors comprising a thermal sensor and a physiological sensor selected from the group consisting of: an optical sensor; a chemical sensor; a mechanical sensor, an inertial sensor, an acoustic sensor, and an electric signal detector;

a multiprotocol wireless radio frequency telemetry system configured to (a) transmit the sensor data, and to (b) transmit an alarm signal, using electrical power, wherein the multiprotocol telemetry system has:

a first protocol of operation compatible with at least one of wireless communication technologies which communicates error correction and detection encoded data through a first antenna, and a second protocol of operation which communicates error correction and detection encoded data using radio frequency backscatter within a frequency range of 30 kHz to 30 MHz through a second antenna comprising a coil;

the multiprotocol telemetry system being configured to select between multiple concurrently available communication partners to establish a communication link;

an energy harvesting system configured to harvest energy from an environment within the host using the second antenna, and to provide at least sufficient electrical power for the transmission of the sensor data by the multiprotocol telemetry system using the second protocol of operation and insufficient electrical power for the transmission of the sensor data by the multiprotocol telemetry system using the first protocol of operation;

a memory;

a microcontroller, configured to operate absent availability of the at least sufficient electrical power to:

receive the sensor data, process the sensor data for storage as information in the memory, determine an alarm state dependent on the sensor data and an alarm threshold, and control communications through the multiprotocol telemetry system to:

select at least one of the first protocol of operation and the second protocol of operation of the multiprotocol telemetry system and control the multiprotocol telemetry system to select a reliable one of the multiple concurrently available communication partners to establish the communication link, wherein the first protocol is selected in preference to the second protocol, transmit the sensor data through the communication link, and transmit the alarm signal through the communication link dependent on the determined alarm state using the selected at least one of the first protocol of operation and the second protocol of operation of the multiprotocol telemetry system; and an electrochemical energy source configured to provide at least a portion of the electrical power for operating the microcontroller, the memory, and the transmission of the alarm signal by the multiprotocol telemetry system, wherein each of the plurality of sensors, the multiprotocol wireless radio frequency telemetry system comprising the first antenna and the second antenna, the energy harvesting system, the memory, the microcontroller, and the electrochemical energy source together are disposed within the implantable, biocompatible shell having dimensions of 1.5-3 mm×1.5-3 mm×5-25 mm.

2. The implantable device of claim 1, wherein the plurality of sensors comprise an optical sensor comprising a light source and an optical detector.

3. The implantable device of claim 1, wherein the plurality of sensors comprise at least one of a potentiometric chemical sensor and an amperometric chemical sensor.

4. The implantable device of claim 1, wherein the first protocol of operation is compatible with communication through a frequency hopping spread spectrum protocol and the second protocol of operation is compatible with a near-field communication (NFC) protocol.

5. The implantable device of claim 1, wherein the plurality of sensors are selected from the group consisting of a glucose level detector, an ion-specific sensor, a lactic acid detector, a pH sensor, a carbon dioxide detector, an electrochemical reaction sensor, a colorimetric sensor, and a fluorometric sensor.

6. The implantable device of claim 1, wherein the plurality of sensors are selected from the group consisting of a bioelectric activity sensor, an electromyographic detector, an electrocardiographic detector, and an electroencephalographic sensor, and has electrodes exposed on an exterior of the implantable, biocompatible shell.

7. The implantable device of claim 1, wherein:

the multiprotocol telemetry system has the second protocol of operation compatible with a near field communication (NFC) system, the electrochemical energy source comprises a rechargeable battery;

the energy harvesting system captures sufficient radio frequency energy from the second antenna during operation according to the second protocol to at least operate the microcontroller and charge the electrochemical energy source, and the microcontroller is further configured to write data received through the near field communication system (NFC) using electrical power from the energy harvesting system into the memory.

8. The implantable device of claim 1, wherein the multiprotocol telemetry system has the second protocol of operation that operates at a radio frequency communications frequency of 13.56 MHz, the second antenna comprises the coil and a magnetic core, and the biocompatible shell has dimensions of 2-3 mm×2-3 mm×15-25 mm.

9. The implantable device of claim 1, wherein the plurality of sensors comprise an optical glucose sensor, comprising a light source and an optical detector.

10. The implantable device of claim 1, wherein the second antenna comprising the coil of the multiprotocol telemetry system is configured to interact with an external inductive power transfer coil to power the energy harvesting system and the microcontroller is further configured to determine the alarm state dependent on the sensor data and the alarm threshold value at least every ten minutes.

11. The implantable device of claim 1, wherein the microcontroller is further configured to:

process the sensor data to represent a glycemic state of the host, information stored in the memory representing at least the glycemic state;

determine a hypoglycemic state of the host in real time dependent on the sensor data, by comparing the glycemic state of the host with the alarm threshold;

selectively actively transmit at least an indicium of hypoglycemia as the alarm signal according to the first protocol through a local area network or personal area network transceiver of the multiprotocol telemetry system dependent on the determined alarm state;

receive harvested energy from the energy harvesting system to power the processing of the sensor data and the determining of the hypoglycemic state during operation according to the second protocol; and receive electrical power from the electrochemical energy source, wherein the electrochemical energy source comprises a secondary energy source, to power the multiprotocol telemetry system for reliable active transmission of the indicium of hypoglycemia during operation according to the first protocol.

12. The implantable device of claim 1, wherein the electrochemical energy source comprises a rechargeable electrical device configured to receive excess power from the energy harvesting system for recharging the rechargeable electrical device.

13. The implantable device of claim 12, wherein the rechargeable electrical device is a lithium battery.

14. The implantable device of claim 1, wherein the second protocol of the multiprotocol telemetry system communicates through a near-field communication (NFC) protocol.

15. The implantable device of claim 14, wherein the first protocol of operation is compatible with Class 2 IEEE-802.11 b/g/n/ac/ad/ax.

16. An implantable device, comprising:

an implantable, biocompatible shell having dimensions of 2-3 mm×2-3 mm×15-25 mm;

an analyte sensor configured to produce analyte sensor data corresponding to an analyte level associated with a physiological condition of a host;

a wireless radio frequency multiprotocol telemetry system configured to transmit the analyte sensor data, and to transmit a status signal, using electrical power, wherein the multiprotocol telemetry system has:

a first error detection and correction encoded protocol of operation which communicates in a 2.4 GHz band using a first antenna, and a second error detection and correction encoded protocol of operation which communicates within a frequency range of 30 kHz to 30 MHz using radio frequency backscatter through a second antenna comprising a coil;

wherein the multiprotocol telemetry system is configured to select between multiple concurrently available communication partners to establish a communication link;

an energy harvesting system configured to harvest radio frequency energy from an environment within the host to power transmission of the analyte sensor data using the second error detection and correction encoded protocol of operation, the energy harvesting system being configured to supply insufficient electrical power to operate the multiprotocol telemetry system in the first error detection and correction encoded protocol of operation and sufficient electrical power to operate the multiprotocol telemetry system in the second error detection and correction encoded protocol of operation;

a memory which uses electrical power;

a microcontroller which uses electrical power, configured to operate absent availability of the harvested radio frequency energy to:

receive and process the analyte sensor data for storage as information in the memory;

communicate the stored information in the memory; and determine a state of the host dependent on the analyte sensor data and a criterion at least once every ten minutes; and control communications through the multiprotocol telemetry system to select one of the first error detection and correction encoded protocol and the second error detection and correction encoded protocol of the multiprotocol telemetry system for transmission of the determined state, and to select one of the concurrently available communication partners to establish the communication link, wherein the first error detection and correction encoded protocol is selected in preference to the second error detection and correction encoded protocol to conserve electrical power; and an electrochemical energy source configured to provide at least a portion of the electrical power for operating the microcontroller, the memory, and the transmission of the determined state by the multiprotocol telemetry system using the first protocol, wherein each of the analyte sensor, the wireless radio frequency multiprotocol telemetry system comprising the first antenna and the second antenna, the energy harvesting system, the memory, the microcontroller, and the electrochemical energy source together are disposed within the implantable, biocompatible shell having dimensions of 2-3 mm×2-3 mm×15-25 mm×5-25 mm.

17. The implantable device of claim 16, wherein: the multiprotocol telemetry system has:

the first error detection and correction encoded protocol of operation compatible with a spread spectrum protocol;

the second antenna comprises the coil and a magnetic core; and the second error detection and correction encoded protocol compatible with a near-field communication (NFC) protocol at a frequency of 13.56 MHz; and the electrochemical energy source is a rechargeable battery which is recharged with energy received through the second antenna.

18. The implantable device of claim 16, wherein the analyte sensor comprises a light emitting diode and optical detector, and the determined state is hypoglycemia.

19. An implantable device, comprising:

an implantable, biocompatible shell having dimensions of 1.5-3 mm×1.5-3 mm×5-25 mm;

an optical, chemical, or bioelectric signal sensor within the implantable, biocompatible shell configured to produce sensor data corresponding to a physiological state of a host;

a multiprotocol telemetry system adapted to operate in an environment having a plurality of compatible transceivers with which the multiprotocol telemetry system is configured to communicate, within the implantable, biocompatible shell configured to transmit the sensor data, and to transmit a signal, by wireless radio frequency communications using electrical power, having:

a first encrypted error detection and correction encoded spread spectrum protocol of operation which communicates through a first antenna, and a second encrypted error detection and correction encoded protocol of operation using radio frequency backscatter within a frequency range of 30 kHz to 30 MHz through a second antenna comprising a coil;

an energy harvesting system within the implantable, biocompatible shell linked to the second antenna, configured to harvest radio frequency energy from an environment within the host using the second antenna, and to provide at least sufficient electrical power for the transmission of the sensor data by the multiprotocol telemetry system using the second encrypted error detection and correction encoded protocol of operation;

a memory within the implantable, biocompatible shell which uses electrical power;

a microcontroller within the implantable, biocompatible shell which uses electrical power, configured to:

encrypt and perform error detection and correction encode communications for transmission;

decrypt and perform error detection and correction decode received communications;

receive the sensor data, process the sensor data for storage as information in the memory, determine a threshold state dependent on the sensor data and a threshold value, select at least one of the first encrypted error detection and correction encoded protocol of operation and the second encrypted error detection and correction encoded protocol of operation of the multiprotocol telemetry system, wherein the first encrypted error detection and correction encoded protocol of operation is selected in preference to the second encrypted error detection and correction encoded protocol of operation to conserve electrical power, transmit the sensor data through the multiprotocol telemetry system as encrypted error detection and correction encoded data, and control communications through the multiprotocol telemetry system to transmit the signal as encrypted error detection and correction encoded data dependent on the determined threshold state the using the selected at least one of the first encrypted error detection and correction encoded protocol of operation and the second encrypted error detection and correction encoded protocol of operation of the multiprotocol telemetry system; and a rechargeable battery within the implantable, biocompatible shell configured to receive energy for recharging from the energy harvesting system, and to provide at least a portion of the electrical power for operating the microcontroller, the memory, and the multiprotocol telemetry system, wherein each of the optical, chemical, or bioelectric signal sensor, the multiprotocol telemetry system comprising the first antenna and the second antenna, the energy harvesting system, the memory, the microcontroller, and the rechargeable battery together are disposed within the implantable, biocompatible shell having dimensions of 1.5-3 mm×1.5-3 mm×5-25 mm.

20. The implantable device according to claim 19, wherein the implantable, biocompatible shell has dimensions of 2-3 mm×2-3 mm×15-25 mm;

the physiological state of the host comprises a glucose level;

the first encrypted error detection and correction encoded protocol of operation operates in a 2.4 GHz band using a TCP/IP protocol;

the second encrypted error detection and correction encoded protocol operates at 13.56 MHz using a near-field communication (NFC) protocol; and the microcontroller is configured to determine the threshold state dependent on the sensor data and the threshold value at least every ten minutes, and select the at least one of the first encrypted, error detection and correction encoded protocol of operation and the second encrypted, error detection and correction encoded protocol of operation of the multiprotocol telemetry system in dependence on whether the second antenna is within range of an active near-field communication (NFC) interrogator.

* * * * *